US012145945B2

(12) United States Patent
Corella et al.

(10) Patent No.: US 12,145,945 B2
(45) Date of Patent: Nov. 19, 2024

(54) COMPOUNDS, COMPOSITIONS, AND THERAPEUTIC USES THEREOF

(71) Applicant: Breakpoint Therapeutics GmbH, Hamburg (DE)

(72) Inventors: Andrea Guerrero Corella, Abingdon (GB); Stuart Robert Flanagan, Abingdon (GB); Jonathan Hollick, Hamburg (DE); Julien Gilbert Jacques Malassis, Toulouse (FR); Matthew Raymond Smith, Abingdon (GB); Ian Andrew Yule, Abingdon (GB); Jonathan Mark Bentley, Abingdon (GB)

(73) Assignee: Breakpoint Therapeutics GmbH, Hamburg (DE)

( * ) Notice: Subject to any disclaimer, the term of this patent is extended or adjusted under 35 U.S.C. 154(b) by 0 days.

(21) Appl. No.: 18/600,352

(22) Filed: Mar. 8, 2024

(65) Prior Publication Data
US 2024/0327430 A1    Oct. 3, 2024

(30) Foreign Application Priority Data

Mar. 10, 2023  (GB) ..................... 2303582
Jun. 12, 2023  (GB) ..................... 2308738
Aug. 11, 2023  (GB) ..................... 2312354

(51) Int. Cl.
*C07D 513/04*    (2006.01)
*A61K 31/4545*    (2006.01)

(52) U.S. Cl.
CPC ........ *C07D 513/04* (2013.01); *A61K 31/4545* (2013.01)

(58) Field of Classification Search
CPC .......................... C07D 513/04; A61K 31/4545
USPC ........................................................ 514/301
See application file for complete search history.

(56) References Cited

U.S. PATENT DOCUMENTS

2010/0249119 A1    9/2010    Hirose et al.

FOREIGN PATENT DOCUMENTS

| CN | 110128419 A | 8/2019 |
|---|---|---|
| EP | 2532661 A1 | 12/2012 |
| WO | WO-2020/243459 A1 | 12/2020 |
| WO | WO-2022/118210 A1 | 6/2022 |
| WO | WO-2022/240213 A1 | 11/2022 |
| WO | WO-2022/259204 A1 | 12/2022 |
| WO | WO-2023/050007 A1 | 4/2023 |
| WO | WO-2023/060573 A1 | 4/2023 |
| WO | WO-2023/061415 A1 | 4/2023 |
| WO | WO-2023/067515 A1 | 4/2023 |
| WO | WO-2023/134708 A1 | 7/2023 |
| WO | WO-2023/134739 A1 | 7/2023 |
| WO | WO-2023/202623 A1 | 10/2023 |
| WO | WO-2023/233295 A1 | 12/2023 |
| WO | WO-2024/069592 A1 | 4/2024 |
| WO | WO-2024/088407 A1 | 5/2024 |

OTHER PUBLICATIONS

Mao et al., "Synthesis and biological evaluation of novel N-pyridylpyrazolecarboxamides containing benzothiazole", Phosphorus, Sulfur, and Silicon and the Related Elements 192.1: 42-46 (2017).
Namani et al., "Design, Synthesis and Biological Evaluation of Benzimidazolyl and Benzothiazolyl Picolinamide Derivatives as Antimicrobial Agents", Asian Journal of Chemistry 27.12: 4575-4578 (2015).
United Kingdom Search Report for GB Application No. GB2303582.7 dated Jan. 31, 2024.
English machine translation of WO 2023/134739 A1 document (2024).
Notice of Allowance for U.S. Appl. No. 18/600,365 dated Jun. 7, 2024.
Database PubChem [Online] "N-(4-methyl-1,3-benzothiazol-2-yl)-2-morp holin-4-ylpyridine-3-carboxamide", XP093162261, Database accession No. 29417748 (2009).
Database PubChem [Online] NCBI; "N,2-bis(1,3-benzothiazol-2-yl)pyridine-3-carboxamide | C20H12N4OS2 | CID 18858909", XP093162239, Database accession No. 18858909 (2007).
Database PubChem [Online] NCBI; N-(4,6-dimethyl-1,3-benzothiazol-2-yl)-2-(1,2,4-triazol-l-yl)pyridine-3-carboxamide II XP093162267, (2009).

(Continued)

*Primary Examiner* — Kahsay Habte
(74) *Attorney, Agent, or Firm* — Foley Hoag LLP; David P. J. Halstead D.; Alexander J. J. Chatterley D.

(57) ABSTRACT

The present invention relates to a compound of the Formula:

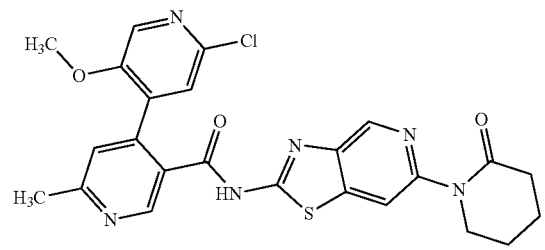

and pharmaceutically salts thereof.
The compound of the present invention inhibits Polθ. This novel therapeutic compound is therefore useful for the treatment and/or prevention of diseases and conditions in which Polθ activity is implicated, such as, for example but not limited to, the treatment and/or prevention of cancer. The present invention also relates to pharmaceutical compositions comprising the novel therapeutic compound defined herein, to processes for synthesising the compound and to their use for the treatment of diseases and/or conditions in which Polθ activity is implicated.

4 Claims, No Drawings

(56) References Cited

OTHER PUBLICATIONS

Database PubChem [Online] NCBI; "N-(4,6-dimethyl-1,3-benzothiazol-2-yl)-2-pyrrolidin-1-ylpyridine-3-carboxamide", XP093162269, Database accession No. 32990616 (2009).
Database PubChem [Online] NCBI; "N-(4-methyl-1,3-benzothiazol-2-yl)-2-pyrrolidin-1-ylpyridine-3-carboxamide", XP093162293, Database accession No. 78806042 (2014).
Database PubChem [Online] NCBI; "N-(5,6-difluoro-1,3-benzothiazol-2-yl)-2-morpholin-4-ylpyridine-3-carboxamide", XP093162290, Database accession No. 56205243 (2012).
Database PubChem [Online] NCBI; "N-(6-chloro-1,3-benzothiazol-2-yl)-2-piperidin-1-ylpyridine-3-carboxamide", XP093162283, Database accession No. 55756051 (2012).
Database PubChem [Online] NCBI; "N-(6-methyl-1,3-benzothiazol-2-yl)-2-morpholin-4-ylpyridine-3-carboxamide", XP093162279, Database accession No. 36297775 (2009).
Database PubChem [Online] NCBI; "N-(6-methyl-1,3-benzothiazol-2-yl)-2-pyrrolidin-1-ylpyridine-3-carboxamide", XP093162273, Database accession No. 32991085 (2009).
International Search Report and Written Opinion for Application No. PCT/IB2024/052261 dated May 24, 2024.
Supplemental Search Report from the UKIPO dated Jan. 30, 2024.
U.S. Appl. No. 18/600,347, Pending.
U.S. Appl. No. 18/600,365, Allowed.

COMPOUNDS, COMPOSITIONS, AND THERAPEUTIC USES THEREOF

RELATED APPLICATIONS

This application claims the benefit of priority to GB Application No.: 2303582.7, filed Mar. 10, 2023, GB Application No.: 2308738.0, filed Jun. 12, 2023, and GB Application No.: 2312354.0, filed Aug. 11, 2023; the contents of each of which are fully incorporated by reference herein.

INTRODUCTION

The present invention relates to novel therapeutic compounds. More specifically, the present invention relates to novel therapeutic compounds that inhibit Polθ. The novel therapeutic compounds are therefore useful for the treatment and/or prevention of diseases and conditions in which Polθ activity is implicated, such as, for example but not limited to, the treatment and/or prevention of cancer. The present invention also relates to pharmaceutical compositions comprising the novel therapeutic compounds defined herein, to processes for synthesising these compounds and to their use for the treatment of diseases and/or conditions in which Polθ activity is implicated.

BACKGROUND OF THE INVENTION

The Maintenance of genome integrity is of upmost importance for cell survival since genomic aberration is a major cause of disease, notably cancer[1]. The genome is continuously challenged by a various types of DNA damage, amongst which double strand breaks (DSBs) are considered the most toxic as they are a source of dramatic genomic rearrangements if not repaired or repaired inaccurately[2].

DNA polymerase theta (Polθ, encoded by POLQ) is a multifunctional enzyme comprising a C-terminal DNA polymerase domain, an N-terminal ATPase/helicase domain and a less structured central domain with protein interaction partner binding function[3]. Both enzymatic functions have been shown to have mechanistic activity in DNA repair processes. The helicase domain disrupts Rad51 nucleofilament formation, removes RPA from single stranded DNA and stimulates ssDNA annealing. The polymerase domain extends single stranded DNA ends to close ssDNA gaps.

Polθ expression is largely absent in normal cells, but expression has been shown to be upregulated in multiple cancers and increased expression correlates with poor prognosis[4,5,6]. In normal mammalian cells, Homologous Recombination (HR) and Non-Homologous End Joining (NHEJ) are the two major pathways for repairing DSBs faithfully. Other alternative pathways referred to as Alternative-NHEJ (ALT-NHEJ) are also involved in DSB repair, mostly in the absence of HR and NHEJ, as back-up pathways[7,4,8]. The most characterised ALT-NHEJ pathway is Micro-Homology End Joining (MMEJ), which relies on micro-homologies flanking the breaks to repair the lesion. In doing so, MMEJ inherently leads to deletions and therefore contributes genomic instability[9,10]. Polθ is a prominent actor in MMEJ which has been shown to process and anneal the single strand DNA ends, as well as to synthesise DNA to complete the repair[11,12,13].

DNA Damage Response (DDR) deficiency, such as loss of HR, results in genomic instability and is often associated with cancer. However, DDR deficient cancers can become critically dependent on back-up DNA repair pathways, which present an Achilles heel that can be targeted to eliminate cancer cells. For example, PARP1 inhibitors are selectively lethal in cancer cells deficient in components of HR (e.g. ATM, BARD1, PALB2, BRCA1, BRCA2 etc.)[14].

Likewise, selective lethality is observed when Polθ functions are abrogated in the context of HR and NHEJ deficiencies. MMEJ is infrequently used when HR and NHEJ are available[15] but becomes necessary when the canonical pathways are impaired during carcinogenesis, rendering these cancer cells specifically dependent on Polθ[4,16].

PARP inhibitors are used in the treatment for HR deficient cancers but inherent or acquired drug resistance is a significant limitation. Two of the most frequent mechanisms of resistance to PARPi, could be counteracted by inhibition of Polθ:

(i) The main mechanism of resistance observed in clinical samples, is the reactivation of HR through reversion of the mutation that caused the HR deficiency[17]. A significant proportion of such reversion mutations are thought to be acquired through the action of Polθ in MMEJ[18,19].

(ii) Restoration of HR activity in BRCA1 deficient cancer through loss of SHLD/53BP1 complex has been shown to lead to PARP inhibitor resistance[20,21,22,23]. Polθ inhibitors are anticipated to be useful in treating such tumours[24] and deficiency in both the SHLD/53BP1 complex and BRCA1 is demonstrated to result in vulnerability to Polθ inhibition[25,26].

In addition to the synthetic lethality observed in HR and NHEJ deficient cancer, Polθ loss has been reported to sensitise cancer cells to many standard of care agents. Depletion of Polθ leads to potentiation of various chemotherapies, such as topo-isomerase1/2 inhibitors[27] hydroxyurea, platinum agents[28], bleomycin, as well as irradiation[29,30]. Furthermore, loss of Polθ was also shown to enhance effects of DNA repair targeted inhibitors: e.g. PARP[31], ATM[27], ATR[32] and DNAPK[32].

Considering the numerous evidence of sensitisation to DNA repair associated therapies, Polθ is a promising target for combination with already established standard of care agents.

There is therefore a need for new and improved agents capable of targeting Polθ and inhibiting its activity. Furthermore, there is a need for improved agents that possess one or more favourable pharmaceutical properties, such as, for example, improved potency, improved human metabolic stability, improved cell permeability or improved solubility. The present invention was devised with the foregoing in mind.

REFERENCES

1. Helleday T., et al, Nat Rev Genet. (2014); 15:585-98
2. Ceccaldi R., et al, Trends Cell Biol. (2016); 26:52-64
3. Seki M. et al., Nucleic Acids Res., (2003); 31:6117-26
4. Ceccaldi R., et al., Nature (2015); 518:258-62
5. Lemée F., et al, PNAS (2010); 107:13390-5
6. Higgins G. S., et al., Oncotarget (2010); 1:175-84
7. Kabotyanski E. B., et al, Nucleic Acids Res. (1998); 26:5333-42
8. Ahrabi S., et al, Nucleic Acids Res. (2016); 44:5743-57
9. McVey M., et al., Trends Genet. (2008); 24:529-38
10. Sfeir A., et al, Biochem Sci. (2015); 40:701-14)
11. Chan S. H., et al., PLoS Genet. (2010); 6:e1001005
12. Wyatt D. W., et al, Mol Cell. (2016); 63:662-673
13. Black S. J., et al., Nat Commun. (2019); 10:4423
14. Audeh M. W., et al., Lancet (2010); 376 (9737):245-51
15. Truong W., et al., PNAS (2013); 110:7720-7725

16. Mateos-Gomez P. A., et al., Nature (2015); 518:254-57
17. Noordermeer S. M., et al., Trends Cell Biol. (2019); 29:820-834
18. Edwards S. L., et al., Nature (2008); 451(7182):1111-5
19. Lukashchuk N., et al., J Clin Oncol (2022) 40(16_suppl): 5559-5559)
20. Jaspers J. E., et al., Cancer Discov. (2013); 3(1):68
21. Pettitt S. J., et al., Nat Commun. (2018); 9:1849;
22. Noordermeer S. M., et al., Nature (2018) 560:117
23. Nacson J., et al, Cell Rep. (2018); 25(5):1384)
24. Higgins G., et al, Science (2018); 359(6381):1217-1218
25. Zatreanu D., et al, Nat Commun. (2021); 12(1):3636
26. Feng W., et al, Nat Commun. (2019); 10(1):4286
27. Wang Z I et al., J Biol Chem. 2019 Mar. 15; 294(11): 3909-3919
28. Dai C H et al., Oncotarget. 2016; 7(40):65157-65170
29. Yousefzadeh M J et al., PLoS Genet. 2014 Oct. 2; 10(10):e1004654
30. Higgins G et al. Cancer Res. 2010 Apr. 1; 70(7):2984-93
31. Schrempf et al., Trends Cancer. 2021; 7(2):98-111
32. Kumar R J et al., NAR Cancer. 2020 December; 2(4): zcaa038

SUMMARY OF THE INVENTION

In one aspect, the present invention provides a compound of Formula I as defined herein, and/or a pharmaceutically acceptable salt, hydrate or solvate thereof.

In another aspect, the present invention provides a pharmaceutical composition which comprises a compound of Formula I as defined herein, or a pharmaceutically acceptable salt, hydrate or solvate thereof, and one or more pharmaceutically acceptable excipients.

In another aspect, the present invention provides a compound of Formula I as defined herein, or a pharmaceutically acceptable salt, hydrate or solvate thereof, or a pharmaceutical composition as defined herein, for use in therapy.

In another aspect, the present invention provides a compound of Formula I as defined herein, or a pharmaceutically acceptable salt, hydrate or solvate thereof, or a pharmaceutical composition as defined herein, for use in the treatment of a disease or condition in which Polθ activity is implicated.

In another aspect, the present invention provides a compound of Formula I as defined herein, or a pharmaceutically acceptable salt, hydrate or solvate thereof, or a pharmaceutical composition as defined herein, for use in the treatment of a disease or condition associated with aberrant activity of Polθ.

In another aspect, the present invention provides a compound of Formula I as defined herein, or a pharmaceutically acceptable salt, hydrate or solvate thereof, or a pharmaceutical composition as defined herein, for use in the treatment of cancer or benign neoplasms.

In another aspect, the present invention provides a compound of Formula I as defined herein, or a pharmaceutically acceptable salt, hydrate or solvate thereof, or a pharmaceutical composition as defined herein, for use in the treatment of a cancer.

In another aspect, the present invention provides the use of a compound of Formula I as defined herein, or a pharmaceutically acceptable salt, hydrate or solvate thereof, in the manufacture of a medicament for use in the treatment of a disease or condition in which Polθ activity is implicated.

In another aspect, the present invention provides the use of a compound of Formula I as defined herein, or a pharmaceutically acceptable salt, hydrate or solvate thereof, in the manufacture of a medicament for use in the treatment of a disease or condition associated with aberrant activity of Polθ.

In another aspect, the present invention provides the use of a compound of Formula I as defined herein, or a pharmaceutically acceptable salt, hydrate or solvate thereof, in the manufacture of a medicament for use in the treatment of cancer or benign neoplasms.

In another aspect, the present invention the use of a compound of Formula I as defined herein, or a pharmaceutically acceptable salt, hydrate or solvate thereof, in the manufacture of a medicament for use in the treatment of a cancer.

In another aspect, the present invention provides a method of treating a disease or condition in which Polθ activity is implicated, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a method of treating a disease or condition associated with aberrant activity of Polθ, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a method of treating cancer or benign neoplasms, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a method of treating cancer, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a combination treatment comprising a compound of Formula I, or a pharmaceutically acceptable salt, hydrate or solvate thereof, as defined herein, with one or more additional therapeutic agents.

In another aspect, the present invention provides processes for preparing compounds of Formula I as defined herein, or a pharmaceutically acceptable salt, hydrate or solvate thereof, as defined herein, with one or more additional therapeutic agents.

In a further aspect, the present invention provides the use of a compound of Formula I or a salt, hydrate or solvate thereof, for CRISPR gene editing in vitro or in vivo.

In another aspect, the present invention provides the use of a compound of Formula I or a salt, hydrate or solvate thereof, for increasing the efficiency of CRISPR gene editing in vitro or in vivo.

In another aspect, the present invention provides a compound of Formula I, or a salt, hydrate or solvate thereof, for use in CRISPR gene editing in vivo.

In another aspect, the present invention provides a compound of Formula I, or a salt, hydrate or solvate thereof, for use in increasing the efficiency of CRISPR gene editing in vivo.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

References to "Polθ" refer to DNA polymerase theta (encoded by POLQ).

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I", "compounds of the invention" and the more general term "compounds" refer to and include any and all compounds described by and/or with reference to Formula I herein. It should also be understood that these terms encompasses all stereoisomers, i.e. cis and trans isomers, as well as optical isomers, i.e. R and S enantiomers, of such compounds, in substantially pure form and/or any mixtures of the foregoing in any ratio. This understanding extends to pharmaceutical compositions and methods of treatment that employ or comprise one or more compounds of the Formula I, either by themselves or in combination with additional agents.

Unless specified otherwise, atoms are referred to herein by their chemical symbol as appearing in the IUPAC periodic table of the Elements. For example, "C" refers to a carbon atom.

The term "(m-nC)" or "(m-nC) group" used alone or as a prefix, refers to any group having m to n carbon atoms.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For Example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

An "alkylene" group is an alkyl group that is positioned between and serves to connect two other chemical groups.

Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(3-6C)cycloalkyl" means a hydrocarbon ring containing from 3 to 6 carbon atoms, for example, cyclopropyl, cyclobutyl, cyclopentyl, cyclohexyl, cycloheptyl or bicyclo[2.2.1]heptyl.

The term "halo" or "halogeno" refers to fluoro, chloro, bromo and iodo.

As used herein by themselves or in conjunction with another term or terms, "haloalkyl" and "haloalkyl group" refer to alkyl groups in which one or more hydrogen atoms are replaced by halogen atoms. Representative examples include, but are not limited to, —$CF_3$, —$CHF_2$, —$CH_2F$, —$CF_2CF_3$, —$CHFCF_3$, and —$CH_2CF_3$. Suitably, a haloalkyl group is selected from —$CHF_2$ and —$CF_3$, suitably —$CF_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Representative examples include, but are not limited to, —$OCF_3$, —$OCHF_2$, —$OCH_2F$, and —$OCF_2CF_3$. Suitably, a haloalkyloxy group is selected from —$OCHF_2$ and —$OCF_3$, suitably —$OCF_3$.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as, but not limited to, oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydrooxathiolyl, tetrahydrooxazolyl, tetrahydro-oxadiazolyl, tetrahydrodioxazolyl, tetrahydrooxathiazolyl, hexahydrotriazinyl, tetrahydrooxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as, but not limited to, tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bicyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

The term "heteroaryl" or "heteroaromatic" means an aromatic mono-, bi-, or polycyclic ring incorporating one or more (for example 14, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzoisoquinolinyl, pyridopyrazinyl, thieno[2,3b]-furanyl-, 2H-furo[3,2b]-pyranyl-, 5H-pyrido[2,3-d]-oxazinyl-, 1H-pyrazolo[4,3-d]-oxazolyl, 4H-imidazo[4,5d]thiazolyl, pyrazino[2,3d]pyridazinyl, -imidazo[2,1b]thiazolyl, -imidazo[1,2b][1,2,4]-triazinyl. "Heteroaryl" also covers partially aromatic bi- or polycyclic ring systems wherein at least one ring is an aromatic ring and one or more of the other ring(s) is a nonaromatic, saturated or partially saturated ring, provided at least one ring contains one or more heteroatoms selected from nitrogen, oxygen or -sulfur-. Examples of partially aromatic heteroaryl groups include for example, tetrahydroisoquinolinyl, tetrahydroquinolinyl, 2-oxo-1,2,3,4-tetrahydroquinolinyl, dihydrobenzothienyl, dihydrobenzofuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl, 3,4-dihydro-2H-pyrido[3,2-b][1,4]oxazinyl and 6,8-dihydro-5H-[1,2,4]triazolo[4,3-a]pyrazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

Heteroaryl groups include ring systems such as pyridones, which can exist in heteroaromatic form, as illustrated below.

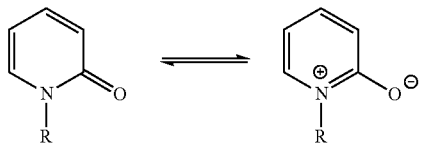

A bicyclic heteroaryl group may be, for example, a group selected from:
- a benzene ring fused to a 5- or 6-membered ring containing 1, 2 or 3 ring heteroatoms;
- a pyridine ring fused to a 5- or 6-membered ring containing 1, 2 or 3 ring heteroatoms;
- a pyrimidine ring fused to a 5- or 6-membered ring containing 1 or 2 ring heteroatoms;
- a pyrrole ring fused to a 5- or 6-membered ring containing 1, 2 or 3 ring heteroatoms;
- a pyrazole ring fused to a 5- or 6-membered ring containing 1 or 2 ring heteroatoms;
- a pyrazine ring fused to a 5- or 6-membered ring containing 1 or 2 ring heteroatoms;
- an imidazole ring fused to a 5- or 6-membered ring containing 1 or 2 ring heteroatoms;
- an oxazole ring fused to a 5- or 6-membered ring containing 1 or 2 ring heteroatoms;
- an isoxazole ring fused to a 5- or 6-membered ring containing 1 or 2 ring heteroatoms;
- a thiazole ring fused to a 5- or 6-membered ring containing 1 or 2 ring heteroatoms;
- an isothiazole ring fused to a 5- or 6-membered ring containing 1 or 2 ring heteroatoms;
- a thiophene ring fused to a 5- or 6-membered ring containing 1, 2 or 3 ring heteroatoms;
- a furan ring fused to a 5- or 6-membered ring containing 1, 2 or 3 ring heteroatoms;
- a cyclohexyl ring fused to a 5- or 6-membered heteroaromatic ring containing 1, 2 or 3 ring heteroatoms; and
- a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "aryl(1-2C)alkyl" means an aryl group covalently attached to a (1-2C)alkylene group, both of which are defined herein. Examples of aryl-(1-2C)alkyl groups include benzyl, phenylethyl, and the like.

"Heteroaryl(1-3C)alkyl" means a heteroaryl group covalently attached to a (1-3C)alkylene group, both of which are defined herein. Examples of heteroaryl-alkyl groups include pyridin-3-ylmethyl, 2-(benzofuran-2-yl)ethyl, and the like.

"Heterocyclyl(1-2C)alkyl" means a heterocyclyl group covalently attached to a (1-2C)alkylene group, both of which are defined herein.

"(3-6C)cycloalkyl-(1-2C)alkyl" means a (3-6C)cycloalkyl group covalently attached to a (1-2C)alkylene group, both of which are defined herein.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

A wavy bond () is used herein to show a point of attachment.

The phrase "compound of the invention" means those compounds which are disclosed herein, both generically and specifically.

As used herein by itself or in conjunction with another term or terms, "pharmaceutically acceptable" refers to materials that are generally chemically and/or physically compatible with other ingredients (such as, for example, with reference to a formulation), and/or are generally physiologically compatible with the recipient (such as, for example, a subject) thereof.

As used herein by themselves or in conjunction with another term or terms, "subject(s)" and "patient(s)", suitably refer to mammals, in particular humans.

COMPOUNDS OF THE INVENTION

In a first aspect, the present invention relates to a compound, or pharmaceutically acceptable salt thereof, having the structural formula I shown below:

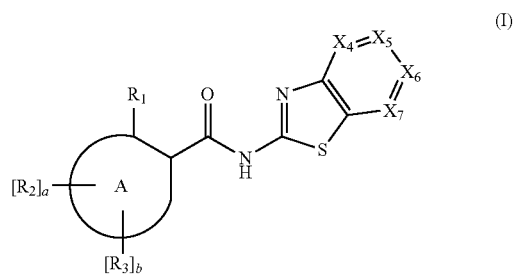

wherein:

ring A is selected from the group consisting of phenyl and a 5- to 10-membered heteroaryl;

$R_1$ is selected from the group consisting of phenyl, 5- to 6-membered heteroaryl, 5- to 6-membered heterocyclyl, 6- to 10-membered bicyclic heterocyclyl, 6- to 10-membered bridged heterocyclyl, and 6- to 12-membered spiroheterocyclyl, wherein:

(i) $R_1$ is optionally substituted with one or more $R_{100}$ substituents; or two $R_{100}$ substituents on adjacent ring atoms in $R_1$ may be linked to form a fused (3-6C)cycloalkyl ring; or (ii) when $R_1$ is 5- to 6-membered heterocyclyl, 6- to 10-membered bicyclic heterocyclyl, 6- to 10-membered bridged heterocyclyl, and 6- to 12-membered spiroheterocyclyl, it is optionally substituted by oxo;

and wherein $R_{100}$ is selected from the group consisting of halo, (1-4C)alkyl, (1-4C)haloalkyl, (1-4C)haloalkoxy, (3-6C)cycloalkyl, (3-6C)cycloalkyloxy, -$Q_{100}$-OH, -$Q_{100}$-O-(1-4C)alkyl, —C(O)-(1-4C)alkyl and -$Q_{100}$-cyano: wherein $Q_{100}$ is a bond or (1-4C)alkylene;

integers a and b are each independently 0 or 1;

$R_2$ and $R_3$, when present, are each independently selected from the group consisting of halo, cyano, (1-4C)alkyl, (1-4C)alkoxy, (1-4C)haloalkyl, (1-4C)hydroxyalkyl, (1-4C)haloalkoxy, -$Q_1$-O-(1-4C)alkyl and —C(O)OH, wherein $Q_1$ is a bond or (1-4C)alkylene;

$X_4$ is selected from $CR_{x4}$ or N;

$X_5$ is selected from $CR_{x5}$ or N;

$X_6$ is selected from $CR_{x6}$ or N;

$X_7$ is selected from $CR_{x7}$ or N;

$R_{x4}$ is hydrogen, fluoro, chloro, methyl or a group of the formula:

—Y-Q wherein:

Y is —O—, —S—, —NH— or —$CH_2$—;

Q is selected from hydrogen (1-6C)alkyl, (3-8C)cycloalkyl, phenyl, heteroaryl, 4- to 7-membered heterocyclyl, 6- to 10-membered bicyclic heterocyclyl, 6- to 10-membered bridged heterocyclyl, and 6- to 12-membered spiroheterocyclyl, each of which is optionally substituted by one or more $R_{100}$ substituents and a (3-8C)cycloalkyl, 4- to 7-membered heterocyclyl, 6- to 10-membered bicyclic heterocyclyl, 6- to 10-membered bridged heterocyclyl, and 6- to 12-membered spiroheterocyclyl is optionally substituted by oxo;

$R_{x5}$ or $R_{x6}$ are selected from:
hydrogen, halo, cyano, nitro or a group of the formula:

-L$_1$-Y$_1$-L$_2$-Q$_1$ wherein:
L$_1$ is absent or (1-2C)alkylene;
Y$_1$ is absent or —O—, —S—, —SO—, —SO$_2$—, —S(O)(=NR$_{y1}$)—, —N(R$_{y1}$)—, —C(O)—, —C(O)O—, —OC(O)—, —C(O)N(R$_{y1}$)—, —N(R$_{y1}$)C(O)—, —S(O)$_2$N(R$_{y1}$)—, —N(R$_{y1}$)SO$_2$— or —N(R$_{y1a}$)C(O)—N(R$_{y1}$)—, wherein R$_{y1}$ and R$_{y1a}$ are selected from hydrogen or (1-2C)alkyl;
L$_2$ is absent or (1-2C)alkylene; and
Q$_1$ is hydrogen, (1-6C)alkyl, (2-6C)alkenyl, (2-6C)alkynyl, (3-8C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl,
wherein:
(i) when Q$_1$ is (1-6C)alkyl, (2-6C)alkenyl or (2-6C)alkynyl, it is optionally further substituted by one or more substituent groups independently selected from oxo, halo, cyano, or by one or more group(s) of the formula:

—Y$_2$-Q$_2$ wherein:
Y$_2$ is absent or selected from or —O—, —S—, —SO—, —SO$_2$, —N(R$_{y2}$)—, —C(O)—, —C(O)O—, —OC(O)—, —C(O)N(R$_{y2}$)—, —N(R$_{y2}$)C(O)—, —S(O)$_2$N(R$_{y2}$)—, or —N(R$_{y2}$)SO$_2$—, wherein R$_{y2}$ is selected from hydrogen or (1-2C)alkyl;
Q$_2$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;
(ii) when Q$_1$ is (3-8C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—Y$_3$-Q$_3$ wherein:
Y$_3$ is absent or selected from or —O—, —S—, —SO—, —SO$_2$—, —N(R$_{y2}$)—, —C(O)—, —C(O)O—, —OC(O)—, —C(O)N(R$_{y3}$)—, —N(R$_{y3}$)C(O)—, —S(O)$_2$N(R$_{y3}$)—, or —N(R$_{y3}$)SO$_2$—, wherein R$_{y3}$ is selected from hydrogen or (1-2C)alkyl;
Q$_3$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;
(iii) when Q$_1$ is phenyl or 5- to 6-membered heteroaryl, it is optionally further substituted by one or more substituent groups independently selected from halo, cyano, or by one or more group(s) of the formula —Y$_3$-Q$_3$ defined above;
R$_{x7}$ is selected from hydrogen, fluoro, chloro, hydroxy, NH$_2$, methyl, or CF$_3$;
or R$_{x4}$ and R$_{x5}$, R$_{x5}$ and R$_{x6}$ or R$_{x6}$ and R$_{x7}$ are linked such that, together with the carbon atoms to which they are attached, they form a fused (5-6C)cycloalkyl, phenyl, 5- or 6-membered heteroaryl or 5- or 6-membered heterocyclic ring, each of which is optionally substituted by fluoro, chloro, methyl or hydroxy;
with the proviso that:
(i) when X$_5$ is CR$_{x5}$ and R$_{x5}$ is a group of the formula -L$_1$-Y$_1$-L$_2$-Q$_1$ then X$_6$ is selected from N, C—H, C—F, C—CN, C—Cl or C-Me; and
(ii) when X$_6$ is CR$_{x6}$ and R$_{x6}$ is a group of the formula -L$_1$-Y$_1$-L$_2$-Q$_1$ then X$_5$ is selected from N, C—H, C—F, C—CN, C—Cl or C-Me.

In another aspect, the present invention relates to a compound, or pharmaceutically acceptable salt thereof, having the structural formula I shown below:

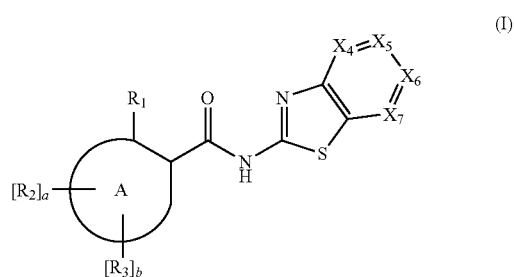

(I)

wherein:
ring A is selected from the group consisting of phenyl and a 5- to 10-membered heteroaryl;
R$_1$ is selected from the group consisting of phenyl, 5- to 6-membered heteroaryl, 5- to 6-membered heterocyclyl, 6- to 10-membered bicyclic heterocyclyl, 6- to 10-membered bridged heterocyclyl, and 6- to 12-membered spiroheterocyclyl, wherein:
(i) R$_1$ is optionally substituted with one or more R$_{100}$ substituents; or two R$_{100}$ substituents on adjacent ring atoms in R$_1$ may be linked to form a fused (3-6C)cycloalkyl ring; or
(ii) when R$_1$ is 5- to 6-membered heterocyclyl, 6- to 10-membered bicyclic heterocyclyl, 6- to 10-membered bridged heterocyclyl, and 6- to 12-membered spiroheterocyclyl, it is optionally substituted by oxo;
and wherein R$_{100}$ is selected from the group consisting of halo, (1-4C)alkyl, (1-4C)haloalkyl, (1-4C)haloalkoxy, (3-6C)cycloalkyl, (3-6C)cycloalkyloxy, -Q$_{100}$-OH, Q$_{100}$-O-(1-4C)alkyl, —C(O)-(1-4C)alkyl and -Q$_{100}$-cyano; wherein Q$_{100}$ is a bond or (1-4C)alkylene;
integers a and b are each independently 0 or 1;
R$_2$ and R$_3$, when present, are each independently selected from the group consisting of halo, cyano, —O$^-$, (1-4C)alkyl, (1-4C)alkoxy, (1-4C)haloalkyl, (1-4C)hydroxyalkyl, (1-4C)haloalkoxy, -$Q_1$-O-(1-4C)alkyl, —C(O)OH, -$Q_1$-C(O)—$NH_2$, -$Q_1$-C(O)—NHMe and -$Q_1$-C(O)—$NMe_2$, wherein
$Q_1$ is a bond or (1-4C)alkylene;
$X_4$ is selected from $CR_{x4}$ or N;
$X_5$ is selected from $CR_{x5}$ or N;
$X_6$ is selected from $CR_{x6}$ or N;
$X_7$ is selected from $CR_{x7}$ or N;
$R_{x4}$ is hydrogen, fluoro, chloro, methyl or a group of the formula:

—Y-Q wherein:
Y is —O—, —O—$CH_2$—, —S—, —NH—, —$CH_2$— or —$CH_2$—$CH_2$—;
Q is selected from hydrogen (1-6C)alkyl, —C(O)—$NH_2$, —C(O)—NHMe, —C(O)—$NMe_2$, (3-8C)cycloalkyl, phenyl, heteroaryl, 4- to 7-membered heterocyclyl, 6- to 10-membered bicyclic heterocyclyl, 6- to 10-membered bridged heterocyclyl, and 6- to 12-membered spiroheterocyclyl, each of which is optionally substituted by one or more $R_{100}$ substituents and a (3-8C)cycloalkyl, 4- to 7-membered heterocyclyl, 6- to 10-membered bicyclic heterocyclyl, 6- to 10-membered bridged heterocyclyl, and 6- to 12-membered spiroheterocyclyl is optionally substituted by oxo;
$R_{x5}$ or $R_{x6}$ are selected from:
hydrogen, halo, cyano, nitro or a group of the formula:

-$L_1$-$Y_1$-$L_2$-$Q_1$ wherein:
$L_1$ is absent or (1-2C)alkylene;
$Y_1$ is absent or —O—, —S—, —SO—, —$SO_2$—, —S(O)(=$NR_{y1}$)—, —N($R_{y1}$)—, —C(O)—, —C(O)O—, —OC(O)—, —C(O)N($R_{y1}$)—, —N($R_{y1}$)C(O)—, —S(O)$_2$N($R_{y1}$)—, —N($R_{y1}$)$SO_2$— or —N($R_{y1a}$)C(O)—N($R_{y1}$)—, wherein $R_{y1}$ and $R_{y1a}$ are selected from hydrogen or (1-2C)alkyl;
$L_2$ is absent or (1-2C)alkylene; and
$Q_1$ is hydrogen, (1-6C)alkyl, (2-6C)alkenyl, (2-6C)alkynyl, (3-8C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl,
wherein:
(i) when $Q_1$ is (1-6C)alkyl, (2-6C)alkenyl or (2-6C)alkynyl, it is optionally further substituted by one or more substituent groups independently selected from oxo, halo, cyano, or by one or more group(s) of the formula:

—$Y_2$-$Q_2$ wherein:
$Y_2$ is absent or selected from or —O—, —S—, —SO—, —$SO_2$—, —N($R_{y2}$)—, —C(O)—, —C(O)O—, —OC(O)—, —C(O)N($R_{y2}$)—, —N($R_{y2}$)C(O)—, —S(O)$_2$N($R_{y2}$)—, or —N($R_{y2}$)$SO_2$—, wherein $R_{y2}$ is selected from hydrogen or (1-2C)alkyl;
$Q_2$ is selected from:
hydrogen;
a (1-4C)alkyl which is optionally substituted by one or more substituents selected from halo, hydroxy, cyano, amino or (1-4C)alkoxy; or a 4 to 7-membered heterocyclic ring which is optionally substituted by one or more substituents selected from halo, hydroxy, cyano, amino, (1-4C)alkyl or (1-4C)alkoxy;
(ii) when $Q_1$ is (3-8C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—$Y_3$-$Q_3$ wherein:
$Y_3$ is absent or selected from or —O—, —S—, —SO—, —$SO_2$—, —N($R_{y2}$)—, —C(O)—, —C(O)O—, —OC(O)—, —C(O)N($R_{y3}$)—, —N($R_{y3}$)C(O)—, —S(O)$_2$N($R_{y3}$)—, or —N($R_{y3}$)$SO_2$—, wherein $R_{y3}$ is selected from hydrogen or (1-2C)alkyl;
$Q_3$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;
(iii) when $Q_1$ is phenyl or 5- to 6-membered heteroaryl, it is optionally further substituted by one or more substituent groups independently selected from halo, cyano, or by one or more group(s) of the formula —$Y_3$-$Q_3$ defined above;
$R_{x7}$ is selected from hydrogen, fluoro, chloro, hydroxy, $NH_2$, methyl, or $CF_3$;
or $R_{x4}$ and $R_{x5}$, $R_{x5}$ and $R_{x6}$ or $R_{x6}$ and $R_{x7}$ are linked such that, together with the carbon atoms to which they are attached, they form a fused (5-6C)cycloalkyl, phenyl, 5- or 6-membered heteroaryl or 5- or 6-membered heterocyclic ring, each of which is optionally substituted by fluoro, chloro, methyl or hydroxy;
with the proviso that:
(i) when $X_5$ is $CR_{x5}$ and $R_{x5}$ is a group of the formula -$L_1$-$Y_1$-$L_2$-$Q_1$ then $X_6$ is selected from N, C—H, C—F, C—CN, C—Cl or C-Me; and
(ii) when $X_6$ is $CR_{x6}$ and $R_{x6}$ is a group of the formula -$L_1$-$Y_1$-$L_2$-$Q_1$ then $X_5$ is selected from N, C—H, C—F, C—CN, C—Cl or C-Me.
Suitably, when $X_5$ is $CR_{x5}$ and $R_{x5}$ is cyano or a group of the formula -$L_1$-$Y_1$-$L_2$-$Q_1$ then:
$X_4$ is selected from N, C—H, C—F, C—Cl or C-Me;
$X_6$ is selected from N, C—H, C—F, C—CN, C—Cl or C-Me;
$X_7$ is selected from N, C—H, C—F, C—Cl or C-Me.
In an embodiment, when $X_5$ is $CR_{x5}$ and $R_{x5}$ is cyano or a group of the formula -$L_1$-$Y_1$-$L_2$-$Q_1$ then:
$X_4$ is selected from N, C—H or C—F;
$X_6$ is selected from N, C—H, C—F, C—Cl or C-Me;
$X_7$ is selected from N, C—H, or C—F.
In a further embodiment, when $X_5$ is $CR_{x5}$ and $R_{x5}$ is cyano or a group of the formula -$L_1$-$Y_1$-$L_2$-$Q_1$ then:
$X_4$ is selected from N or C—H or C—F;
$X_6$ is selected from N, C—H, C—F, C—Cl or C-Me;
$X_7$ is selected from N or C—H.

In a further embodiment, when $X_5$ is $CR_{x5}$ and $R_{x5}$ is cyano or a group of the formula -$L_1$-$Y_1$-$L_2$-$Q_1$ then:
  $X_4$ is C—H;
  $X_6$ is selected from N, C—H, C—F, C—Cl or C-Me;
  $X_7$ is selected from N or C—H.

In a further embodiment, when $X_5$ is $CR_{x5}$ and $R_{x5}$ is cyano or a group of the formula -$L_1$-$Y_1$-$L_2$-$Q_1$ then:
  $X_4$ is C—H;
  $X_6$ is C—H;
  $X_7$ is N or C—H.

In a further embodiment, when $X_5$ is $CR_{x5}$ and $R_{x5}$ is cyano or a group of the formula -$L_1$-$Y_1$-$L_2$-$Q_1$ then:
  $X_4$ is C—H;
  $X_6$ is C—H;
  $X_7$ is C—H.

Suitably, when $X_6$ is $CR_{x6}$ and $R_{x6}$ is cyano or a group of the formula -$L_1$-$Y_1$-$L_2$-$Q_1$ then:
  $X_4$ is selected from N, C—H or C—F;
  $X_5$ is selected from N, C—H, C—F, C—Cl or C-Me;
  $X_7$ is selected from N, C—H or C—F.

In an embodiment, when $X_6$ is $CR_{x6}$ and $R_{x6}$ is cyano or a group of the formula -$L_1$-$Y_1$-$L_2$-$Q_1$ then:
  $X_4$ is selected from N, C—H or C—F;
  $X_5$ is selected from N, C—H or C—F;
  $X_7$ is selected from N, C—H or C—F.

In a further embodiment, when $X_6$ is $CR_{x6}$ and $R_{x6}$ is cyano or a group of the formula -$L_1$-$Y_1$-$L_2$-$Q_1$ then:
  $X_4$ is selected from N, C—H or C—F;
  $X_5$ is selected from N, C—H or C—F;
  $X_7$ is selected from N, C—H or C—F.

In a further embodiment, when $X_6$ is $CR_{x6}$ and $R_{x6}$ is cyano or a group of the formula -$L_1$-$Y_1$-$L_2$-$Q_1$ then:
  $X_4$ is selected from N or C—H;
  $X_5$ is selected from N, C—H or C—F;
  $X_7$ is selected from N or C—H.

In a further embodiment, when $X_6$ is $CR_{x6}$ and $R_{x6}$ is cyano or a group of the formula -$L_1$-$Y_1$-$L_2$-$Q_1$ then:
  $X_4$ is C—H;
  $X_5$ is selected from N or C—H;
  $X_7$ is selected from N or C—H.

Particular compounds of the invention include, for example, compounds of the formula I, or pharmaceutically acceptable salts, hydrates and/or solvates thereof, wherein, unless otherwise stated, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, integer c, $R_{100a}$, integer d, $R_{100b}$, integer e and $R_{100c}$ each have any of the meanings defined hereinbefore or are as defined in any one of paragraphs (1) to (89) hereinafter:—

(1) ring A is selected from phenyl or 5-, 6-, 9- or 10-membered heteroaryl;
(2) ring A is selected from phenyl or 5- or 6-membered heteroaryl;
(3) ring A is selected from phenyl or 6-membered heteroaryl;
(4) ring A is a 5-, 6-, 9- or 10-membered heteroaryl;
(5) ring A is a 5- or 6-membered heteroaryl;
(6) ring A is phenyl, pyridinyl, pyridazinyl, pyrimidinyl, imidazolyl, pyrazolyl, triazolyl, imidazo[1,2-a]pyridinyl, [1,2,3]triazolo[1,5-a]pyridinyl, imidazo[1,5-a]pyridinyl, pyrrolo[2,3-b]pyridinyl, pyrrolo[3,2-b]pyridinyl, pyrazolo[1,5-a]pyridinyl, [1,2,4]triazolo[1,5-a]pyridinyl, 1,6-naphthyridinyl, or 1,7-naphthyridinyl;
(7) ring A is phenyl, pyridinyl, pyrimidinyl, and imidazo[1,2-a]pyridinyl, 1,2,3-triazole, pyrazolyl, isoxazolyl, imidazo [1,5-a]pyridinyl
(8) ring A is phenyl, pyridinyl, pyrimidinyl, and imidazo[1,2-a]pyridinyl
(9) ring A is phenyl or pyridyl;
(10) ring A is phenyl;
(11) ring A is pyridyl;
(12) ring A is selected from:

[Chemical structures showing various ring A options with $R_1$, $[R_2]_a$, $[R_3]_b$ substituents]

wherein ⌇⌇⌇ denotes the point of attachment to the amide group of formula I; and $R_1$, $R_2$, $R_3$, a and b are each as defined herein;

(13) ring A is selected from:

[Chemical structures showing ring A options with $R_1$, $[R_2]_a$, $[R_3]_b$ substituents]

wherein ⌇ denotes the point of attachment to the amide group of formula I; and $R_1$, $R_2$, $R_3$, a and b are each as defined herein;

(14) ring A is selected from:

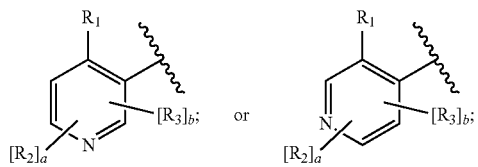

wherein ⌇ denotes the point of attachment to the amide group of formula I; and $R_1$, $R_2$, $R_3$, a and b are each as defined herein;

(15) ring A is selected from:

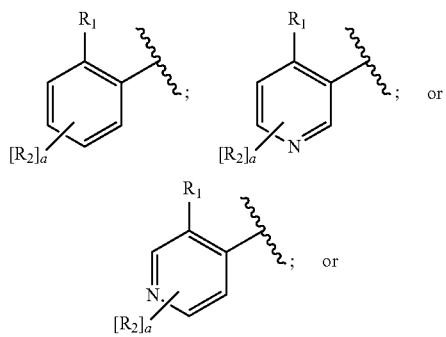

wherein ⌇ denotes the point of attachment to the amide group of formula I; and $R_1$, $R_2$, $R_3$, a and b are each as defined herein;

(16) ring A is selected from:

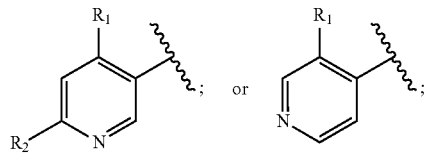

wherein ⌇ denotes the point of attachment to the amide group of formula I; and $R_1$, $R_2$, $R_3$, a and b are each as defined herein;

(17) ring A is:

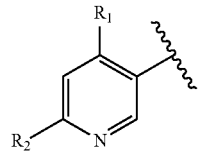

wherein ⌇ denotes the point of attachment to the amide group of formula I; and $R_1$, $R_2$, $R_3$, a and b are each as defined herein;

(18) ring A is:

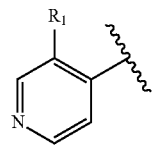

wherein ⌇ denotes the point of attachment to the amide group of formula I; and $R_1$, $R_2$, $R_3$, a and b are each as defined herein;

(19) $R_1$ is selected from phenyl or a 5- to 6-membered heteroaryl, each of which is optionally substituted with one or more $R_{100}$ as defined hereinbefore and any one of paragraphs (25) to (31) below; or two $R_{100}$ substituents on adjacent ring atoms in $R_1$ may be linked to form a fused (3-6C)cycloalkyl ring;

(20) $R_1$ is selected from phenyl or a 6-membered heteroaryl, each of which is optionally substituted with one or more $R_{100}$ as defined hereinbefore and any one of paragraphs (25) to (31) below; or two $R_{100}$ substituents on adjacent ring atoms in $R_1$ may be linked to form a fused (3-6C)cycloalkyl ring;

(21) $R_1$ is a group of the formula:

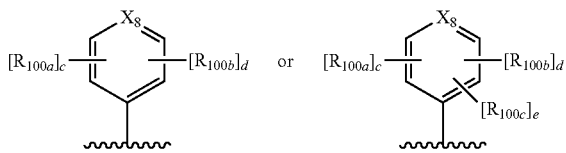

wherein:

⌇ denotes the point of attachment to ring A of formula I;

$X_8$ is CH or N;

$R_{100a}$, $R_{100b}$ and $R_{100c}$ are substituent groups $R_{100}$ as defined hereinbefore and any one of paragraphs (25) to (31) below; and integers c, d and e are 0, 1 or 2;

(22) $R_1$ is a group of the formula:

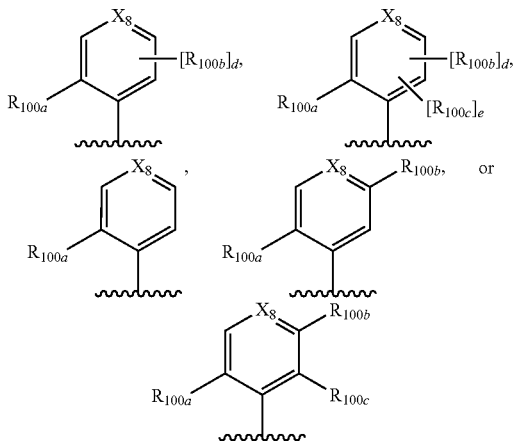

wherein:
 ⁓ denotes the point of attachment to ring A of formula I;
 $X_8$ is CH or N;
 $R_{100a}$, $R_{100b}$ and $R_{100c}$ are substituent groups $R_{100}$ as defined hereinbefore and any one of paragraphs (25) to (31) below; and
 integers d and e are 0 or 1;
(23) $R_1$ is a group of the formula:

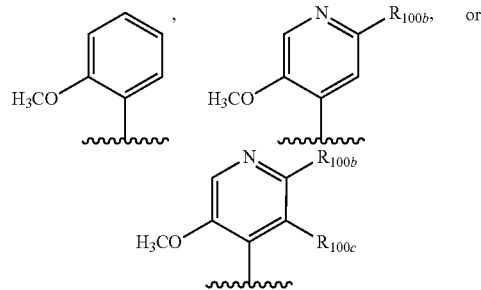

wherein:
 ⁓ denotes the point of attachment to ring A of formula I;
 $R_{100b}$ is methyl, fluoro or chloro;
 $R_{100c}$ is fluoro or chloro, especially fluoro;
(24) $R_1$ is a group of the formula:

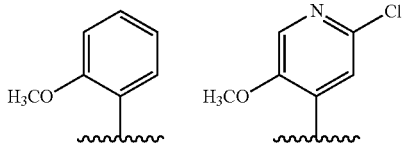 [SMILES: *c1ccccc1OC ; *c1cc(Cl)ncc1OC]

wherein:
 ⁓ denotes the point of attachment to ring A of formula I.
(25) $R_{100}$ is selected from halo, (1-3C)alkyl, (1-3C)haloalkyl, (1-3C)haloalkoxy, (3-6C)cycloalkyl, (3-6C)cycloalkyloxy, -$Q_{100}$-OH, -$Q_{100}$-O-(1-3C)alkyl, —C(O)-(1-3C)alkyl and -$Q_{100}$-cyano; wherein $Q_{100}$ is a bond or (1-3C)alkylene;
(26) $R_{100}$ is selected from halo, (1-2C)alkyl, (1-2C)haloalkyl, (1-2C)haloalkoxy, (3-6C)cycloalkyl, (3-6C)cycloalkyloxy, -$Q_{100}$-OH, -$Q_{100}$-O-(1-2C)alkyl, —C(O)-(1-2C)alkyl and -$Q_{100}$-cyano; wherein $Q_{100}$ is a bond or (1-2C)alkylene;
(27) $R_{100}$ is selected from halo, (1-2C)alkyl, (1-2C)fluoroalkyl, (1-2C)fluoroalkoxy, (3-6C)cycloalkyl, (3-6C)cycloalkyloxy, -$Q_{100}$-OH, -$Q_{100}$-O-(1-2C)alkyl, —C(O)-(1-2C)alkyl and -$Q_{100}$-cyano; wherein $Q_{100}$ is a bond or (1-2C)alkylene;
(28) $R_{100}$ is selected from halo, (1-2C)alkyl, (1-2C)fluoroalkyl, -$Q_{100}$-OH, -$Q_{100}$-O-(1-2C)alkyl, —C(O)-(1-2C)alkyl and -$Q_{100}$-cyano; wherein $Q_{100}$ is a bond or (1-2C)alkylene;
(29) $R_{100}$ is selected from halo, (1-2C)alkyl, (1-2C)fluoroalkyl, -$Q_{100}$-OH and -$Q_{100}$-O-(1-2C)alkyl; wherein $Q_{100}$ is a bond or (1-2C)alkylene;
(30) $R_{100}$ is selected from fluoro, chloro, (1-2C)alkyl, (1-2C)fluoroalkyl, -$Q_{100}$-OH and -$Q_{100}$-O-(1-2C)alkyl; wherein $Q_{100}$ is a bond or (1-2C)alkylene;
(31) $R_{100}$ is selected from fluoro, chloro, methyl, (1-2C)fluoromethyl and -$Q_{100}$-O-(1-2C)alkyl; wherein $Q_{100}$ is a bond or methylene.
(32) integer a is 0 or 1 and integer b is 0;
(33) integer a is 0 and integer b is 0;
(34) integer a is 1 and integer b is 0;
(35) $R_2$ and $R_3$, when present, are each independently selected from the group consisting of fluoro, chloro, (1-2C)alkyl, (1-2C)alkoxy, (1-2C)haloalkyl, (1-2C)hydroxyalkyl, (1-2C)haloalkoxy, -$Q_1$-O-(1-2C)alkyl and —C(O)OH, wherein $Q_1$ is a bond or (1-2C)alkylene;
(36) $R_2$ and $R_3$, when present, are each independently selected from the group consisting of fluoro, chloro, (1-2C)alkyl, (1-2C)alkoxy or (1-2C)haloalkyl;
(37) $R_2$ and $R_3$, when present, are each independently selected from the group consisting of fluoro, (1-2C)alkyl or (1-2C)alkoxy;
(38) $R_2$ and $R_3$, when present, are methyl;
(39) $X_4$ is selected from $CR_{x4}$; $X_5$ is selected from $CR_{x5}$ or N; $X_6$ is selected from $CR_{x6}$; $X_7$ is selected from $CR_{x7}$ or N; wherein $R_{x4}$, $R_{x5}$, $R_{x6}$ and $R_{x7}$ are each as defined hereinbefore or $R_{x4}$ is as defined in any one of paragraphs (50) to (58); $R_{x5}$ is as defined in any one of paragraphs (59) to (62); $R_{x6}$ is as defined in any one of paragraphs (59) to (62); or $R_{x7}$ is as defined in any one of paragraphs (63) or (64);
(40) $X_4$ is selected from $CR_{x4}$; $X_5$ is selected from $CR_{x5}$ or N; $X_6$ is selected from $CR_{x6}$; $X_7$ is selected from CH or N; wherein $R_{x4}$, $R_{x5}$ and $R_{x6}$ are each as defined hereinbefore or $R_{x4}$ is as defined in any one of paragraphs (50) to (58); $R_{x5}$ is as defined in any one of paragraphs (59) to (62); or $R_{x6}$ is as defined in any one of paragraphs (59) to (62);
(41) $X_4$ is selected from CH; $X_5$ is selected from $CR_{x5}$ or N; $X_6$ is selected from $CR_{x6}$; $X_7$ is selected from CH or N; wherein $R_{x5}$ and $R_{x6}$ are each as defined hereinbefore or $R_{x5}$ is as defined in any one of paragraphs (59) to (62) and $R_{x6}$ is as defined in any one of paragraphs (59) to (62);
(42) $X_4$ is selected from CH; $X_5$ is selected from CH or N; $X_6$ is selected from $CR_{x6}$; $X_7$ is selected from CH or N; wherein $R_{x6}$ is as defined hereinbefore or in any one of paragraphs (59) to (62);
(43) $X_4$ is selected from CH; $X_5$ is selected from CH; $X_6$ is selected from $CR_{x6}$; $X_7$ is selected from CH or N; wherein $R_{x6}$ is as defined hereinbefore or in any one of paragraphs (59) to (62);
(44) $X_4$ is selected from CH; $X_5$ is selected from CH or N; $X_6$ is selected from $CR_{x6}$; $X_7$ is selected from CH; wherein $R_{x6}$ is as defined hereinbefore or in any one of paragraphs (59) to (62);
(45) $X_4$ is selected from CH; $X_5$ is selected from CH; $X_6$ is selected from $CR_{x6}$; $X_7$ is selected from CH; wherein $R_{x6}$ is as defined hereinbefore or in any one of paragraphs (59) to (62);
(46) $X_4$ is selected from CH; $X_5$ is selected from N; $X_6$ is selected from $CR_{x6}$; $X_7$ is selected from CH; wherein $R_{x6}$ is as defined hereinbefore or in any one of paragraphs (59) to (62);
(47) $X_4$ is selected from CH; $X_5$ is selected from CH; $X_6$ is selected from $CR_{x6}$; $X_7$ is selected from N; wherein $R_{x6}$ is as defined hereinbefore or in any one of paragraphs (59) to (62);
(48) $X_4$ is selected from CH; $X_5$ is selected from N; $X_6$ is selected from $CR_{x6}$; $X_7$ is selected from N; wherein $R_{x6}$ is as defined hereinbefore or in any one of paragraphs (59) to (62);

(49) $X_4$ is selected from CH or N; $X_5$ is selected from $CR_{x5}$; $X_6$ is selected from CH or N; $X_7$ is selected from CH or N; wherein $R_{x5}$ is as defined hereinbefore or in any one of paragraphs (59) to (62);

(50) $X_4$ is selected from CH; $X_5$ is selected from $CR_{x5}$; $X_6$ is selected from CH; $X_7$ is selected from CH; wherein $R_{x5}$ is as defined hereinbefore or in any one of paragraphs (59) to (62);

(51) $X_4$ is selected from CH; $X_5$ is selected from $CR_{x5}$; $X_6$ is selected from N; $X_7$ is selected from CH; wherein $R_{x5}$ is as defined hereinbefore or in any one of paragraphs (59) to (62);

(52) $X_4$ is selected from CH; $X_5$ is selected from $CR_{x5}$; $X_6$ is selected from CH; $X_7$ is selected from N; wherein $R_{x5}$ is as defined hereinbefore or in any one of paragraphs (59) to (62);

(53) $X_4$ is selected from N; $X_5$ is selected from $CR_{x5}$; $X_6$ is selected from CH; $X_7$ is selected from CH; wherein $R_{x5}$ is as defined hereinbefore or in any one of paragraphs (59) to (62);

(54) $X_4$ is selected from N; $X_5$ is selected from $CR_{x5}$; $X_6$ is selected from N; $X_7$ is selected from CH; wherein $R_{x5}$ is as defined hereinbefore or in any one of paragraphs (59) to (62);

(55) $R_{x4}$ is selected from hydrogen, fluoro, chloro, methyl or a group of the formula:

—Y-Q wherein:
Y is —O—, —S—, —NH— or —$CH_2$—;
Q is selected from hydrogen (1-4C)alkyl, (3-6C)cycloalkyl, phenyl, 5- or 6-membered heteroaryl, 4- to 7-membered heterocyclyl, each of which is optionally substituted by one or more $R_{100}$ substituents and a (3-8C)cycloalkyl and 4- to 7-membered heterocyclyl is optionally substituted by oxo;

(56) $R_{x4}$ is selected from hydrogen, fluoro, methyl or a group of the formula:

—Y-Q wherein:
Y is —O—, —S—, —NH— or —$CH_2$—;
Q is selected from hydrogen, (1-4C)alkyl, (3-6C)cycloalkyl, phenyl, 5- or 6-membered heteroaryl, 4- to 7-membered heterocyclyl;

(57) $R_{x4}$ is selected from hydrogen, fluoro, chloro or methyl;

(58) $R_{x4}$ is hydrogen;

(59) $R_{x5}$ or $R_{x6}$ are selected from hydrogen, halo, cyano, nitro or a group of the formula:

-$L_1$-$Y_1$-$L_2$-$Q_1$ wherein:
$L_1$ is absent or (1-2C)alkylene;
$Y_1$ is absent or —O—, —S—, —SO—, —$SO_2$—, —S(O)(=$NR_{y1}$)—, —N($R_{y1}$)—, —C(O)—, —C(O)O—, —OC(O)—, —C(O)N($R_{y1}$)—, —N($R_{y1}$)C(O)—, —S(O)$_2$N($R_{y1}$)—, —N($R_{y1}$)$SO_2$— or —N($R_{y1a}$)C(O)—N($R_{y1}$)—, wherein $R_{y1}$ and $R_{y1a}$ are selected from hydrogen or (1-2C)alkyl;
$L_2$ is absent or (1-2C)alkylene; and
$Q_1$ is hydrogen, (1-6C)alkyl, (3-8C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl, wherein:
(i) when $Q_1$ is (1-6C)alkyl, it is optionally further substituted by one or more substituent groups independently selected from oxo, halo, cyano, or by one or more group(s) of the formula:

—$Y_2$-$Q_2$ wherein:
$Y_2$ is absent or selected from or —O—, —$SO_2$—, —N($R_{y2}$)—, —C(O)—, —C(O)N($R_{y2}$)—, —N($R_{y2}$)C(O)—, —S(O)$_2$N($R_{y2}$)—, or —N($R_{y2}$)$SO_2$—, wherein $R_{y2}$ is selected from hydrogen or methyl;
$Q_2$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;

(ii) when $Q_1$ is (3-8C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—$Y_3$-$Q_3$ wherein:
$Y_3$ is absent or selected from or —O—, —$SO_2$—, —N($R_{y3}$)—, —C(O)—, —C(O)N($R_{y3}$)—, —N($R_{y3}$)C(O)—, —S(O)$_2$N($R_{y3}$)—, or —N($R_{y3}$)$SO_2$—,
wherein $R_{y3}$ is selected from hydrogen or methyl;
$Q_3$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;

(iii) when $Q_1$ is phenyl or 5- to 6-membered heteroaryl, it is optionally further substituted by one or more substituent groups independently selected from halo, cyano, or by one or more group(s) of the formula —$Y_3$-$Q_3$ defined above

(60) $R_{x5}$ or $R_{x6}$ are selected from hydrogen, halo, cyano, nitro or a group of the formula:

-$L_1$-$Y_1$-$L_2$-$Q_1$ wherein:
$L_1$ is absent or methylene;
$Y_1$ is absent or —O—, —$SO_2$—, —S(O)(=$NR_{y1}$)—, —N($R_{y1}$)—, —C(O)N($R_{y1}$)—, —N($R_{y1}$)C(O)—, —S(O)$_2$N($R_{y1}$)—, or —N($R_{y1}$)$SO_2$—, wherein $R_{y1}$ and $R_{y1a}$ are selected from hydrogen or (1-2C)alkyl;
$L_2$ is absent or methylene; and
$Q_1$ is hydrogen, (1-4C)alkyl, (3-4C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl, wherein:
  (i) when $Q_1$ is (1-4C)alkyl, it is optionally further substituted by one or more substituent groups independently selected from halo, cyano, or by one or more group(s) of the formula:

—$Y_2$-$Q_2$ wherein:
    $Y_2$ is absent or selected from or —O—, —SO$_2$—, —N($R_{y2}$)—, —C(O)—, —C(O)N($R_{y2}$)—, or —N($R_{y2}$)C(O)—, —S(O)$_2$N($R_{y2}$)—, or —N($R_{y2}$)SO$_2$—, wherein $R_{y2}$ is selected from hydrogen or methyl;
    $Q_2$ is selected from:
      hydrogen;
      a (1-4C)alkyl optionally substituted by one or more halo;
      or
      a 4 to 7-membered heterocyclic ring;
  (ii) when $Q_1$ is (3-6C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—$Y_3$-$Q_3$ wherein:
    $Y_3$ is absent or selected from or —O—, —SO$_2$—, —N($R_{y3}$)—, —C(O)—, —C(O)N($R_{y3}$)—, —N($R_{y3}$)C(O)—, —S(O)$_2$N($R_{y3}$)—, or —N($R_{y3}$)SO$_2$—,
    wherein $R_{y3}$ is selected from hydrogen or methyl;
    $Q_3$ is selected from:
      hydrogen;
      a (1-4C)alkyl optionally substituted by one or more halo;
      or
      a 4 to 7-membered heterocyclic ring;
  (iii) when $Q_1$ is phenyl or 5- to 6-membered heteroaryl, it is optionally further substituted by one or more substituent groups independently selected from halo, cyano, or by one or more group(s) of the formula —$Y_3$-$Q_3$ defined above;
(61) $R_{x5}$ or $R_{x6}$ are selected from hydrogen, halo, cyano, nitro or a group of the formula:

-$L_1$-$Y_1$-$L_2$-$Q_1$ wherein:
$L_1$ is absent or methylene;
$Y_1$ is absent or —O—, —SO$_2$—, —S(O)(=N$R_{y1}$)—, —N($R_{y1}$)—, —C(O)N($R_{y1}$)—, —N($R_{y1}$)C(O)—, —S(O)$_2$N($R_{y1}$)—, or —N($R_{y1}$)SO$_2$—, wherein $R_{y1}$ and $R_{y1a}$ are selected from hydrogen or (1-2C)alkyl;
$L_2$ is absent or methylene; and
$Q_1$ is hydrogen, (1-4C)alkyl, (3-4C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl,
wherein:
  (i) when $Q_1$ is (1-4C)alkyl, it is optionally further substituted by one or more substituent groups independently selected from halo, cyano, or by one or more group(s) of the formula:

—$Y_2$-$Q_2$ wherein:
    $Y_2$ is absent or selected from or —O—, —SO$_2$— or —N($R_{y2}$)—, wherein
    $R_{y2}$ is selected from hydrogen or methyl;
    $Q_2$ is selected from:
      hydrogen;
      a (1-4C)alkyl optionally substituted by one or more halo;
      or
      a 4 to 7-membered heterocyclic ring;
  (ii) when $Q_1$ is (3-6C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—$Y_3$-$Q_3$ wherein:
    $Y_3$ is absent or selected from or —O—, —SO$_2$— or —N($R_{y3}$)—, wherein
    $R_{y3}$ is selected from hydrogen or methyl;
    $Q_3$ is selected from:
      hydrogen;
      a (1-4C)alkyl optionally substituted by one or more halo;
      or
      a 4 to 7-membered heterocyclic ring;
  (iii) when $Q_1$ is phenyl or 5- to 6-membered heteroaryl, it is optionally further substituted by one or more substituent groups independently selected from halo, cyano, or by one or more group(s) of the formula —$Y_3$-$Q_3$ defined above;
(62) $R_{x5}$ or $R_{x6}$ are selected from hydrogen, halo, cyano, nitro or a group of the formula:

-$L_1$-$Y_1$-$L_2$-$Q_1$ wherein:
$L_1$ is absent;
$Y_1$ is absent or —O—, —SO$_2$—, —S(O)(=N$R_{y1}$)—, —N($R_{y1}$)—, —C(O)N($R_{y1}$)—, —N($R_{y1}$)C(O)—, —S(O)$_2$N($R_{y1}$)—, or —N($R_{y1}$)SO$_2$—, wherein $R_{y1}$ and $R_{y1a}$ are selected from hydrogen or (1-2C)alkyl;
$L_2$ is absent or methylene; and
$Q_1$ is hydrogen, (1-4C)alkyl, (3-4C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl,
wherein:
  (i) when $Q_1$ is (1-4C)alkyl, it is optionally further substituted by one or more substituent groups independently selected from halo, cyano, or by one or more group(s) of the formula:

—$Y_2$-$Q_2$ wherein:
    $Y_2$ is absent or —O—;
    $Q_2$ is selected from:
      hydrogen;
      a (1-4C)alkyl optionally substituted by one or more halo;

or
a 4 to 7-membered heterocyclic ring;
(ii) when $Q_1$ is (3-6C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—$Y_3$-$Q_3$ wherein:
$Y_3$ is absent or —O—;
$Q_3$ is selected from:
hydrogen;
a (1-4C)alkyl optionally substituted by one or more halo;
or
a 4 to 7-membered heterocyclic ring;
(iii) when $Q_1$ is phenyl or 5- to 6-membered heteroaryl, it is optionally further substituted by one or more substituent groups independently selected from halo, cyano, or by one or more group(s) of the formula —$Y_3$-$Q_3$ defined above;
(63) $R_{x7}$ is selected from hydrogen, fluoro, chloro or methyl;
(64) $R_{x7}$ is hydrogen;
(65) $X_8$ is N;
(66) $X_8$ is CH;
(67) integer c is 1 and integer d is 0 or 1;
(68) $R_{100a}$ and $R_{100b}$ are both $R_{100}$ as defined in hereinbefore;
(69) $R_{100a}$ and $R_{100b}$ are both $R_{100}$ as defined in paragraph (25) above;
(70) $R_{100a}$ and $R_{100b}$ are both $R_{100}$ as defined in paragraph (26) above;
(71) $R_{100a}$ and $R_{100b}$ are both $R_{100}$ as defined in paragraph (27) above;
(72) $R_{100a}$ and $R_{100b}$ are both $R_{100}$ as defined in paragraph (28) above;
(73) $R_{100a}$ and $R_{100b}$ are both $R_{100}$ as defined in paragraph (29) above;
(74) $R_{100a}$ and $R_{100b}$ are both $R_{100}$ as defined in paragraph (30) above;
(75) $R_{100a}$ and $R_{100b}$ are both $R_{100}$ as defined in paragraph (31) above;
(76) integer e is 0 or 1;
(77) $R_{100c}$ is as defined in as defined in paragraph (23) above;
(78) $R_{100c}$ is as defined in as defined in paragraph (26) above;
(79) $R_{100c}$ is as defined in as defined in paragraph (27) above;
(80) $R_{100c}$ is as defined in as defined in paragraph (28) above;
(81) $R_{100c}$ is as defined in as defined in paragraph (29) above;
(82) $R_{100c}$ is as defined in as defined in paragraph (30) above;
(83) $R_{100c}$ is as defined in as defined in paragraph (31) above;
(84) $R_2$ and $R_3$, when present, are each independently selected from the group consisting of fluoro, oxo, (1-2C)alkyl, (1-2C)alkoxy, —$CH_2$—C(O)—$NH_2$, —$CH_2$—C(O)—NHMe or —$CH_2$—C(O)—$NMe_2$;
(85) $R_2$ and $R_3$, when present, are methyl, oxo or —$CH_2$—C(O)—$NMe_2$;
(86) $R_{x4}$ is selected from hydrogen, fluoro, chloro, bromo, methyl or a group of the formula:

—Y-Q wherein:
Y is —O—, —O—$CH_2$—, —S—, —NH—, —$CH_2$— or —$CH_2$—$CH_2$—;
Q is selected from hydrogen, (1-4C)alkyl, —C(O)—$NH_2$, —C(O)—NHMe, —C(O)—$NMe_2$, (3-6C)cycloalkyl, phenyl, 5- or 6-membered heteroaryl, 4- to 7-membered heterocyclyl;
(87) $R_{x4}$ is selected from hydrogen, fluoro, chloro, bromo or methyl;
(88) $R_{x5}$ or $R_{x6}$ are selected from hydrogen, halo, cyano, nitro or a group of the formula:

-$L_1$-$Y_1$-$L_2$-$Q_1$ wherein:
$L_1$ is absent or methylene;
$Y_1$ is absent or —O—, —$SO_2$—, —S(O)(=$NR_{y1}$)—, —N($R_{y1}$)—, —C(O)N($R_{y1}$)—, —N($R_{y1}$)C(O)—, —S(O)$_2$N($R_{y1}$)—, or —N($R_{y1}$)$SO_2$—, wherein $R_{y1}$ and $R_{y1a}$ are selected from hydrogen or (1-2C)alkyl;
$L_2$ is absent or (1-2C)alkylene; and
$Q_1$ is hydrogen, (1-4C)alkyl, (3-4C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl,
wherein:
(i) when $Q_1$ is (1-4C)alkyl, it is optionally further substituted by one or more substituent groups independently selected from oxo, halo, cyano, or by one or more group(s) of the formula:

—$Y_2$-$Q_2$ wherein:
$Y_2$ is absent or selected from or —O—, —$SO_2$—, —O—C(O)—, —N($R_{y2}$)—, —C(O)N($R_{y2}$)— or —N($R_{y2}$)C(O)—, wherein $R_{y2}$ is selected from hydrogen or methyl;
$Q_2$ is selected from:
hydrogen;
a (1-4C)alkyl optionally substituted by one or more halo;
or
a 4 to 7-membered heterocyclic ring;
(ii) when $Q_1$ is (3-6C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—$Y_3$-$Q_3$ wherein:
$Y_3$ is absent or selected from or —O—, —$SO_2$— or —N($R_{y3}$)—, wherein $R_{y3}$ is selected from hydrogen or methyl;
$Q_3$ is selected from:
  hydrogen;
  a (1-4C)alkyl optionally substituted by one or more halo;
  or
  a 4 to 7-membered heterocyclic ring;
(iii) when $Q_1$ is phenyl or 5- to 6-membered heteroaryl, it is optionally further substituted by one or more substituent groups independently selected from halo, cyano, or by one or more group(s) of the formula —$Y_3$-$Q_3$ defined above;

(89) $R_{x5}$ or $R_{x6}$ are selected from hydrogen, halo, cyano, nitro or a group of the formula:

-$L_1$-$Y_1$-$L_2$-$Q_1$ wherein:
$L_1$ is absent;
$Y_1$ is absent or —O—, —SO$_2$—, —S(O)(=NR$_{y1}$)—, —N(R$_{y1}$)—, —C(O)N(R$_{y1}$)—, —N(R$_{y1}$)C(O)—, —S(O)$_2$N(R$_{y1}$)—, or —N(R$_{y1}$)SO$_2$—, wherein $R_{y1}$ and $R_{y1a}$ are selected from hydrogen or (1-2C)alkyl;
$L_2$ is absent or (1-2C)alkylene; and
$Q_1$ is hydrogen, (1-4C)alkyl, (3-4C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl,
wherein:
(i) when $Q_1$ is (1-4C)alkyl, it is optionally further substituted by one or more substituent groups independently selected from oxo, halo, cyano, or by one or more group(s) of the formula:

—$Y_2$-$Q_2$ wherein:
$Y_2$ is absent, —O—, —O—C(O)—, —C(O)NH— or —C(O)NMe-;
$Q_2$ is selected from:
  hydrogen;
  a (1-4C)alkyl optionally substituted by one or more halo;
  or
  a 4 to 7-membered heterocyclic ring;
(ii) when $Q_1$ is (3-6C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—$Y_3$-$Q_3$ wherein:
$Y_3$ is absent or —O—;
$Q_3$ is selected from:
  hydrogen;
  a (1-4C)alkyl optionally substituted by one or more halo;
  or
  a 4 to 7-membered heterocyclic ring;
(iii) when $Q_1$ is phenyl or 5- to 6-membered heteroaryl, it is optionally further substituted by one or more substituent groups independently selected from halo, cyano, or by one or more group(s) of the formula —$Y_3$-$Q_3$ defined above.

Suitably, in the compounds of formula I, ring A is as defined hereinbefore or as defined in any one of paragraphs (1) to (18) above. More suitably, ring A is as defined in paragraphs (12) to (18) above. Most suitably, ring A is as defined in paragraphs (15) or paragraph (16) above.

Suitably, in the compounds of formula I, $R_1$ is as defined hereinbefore or is as defined in any one of paragraphs (19) to (24) above. More suitably, $R_1$ is as defined in paragraphs (21) to (23) above. Most suitably, $R_1$ is as defined in paragraphs (22) or paragraph (23) above.

Suitably, in the compounds of formula I, $R_{100}$ is as defined hereinbefore or is as defined in any one of paragraphs (25) to (31) above. More suitably, $R_{100}$ is as defined in paragraphs (27) to (31) above. Most suitably, $R_{100}$ is as defined in paragraphs (27) or paragraph (30) above.

Suitably, in the compounds of formula I, integers a and b are as defined hereinbefore or are as defined in any one of paragraphs (32) to (34) above. More suitably, integers a and b are as defined in paragraph (32) or paragraph (33) above. Most suitably, integers a and b are as defined in paragraphs (32) above.

Suitably, in the compounds of formula I, $R_2$ and $R_3$ are as defined hereinbefore or are as defined in any one of paragraphs (35) to (38), (84) or (85) above. More suitably, $R_2$ and $R_3$ are as defined in paragraph (36) to (38) or (85) above. Most suitably, $R_2$ and $R_3$ are as defined in paragraphs (36) or paragraph (37) above.

Suitably, in the compounds of formula I, $X_4$, $X_5$, $X_6$ and $X_7$ are as defined hereinbefore or are as defined in any one of paragraphs (39) to (54) above. More suitably, $X_4$, $X_5$, $X_6$ and $X_7$ are as defined in paragraph (40) above. Most suitably, $X_4$, $X_5$, $X_6$ and $X_7$ are as defined in paragraphs (41), (42), (49) or (50) above.

Suitably, in the compounds of formula I, $R_{x4}$ is as defined hereinbefore or is as defined in any one of paragraphs (55) to (58), (86) or (87) above. More suitably, $R_{x4}$ is as defined in paragraphs (56) to (58) or (87) above. Most suitably, $R_{x4}$ is as defined in paragraphs (57) or paragraph (58) above.

Suitably, in the compounds of formula I, $R_{x5}$ is as defined hereinbefore or is as defined in any one of paragraphs (59) to (62), (88) or (89) above. More suitably, $R_{x5}$ is as defined in paragraph (60) or (89) above. Most suitably, $R_{x5}$ is as defined in paragraphs (61) or paragraph (62) above.

Suitably, in the compounds of formula I, $R_{x6}$ is as defined hereinbefore or is as defined in any one of paragraphs (59) to (62), (88) or (89) above. More suitably, $R_{x6}$ is as defined in paragraph (60) or (89) above. Most suitably, $R_{x6}$ is as defined in paragraphs (61) or paragraph (62) above.

Suitably, at least one of $R_{x5}$ and $R_{x6}$ is not hydrogen. In an embodiment, when $R_{x5}$ and $R_{x6}$ are both present, then $R_{x6}$ is not hydrogen. In another embodiment, when $R_{x5}$ and $R_{x6}$ are both present, then $R_{x5}$ is not hydrogen. In an embodiment, when $R_{x5}$ and $R_{x6}$ are both present and $R_{x5}$ is hydrogen, then $R_{x6}$ is not hydrogen. In an embodiment, when $R_{x5}$ and $R_{x6}$ are both present and $R_{x6}$ is hydrogen, then $R_{x5}$ is not hydrogen.

In an embodiment, $R_{x5}$ and $R_{x6}$ are as defined hereinbefore with the proviso that at least one of $R_{x5}$ and $R_{x6}$ is not hydrogen. In another embodiment, $R_{x5}$ and $R_{x6}$ are as defined in paragraph (59) above, with the proviso that at least one of $R_{x5}$ and $R_{x6}$ is not hydrogen. In another embodiment, $R_{x5}$ and $R_{x6}$ are as defined in paragraph (60) above, with the proviso that at least one of $R_{x5}$ and $R_{x6}$ is not hydrogen. In another embodiment, $R_{x5}$ and $R_{x6}$ areas defined in paragraph (61) above, with the proviso that at least one of $R_{x5}$ and $R_{x6}$ is not hydrogen. In another embodiment, $R_{x5}$ and $R_{x6}$ are as defined in paragraph (62) above, with the proviso that at least one of $R_{x5}$ and $R_{x6}$ is not hydrogen. In another embodiment, $R_{x6}$ is as defined in paragraph (59) above, with the proviso that $R_{x6}$ is not hydrogen. In another embodiment, $R_{x6}$ is as defined in paragraph (60) above, with the proviso that $R_{x6}$ is not hydrogen. In another embodiment, $R_{x6}$ is as defined in paragraph (61) above, with the proviso that $R_{x6}$ is not hydrogen. In another embodiment, $R_{x6}$ is as defined in paragraph (62) above, with the proviso that $R_{x6}$ is not hydrogen. In another embodiment, $R_{x5}$ and $R_{x6}$ are as defined in paragraph (88) above, with the proviso that at least one of $R_{x5}$ and $R_{x6}$ is not hydrogen. In another embodiment, $R_{x5}$ and $R_{x6}$ are as defined in paragraph (89) above, with the proviso that at least one of $R_{x5}$ and $R_{x6}$ is not hydrogen. In another embodiment, $R_{x6}$ is as defined in paragraph (88) above, with the proviso that $R_{x6}$ is not hydrogen. In another embodiment, $R_{x6}$ is as defined in paragraph (89) above, with the proviso that $R_{x6}$ is not hydrogen.

Suitably, in the compounds of formula I, $R_{x7}$ is as defined hereinbefore or is as defined in any one of paragraphs (63) or (64) above. More suitably, $R_{x7}$ is as defined in paragraph (63) above. Most suitably, $R_{x7}$ is as defined in paragraph (64) above.

Suitably, in the compounds of formula I, $X_8$ is as defined hereinbefore or is as defined in any one of paragraphs (65) or (66). More suitably, $X_8$ is as defined in paragraph (65) above.

Suitably, in the compounds of formula I, integers c and d are as defined hereinbefore or are as defined in any one of paragraph (67) above.

Suitably, in the compounds of formula I, integer e is as defined hereinbefore or are as defined in any one of paragraph (76) above.

Suitably, in the compounds of formula I, $R_{100a}$ and $R_{100b}$ are as defined hereinbefore or are as defined in any one of paragraphs (68) to (75) above. More suitably, $R_{100a}$ and $R_{100b}$ are as defined in paragraph (70). Most suitably, $R_{100a}$ and $R_{100b}$ are as defined in paragraphs (72) or paragraph (73) above.

Suitably, in the compounds of formula I, $R_{100c}$ is as defined hereinbefore in paragraph (23) above.

In a particular group of compounds of formula I, the compounds, or a pharmaceutically acceptable salt thereof, have one of the structural formulae Ia to Iam shown below:

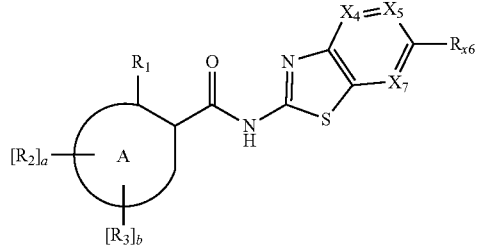

Ia

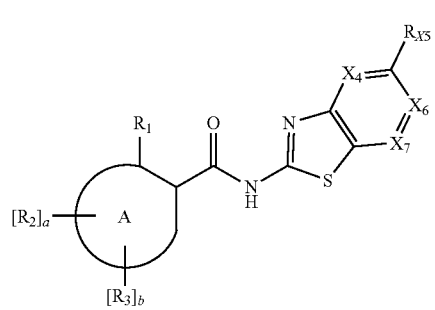

Ib

-continued

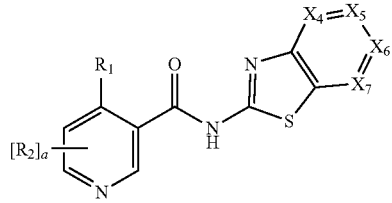

Ic

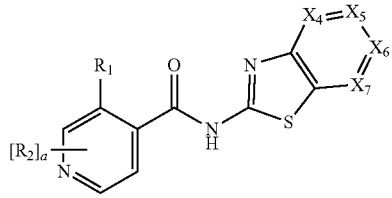

Id

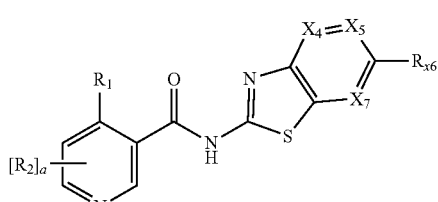

Ie

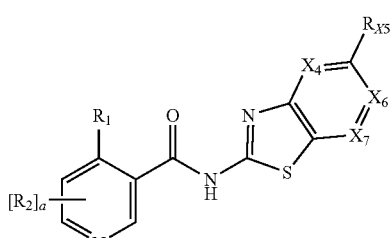

If

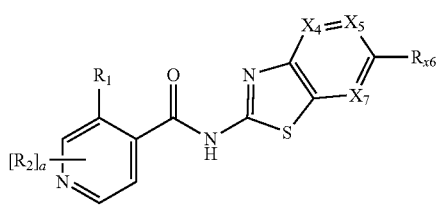

Ig

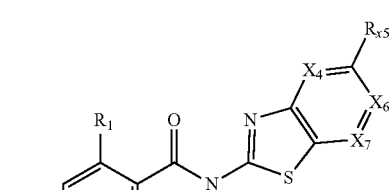

Ih

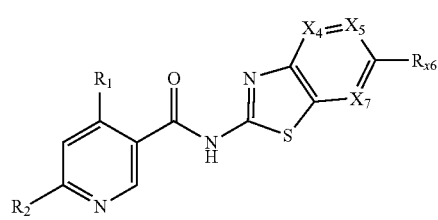

Ii

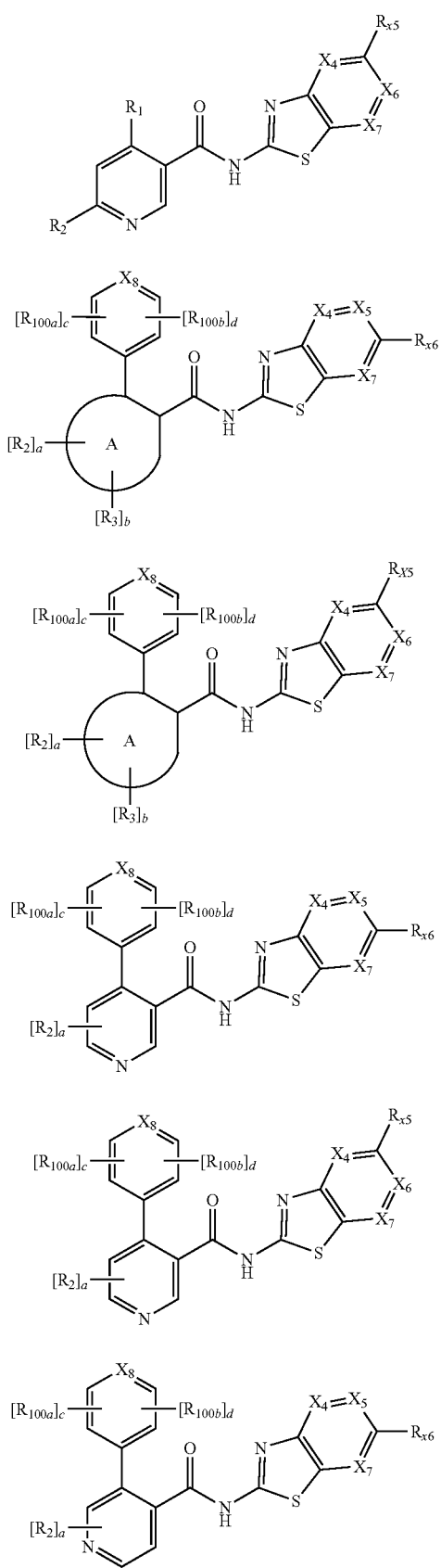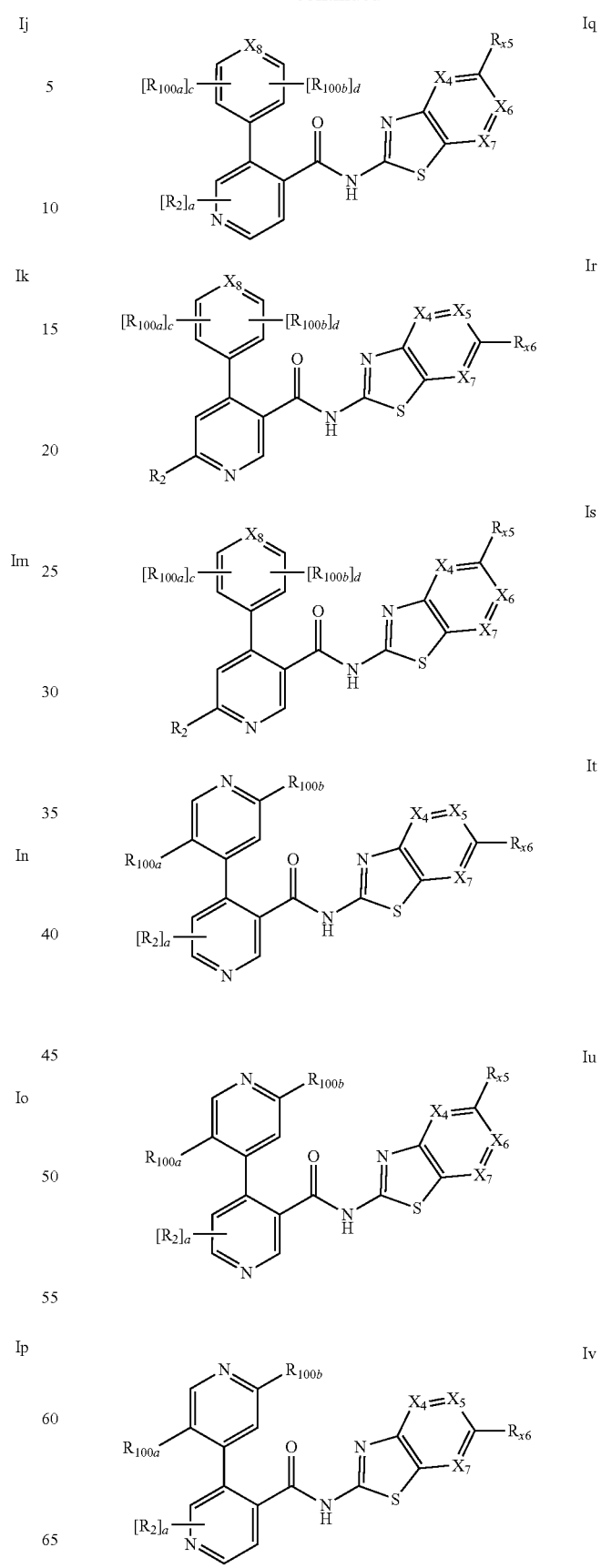

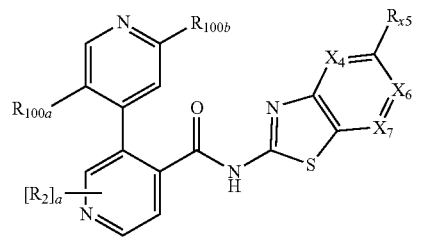
Iw
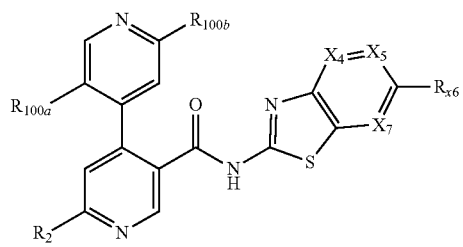
Ix
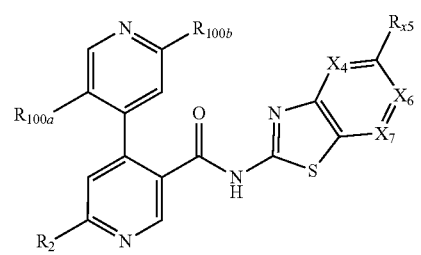
Iy
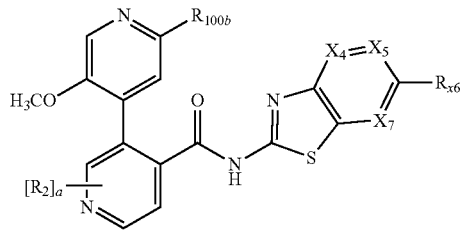
Iz
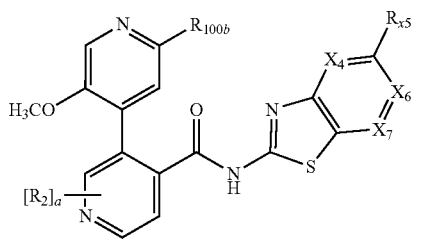
Iaa
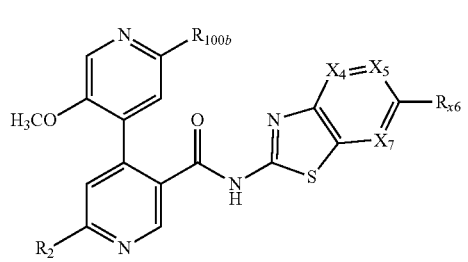
Iab
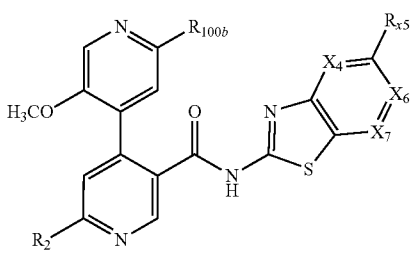
Iac
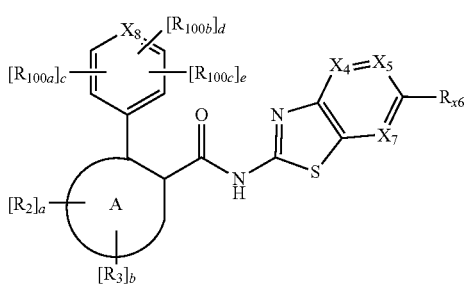
Iad
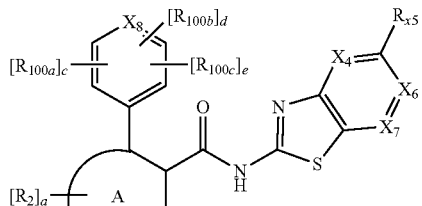
Iae
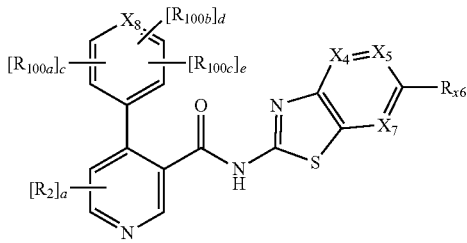
Iaf
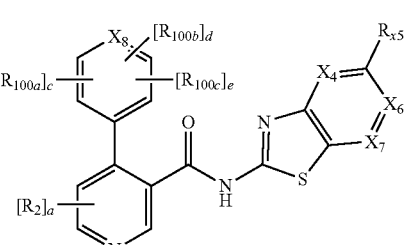
Iag
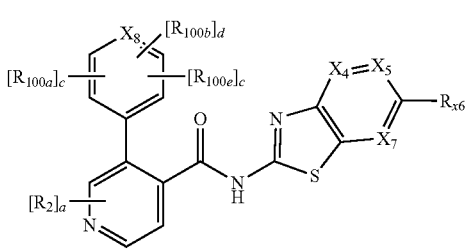
Iah wherein:
ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, integer c, $R_{100a}$, integer d, $R_{100b}$, integer e and $R_{100c}$ each have any of the meanings defined hereinbefore, or are as defined in any one of paragraphs (1) to (89) above.

In a particular group of compounds of the invention, the compounds have the structural formula Ia shown above.

In a particular group of compounds of the invention, the compounds have the structural formula Ib shown above.

In a particular group of compounds of the invention, the compounds have the structural formula Ic shown above.

In a particular group of compounds of the invention, the compounds have the structural formula Id shown above.

In a particular group of compounds of the invention, the compounds have the structural formula Ie shown above.

In a particular group of compounds of the invention, the compounds have the structural formula If shown above.

In a particular group of compounds of the invention, the compounds have the structural formula Ig shown above.

In a particular group of compounds of the invention, the compounds have the structural formula Ih shown above.

In a particular group of compounds of the invention, the compounds have the structural formula Ii shown above.

In a particular group of compounds of the invention, the compounds have the structural formula Ij shown above.

In a particular group of compounds of the invention, the compounds have the structural formula Ik shown above.

In a particular group of compounds of the invention, the compounds have the structural formula Im shown above.

In a particular group of compounds of the invention, the compounds have the structural formula In shown above.

In a particular group of compounds of the invention, the compounds have the structural formula Io shown above.

In a particular group of compounds of the invention, the compounds have the structural formula Ip shown above.

In a particular group of compounds of the invention, the compounds have the structural formula Iq shown above.

In a particular group of compounds of the invention, the compounds have the structural formula Ir shown above.

In a particular group of compounds of the invention, the compounds have the structural formula Is shown above.

In a particular group of compounds of the invention, the compounds have the structural formula It shown above.

In a particular group of compounds of the invention, the compounds have the structural formula Iu shown above.

In a particular group of compounds of the invention, the compounds have the structural formula Iv shown above.

In a particular group of compounds of the invention, the compounds have the structural formula Iw shown above.

In a particular group of compounds of the invention, the compounds have the structural formula Ix shown above.

In a particular group of compounds of the invention, the compounds have the structural formula Iy shown above.

In a particular group of compounds of the invention, the compounds have the structural formula Iz shown above.

In a particular group of compounds of the invention, the compounds have the structural formula Iaa shown above.

In a particular group of compounds of the invention, the compounds have the structural formula Iab shown above.

In a particular group of compounds of the invention, the compounds have the structural formula Iac shown above.

In a particular group of compounds of the invention, the compounds have the structural formula Iad shown above.

In a particular group of compounds of the invention, the compounds have the structural formula Iae shown above.

In a particular group of compounds of the invention, the compounds have the structural formula Iaf shown above.

In a particular group of compounds of the invention, the compounds have the structural formula Iag shown above.

In a particular group of compounds of the invention, the compounds have the structural formula Iah shown above.

In a particular group of compounds of the invention, the compounds have the structural formula Iai shown above.

In a particular group of compounds of the invention, the compounds have the structural formula Iaj shown above.

In a particular group of compounds of the invention, the compounds have the structural formula Ial shown above.

In a particular group of compounds of the invention, the compounds have the structural formula Ial shown above.

In a particular group of compounds of the invention, the compounds have the structural formula Iam shown above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (1) above;
$R_1$ is as defined in paragraph (19) above;
$R_{100}$ is as defined in paragraph (25) above;
$R_2$ is as defined in paragraph (35) above;
$R_3$ is as defined in paragraph (35) above;
integer a is as defined in paragraph (32) above;
integer b is as defined in paragraph (32) above;
$X_4$ is as defined in paragraph (39) above;
$X_5$ is as defined in paragraph (39) above;
$X_6$ is as defined in paragraph (39) above;
$X_7$ is as defined in paragraph (39) above;
$R_{x4}$ is as defined in paragraph (55) above;
$R_{x5}$ is as defined in paragraph (59) above;
$R_{x6}$ is as defined in paragraph (59) above;
$R_{x7}$ is as defined in paragraph (63) above;
$X_8$ is as defined in paragraph (65) above;
integer c is as defined in paragraph (67) above;
integer d is as defined in paragraph (67) above;
$R_{100a}$ is as defined in paragraph (69) above;
$R_{100b}$ is as defined in paragraph (69) above;
integer e is as defined in paragraph (76) above;
$R_{100c}$ is as defined in paragraph (78) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (3) above;
$R_1$ is as defined in paragraph (18) above;
$R_{100}$ is as defined in paragraph (26) above;
$R_2$ is as defined in paragraph (36) above;
$R_3$ is as defined in paragraph (36) above;
integer a is as defined in paragraph (32) above;
integer b is as defined in paragraph (32) above;
$X_4$ is as defined in paragraph (39) above;
$X_5$ is as defined in paragraph (39) above;
$X_6$ is as defined in paragraph (39) above;
$X_7$ is as defined in paragraph (39) above;
$R_{x4}$ is as defined in paragraph (56) above;
$R_{x5}$ is as defined in paragraph (60) above;
$R_{x6}$ is as defined in paragraph (60) above;
$R_{x7}$ is as defined in paragraph (63) above;
$X_8$ is as defined in paragraph (65) above;
integer c is as defined in paragraph (67) above;
integer d is as defined in paragraph (67) above;
$R_{100a}$ is as defined in paragraph (70) above;
$R_{100b}$ is as defined in paragraph (70) above;
integer e is as defined in paragraph (76) above;
$R_{100c}$ is as defined in paragraph (23) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (12) above;
$R_1$ is as defined in paragraph (21) above;
$R_{100}$ is as defined in paragraph (27) above;
$R_2$ is as defined in paragraph (36) above;
$R_3$ is as defined in paragraph (36) above;
integer a is as defined in paragraph (32) above;
integer b is as defined in paragraph (32) above;
$X_4$ is as defined in paragraph (41) above;
$X_5$ is as defined in paragraph (41) above;
$X_6$ is as defined in paragraph (41) above;
$X_7$ is as defined in paragraph (41) above;
$R_{x5}$ is as defined in paragraph (60) above;
$R_{x6}$ is as defined in paragraph (60) above;
$X_8$ is as defined in paragraph (65) above;
integer c is as defined in paragraph (67) above;
integer d is as defined in paragraph (67) above;
$R_{100a}$ is as defined in paragraph (72) above;
$R_{100b}$ is as defined in paragraph (72) above;
integer e is as defined in paragraph (76) above;
$R_{100c}$ is as defined in paragraph (23) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (15) above;
$R_1$ is as defined in paragraph (22) above;
$R_{100}$ is as defined in paragraph (30) above;
$R_2$ is as defined in paragraph (37) above;
$R_3$ is as defined in paragraph (37) above;
integer a is as defined in paragraph (32) above;
integer b is as defined in paragraph (32) above;
$X_4$ is as defined in paragraph (41) above;
$X_5$ is as defined in paragraph (41) above;
$X_6$ is as defined in paragraph (41) above;
$X_7$ is as defined in paragraph (41) above;
$R_{x5}$ is as defined in paragraph (61) above;
$R_{x6}$ is as defined in paragraph (61) above;
$X_8$ is as defined in paragraph (65) above;
integer c is as defined in paragraph (67) above;
integer d is as defined in paragraph (67) above;
$R_{100a}$ is as defined in paragraph (73) above;
$R_{100b}$ is as defined in paragraph (73) above;
integer e is as defined in paragraph (76) above;
$R_{100c}$ is as defined in paragraph (23) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (16) above;
$R_1$ is as defined in paragraph (23) above;
$R_{100}$ is as defined in paragraph (30) above;
$R_2$ is as defined in paragraph (37) above;
$R_3$ is as defined in paragraph (37) above;
integer a is as defined in paragraph (32) above;
integer b is as defined in paragraph (32) above;
$X_4$ is as defined in paragraph (41) above;
$X_5$ is as defined in paragraph (41) above;
$X_6$ is as defined in paragraph (41) above;
$X_7$ is as defined in paragraph (41) above;
$R_{x5}$ is as defined in paragraph (61) above;
$R_{x6}$ is as defined in paragraph (61) above;
$X_8$ is as defined in paragraph (65) above;
integer c is as defined in paragraph (67) above;
integer d is as defined in paragraph (67) above;
$R_{100a}$ is as defined in paragraph (73) above;
$R_{100b}$ is as defined in paragraph (73) above;
integer e is as defined in paragraph (76) above;
$R_{100c}$ is as defined in paragraph (23) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:

ring A is as defined in paragraph (1) above;
$R_1$ is as defined in paragraph (19) above;
$R_{100}$ is as defined in paragraph (25) above;
$R_2$ is as defined in paragraph (84) above;
$R_3$ is as defined in paragraph (84) above;
integer a is as defined in paragraph (32) above;
integer b is as defined in paragraph (32) above;
$X_4$ is as defined in paragraph (39) above;
$X_5$ is as defined in paragraph (39) above;
$X_6$ is as defined in paragraph (39) above;
$X_7$ is as defined in paragraph (39) above;
$R_{x4}$ is as defined in paragraph (86) above;
$R_{x5}$ is as defined in paragraph (88) above;
$R_{x6}$ is as defined in paragraph (88) above;
$R_{x7}$ is as defined in paragraph (63) above;
$X_8$ is as defined in paragraph (65) above;
integer c is as defined in paragraph (67) above;
integer d is as defined in paragraph (67) above;
$R_{100a}$ is as defined in paragraph (69) above;
$R_{100b}$ is as defined in paragraph (69) above;
integer e is as defined in paragraph (76) above;
$R_{100c}$ is as defined in paragraph (78) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (3) above;
$R_1$ is as defined in paragraph (19) above;
$R_{100}$ is as defined in paragraph (26) above;
$R_2$ is as defined in paragraph (85) above;
$R_3$ is as defined in paragraph (85) above;
integer a is as defined in paragraph (32) above;
integer b is as defined in paragraph (32) above;
$X_4$ is as defined in paragraph (39) above;
$X_5$ is as defined in paragraph (39) above;
$X_6$ is as defined in paragraph (39) above;
$X_7$ is as defined in paragraph (39) above;
$R_{x4}$ is as defined in paragraph (87) above;
$R_{x5}$ is as defined in paragraph (89) above;
$R_{x6}$ is as defined in paragraph (89) above;
$R_{x7}$ is as defined in paragraph (63) above;
$X_8$ is as defined in paragraph (65) above;
integer c is as defined in paragraph (67) above;
integer d is as defined in paragraph (67) above;
$R_{100a}$ is as defined in paragraph (70) above;
$R_{100b}$ is as defined in paragraph (70) above;
integer e is as defined in paragraph (76) above;
$R_{100c}$ is as defined in paragraph (23) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (12) above;
$R_1$ is as defined in paragraph (21) above;
$R_{100}$ is as defined in paragraph (27) above;
$R_2$ is as defined in paragraph (85) above;
$R_3$ is as defined in paragraph (85) above;
integer a is as defined in paragraph (32) above;
integer b is as defined in paragraph (32) above;
$X_4$ is as defined in paragraph (41) above;
$X_5$ is as defined in paragraph (41) above;
$X_6$ is as defined in paragraph (41) above;
$X_7$ is as defined in paragraph (41) above;
$R_{x5}$ is as defined in paragraph (89) above;
$R_{x6}$ is as defined in paragraph (89) above;
$X_8$ is as defined in paragraph (65) above;
integer c is as defined in paragraph (67) above;
integer d is as defined in paragraph (67) above;
$R_{100a}$ is as defined in paragraph (72) above;
$R_{100b}$ is as defined in paragraph (72) above;
integer e is as defined in paragraph (76) above;
$R_{100c}$ is as defined in paragraph (23) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (15) above;
$R_1$ is as defined in paragraph (22) above;
$R_{100}$ is as defined in paragraph (30) above;
$R_2$ is as defined in paragraph (85) above;
$R_3$ is as defined in paragraph (85) above;
integer a is as defined in paragraph (32) above;
integer b is as defined in paragraph (32) above;
$X_4$ is as defined in paragraph (41) above;
$X_5$ is as defined in paragraph (41) above;
$X_6$ is as defined in paragraph (41) above;
$X_7$ is as defined in paragraph (41) above;
$R_{x5}$ is as defined in paragraph (89) above;
$R_{x6}$ is as defined in paragraph (89) above;
$X_8$ is as defined in paragraph (65) above;
integer c is as defined in paragraph (67) above;
integer d is as defined in paragraph (67) above;
$R_{100a}$ is as defined in paragraph (73) above;
$R_{100b}$ is as defined in paragraph (73) above;
integer e is as defined in paragraph (76) above;
$R_{100c}$ is as defined in paragraph (23) above.

A particular group of compounds have any one of the formulae Ia to Iam above, wherein, and where present, each of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ each the following definitions:
ring A is as defined in paragraph (16) above;
$R_1$ is as defined in paragraph (23) above;
$R_{100}$ is as defined in paragraph (30) above;
$R_2$ is as defined in paragraph (85) above;
$R_3$ is as defined in paragraph (85) above;
integer a is as defined in paragraph (32) above;
integer b is as defined in paragraph (32) above;
$X_4$ is as defined in paragraph (41) above;
$X_5$ is as defined in paragraph (41) above;
$X_6$ is as defined in paragraph (41) above;
$X_7$ is as defined in paragraph (41) above;
$R_{x5}$ is as defined in paragraph (89) above;
$R_{x6}$ is as defined in paragraph (89) above;
$X_8$ is as defined in paragraph (65) above;
integer c is as defined in paragraph (67) above;
integer d is as defined in paragraph (67) above;
$R_{100a}$ is as defined in paragraph (73) above;
$R_{100b}$ is as defined in paragraph (73) above;
integer e is as defined in paragraph (76) above;
$R_{100c}$ is as defined in paragraph (23) above.

A particular group of compounds have any one of the formulae Ia to Iam above, wherein, and where present, each of $R_{100}$, $R_2$, $R_3$, integer a, integer b, $R_{x4}$, $R_{x5}$, $R_{x6}$, $R_{x7}$, $X_8$, $R_{100a}$ and $R_{100b}$ have any of the definitions described herein and each of ring A, $R_1$, $X_4$, $X_5$, $X_6$ and $X_7$ have the following definitions:
ring A is as defined in paragraph (12) above;
$R_1$ is as defined in paragraph (21) above;
$X_4$ is selected from CH;
$X_5$ is selected from N;

$X_6$ is selected from $CR_{x6}$; and
$X_7$ is selected from N or CH.
A particular group of compounds have any one of the formulae Ia to Iam above, wherein, and where present, each of $R_{100}$, $R_2$, $R_3$, integer a, integer b, $R_{x4}$, $R_{x5}$, $R_{x6}$, $R_7$, $X_8$, $R_{100a}$ and $R_{100b}$ have any of the definitions described herein and each of ring A, $R_1$, $X_4$, $X_5$, $X_6$ and $X_7$ have the following definitions:
ring A is as defined in paragraph (15) above;
$R_1$ is as defined in paragraph (22) above;
$X_4$ is selected from CH;
$X_5$ is selected from N;
$X_6$ is selected from $CR_{x6}$; and
$X_7$ is selected from N or CH.
A particular group of compounds have any one of the formulae Ia to Iam above, wherein, and where present, each of $R_{100}$, $R_2$, $R_3$, integer a, integer b, $R_{x4}$, $R_{x5}$, $R_{x6}$, $R_{x7}$, $X_8$, $R_{100a}$ and $R_{100b}$ have any of the definitions described herein and each of ring A, $R_1$, $X_4$, $X_5$, $X_6$ and $X_7$ have the following definitions:
ring A is as defined in paragraph (17) above;
$R_1$ is as defined in paragraph (23) above;
$X_4$ is selected from CH;
$X_5$ is selected from N;
$X_6$ is selected from $CR_{x6}$; and
$X_7$ is selected from N or CH.
A particular group of compounds have any one of the formulae Ia to Iam above, wherein, and where present, each of $R_{100}$, $R_2$, $R_3$, integer a, integer b, $R_{x4}$, $R_{x5}$, $R_{x6}$, $R_{x7}$, $X_8$, $R_{100a}$ and $R_{100b}$ have any of the definitions described herein and each of ring A, $R_1$, $X_4$, $X_5$, $X_6$ and $X_7$ have the following definitions:
ring A is as defined in paragraph (18) above;
$R_1$ is as defined in paragraph (24) above;
$X_4$ is selected from CH;
$X_5$ is selected from N;
$X_6$ is selected from $CR_{x6}$; and
$X_7$ is selected from N or CH.
In a group of compounds of the invention, including compounds of formula I, and any of formulae Ia through to Iam defined above, $R_{x4}$ and $R_{x5}$, $R_{x5}$ and $R_{x6}$ or $R_{x6}$ and $R_{x7}$ may be linked such that, together with the carbon atoms to which they are attached, they form a fused (5-6C)cycloalkyl, phenyl, 5- or 6-membered heteroaryl or 5- or 6-membered heterocyclic ring, each of which is optionally substituted by fluoro, chloro, methyl or hydroxy. In such compounds, all other variable groups may have any one of the definitions set out herein.
In such compounds, $R_{x4}$ and $R_{x5}$ are suitably linked such that, together with the carbon atoms to which they are attached, they form a fused 5- or 6-membered heteroaryl or 5- or 6-membered heterocyclic ring, each of which is optionally substituted by fluoro, chloro, methyl or hydroxy.
In a particular group of compounds of the invention, including compounds of formula I, and any of formulae Ia through to Iam defined above, $R_{x4}$ and $R_{x5}$ may be linked such that, together with the carbon atoms to which they are attached, they form a fused (5-6C)cycloalkyl, phenyl, 5- or 6-membered heteroaryl or 5- or 6-membered heterocyclic ring, each of which is optionally substituted by fluoro, chloro, methyl or hydroxy.
In such compounds, $R_{x4}$ and $R_{x5}$ are suitably linked such that, together with the carbon atoms to which they are attached, they form a fused 5- or 6-membered heteroaryl or 5- or 6-membered heterocyclic ring, each of which is optionally substituted by fluoro, chloro, methyl or hydroxy.

Particular compounds of the present invention include any of the compounds described in the example section of the present application, or a pharmaceutically acceptable salt thereof, and, in particular, any of the following:
N-(6-chloro-1,3-benzothiazol-2-yl)-4-(2-chloro-5-methoxy-4-pyridyl)-6-methyl-pyridine-3-carboxamide;
2'-chloro-N-(6-methanesulfonyl-1,3-benzothiazol-2-yl)-5'-methoxy-6-methyl-[4,4'-bipyridine]-3-carboxamide;
2'-chloro-N-(6-cyano-1,3-benzothiazol-2-yl)-5'-methoxy-6-methyl-[4,4'-bipyridine]-3-carboxamide;
2'-chloro-N-(6-iodo-1,3-benzothiazol-2-yl)-5'-methoxy-6-methyl-[4,4'-bipyridine]-3-carboxamide;
N-(6-bromo-1,3-benzothiazol-2-yl)-2'-chloro-5'-methoxy-6-methyl-[4,4'-bipyridine]-3-carboxamide;
2'-chloro-N-{5-chloro-[1,3]thiazolo[5,4-d]pyrimidin-2-yl}-5'-methoxy-6-methyl-[4,4'-bipyridine]-3-carboxamide;
2'-chloro-N-{5-chloro-[1,3]thiazolo[5,4-b]pyridin-2-yl}-5'-methoxy-6-methyl-[4,4'-bipyridine]-3-carboxamide;
3-(2-methoxyphenyl)-N-{[1,3]thiazolo[5,4-d]pyrimidin-2-yl}pyridine-4-carboxamide;
N-(6-bromo-1,3-benzothiazol-2-yl)-3-(2-methoxyphenyl)pyridine-4-carboxamide;
3-(2-methoxyphenyl)-N-{[1,3]thiazolo[4,5-c]pyridin-2-yl}pyridine-4-carboxamide;
3-(2-methoxyphenyl)-N-{[1,3]thiazolo[4,5-b]pyridin-2-yl}pyridine-4-carboxamide;
3-(2-methoxyphenyl)-N-[5-(trifluoromethyl)-1,3-benzothiazol-2-yl]pyridine-4-carboxamide;
N-(5-chloro-1,3-benzothiazol-2-yl)-3-(2-methoxyphenyl)pyridine-4-carboxamide;
3-(2-methoxyphenyl)-N-{[1,3]thiazolo[5,4-b]pyridin-2-yl}pyridine-4-carboxamide;
N-(1,3-benzothiazol-2-yl)-3-(2-methoxyphenyl)pyridine-4-carboxamide;
N-(5-cyano-1,3-benzothiazol-2-yl)-3-(2-methoxyphenyl)pyridine-4-carboxamide;
2'-chloro-5'-methoxy-6-methyl-N-[6-(morpholin-4-yl)-1,3-benzothiazol-2-yl]-[4,4'-bipyridine]-3-carboxamide;
2'-chloro-5'-methoxy-6-methyl-N-(6-nitro-1,3-benzothiazol-2-yl)-[4,4'-bipyridine]-3-carboxamide;
4-(2-chloro-5-methoxy-4-pyridyl)-N-[5-[(3R)-3-hydroxypyrrolidin-1-yl]thiazolo[5,4-d]pyrimidin-2-yl]-6-methyl-pyridine-3-carboxamide;
2'-chloro-5'-methoxy-6-methyl-N-[5-(piperidin-1-yl)-[1,3]thiazolo[5,4-d]pyrimidin-2-yl]-[4,4'-bipyridine]-3-carboxamide;
2'-chloro-N-[5-(4,4-difluoropiperidin-1-yl)-[1,3]thiazolo[5,4-d]pyrimidin-2-yl]-5'-methoxy-6-methyl-[4,4'-bipyridine]-3-carboxamide;
2'-chloro-5'-methoxy-6-methyl-N-[5-(morpholin-4-yl)-[1,3]thiazolo[5,4-d]pyrimidin-2-yl]-[4,4'-bipyridine]-3-carboxamide;
2'-chloro-N-{5-[(3S)-3-hydroxypyrrolidin-1-yl]-[1,3]thiazolo[5,4-d]pyrimidin-2-yl}-5'-methoxy-6-methyl-[4,4'-bipyridine]-3-carboxamide;
2'-chloro-5'-methoxy-6-methyl-N-[5-(pyrrolidin-1-yl)-[1,3]thiazolo[5,4-d]pyrimidin-2-yl]-[4,4'-bipyridine]-3-carboxamide;
2'-chloro-N-[5-(3,3-difluoropyrrolidin-1-yl)-[1,3]thiazolo[5,4-d]pyrimidin-2-yl]-5'-methoxy-6-methyl-[4,4'-bipyridine]-3-carboxamide;
2'-chloro-N-{5-[(3R)-3-hydroxypyrrolidin-1-yl]-[1,3]thiazolo[5,4-d]pyrimidin-2-yl}-5'-methoxy-6-methyl-[4,4'-bipyridine]-3-carboxamide;
2'-chloro-N-[5-(1,1-dioxo-1$\lambda^6$-thiomorpholin-4-yl)-[1,3]thiazolo[5,4-d]pyrimidin-2-yl]-5'-methoxy-6-methyl-[4,4'-bipyridine]-3-carboxamide;

2'-chloro-5'-methoxy-6-methyl-N-[5-(4-methylpiperazin-1-yl)-[1,3]thiazolo[5,4-d]pyrimidin-2-yl]-[4,4'-bipyridine]-3-carboxamide;

2'-chloro-5'-methoxy-6-methyl-N-(5-{2-oxa-6-azaspiro[3.3]heptan-6-yl}-[1,3]thiazolo[5,4-d]pyrimidin-2-yl)-[4,4'-bipyridine]-3-carboxamide;

2'-chloro-5'-methoxy-N-{5-[(2-methoxyethyl)amino]-[1,3]thiazolo[5,4-d]pyrimidin-2-yl}-6-methyl-[4,4'-bipyridine]-3-carboxamide;

2'-chloro-N-[5-(3-hydroxyazetidin-1-yl)-[1,3]thiazolo[5,4-d]pyrimidin-2-yl]-5'-methoxy-6-methyl-[4,4'-bipyridine]-3-carboxamide;

2'-chloro-5'-methoxy-N-[5-(3-methoxypyrrolidin-1-yl)-[1,3]thiazolo[5,4-d]pyrimidin-2-yl]-6-methyl-[4,4'-bipyridine]-3-carboxamide;

2'-chloro-N-[5-(4-hydroxypiperidin-1-yl)-[1,3]thiazolo[5,4-d]pyrimidin-2-yl]-5'-methoxy-6-methyl-[4,4'-bipyridine]-3-carboxamide;

2'-chloro-5'-methoxy-6-methyl-N-{5-[(1S,4S)-2-oxa-5-azabicyclo[2.2.1]heptan-5-yl]-[1,3]thiazolo[5,4-d]pyrimidin-2-yl}-[4,4'-bipyridine]-3-carboxamide;

2'-chloro-N-[5-(3-cyanopiperidin-1-yl)-[1,3]thiazolo[5,4-d]pyrimidin-2-yl]-5'-methoxy-6-methyl-[4,4'-bipyridine]-3-carboxamide;

N-(6-amino-1,3-benzothiazol-2-yl)-4-(2-chloro-5-methoxy-4-pyridyl)-6-methyl-pyridine-3-carboxamide;

2'-chloro-5'-methoxy-6-methyl-N-[6-(2-oxopiperidin-1-yl)-1,3-benzothiazol-2-yl]-[4,4'-bipyridine]-3-carboxamide;

4-(2-chloro-5-methoxy-4-pyridyl)-N-[5-(3,6-dihydro-2H-pyran-5-yl)thiazolo[5,4-b]pyridin-2-yl]-6-methyl-pyridine-3-carboxamide;

4-(2-chloro-5-methoxy-4-pyridyl)-N-[6-(5-chloro-2-pyridyl)-1,3-benzothiazol-2-yl]-6-methyl-pyridine-3-carboxamide;

N-[6-(5-chloropyridin-2-yl)-1,3-benzothiazol-2-yl]-3-(2-methoxyphenyl)pyridine-4-carboxamide;

2'-chloro-N-[6-(3-hydroxyoxolan-3-yl)-1,3-benzothiazol-2-yl]-5'-methoxy-6-methyl-[4,4'-bipyridine]-3-carboxamide;

2'-chloro-N-(6-methanesulfonamido-1,3-benzothiazol-2-yl)-5'-methoxy-6-methyl-[4,4'-bipyridine]-3-carboxamide;

2'-chloro-5'-methoxy-6-methyl-N-{[1,3]thiazolo[5,4-d]pyrimidin-2-yl}-[4,4'-bipyridine]-3-carboxamide;

2'-chloro-5'-methoxy-6-methyl-N-[6-(methylsulfanyl)-1,3-benzothiazol-2-yl]-[4,4'-bipyridine]-3-carboxamide;

2'-chloro-5'-methoxy-6-methyl-N-{[1,3]thiazolo[5,4-c]pyridin-2-yl}-[4,4'-bipyridine]-3-carboxamide;

N-[5-(4-acetylpiperazin-1-yl)-[1,3]thiazolo[5,4-d]pyrimidin-2-yl]-2'-chloro-5'-methoxy-6-methyl-[4,4'-bipyridine]-3-carboxamide;

2'-chloro-N-{5-[(2-hydroxyethyl)amino]-[1,3]thiazolo[5,4-d]pyrimidin-2-yl}-5'-methoxy-6-methyl-[4,4'-bipyridine]-3-carboxamide;

2'-chloro-5'-methoxy-N-[5-(3-methoxyazetidin-1-yl)-[1,3]thiazolo[5,4-d]pyrimidin-2-yl]-6-methyl-[4,4'-bipyridine]-3-carboxamide;

2'-chloro-N-{5-[(4-hydroxycyclohexyl)amino]-[1,3]thiazolo[5,4-d]pyrimidin-2-yl}-5'-methoxy-6-methyl-[4,4'-bipyridine]-3-carboxamide;

rac-2'-chloro-N-(5-{[(1R,3S)-3-hydroxycyclopentyl]amino}-[1,3]thiazolo[5,4-d]pyrimidin-2-yl)-5'-methoxy-6-methyl-[4,4'-bipyridine]-3-carboxamide;

2'-chloro-5'-methoxy-6-methyl-N-{5-[(3R)-3-methylmorpholin-4-yl]-[1,3]thiazolo[5,4-d]pyrimidin-2-yl}-[4,4'-bipyridine]-3-carboxamide;

2'-chloro-5'-methoxy-6-methyl-N-{5-[(3S)-3-methylmorpholin-4-yl]-[1,3]thiazolo[5,4-d]pyrimidin-2-yl}-[4,4'-bipyridine]-3-carboxamide;

2'-chloro-5'-methoxy-6-methyl-N-{5-[(propan-2-yl)amino]-[1,3]thiazolo[5,4-d]pyrimidin-2-yl}-[4,4'-bipyridine]-3-carboxamide;

2'-chloro-5'-methoxy-N-(5-{2-oxa-7-azaspiro[3.5]nonan-7-yl}-[1,3]thiazolo[5,4-d]pyrimidin-2-yl)-[4,4'-bipyridine]-3-carboxamide;

2'-chloro-N-(5-{3,8-diazabicyclo[3.2.1]octan-3-yl}-[1,3]thiazolo[5,4-d]pyrimidin-2-yl)-5'-methoxy-6-methyl-[4,4'-bipyridine]-3-carboxamide;

2'-chloro-5'-methoxy-6-methyl-N-[5-(piperazin-1-yl)-[1,3]thiazolo[5,4-d]pyrimidin-2-yl]-[4,4'-bipyridine]-3-carboxamide;

2'-chloro-5'-methoxy-6-methyl-N-[6-(2-oxopyrrolidin-1-yl)-1,3-benzothiazol-2-yl]-[4,4'-bipyridine]-3-carboxamide;

2'-chloro-5'-methoxy-6-methyl-N-[6-(3-oxomorpholin-4-yl)-1,3-benzothiazol-2-yl]-[4,4'-bipyridine]-3-carboxamide;

2'-chloro-5'-methoxy-6-methyl-N-[6-(3-methyl-2-oxoimidazolidin-1-yl)-1,3-benzothiazol-2-yl]-[4,4'-bipyridine]-3-carboxamide;

2'-chloro-5'-methoxy-6-methyl-N-[6-(2-oxo-1,3-oxazolidin-3-yl)-1,3-benzothiazol-2-yl]-[4,4'-bipyridine]-3-carboxamide;

2'-chloro-5'-methoxy-6-methyl-N-[6-(2-oxoimidazolidin-1-yl)-1,3-benzothiazol-2-yl]-[4,4'-bipyridine]-3-carboxamide;

2'-chloro-5'-methoxy-6-methyl-N-[6-(2-oxopiperidin-1-yl)-[1,3]thiazolo[4,5-c]pyridin-2-yl]-[4,4'-bipyridine]-3-carboxamide;

2'-chloro-5'-methoxy-6-methyl-N-{[1,3]thiazolo[4,5-c]pyridin-2-yl}-[4,4'-bipyridine]-3-carboxamide;

2'-chloro-N-{6-chloro-[1,3]thiazolo[5,4-c]pyridin-2-yl}-5'-methoxy-6-methyl-[4,4'-bipyridine]-3-carboxamide;

2'-chloro-N-{6-chloro-[1,3]thiazolo[4,5-c]pyridin-2-yl}-5'-methoxy-6-methyl-[4,4'-bipyridine]-3-carboxamide;

2'-chloro-5'-methoxy-6-methyl-N-[6-(morpholin-4-yl)-[1,3]thiazolo[4,5-c]pyridin-2-yl]-[4,4'-bipyridine]-3-carboxamide;

2'-chloro-N-[6-(dimethylsulfamoyl)-1,3-benzothiazol-2-yl]-5'-methoxy-6-methyl-[4,4'-bipyridine]-3-carboxamide;

2'-chloro-5'-methoxy-6-methyl-N-[6-(morpholin-4-yl)-[1,3]thiazolo[4,5-b]pyridin-2-yl]-[4,4'-bipyridine]-3-carboxamide;

2'-chloro-N-[6-(4-hydroxypiperidin-1-yl)-[1,3]thiazolo[4,5-c]pyridin-2-yl]-5'-methoxy-6-methyl-[4,4'-bipyridine]-3-carboxamide;

N-(1,3-benzothiazol-2-yl)-2'-chloro-5'-methoxy-6-methyl-[4,4'-bipyridine]-3-carboxamide;

2'-chloro-5'-methoxy-6-methyl-N-[6-(2-oxopiperidin-1-yl)-[1,3]thiazolo[4,5-b]pyridin-2-yl]-[4,4'-bipyridine]-3-carboxamide;

2'-chloro-N-[6-(4-hydroxypiperidin-1-yl)-[1,3]thiazolo[4,5-b]pyridin-2-yl]-5'-methoxy-6-methyl-[4,4'-bipyridine]-3-carboxamide;

2'-chloro-5'-methoxy-6-methyl-N-[5-(morpholin-4-yl)-[1,3]thiazolo[5,4-b]pyridin-2-yl]-[4,4'-bipyridine]-3-carboxamide;

2'-chloro-5'-methoxy-6-methyl-N-[5-(2-oxopiperidin-1-yl)-[1,3]thiazolo[5,4-b]pyridin-2-yl]-[4,4'-bipyridine]-3-carboxamide;

2'-chloro-N-[5-(4-hydroxypiperidin-1-yl)-[1,3]thiazolo[5,4-b]pyridin-2-yl]-5'-methoxy-6-methyl-[4,4'-bipyridine]-3-carboxamide;

2'-chloro-5'-methoxy-N-{5-methoxy-[1,3]thiazolo[5,4-d]pyrimidin-2-yl}-6-methyl-[4,4'-bipyridine]-3-carboxamide;

2'-chloro-5'-methoxy-6-methyl-N-(5-{2-oxa-6-azaspiro[3.4]octan-6-yl}-[1,3]thiazolo[5,4-d]pyrimidin-2-yl)-[4,4'-bipyridine]-3-carboxamide;

2'-chloro-N-{5-[(2-hydroxy-2-methylpropyl)amino]-[1,3]thiazolo[5,4-d]pyrimidin-2-yl}-5'-methoxy-6-methyl-[4,4'-bipyridine]-3-carboxamide;

2'-chloro-5'-methoxy-6-methyl-N-{5-[(2-methylpropyl)amino]-[1,3]thiazolo[5,4-d]pyrimidin-2-yl}-[4,4'-bipyridine]-3-carboxamide;

2'-chloro-N-[5-(cyclobutylamino)-[1,3]thiazolo[5,4-d]pyrimidin-2-yl]-5'-methoxy-6-methyl-[4,4'-bipyridine]-3-carboxamide;

2'-chloro-5'-methoxy-N-[5-(4-methoxypiperidin-1-yl)-[1,3]thiazolo[5,4-d]pyrimidin-2-yl]-6-methyl-[4,4'-bipyridine]-3-carboxamide;

2'-chloro-N-(5-{6-hydroxy-2-azaspiro[3.3]heptan-2-yl}-[1,3]thiazolo[5,4-d]pyrimidin-2-yl)-5'-methoxy-6-methyl-[4,4'-bipyridine]-3-carboxamide;

2'-chloro-5'-methoxy-6-methyl-N-(5-{6-oxa-2-azaspiro[3.4]octan-2-yl}-[1,3]thiazolo[5,4-d]pyrimidin-2-yl)-[4,4'-bipyridine]-3-carboxamide;

2'-chloro-N-{6-[imino(methyl)oxo-$\lambda^6$-sulfanyl]-1,3-benzothiazol-2-yl}-5'-methoxy-6-methyl-[4,4'-bipyridine]-3-carboxamide;

2'-chloro-N-[6-(1,1-dioxo-1$\lambda^6$,2-thiazolidin-2-yl)-1,3-benzothiazol-2-yl]-5'-methoxy-6-methyl-[4,4'-bipyridine]-3-carboxamide;

2'-chloro-N-{6-[(4R)-4-hydroxy-2-oxopiperidin-1-yl]-1,3-benzothiazol-2-yl}-5'-methoxy-6-methyl-[4,4'-bipyridine]-3-carboxamide;

2'-chloro-5'-methoxy-6-methyl-N-[6-(4-methyl-2-oxopiperazin-1-yl)-1,3-benzothiazol-2-yl]-[4,4'-bipyridine]-3-carboxamide;

2'-chloro-N-[5-(3,6-dihydro-2H-pyran-4-yl)-[1,3]thiazolo[5,4-d]pyrimidin-2-yl]-5'-methoxy-6-methyl-[4,4'-bipyridine]-3-carboxamide;

N-[5-(4-hydroxypiperidin-1-yl)-[1,3]thiazolo[5,4-d]pyrimidin-2-yl]-5'-methoxy-6-methyl-2'-(trifluoromethyl)-[4,4'-bipyridine]-3-carboxamide;

N-[5-(4-hydroxypiperidin-1-yl)-[1,3]thiazolo[5,4-d]pyrimidin-2-yl]-5'-methoxy-6-methyl-2'-(trifluoromethyl)-[4,4'-bipyridine]-3-carboxamide;

2'-chloro-5'-methoxy-6-methyl-N-[5-(trifluoromethyl)-[1,3]thiazolo[5,4-d]pyrimidin-2-yl]-[4,4'-bipyridine]-3-carboxamide;

2'-chloro-5'-methoxy-6-methyl-N-{5-methyl-[1,3]thiazolo[5,4-d]pyrimidin-2-yl}-[4,4'-bipyridine]-3-carboxamide;

5'-methoxy-2',6-dimethyl-N-[5-(morpholin-4-yl)-[1,3]thiazolo[5,4-d]pyrimidin-2-yl]-[4,4'-bipyridine]-3-carboxamide;

2'-fluoro-5'-methoxy-6-methyl-N-[5-(morpholin-4-yl)-[1,3]thiazolo[5,4-d]pyrimidin-2-yl]-[4,4'-bipyridine]-3-carboxamide;

2'-chloro-5'-methoxy-6-methyl-N-[5-(2-oxopiperidin-1-yl)-[1,3]thiazolo[5,4-d]pyrimidin-2-yl]-[4,4'-bipyridine]-3-carboxamide;

2'-chloro-N-(5-{[(2R)-2-hydroxypropyl]amino}-[1,3]thiazolo[5,4-d]pyrimidin-2-yl)-5'-methoxy-6-methyl-[4,4'-bipyridine]-3-carboxamide;

2'-chloro-N-(5-{[(2S)-2-hydroxypropyl]amino}-[1,3]thiazolo[5,4-d]pyrimidin-2-yl)-5'-methoxy-6-methyl-[4,4'-bipyridine]-3-carboxamide;

2'-chloro-5'-methoxy-N-[5-(3-methoxy-3-methylazetidin-1-yl)-[1,3]thiazolo[5,4-d]pyrimidin-2-yl]-6-methyl-[4,4'-bipyridine]-3-carboxamide;

N-(4-bromo-1,3-benzothiazol-2-yl)-2'-chloro-5'-methoxy-6-methyl-[4,4'-bipyridine]-3-carboxamide;

2'-chloro-N-{4-[2-(dimethylcarbamoyl)ethyl]-1,3-benzothiazol-2-yl}-5'-methoxy-6-methyl-[4,4'-bipyridine]-3-carboxamide;

2'-chloro-N-[5-(cyanomethoxy)-1,3-benzothiazol-2-yl]-5'-methoxy-6-methyl-[4,4'-bipyridine]-3-carboxamide;

2'-chloro-N-{5-[difluoro(methylcarbamoyl)methoxy]-1,3-benzothiazol-2-yl}-5'-methoxy-6-methyl-[4,4'-bipyridine]-3-carboxamide;

N-(5-bromo-1,3-benzothiazol-2-yl)-2'-chloro-5'-methoxy-6-methyl-[4,4'-bipyridine]-3-carboxamide;

2'-chloro-N-{5-[(dimethylcarbamoyl)difluoromethoxy]-1,3-benzothiazol-2-yl}-5'-methoxy-6-methyl-[4,4'-bipyridine]-3-carboxamide;

2'-chloro-5'-methoxy-6-methyl-N-[5-(methylcarbamoyl)-1,3-benzothiazol-2-yl]-[4,4'-bipyridine]-3-carboxamide;

2'-chloro-5'-methoxy-N-(5-methoxy-1,3-benzothiazol-2-yl)-6-methyl-[4,4'-bipyridine]-3-carboxamide;

2'-chloro-5'-methoxy-N-{5-[(2-methoxyethyl)carbamoyl]-1,3-benzothiazol-2-yl}-6-methyl-[4,4'-bipyridine]-3-carboxamide;

2'-chloro-N-{7-[(dimethylcarbamoyl)methoxy]-[1,3]thiazolo[5,4-d]pyrimidin-2-yl}-5'-methoxy-6-methyl-[4,4'-bipyridine]-3-carboxamide;

N-{5-[(1-acetylpiperidin-4-yl)methoxy]-1,3-benzothiazol-2-yl}-2'-chloro-5'-methoxy-6-methyl-[4,4'-bipyridine]-3-carboxamide;

2'-chloro-N-{5-[(dimethylcarbamoyl)methoxy]-1,3-benzothiazol-2-yl}-5'-methoxy-6-methyl-[4,4'-bipyridine]-3-carboxamide;

2'-chloro-5'-methoxy-6-methyl-N-{5-[2-(morpholin-4-yl)ethoxy]-1,3-benzothiazol-2-yl}-[4,4'-bipyridine]-3-carboxamide;

2'-chloro-5'-methoxy-6-methyl-N-[5-(propan-2-yloxy)-1,3-benzothiazol-2-yl]-[4,4'-bipyridine]-3-carboxamide;

2'-chloro-N-{5-[(1,1-dioxo-1-$\lambda^6$-thietan-3-yl)methoxy]-1,3-benzothiazol-2-yl}-5'-methoxy-6-methyl-[4,4'-bipyridine]-3-carboxamide;

2'-chloro-N-(5-ethoxy-1,3-benzothiazol-2-yl)-5'-methoxy-6-methyl-[4,4'-bipyridine]-3-carboxamide;

2'-chloro-5'-methoxy-6-methyl-N-{5-[2-(trifluoromethoxy)ethoxy]-1,3-benzothiazol-2-yl}-[4,4'-bipyridine]-3-carboxamide;

2'-chloro-5'-methoxy-N-[6-(3-methoxyazetidin-1-yl)-[1,3]thiazolo[4,5-c]pyridin-2-yl]-6-methyl-[4,4'-bipyridine]-3-carboxamide;

2'-chloro-N-{6-[(2-hydroxy-2-methylpropyl)amino]-[1,3]thiazolo[4,5-c]pyridin-2-yl}-5'-methoxy-6-methyl-[4,4'-bipyridine]-3 carboxamide;

2'-chloro-5'-methoxy-N-[6-(3-methoxy-3-methylazetidin-1-yl)-[1,3]thiazolo[4,5-c]pyridin-2-yl]-6-methyl-[4,4'-bipyridine]-3-carboxamide;

6-[(dimethylcarbamoyl)methyl]-5'-methoxy-N-{[1,3]thiazolo[5,4d]pyrimidin-2-yl}-2'-(trifluoromethyl)-[4,4'-bipyridine]-3-carboxamide;

N-[5-(4-hydroxypiperidin-1-yl)-[1,3]thiazolo[5,4-d]pyrimidin-2-yl]-5'-methoxy-2',6-dimethyl-[4,4'-bipyridine]-3-carboxamide;

2'-chloro-5'-methoxy-6-methyl-N-[5-(2-oxopiperidin-1-yl)-[1,3]thiazolo[5,4-b]pyridin-2-yl]-[4,4'-bipyridine]-3-carboxamide;

5-[(2-{2'-chloro-5'-methoxy-6-methyl-[4,4'-bipyridine]-3-amido}-[1,3]thiazolo[4,5-c]pyridin-6-yl)amino]pentanoic acid;

5-[(2-{2'-chloro-5'-methoxy-6-methyl-[4,4'-bipyridine]-3-amido}-[1,3]thiazolo[5,4-b]pyridin-5-yl)amino]pentanoic acid;

2'-chloro-5'-methoxy-6-methyl-N-{5-[(2H-1,2,3,4-tetrazol-5-yl)methoxy]-1,3-benzothiazol-2-yl}-[4,4'-bipyridine]-3-carboxamide;

2'-chloro-N-(5-hydroxy-1,3-benzothiazol-2-yl)-5'-methoxy-6-methyl-[4,4'-bipyridine]-3-carboxamide;

2-[(2-{2'-chloro-5'-methoxy-6-methyl-[4,4'-bipyridine]-3-amido}-1,3-benzothiazol-5-yl)oxy]ethyl acetate;

2'-chloro-N-[5-(2-hydroxyethoxy)-1,3-benzothiazol-2-yl]-5'-methoxy-6-methyl-[4,4'-bipyridine]-3-carboxamide;

5-(4-hydroxypiperidin-1-yl)-[1,3]thiazolo[5,4-d]pyrimidin-2-yl 2'-chloro-5'-methoxy-1-methyl-6-oxo-1,6-dihydro-[3,4'-bipyridine]-4-carboxylate;

2'-chloro-N-[7-(cyanomethoxy)-[1,3]thiazolo[5,4-d]pyrimidin-2-yl]-5'-methoxy-6-methyl-[4,4'-bipyridine]-3-carboxamide;

N-[7-(carbamoylmethoxy)-[1,3]thiazolo[5,4-d]pyrimidin-2-yl]-2'-chloro-5'-methoxy-6-methyl-[4,4'-bipyridine]-3-carboxamide;

2'-chloro-5'-methoxy-6-methyl-N-[6-(morpholin-3-yl)-1,3-benzothiazol-2-yl]-[4,4'-bipyridine]-3-carboxamide;

2'-chloro-N-[5-(4-hydroxypiperidin-1-yl)-7-methyl-[1,3]thiazolo[5,4-d]pyrimidin-2-yl]-5'-methoxy-6-methyl-[4,4'-bipyridine]-3-carboxamide;

2'-chloro-N-[5-(2-hydroxy-2-methylpropoxy)-[1,3]thiazolo[5,4-d]pyrimidin-2-yl]-5'-methoxy-6-methyl-[4,4'-bipyridine]-3-carboxamide, or a pharmaceutically acceptable salt thereof.

Though the present invention may relate to any compound or particular group of compounds defined herein by way of optional, preferred or suitable features, or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Numbered Paragraphs

The following numbered paragraphs define particular features of the present invention.

Paragraph 1. A compound, or a pharmaceutically acceptable salt thereof, having the structural formula (I) shown below:

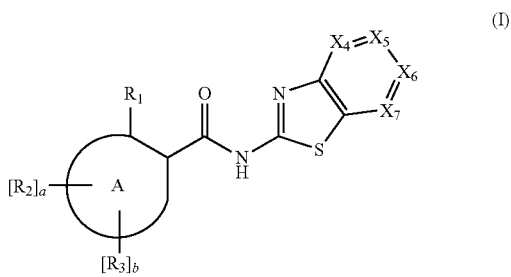

(I)

wherein:

ring A is selected from the group consisting of phenyl and a 5- to 10-membered heteroaryl;

$R_1$ is selected from the group consisting of phenyl, 5- to 6-membered heteroaryl, 5- to 6-membered heterocyclyl, 6- to 10-membered bicyclic heterocyclyl, 6- to 10-membered bridged heterocyclyl, and 6- to 12-membered spiroheterocyclyl, wherein:

(i) $R_1$ is optionally substituted with one or more $R_{100}$ substituents; or two $R_{100}$ substituents on adjacent ring atoms in $R_1$ may be linked to form a fused (3-6C)cycloalkyl ring; or (ii) when $R_1$ is 5- to 6-membered heterocyclyl, 6- to 10-membered bicyclic heterocyclyl, 6- to 10-membered bridged heterocyclyl, and 6- to 12-membered spiroheterocyclyl, it is optionally substituted by oxo;

wherein $R_{100}$ is selected from the group consisting of halo, (1-4C)alkyl, (1-4C)haloalkyl, (1-4C)haloalkoxy, (3-6C)cycloalkyl, (3-6C)cycloalkyloxy, -$Q_{100}$-OH, -$Q_{100}$-O-(1-4C)alkyl, —C(O)-(1-4C)alkyl and -$Q_{100}$-cyano; wherein $Q_{100}$ is a bond or (1-4C)alkylene;

integers a and b are each independently 0 or 1;

$R_2$ and $R_3$, when present, are each independently selected from the group consisting of halo, cyano, —O$^-$, (1-4C)alkyl, (1-4C)alkoxy, (1-4C)haloalkyl, (1-4C)hydroxyalkyl, (1-4C)haloalkoxy, -$Q_1$-O-(1-4C)alkyl, —C(O)OH, -$Q_1$-C(O)—NH$_2$, -$Q_1$-C(O)—NHMe and -$Q_1$-C(O)—NMe$_2$, wherein $Q_1$ is a bond or (1-4C)alkylene;

$X_4$ is selected from $CR_{x4}$ or N;
$X_5$ is selected from $CR_{x5}$ or N;
$X_6$ is selected from $CR_{x6}$ or N;
$X_7$ is selected from $CR_{x7}$ or N;

$R_{x4}$ is hydrogen, fluoro, chloro, methyl or a group of the formula:

—Y-Q wherein:

Y is —O—, —O—CH$_2$—, —S—, —NH—, —CH$_2$— or —CH$_2$CH$_2$—;

Q is selected from hydrogen (1-6C)alkyl, —C(O)—NH$_2$, —C(O)—NHMe, —C(O)—NMe$_2$, (3-8C)cycloalkyl, phenyl, heteroaryl, 4- to 7-membered heterocyclyl, 6- to 10-membered bicyclic heterocyclyl, 6- to 10-membered bridged heterocyclyl, and 6- to 12-membered spiroheterocyclyl, each of which is optionally substituted by one or more $R_{100}$ substituents and a (3-8C)cycloalkyl, 4- to 7-membered heterocyclyl, 6- to 10-membered bicyclic heterocyclyl, 6- to 10-membered bridged heterocyclyl, and 6- to 12-membered spiroheterocyclyl is optionally substituted by oxo;

$R_{x5}$ or $R_{x6}$ are selected from:

hydrogen, halo, cyano, nitro, or a group of the formula:

-$L_1$-$Y_1$-$L_2$-$Q_1$ wherein:

$L_1$ is absent or (1-2C)alkylene;

$Y_1$ is absent or —O—, —S—, —SO—, —SO$_2$—, —S(O)(=NR$_{y1}$)—, —N(R$_{y1}$)—, —C(O)—, —C(O)O—, —OC(O)—, —C(O)N(R$_{y1}$)—, —N(R$_{y1}$)C(O)—, —S(O)$_2$N(R$_{y1}$)—, —N(R$_{y1}$)SO$_2$— or —N(R$_{y1a}$)C(O)—N(R$_{y1}$)—, wherein $R_{y1}$ and $R_{y1a}$ are selected from hydrogen or (1-2C)alkyl;

$L_2$ is absent or (1-2C)alkylene; and $Q_1$ is hydrogen, (1-6C)alkyl, (2-6C)alkenyl, (2-6C)alkynyl, (3-8C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl, wherein:
(i) when $Q_1$ is (1-6C)alkyl, (2-6C)alkenyl or (2-6C)alkynyl, it is optionally further substituted by one or more substituent groups independently selected from oxo, halo, cyano, or by one or more group(s) of the formula:

—$Y_2$-$Q_2$ wherein:
$Y_2$ is absent or selected from or —O—, —S—, —SO—, —SO$_2$—, —N($R_{y2}$)—, —C(O)—, —C(O)O—, —OC(O)—, —C(O)N($R_{y2}$)—, —N($R_{y2}$)C(O)—, —S(O)$_2$N($R_{y2}$)—, or —N($R_{y2}$)SO$_2$—, wherein $R_{y2}$ is selected from hydrogen or (1-2C)alkyl;
$Q_2$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;
(ii) when $Q_1$ is (3-8C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—$Y_3$-$Q_3$ wherein:
$Y_3$ is absent or selected from or —O—, —S—, —SO—, —SO$_2$—, —N($R_{y2}$)—, —C(O)—, —C(O)O—, —OC(O)—, —C(O)N($R_{y3}$)—, —N($R_{y3}$)C(O)—, —S(O)$_2$N($R_{y3}$)—, or —N($R_{y3}$)SO$_2$—, wherein $R_{y3}$ is selected from hydrogen or (1-2C)alkyl;
$Q_3$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;
(iii) when $Q_1$ is phenyl or 5- to 6-membered heteroaryl, it is optionally further substituted by one or more substituent groups independently selected from halo, cyano, or by one or more group(s) of the formula —$Y_3$-$Q_3$ defined above;
$R_{x7}$ is selected from hydrogen, fluoro, chloro, hydroxy, NH$_2$, methyl, or CF$_3$;
or $R_{x4}$ and $R_{x5}$, $R_{x5}$ and $R_{x6}$ or $R_{x6}$ and $R_{x7}$ are linked such that, together with the carbon atoms to which they are attached, they form a fused (5-6C)cycloalkyl, phenyl, 5- or 6-membered heteroaryl or 5- or 6-membered heterocyclic ring, each of which is optionally substituted by fluoro, chloro, methyl or hydroxy;
with the proviso that:
(i) when $X_5$ is $CR_{x5}$ and $R_{x5}$ is a group of the formula -$L_1$-$Y_1$-$L_2$-$Q_1$ then $X_6$ is selected from N, C—H, C—F, C—CN, C—Cl or C-Me; and (ii) when $X_6$ is $CR_{x6}$ and $R_{x6}$ is a group of the formula -$L_1$-$Y_1$-$L_2$-$Q_1$ then $X_5$ is selected from N, C—H, C—F, C—Cn, C—Cl or C-Me.

Paragraph 2. A compound according to Paragraph 1, or a pharmaceutically acceptable salt thereof, wherein:
(i) when $X_5$ is $CR_{x5}$ and $R_{x5}$ is cyano or a group of the formula -$L_1$-$Y_1$-$L_2$-$Q_1$ then:
$X_4$ is selected from N, C—H, C—F, C—Cl or C-Me;
$X_6$ is selected from N, C—H, C—F, C—CN, C—Cl or C-Me;
$X_7$ is selected from N, C—H, C—F, C—Cl or C-Me; and
(ii) when $X_6$ is $CR_{x6}$ and $R_{x6}$ is cyano or a group of the formula -$L_1$-$Y_1$-$L_2$-$Q_1$ then:
$X_4$ is selected from N, C—H, C—F, C—Cl or C-Me;
$X_5$ is selected from N, C—H, C—F, C—Cl or C-Me;
$X_7$ is selected from N, C—H, C—F, C—Cl or C-Me.

Paragraph 3. A compound according to Paragraph 1 or Paragraph 2, or a pharmaceutically acceptable salt thereof, wherein ring A is selected from phenyl or 5-, 6-, 9- or 10-membered heteroaryl.

Paragraph 4. A compound according to any one of the preceding paragraphs, or a pharmaceutically acceptable salt thereof, wherein ring A is selected from:
(i) phenyl, pyridinyl, pyridazinyl, pyrimidinyl, imidazolyl, pyrazolyl, triazolyl, imidazo[1,2-a]pyridinyl, [1,2,3]triazolo[1,5-a]pyridinyl, imidazo[1,5-a]pyridinyl, pyrrolo[2,3-b]pyridinyl, pyrrolo[3,2-b]pyridinyl, pyrazolo[1,5-a]pyridinyl, [1,2,4]triazolo[1,5-a]pyridinyl, 1,6-naphthyridinyl, or 1,7-naphthyridinyl;
(ii) phenyl, pyridinyl, pyrimidinyl, and imidazo[1,2-a]pyridinyl, 1,2,3-triazole, pyrazolyl, isoxazolyl, imidazo[1,5-a]pyridinyl;
(iii) phenyl, pyridinyl, pyrimidinyl, and imidazo[1,2-a]pyridinyl;
(iv) phenyl or pyridyl;
(v) pyridyl.

Paragraph 5. A compound according to any one of the preceding paragraphs, or a pharmaceutically acceptable salt thereof, wherein ring A is selected from:

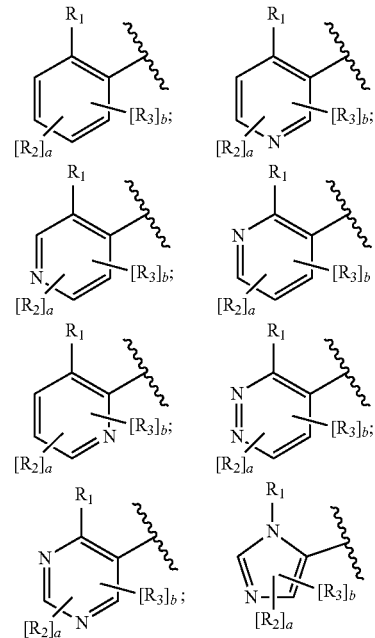

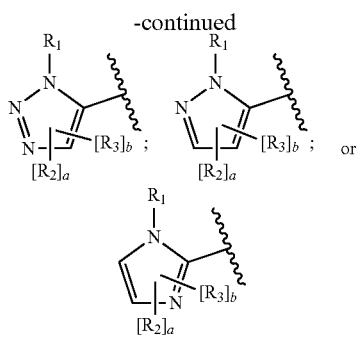

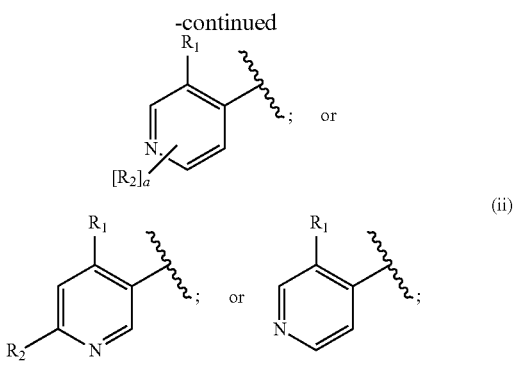

wherein ⌇⌇⌇ denotes the point of attachment to the amide group of formula I; and $R_1$, $R_2$, $R_3$, a and b are as defined in paragraph 1.

Paragraph 6. A compound according to any one of the preceding paragraphs, or a pharmaceutically acceptable salt thereof, wherein ring A is selected from:

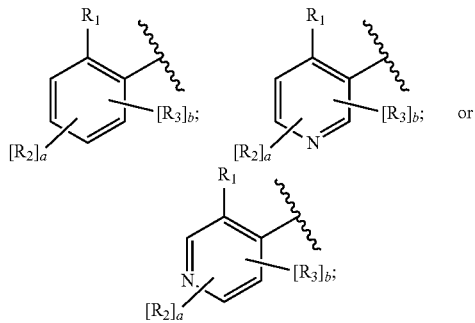

wherein ⌇⌇⌇ denotes the point of attachment to the amide group of formula I; and $R_1$, $R_2$, $R_3$, a and b are each as defined herein.

Paragraph 7. A compound according to any one of the preceding paragraphs, or a pharmaceutically acceptable salt thereof, wherein ring A is selected from:

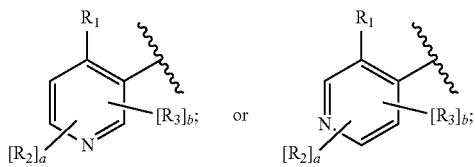

wherein ⌇⌇⌇ denotes the point of attachment to the amide group of formula I; and $R_1$, $R_2$, $R_3$, a and b are as defined in paragraph 1.

Paragraph 8. A compound according to any one of the preceding paragraphs, or a pharmaceutically acceptable salt thereof, wherein ring A is selected from:

(i)

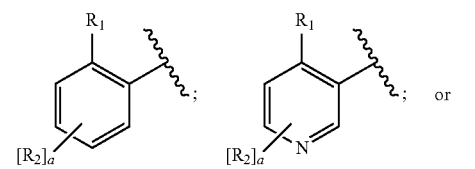

wherein ⌇⌇⌇ denotes the point of attachment to the amide group of formula I; and $R_1$, $R_2$, $R_3$, a and b are as defined in paragraph 1.

Paragraph 9. A compound according to any one of the preceding paragraphs, or a pharmaceutically acceptable salt thereof, wherein $R_1$ is selected from one of the following options:
(i) phenyl or a 5- to 6-membered heteroaryl, each of which is optionally substituted with one or more $R_{100}$ substituents as defined in paragraph 1; or two $R_{100}$ substituents on adjacent ring atoms in $R_1$ may be linked to form a fused (3-6C)cycloalkyl ring; or
(ii) phenyl or a 6-membered heteroaryl, each of which is optionally substituted with one or more $R_{100}$ substituents as defined in paragraph 1; or two $R_{100}$ substituents on adjacent ring atoms in $R_1$ may be linked to form a fused (3-6C)cycloalkyl ring.

Paragraph 10. A compound according to any one of the preceding paragraphs, or a pharmaceutically acceptable salt thereof, wherein $R_1$ is selected from one of the following options:
(i) a group of the formula

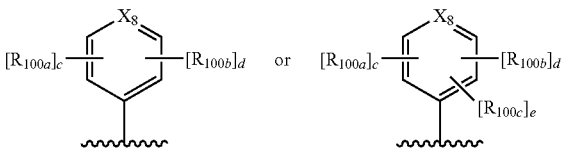

wherein:
⌇⌇⌇ denotes the point of attachment to ring A of formula I;
$X_8$ is CH or N;
$R_{100a}$, $R_{100b}$ and $R_{100c}$ are substituent groups $R_{100}$ as defined in paragraph 1;
and
integers c, d and e are 0, 1 or 2;
(ii) a group of the formula:

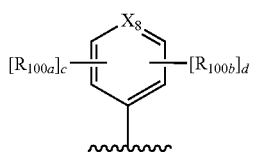

wherein:
⌇⌇⌇ denotes the point of attachment to ring A of formula I;

$X_8$ is CH or N;

$R_{100a}$ and $R_{100b}$ are both substituent groups $R_{100}$ as defined in paragraph 1;

and integers c and d are 0, 1 or 2;

(iii) a group of the formula:

wherein:

∿∿ denotes the point of attachment to ring A of formula I;

$X_8$ is CH or N;

$R_{100a}$, $R_{100b}$ and $R_{100c}$ are substituent groups $R_{100}$ as defined in paragraph 1;

and integers d and e are 0 or 1;

(iv) a group of the formula:

wherein:

∿∿ denotes the point of attachment to ring A of formula I;

$X_8$ is CH or N;

$R_{100a}$ and $R_{100b}$ are both substituent groups $R_{100}$ as defined in paragraph 1; and integer d is 0 or 1;

(v) a group of the formula:

wherein:

∿∿ denotes the point of attachment to ring A of formula I;

$R_{100b}$ is methyl, fluoro or chloro;

$R_{100c}$ is fluoro or chloro, especially fluoro;

(vi) a group of the formula:

wherein:

∿∿ denotes the point of attachment to ring A of formula I;

$R_{100b}$ is fluoro or chloro; or (vii) a group of the formula:

wherein:

∿∿ denotes the point of attachment to ring A of formula I.

Paragraph 11. A compound according to any one of the preceding paragraphs, or a pharmaceutically acceptable salt thereof, wherein $R_{100}$ is selected from one of the following options:

(i) halo, (1-3C)alkyl, (1-3C)haloalkyl, (1-3C)haloalkoxy, (3-6C)cycloalkyl, (3-6C)cycloalkyloxy, -$Q_{100}$-OH, -$Q_{100}$-O-(1-3C)alkyl, —C(O)-(1-3C)alkyl and -$Q_{100}$-cyano; wherein $Q_{100}$ is a bond or (1-3C)alkylene;

(ii) halo, (1-2C)alkyl, (1-2C)haloalkyl, (1-2C)haloalkoxy, (3-6C)cycloalkyl, (3-6C)cycloalkyloxy, -$Q_{100}$-OH, -$Q_{100}$-O-(1-2C)alkyl, —C(O)-(1-2C)alkyl and -$Q_{100}$-cyano; wherein $Q_{100}$ is a bond or (1-2C)alkylene;

(iii) halo, (1-2C)alkyl, (1-2C)fluoroalkyl, (1-2C)fluoroalkoxy, (3-6C)cycloalkyl, (3-6C)cycloalkyloxy, -$Q_{100}$-OH, -$Q_{100}$-O-(1-2C)alkyl, —C(O)-(1-2C)alkyl and -$Q_{100}$-cyano; wherein $Q_{100}$ is a bond or (1-2C)alkylene;

(iv) halo, (1-2C)alkyl, (1-2C)fluoroalkyl, -Q-OH, -$Q_{100}$-O-(1-2C)alkyl, —C(O)-(1-2C)alkyl and -$Q_{100}$-cyano; wherein $Q_{100}$ is a bond or (1-2C)alkylene;

(v) halo, (1-2C)alkyl, (1-2C)fluoroalkyl, -Q-OH and -Q-O-(1-2C)alkyl; wherein Q is a bond or (1-2C) alkylene;

(vi) fluoro, chloro, (1-2C)alkyl, (1-2C)fluoroalkyl, -$Q_{100}$-OH and -$Q_{100}$-O-(1-2C)alkyl; wherein $Q_{100}$ is a bond or (1-2C)alkylene; or (vii) fluoro, chloro, methyl, (1-2C)fluoromethyl and -$Q_{100}$-O-(1-2C)alkyl; wherein $Q_{100}$ is a bond or methylene.

Paragraph 12. A compound according to any one of the preceding paragraphs, or a pharmaceutically acceptable salt thereof, wherein:
(i) integer a is 0 or 1 and integer b is 0;
(ii) integer a is 0 and integer b is 0;
(iii) integer a is 1 and integer b is 0.

Paragraph 13. A compound according to any one of the preceding paragraphs, or a pharmaceutically acceptable salt thereof, wherein $R_2$ and $R_3$, when present, are each independently selected from:
(i) the group consisting of fluoro, chloro, (1-2C)alkyl, (1-2C)alkoxy, (1-2C)haloalkyl, (1-2C)hydroxyalkyl, (1-2C)haloalkoxy, -$Q_1$-O-(1-2C)alkyl and —C(O)OH, wherein $Q_1$ is a bond or (1-2C)alkylene;
(ii) the group consisting of fluoro, chloro, (1-2C)alkyl, (1-2C)alkoxy or (1-2C)haloalkyl;
(iii) the group consisting of fluoro, (1-2C)alkyl or (1-2C)alkoxy; or
(iv) methyl.

Paragraph 14. A compound, or a pharmaceutically acceptable salt thereof, having one of the following formulae Ia to Iac defined hereinbefore; wherein:
ring A, $R_1$, integer a, integer b, $R_2$, $R_3$, $X_4$, $X_5$, $X_6$, $X_7$, $R_{x5}$ and $R_{x6}$ are as defined in any one of paragraphs 1 to 13 or 15 to 21;
$X_8$ is CH or N;
$R_{100a}$, $R_{100b}$ and $R_{100c}$ are both $R_{100}$ as defined in paragraph 1; and
Integers c, d and e are 0 or 1.

Paragraph 15. A compound according to any one of the preceding paragraphs, or a pharmaceutically acceptable salt thereof, wherein $X_4$, $X_5$, $X_6$ and $X_7$ are selected for one of the following options:
(i) $X_4$ is selected from $CR_{x4}$ or N;
    $X_5$ is selected from $CR_{x5}$ or N;
    $X_6$ is selected from $CR_{x6}$;
    $X_7$ is selected from $CR_{x7}$ or N;
(ii) $X_4$ is selected from $CR_{x4}$;
    $X_5$ is selected from $CR_{x5}$ or N;
    $X_6$ is selected from $CR_{x6}$;
    $X_7$ is selected from $CR_{x7}$ or N;
(iii) $X_4$ is selected from $CR_{x4}$;
    $X_5$ is selected from $CR_{x5}$ or N;
    $X_6$ is selected from $CR_{x6}$;
    $X_7$ is selected from CH or N;
(iv) $X_4$ is selected from CH;
    $X_5$ is selected from $CR_{x5}$ or N;
    $X_6$ is selected from $CR_{x6}$;
    $X_7$ is selected from CH or N;
(v) $X_4$ is selected from CH;
    $X_5$ is selected from CH or N;
    $X_6$ is selected from $CR_{x6}$;
    $X_7$ is selected from CH or N;
(vi) $X_4$ is selected from CH;
    $X_5$ is selected from CH;
    $X_6$ is selected from $CR_{x6}$;
    $X_7$ is selected from CH or N;
(vii) $X_4$ is selected from CH;
    $X_5$ is selected from CH or N;
    $X_6$ is selected from $CR_{x6}$;
    $X_7$ is selected from CH;
(viii) $X_4$ is selected from CH;
    $X_5$ is selected from CH;
    $X_6$ is selected from $CR_{x6}$;
    $X_7$ is selected from CH;
(ix) $X_4$ is selected from CH;
    $X_5$ is selected from N;
    $X_6$ is selected from $CR_{x6}$;
    $X_7$ is selected from CH;
(x) $X_4$ is selected from CH;
    $X_5$ is selected from CH;
    $X_6$ is selected from $CR_{x6}$;
    $X_7$ is selected from N;
(xi) $X_4$ is selected from CH;
    $X_5$ is selected from N;
    $X_6$ is selected from $CR_{x6}$;
    $X_7$ is selected from N;
(xii) $X_4$ is selected from CH or N;
    $X_5$ is selected from $CR_{x5}$;
    $X_6$ is selected from CH or N;
    $X_7$ is selected from CH or N;
(xiii) $X_4$ is selected from CH;
    $X_5$ is selected from $CR_{x5}$;
    $X_6$ is selected from CH;
    $X_7$ is selected from CH;
(xiv) $X_4$ is selected from CH;
    $X_5$ is selected from $CR_{x5}$;
    $X_6$ is selected from N;
    $X_7$ is selected from CH;
(xv) $X_4$ is selected from CH;
    $X_5$ is selected from $CR_{x5}$;
    $X_6$ is selected from CH;
    $X_7$ is selected from N;
(xvi) $X_4$ is selected from N;
    $X_5$ is selected from $CR_{x5}$;
    $X_6$ is selected from CH;
    $X_7$ is selected from CH;
(xvii) $X_4$ is selected from N;
    $X_5$ is selected from $CR_{x5}$;
    $X_6$ is selected from N;
    $X_7$ is selected from CH.

Paragraph 16. A compound according to paragraph 14, or a pharmaceutically acceptable salt thereof, wherein $X_4$, $X_5$, $X_6$ and $X_7$ are selected for one of the following options:
(i) $X_4$ is selected from CH;
    $X_5$ is selected from CH or N;
    $X_6$ is selected from $CR_{x6}$;
    $X_7$ is selected from CH or N;
(ii) $X_4$ is selected from CH;
    $X_5$ is selected from CH;
    $X_6$ is selected from $CR_{x6}$;
    $X_7$ is selected from CH or N;
(iii) $X_4$ is selected from CH;
    $X_5$ is selected from CH or N;
    $X_6$ is selected from $CR_{x6}$;
    $X_7$ is selected from CH;
(iv) $X_4$ is selected from CH;
    $X_5$ is selected from CH;
    $X_6$ is selected from $CR_{x6}$;
    $X_7$ is selected from CH;
(v) $X_4$ is selected from CH;
    $X_5$ is selected from N;
    $X_6$ is selected from $CR_{x6}$;
    $X_7$ is selected from CH;
(vi) $X_4$ is selected from CH;
    $X_5$ is selected from CH;
    $X_6$ is selected from $CR_{x6}$;
    $X_7$ is selected from N;
(vii) $X_4$ is selected from CH;
    $X_5$ is selected from N;
    $X_6$ is selected from $CR_{x6}$;
    $X_7$ is selected from N;

(viii) $X_4$ is selected from CH;
$X_5$ is selected from $CR_{x5}$;
$X_6$ is selected from CH;
$X_7$ is selected from CH.

Paragraph 17. A compound according to paragraph 14, or a pharmaceutically acceptable salt thereof, wherein $X_4$, $X_5$, $X_6$ and $X_7$ are selected for one of the following options:
(i) $X_4$ is selected from CH;
$X_5$ is selected from CH;
$X_6$ is selected from $CR_{x6}$;
$X_7$ is selected from CH;
(ii) $X_4$ is selected from CH;
$X_5$ is selected from N;
$X_6$ is selected from $CR_{x6}$;
$X_7$ is selected from CH;
(iii) $X_4$ is selected from CH;
$X_5$ is selected from CH;
$X_6$ is selected from $CR_{x6}$;
$X_7$ is selected from N;
(iv) $X_4$ is selected from CH;
$X_5$ is selected from N;
$X_6$ is selected from $CR_{x6}$;
$X_7$ is selected from N;
(v) $X_4$ is selected from CH;
$X_5$ is selected from $CR_{x5}$;
$X_6$ is selected from CH;
$X_7$ is selected from CH.

Paragraph 18. A compound according to any one of the preceding paragraphs, or a pharmaceutically acceptable salt thereof, wherein $R_{x4}$ is selected from one of the following options:
(i) hydrogen, fluoro, chloro, methyl or a group of the formula:

—Y-Q wherein:
Y is —O—, —S—, —NH— or —CH$_2$—;
Q is selected from hydrogen (1-4C)alkyl, (3-6C)cycloalkyl, phenyl, 5- or 6-membered heteroaryl, 4- to 7-membered heterocyclyl, each of which is optionally substituted by one or more $R_{100}$ substituents and a (3-8C)cycloalkyl and 4- to 7-membered heterocyclyl is optionally substituted by oxo;
(ii) hydrogen, fluoro, methyl or a group of the formula:

—Y-Q wherein:
Y is —O—, —S—, —NH— or —CH$_2$;
Q is selected from hydrogen, (1-4C)alkyl, (3-6C)cycloalkyl, phenyl, 5- or 6-membered heteroaryl, 4- to 7-membered heterocyclyl;
(iii) hydrogen, fluoro, chloro or methyl; or
(iv) hydrogen.

Paragraph 19. A compound according to any one of the preceding paragraphs, or a pharmaceutically acceptable salt thereof, wherein $R_{x5}$ or $R_{x6}$ are selected from hydrogen, halo, cyano, nitro or a group of the formula:

-L$_1$-Y$_1$-L$_2$-Q$_1$ wherein:
L$_1$ is absent or (1-2C)alkylene;
Y$_1$ is absent or —O—, —S—, —SO—, —SO$_2$—, —S(O)(=NR$_{y1}$)—, —N(R$_{y1}$)—, —C(O)—, —C(O)O—, —OC(O)—, —C(O)N(R$_{y1}$)—, —N(R$_{y1}$)C(O)—, —S(O)$_2$N(R$_{y1}$)—, —N(R$_{y1}$)SO$_2$— or —N(R$_{y1a}$)C(O)—N(R$_{y1}$)—, wherein R$_{y1}$ and R$_{y1a}$ are selected from hydrogen or (1-2C)alkyl;
L$_2$ is absent or (1-2C)alkylene; and
Q$_1$ is hydrogen, (1-6C)alkyl, (3-8C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl, wherein:
(i) when Q$_1$ is (1-6C)alkyl, it is optionally further substituted by one or more substituent groups independently selected from oxo, halo, cyano, or by one or more group(s) of the formula:

—Y$_2$-Q$_2$ wherein:
Y$_2$ is absent or selected from or —O—, —SO$_2$—, —N(R$_{y2}$)—, —C(O)—, —C(O)N(R$_{y2}$)—, —N(R$_{y2}$)C(O)—, —S(O)$_2$N(R$_{y2}$)—, or —N(R$_{y2}$)SO$_2$—, wherein R$_{y2}$ is selected from hydrogen or methyl;
Q$_2$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;
(ii) when Q$_1$ is (3-8C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—Y$_3$-Q$_3$ wherein:
Y$_3$ is absent or selected from or —O—, —SO$_2$—, —N(R$_{y3}$)—, —C(O)—, —C(O)N(R$_{y3}$)—, —N(R$_{y3}$)C(O)—, —S(O)$_2$N(R$_{y3}$)—, or —N(R$_{y3}$)SO$_2$—, wherein R$_{y3}$ is selected from hydrogen or methyl;
Q$_3$ is selected from:
hydrogen;
a (1-4C)alkyl which is optionally substituted by one or more substituents selected from halo, hydroxy, cyano, amino or (1-4C)alkoxy; or
a 4 to 7-membered heterocyclic ring which is optionally substituted by one or more substituents selected from halo, hydroxy, cyano, amino, (1-4C)alkyl or (1-4C)alkoxy;
(iii) when Q$_1$ is phenyl or 5- to 6-membered heteroaryl, it is optionally further substituted by one or more substituent groups independently selected from halo, cyano, or by one or more group(s) of the formula —Y$_3$-Q$_3$ defined above.

Paragraph 20. A compound according any one of the preceding paragraphs, or a pharmaceutically acceptable salt thereof, wherein $R_{x5}$ or $R_{x6}$ are selected from hydrogen, halo, cyano, nitro or a group of the formula:

-L$_1$-Y$_1$-L$_2$-Q$_1$ wherein:
L$_1$ is absent or methylene;
Y$_1$ is absent or —O—, —SO$_2$—, —S(O)(=NR$_{y1}$)—, —N(R$_{y1}$)—, —C(O)N(R$_{y1}$)—, —N(R$_{y1}$)C(O)—, —S(O)$_2$N(R$_{y1}$)—, or —N(R$_{y1}$)SO$_2$—, wherein R$_{y1}$ and R$_{y1a}$ are selected from hydrogen or (1-2C)alkyl;

L$_2$ is absent or methylene; and

Q$_1$ is hydrogen, (1-4C)alkyl, (3-4C)cycloalkyl, phenyl, 5- to 6-membered heteroaryl, 4- to 7-membered heterocyclyl, 6- to 10-membered bicyclic heterocyclyl, 6- to 10-membered bridged heterocyclyl, and 6- to 12-membered spiroheterocyclyl, wherein:
(i) when Q$_1$ is (1-4C)alkyl, it is optionally further substituted by one or more substituent groups independently selected from halo, cyano, or by one or more group(s) of the formula:

—Y$_2$-Q$_2$ wherein:
Y$_2$ is absent or selected from or —O—, —SO$_2$—, —N(R$_{y2}$)—, —C(O)—, —C(O)N(R$_{y2}$)—, or —N(R$_{y2}$)C(O)—, —S(O)$_2$N(R$_{y2}$)—, or —N(R$_{y2}$)SO$_2$—, wherein R$_{y2}$ is selected from hydrogen or methyl;

Q$_2$ is selected from:
hydrogen;
a (1-4C)alkyl optionally substituted by one or more halo;
or
a 4 to 7-membered heterocyclic ring;

(ii) when Q$_1$ is (3-6C)cycloalkyl, 4- to 7-membered heterocyclyl, 6- to 10-membered bicyclic heterocyclyl, 6- to 10-membered bridged heterocyclyl, and 6- to 12-membered spiroheterocyclyl, it is optionally further substituted by one or more substituent groups independently selected from oxo, halo, cyano, or by one or more group(s) of the formula:

—Y$_3$-Q$_3$ wherein:
Y$_3$ is absent or selected from or —O—, —SO$_2$—, —N(R$_{y3}$)—, —C(O)—, —C(O)N(R$_{y3}$)—, —N(R$_{y3}$)C(O)—, —S(O)$_2$N(R$_{y3}$)—, or —N(R$_{y3}$)SO$_2$—, wherein R$_{y3}$ is selected from hydrogen or methyl;

Q$_3$ is selected from:
hydrogen;
a (1-4C)alkyl optionally substituted by one or more halo;
or
a 4 to 7-membered heterocyclic ring;

(iii) when Q$_1$ is phenyl or 5- to 6-membered heteroaryl, it is optionally further substituted by one or more substituent groups independently selected from halo, cyano, or by one or more group(s) of the formula —Y$_3$-Q$_3$ defined above.

Paragraph 21. A compound according any one of the preceding paragraphs, or a pharmaceutically acceptable salt thereof, wherein R$_{x7}$ is selected from one of the following options:
(i) hydrogen, fluoro, chloro or methyl; or
(ii) hydrogen.

Paragraph 22. A compound according any one of paragraphs 14 to 21, or a pharmaceutically acceptable salt thereof, wherein:
(i) X$_8$ is N;
R$_{100a}$ and R$_{100b}$ are both R$_{100}$ as defined in paragraph 1 or paragraph 11; and integers c and d are 0 or 1;

(ii) X$_8$ is CH;
R$_{100a}$ and R$_{100b}$ are both R$_{100}$ as defined in paragraph 1 or paragraph 11; and integers c and d are 0 or 1;
(iii) X$_8$ is N;
R$_{100a}$ and R$_{100b}$ are both R$_{100}$ as defined in paragraph 11; and
integers c and d are 0 or 1;
(iv) X$_8$ is CH;
R$_{100a}$ and R$_{100b}$ are both R$_{100}$ as defined in paragraph 11; and
integers c and d are 0 or 1.

Paragraph 23. A compound according to any one of paragraphs 1-22, or a pharmaceutically acceptable salt thereof, wherein X$_4$, X$_5$, X$_6$ and X$_7$ are selected from one of the following options:
(i) X$_4$ is selected from CH;
X$_5$ is selected from N;
X$_6$ is selected from CR$_{x6}$; and
X$_7$ is selected from N; or
(ii) X$_4$ is selected from CH;
X$_5$ is selected from N;
X$_6$ is selected from CR$_{x6}$; and
X$_7$ is selected from CH.

Paragraph 24. A compound according to paragraph 23, or a pharmaceutically acceptable salt thereof, wherein R$_1$ is selected from a group of the formula:

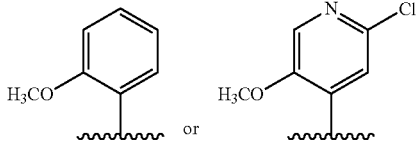 [SMILES: *c1ccccc1OC ; *c1cc(Cl)ncc1OC]

wherein ∿∿∿ denotes the point of attachment to ring A of formula I.

Paragraph 25. A compound according to paragraph 23 or 24, or a pharmaceutically acceptable salt thereof, wherein ring A is selected from:

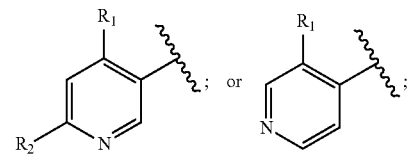

wherein ∿∿∿ denotes the point of attachment to the amide group of formula I; and R$_1$ and R$_2$ are as defined in paragraph 1.

Paragraph 26. A compound selected from any one of the examples set out herein, or a pharmaceutically acceptable salt thereof.

Paragraph 27. A pharmaceutical composition comprising a compound according to any one of paragraphs 1 to 26, or a pharmaceutically acceptable salt thereof, and at least one pharmaceutically acceptable excipient.

Salts and Solvates

The compounds (including final products and intermediates) described herein may be isolated and used per se or may be isolated in the form of a sat, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I and sub-formulae thereof are isolated as pharmaceutically acceptable salts.

A suitable pharmaceutically acceptable salt of a compound of the invention is, for example, an acid addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. -In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable-cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as, but not limited to, sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I and sub-formulae thereof may exist in solvated as well as unsolvated forms such as, for example, hydrated forms. It is to be understood that the invention encompasses all such solvated forms that possess the biological activity described herein.

Polymorphs

It is also to be understood that certain compounds of the Formula I and sub-formulae thereof may exhibit polymorphism, and that the invention encompasses all such forms that possess the biological activity described herein.

N-Oxides

Compounds of the Formula I and sub-formulae thereof containing an amine function may also form N-oxides. A reference herein to a compound of the Formula I and sub-formulae thereof that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as, but not limited to, hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as, but not limited to, dichloromethane.

Tautomers

Compounds of the Formula I and sub-formulae thereof may exist in a number of different tautomeric forms and references to compounds of the Formula I and sub-formulae thereof include all such forms. For the avoidance of doubt, where a compound can exist in one of several tautomeric forms, and only one is specifically described or shown, all others are nevertheless embraced by Formula I and sub-formulae thereof. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

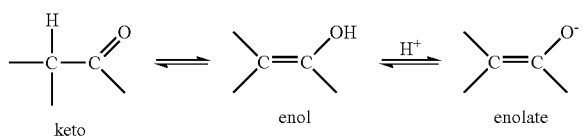

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are nonsuperimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R and S sequencing rules of Cahn and Prelog, or by the manner in which the molecule rotates the plane of polarized light and designated as dextrorotatory or levorotatory (i.e., as (+) or (−)isomers respectively). A chiral compound can exist as either individual enantiomer or as a mixture thereof. A mixture containing equal proportions of the enantiomers is called a "racemic mixture".

Certain compounds of Formula I and sub-formulae thereof may have one or more asymmetric centres and therefore can exist in a number of stereoisomeric configurations. Consequently, such compounds can be synthesized and/or isolated as mixtures of enantiomers and/or as individual (pure) enantiomers, and, in the case of two or more asymmetric centres, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of Formula I and sub-formulae thereof may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I and sub-formulae thereof.

Accordingly, the present invention includes those compounds of the Formula I and sub-formulae thereof as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I and sub-formulae thereof may be a synthetically-produced compound or a metabolically-produced compound.

A suitable pharmaceutically acceptable pro-drug of a compound of the Formula I and sub-formulae thereof is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
C) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 2, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I and sub-formulae thereof that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as, but not limited to, methyl, ethyl and tert-butyl, $C_{1-6}$alkoxymethyl esters such as, but not limited to, methoxymethyl esters, $C_{1-6}$alkanoyloxymethyl esters such as, but not limited to, pivaloyloxymethyl esters, 3-phthalidyl esters, $C_{3-8}$cycloalkylcarbonyloxy-$C_{1-6}$alkyl esters such as, but not limited to, cyclopentylcarbonyloxymethyl and 1-cyclohexylcarbonyloxyethyl esters, 2-oxo-1,3-dioxolenylmethyl esters such as, but not limited to, 5-methyl-2-oxo-1,3-dioxolen-4-ylmethyl esters and $C_{1-6}$alkoxycarbonyloxy-$C_{1-6}$alkyl esters such as, but not limited to, methoxycarbonyloxymethyl and 1-methoxycarbonyloxyethyl esters.

A suitable pharmaceutically acceptable pro-drug of a compound of the Formula I and sub-formulae thereof that possesses a hydroxy group is, for example, an in vivo cleavable ester or ether thereof. An in vivo cleavable ester or ether of a compound of the Formula I and sub-formulae thereof containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as, but not limited to, phosphate esters (including phosphoramidic cyclic esters). Further suitable pharmaceutically acceptable ester forming groups for a hydroxy group include $C_{1-10}$alkanoyl groups such as, but not limited to, acetyl, benzoyl, phenylacetyl and substituted benzoyl and phenylacetyl groups, $C_{1-10}$alkoxycarbonyl groups such as, but not limited to, ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as, but not limited to, acetoxymethyl and pivaloyloxymethyl groups.

A suitable pharmaceutically acceptable pro-drug of a compound of the Formula I and sub-formulae thereof that possesses a carboxy group is, for example, an in vivo cleavable amide thereof, for example an amide formed with an amine such as, but not limited to, ammonia, a $C_{1-4}$alkylamine such as, but not limited to, methylamine, a $(C_{1-4}alkyl)_2$amine such as, but not limited to, dimethylamine, N-ethyl-N-methylamine or diethylamine, a $C_{1-4}$alkoxy-$C_{2-4}$alkylamine such as, but not limited to, 2-methoxyethylamine, a phenyl-$C_{1-4}$alkylamine such as, but not limited to, benzylamine and amino acids such as, but not limited to, glycine or an ester thereof.

A suitable pharmaceutically acceptable pro-drug of a compound of the Formula I and sub-formulae thereof that possesses an amino group is, for example, an in vivo cleavable amide derivative thereof. Suitable pharmaceutically acceptable amides from an amino group include, for example an amide formed with $C_{1-10}$alkanoyl groups such as, but not limited to, an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the Formula I and sub-formulae thereof may be exerted in part by one or more metabolites that are formed within the human or animal body after administration of a compound of the Formula I and sub-formulae thereof. As stated hereinbefore, the in vivo effects of a compound of the Formula I and sub-formulae thereof may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 1.5 g of active agent (more suitably from 0.5 to 600 mg, for example from 1 to 200 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well-known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used.

For the compounds of the present invention, oral administration is particularly suitable. The compounds of the present invention may be formulated as a tablet, capsule or solution for oral administration. Suitably, the compound of the present invention is formulated in a unit dosage form (e.g. a tablet or capsule) for oral administration. Typically, unit dosage forms will contain about 0.5 mg to 1.5 g of a compound of this invention.

Synthesis

The compounds of the present invention can be prepared by any suitable technique known in the art. Particular methods for forming compounds of formula I defined herein are shown in the accompanying example section.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For Examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as, but not limited to, acetyl, an alkoxycarbonyl group, for example a methoxycarbonyl, ethoxycarbonyl or tbutoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as, but not limited to, an alkali metal hydroxide, for example lithium or sodium hydroxide. Alternatively an acyl group such as a tertbutoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively, an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium on carbon.

Resins may also be used as a protecting group.

The methodology employed to synthesise a compound of formula (I) will vary depending on the nature of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ and any substituent groups associated therewith. Suitable processes for their preparation are described further in the accompanying example section.

Once a compound of formula (I) has been synthesised by any one of the processes defined herein, the processes may then further comprise one or more of the additional steps of:
(i) removing any residual protecting groups present;
(ii) converting the compound formula (I) into another compound of formula (I);
(iii) forming a pharmaceutically acceptable salt, hydrate or solvate of the compound of formula I; and/or
(iv) forming a prodrug of the compound of formula I.

An example of (ii) above is when a compound of formula (I) is synthesised and then one or more of the groups of ring A, $R_1$, $R_{100}$, $R_2$, $R_3$, integer a, integer b, $X_4$, $X_5$, $X_6$, $X_7$, $R_{x4}$, $R_{x5}$, $R_{x6}$, $R_{x7}$, $X_8$, $R_{100a}$ and $R_{100b}$ may be further reacted to change the nature of the group and provide an alternative compound of formula (I).

The resultant compounds of formula (I) can be isolated and purified using techniques well known in the art.

Therapeutic Uses and Applications

The compounds of the present invention are potent inhibitors of Polθ. Data showing the Polθ inhibition for the exemplified compounds is presented in the accompanying example section.

Accordingly, the compounds of formula I are useful for the treatment and/or prevention of diseases and conditions in which Polθ activity is implicated, such as, for example, but not limited to, the treatment and/or prevention of cancer and/or benign neoplasms.

In one aspect, the present invention provides a compound of Formula I as defined herein, or a pharmaceutically acceptable salt, hydrate or solvate thereof, or a pharmaceutical composition as defined herein, for use in therapy.

In another aspect, the present invention provides a compound of Formula I as defined herein, or a pharmaceutically acceptable salt, hydrate or solvate thereof, or a pharmaceutical composition as defined herein, for use in the treatment of a disease or condition in which Polθ activity is implicated.

In another aspect, the present invention provides the use of a compound of Formula I as defined herein, or a pharmaceutically acceptable salt, hydrate or solvate thereof, in the manufacture of a medicament for use in the treatment of a disease or condition in which Polθ activity is implicated.

In another aspect, the present invention provides a method of treating a disease or condition in which Polθ activity is implicated, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a compound of Formula I as defined herein, or a pharmaceutically acceptable salt, hydrate or solvate thereof, or a pharmaceutical composition as defined herein, for use in the treatment of a disease or condition associated with aberrant activity of Polθ.

In another aspect, the present invention provides the use of a compound of Formula I as defined herein, or a pharmaceutically acceptable salt, hydrate or solvate thereof, in the manufacture of a medicament for use in the treatment of a disease or condition associated with aberrant activity of Polθ.

In another aspect, the present invention provides a method of treating a disease or condition associated with aberrant activity of Polθ, said method comprising administering to a subject in need thereof an effective amount of a compound of Formula I as defined herein, or a pharmaceutically acceptable salt, hydrate or solvate thereof, or a pharmaceutical composition as defined herein.

In another aspect, the present invention provides a compound of Formula I as defined herein, or a pharmaceutically acceptable salt, hydrate or solvate thereof, or a pharmaceutical composition as defined herein, for use in the treatment of cancer or benign neoplasms.

In another aspect, the present invention provides the use of a compound of Formula I as defined herein, or a pharmaceutically acceptable salt, hydrate or solvate thereof, in the manufacture of a medicament for use in the treatment of cancer or benign neoplasms.

In another aspect, the present invention provides a method of treating a cancer or a benign neoplasm, said method comprising administering to a subject in need thereof an effective amount of a compound of Formula I as defined herein, or a pharmaceutically acceptable salt, hydrate or solvate thereof, or a pharmaceutical composition as defined herein.

A benign neoplasm may be, for example, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas or pituitary adenomas. The benign neoplasm may be endometrial implants or a keratocystic odontogenic tumor.

In another aspect, the present invention provides a compound of Formula I as defined herein, or a pharmaceutically acceptable salt, hydrate or solvate thereof, or a pharmaceutical composition as defined herein, for use in the treatment of a cancer.

In another aspect, the present invention the use of a compound of Formula I as defined herein, or a pharmaceutically acceptable salt, hydrate or solvate thereof, in the manufacture of a medicament for use in the treatment of a cancer.

In another aspect, the present invention provides a method of treating cancer, said method comprising administering to a subject in need thereof an effective amount of a compound of Formula I as defined herein, or a pharmaceutically acceptable salt, hydrate or solvate thereof, or a pharmaceutical composition as defined herein.

The compounds of the present invention, or pharmaceutically acceptable salts thereof, may be for used in the treatment of a homologous recombinant (HR) deficient cancer.

The compounds of the present invention, or pharmaceutically acceptable salts thereof, may be for used in the treatment of cancer characterized by a reduction or absence of the components of Homologous Recombination (HR).

For this reason, the compounds of the present invention may be used in the treatment of cancers characterized by a reduction or absence of one or more of ATM, BARD1, PALB2, BRCA1 and BRCA2, the absence of one or more of the ATM, BARD1, PALB2, BRCA1 and BRCA2 genes, or a reduced function of ATM, BARD1, PALB2, BRCA1 and BRCA2 protein.

In a particular aspect of the invention, the compounds of the present invention, or pharmaceutically acceptable salts thereof, may be for used in the treatment of cancer characterized by a reduction or absence of BRCA gene expression, the absence of the BRCA gene, or a reduced function of BRCA protein.

In a further aspect, the present invention relates to compounds of the present invention, or pharmaceutically acceptable salts thereof, for use in the treatment of cancers that are resistant to PARP inhibitor treatment.

The compounds of the present invention may be useful for the treatment of the adult population. The compounds of the present invention may also be useful for the treatment of the paediatric population.

As a consequence of their inhibition of Polθ, the compounds of the present invention will be useful in providing a means of disabling the ability of cells to perform MMEJ. It is therefore anticipated that the compounds may prove useful in treating or preventing proliferative disorders such as cancers. In addition, the compounds of the invention may be useful in the treatment of diseases in which there is a disorder associated with cell accumulation.

In one embodiment, the compounds of the present invention are suitably lethal in BRCA1 and BRCA2 deficient primary and secondary solid tumours, including breast, ovarian, prostate and pancreas. In a further embodiment, the compounds of the present invention are suitably lethal in a variety of primary and secondary solid tumours which are HRD by mechanisms other than BRCA deficiency, such as those with promoter hypermethylation. In these tumours where no DSB repair pathway may be fully down regulated the compound of the present invention may be given along with another DDR modulator such as a PARP inhibitor, a DNA-PK inhibitor, an ATR inhibitor, an ATM inhibitor, a wee1 inhibitor or a CHK1 inhibitor.

In a further embodiment, the compounds of the present invention are suitably lethal in primary and secondary breast, ovarian, prostate and pancreatic tumours retaining BRCA1 deficiency but which, following or not following exposure to PARP inhibitor medication, are resistant to PARP inhibitor treatment.

In a further embodiment, the compounds of the present invention suitably increase the objective response rate (ORR), including the complete response rate (CRR), will delay the onset of PARP inhibitor resistance, will increase the time to relapse and disease free survival (DFS), and will increase the overall survival (OS) of homologous recombination deficiency (HRD, BRCA1/2 deficient and other HRD mechanisms) primary and secondary tumours (breast, ovarian, prostate and pancreas) when given with PARP inhibitor treatment programmes.

In a further embodiment, the compounds of the present invention suitably show synthetic sickness and/or synthetic lethality in a variety of tumours with loss of ATM activity (ATM$^{-/-}$) particularly in the context of WT p53. Tumour types will include around 10% of all solid tumours including gastric, lung, breast, and CRC, along with CLL. Co-medicating with another DDR modifier, such as a DNA-PK inhibitor, PARP inhibitor or ATR inhibitor, may further enhance such activity. Polθ inhibitors will resensitise CLL to classical chemotherapy and chemo-immunotherapy where drug resistance has emerged. Thus, according to a further embodiment, the pharmaceutical composition of the present invention additionally comprises a DNA-PK inhibitor, PARP inhibitor, or ATR inhibitor.

In a further embodiment, the compounds of the present invention suitably show synthetic sickness and/or synthetic lethality in a variety of tumours deficient in the DNA double strand break repair process of non-homologous end-joining (NHEJ-D). Tumour types will include approximately 2-10% of all solid tumours including prostate, pancreatic, cervical, breast, lung, bladder and oesophageal. Co-medicating with another DDR modifier, such as a PARP inhibitor, ATM inhibitor, wee1 inhibitor, CHK inhibitor, or ATR inhibitor, may further enhance such activity. Polθ inhibitors will further sensitise NHEJD cancer cells to DNA double strand breaks (DSB) inducing chemotherapies and to ionising radiation based therapies. Thus, according to a further embodiment, the pharmaceutical composition of the present invention additionally comprises a PARP inhibitor, ATM inhibitor, wee1 inhibitor, CHK inhibitor, or ATR inhibitor.

In a further embodiment, the compounds of the present invention suitably reduce the DNA replication stress response during the chemotherapy of HR proficient tumours such as ovarian, NSCL and breast tumours over-expressing Polθ. This will increase the ORR to treatment and increase OS. Such effects are particularly likely with cytarabine (Ara-C) and hydroxyurea used in a wide variety of leukemias including CML, and the management of squamous cell carcinomas.

In a further embodiment, the compounds of the present invention suitably selectively sensitise solid tumours to radiotherapy, including EBRT and brachytherapy, with little or no sensitisation of normal tissues. In a fractionated curative-intent setting this will increase loco-regional control driving increased survival. This will be particularly evident in the management of non-small cell lung cancer (NSCLC), squamous cell carcinoma of head and neck (SCCH&N), rectal cancer, prostate cancer and pancreatic cancer. In a further embodiment, the compounds of the present invention suitably show synthetic sickness and/or synthetic lethality in PTEN deleted tumours such as CaP, with or without comedication with a PARP inhibitor. Furthermore, such tumours will exhibit exquisite sensitivity to radiotherapy both by dint of the PTEN deletion as well as the Polθ inhibitor induced radiosensitivity.

In a further embodiment, the compounds of the present invention suitably suppress TLS polymerase activity, sensitising primary and secondary solid tumours (e.g. breast, lung, ovarian, CRC) to drugs (e.g. cisplatin, mitomycin and cyclophosphamide) as well as reducing the acquisition of drug-induced mutations implicated in tumour resistance leading to prolongation of remission and increased TTR.

In a further embodiment, the compounds of the present invention suitably resensitise BCR-ABL-positive CML which is has developed imatinib resistance, as well as other solid tumours with elevated ligase IIIa levels, reduced ligase IV levels and increased dependence upon altEJ DSB repair.

In a further embodiment, the compounds of the present invention suitably show synthetic sickness and/or synthetic lethality in aromatase inhibitor resistant ER primary and secondary breast cancers, again showing elevated ligase IIIa levels, reduced ligase IV levels and increased dependence upon altEJ DSB repair.

According to a further aspect of the invention there is a provided a compound of formula (I) as defined herein for use in the treatment of tumours characterised by a deficiency in homologous recombination (HRD).

It will be appreciated that references herein to "deficiency in homologous recombination (HRD)" refer to any genetic variation which results in a deficiency or loss of function of the resultant homologous recombination gene. Examples of said genetic variation include mutations (e.g. point mutations), substitutions, deletions, single nucleotide polymorphisms (SNPs), haplotypes, chromosome abnormalities, Copy Number Variation (CNV), epigenetics, DNA inversions, reduction in expression and mis-localisation.

In one embodiment, said homologous recombination genes are selected from any of: ATM, ATR, BRCA1, BRCA2, BARD1, RAD51C, RAD50, CHEK1, CHEK2, FANCA, FANCB, FANCC, FANCD2, FANCE, FANCF, FANCG, FANCI, FANCL, FANCM, PALB2 (FANCN), FANCP (BTBD12), ERCC4 (FANCQ), PTEN, CDK12, MRE11, NBS1, NBN, CLASPIN, BLM, WRN, SMARCA2, SMARCA4, LIG1, RPA1, RPA2, BRIP1 and PTEN.

It will be appreciated that references herein to "non-homologous end-joining deficiency (NHEJD)" refer to any genetic variation which results in a deficiency or loss of function of the resultant homologous recombination gene. Examples of said genetic variation include mutations (e.g. point mutations), substitutions, deletions, single nucleotide polymorphisms (SNPs), haplotypes, chromosome abnormalities, Copy Number Variation (CNV), epigenetics, DNA inversions, reduction in expression and mis-localisation.

In one embodiment, said non-homologous end-joining genes are selected from any one or more of: LIG4, NHEJ1, POLL, POLM, PRKDC, XRCC4, XRCC5, XRCC6, and DCLRE1C.

According to a further aspect of the invention there is a provided a compound of formula (I) as defined herein for use in the treatment of tumours which overexpress Polθ.

According to a further aspect of the invention there is a provided a compound of formula (I) as defined herein for use in the treatment of tumours which have elevated ligase IIIa levels, reduced ligase IV levels and increased dependence upon altEJ DSB repair.

The cancer may be non-metastatic or metastatic and which may be a solid tumour or a haematological ("liquid") cancer. The cancer may, for example, be selected from:

(1) Carcinoma, including for example tumours derived from stratified squamous epithelia (squamous cell carcinomas) and tumours arising within organs or glands (adenocarcinomas). Examples include breast, colon, lung, prostate, ovary, esophageal carcinoma (including, but not limited to, esophageal adenocarcinoma and squamous cell carcinoma), basal-like breast carcinoma, basal cell carcinoma (a form of skin cancer), squamous cell carcinoma (various tissues), head and neck carcinoma (including, but not limited to, squamous cell carcinomas), stomach carcinoma (including, but not limited to, stomach adenocarcinoma, gastrointestinal stromal tumor), signet ring cell carcinoma, bladder carcinoma (including transitional cell carcinoma (a malignant neoplasm of the bladder)), bronchogenic carcinoma, colorectal carcinoma (including, but not limited to, colon carcinoma and rectal carcinoma), anal carcinoma, gastric carcinoma, lung carcinoma (including but not limited to small cell carcinoma (SCLC) and non-small cell carcinoma of the lung (NSCLC), lung adenocarcinoma, squamous cell carcinoma, large cell carcinoma, bronchioloalveolar carcinoma, and mesothelioma), neuroendocrine tumors (including but not limited to carcinoids of the gastrointestinal tract, breast, and other organs), adrenocortical carcinoma, thyroid carcinoma, pancreatic carcinoma (including, but not limited to, pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumors), breast carcinoma (including, but not limited to, ductal carcinoma, lobular carcinoma, inflammatory breast cancer, clear cell carcinoma, mucinous carcinoma), ovarian carcinoma (including, but not limited to, ovarian epithelial carcinoma or surface epithelial-stromal tumor including serous tumor, endometrioid tumor and mucinous cystadenocarcinoma, sex-cord-stromal tumor), liver and bile duct carcinoma (including, but not limited to, hepatocellular carcinoma, cholangiocarcinoma and hemangioma), prostate carcinoma, adenocarcinoma, brain tumours (including, but not limited to glioma, glioblastoma and medulloblastoma), germ cell tumors, sweat gland carcinoma, sebaceous gland carcinoma, papillary carcinoma, papillary adenocarcinoma, cystadenocarcinoma, kidney carcinoma (including, but not limited to, renal cell carcinoma, clear cell carcinoma and Wilm's tumor), medullary carcinoma, ductal carcinoma in situ or bile duct carcinoma, choriocarcinoma, seminoma, embryonal carcinoma, cervical carcinoma, uterine carcinoma (including, but not limited to, endometrial adenocarcinoma, uterine papillary serous carcinoma, uterine clear-cell carcinoma, uterine sarcomas and leiomyosarcomas, mixed mullerian tumors), testicular carcinoma, osteogenic carcinoma, epithelial carcinoma, sarcomatoid carcinoma, nasopharyngeal carcinoma, laryngeal carcinoma; oral and oropharyngeal squamous carcinoma;

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and hemangioendothelioma (blood vessels); liposarcoma (adipose tissue); glioma and astrocytoma (neurogenic connective tissue found in the brain); myxosarcoma (primitive embryonic connective tissue); chordoma, endotheliosarcoma, lymphangiosarcoma, lymphangioendotheliosarcoma, synovioma, Ewing's sarcoma, mesenchymous and mixed mesodermal tumor (mixed connective tissue types) and other soft tissue sarcomas;

(3) Myeloma and multiple myeloma;

(4) Hematopoietic tumours, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); myelofibrosis.

(5) Lymphomas, including: Hodgkin and Non-Hodgkin lymphomas;

(6) Solid tumors of the nervous system including medulloblastoma, craniopharyngioma, ependymoma, pinealoma, hemangioblastoma, acoustic neuroma, oligodendroglioma, meningioma, neuroblastoma and schwannoma;

(7) Melanoma, uveal melanoma and retinoblastoma; and (8) Mixed Types, including, e.g., adenosquamous carcinoma, mixed mesodermal tumor, carcinosarcoma or teratocarcinoma.

Further examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and pre-malignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, MALT lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Particular examples of cancers that can be targeted with the compounds of the present invention include, but are not limited to lymphoma, rhabdoid tumor, multiple myeloma, uterine cancer, gastric cancer, peripheral nervous system cancer, rhabdomyosarcoma, bone cancer, colorectal cancer, prostate cancer, mesothelioma, breast cancer, ovarian cancer, lung cancer, fibroblast cancer, central nervous system cancer, urinary tract cancer, upper aerodigestive cancer, leukemia, kidney cancer, skin cancer, esophageal cancer, and pancreatic cancer. More particularly, the cancers may be one or more of the following breast cancer, ovary cancer, pancreatic cancer, prostate cancer, lung cancer and/or colorectal cancer.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis. In particular, the compounds of the invention may be useful in the treatment of metastasis and metastatic cancers.

Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body.

Particular cancers include hepatocellular carcinoma, melanoma, oesophageal, renal, colon, colorectal, lung e.g. mesothelioma or lung adenocarcinoma, breast, bladder, gastrointestinal, ovarian and prostate cancers.

The compounds may also be useful in the treatment of tumour growth, pathogenesis, resistance to chemo- and radio-therapy by sensitising cells to chemotherapy and as an anti-metastatic agent.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (e.g. by a patch, plaster, etc.); transmucosal (e.g. by a patch, plaster, etc.); intranasal (e.g. by nasal spray); ocular (e.g. by eye drops, eye ointment etc.); pulmonary (e.g. by inhalation or insufflation therapy, for example via an aerosol, for example by the nose or mouth); rectal (e.g. by suppository or enema); vaginal (e.g. by pessary); parental, for example by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir dosage form, for example subcutaneously or intramuscularly.

The compounds of the present invention are particularly suitable for oral administration.

Combination Therapies

The compounds of the invention and salts, solvates thereof defined hereinbefore may be applied as a sole therapy or may involve, in addition to the compound of the invention, one or more additional therapeutic agents, e.g. an anti-tumour agent.

In the context of cancer treatment, in addition to the compound of the invention, therapy may additionally involve conventional surgery, radiotherapy and/or chemotherapy. Such chemotherapy may include one or more of the following categories of anti-tumour agents:— other antiproliferative/antineoplastic drugs and combinations thereof, as used in medical oncology, such as, but not limited to, alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as, but not limited to, fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

cytostatic agents such as, but not limited to, antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as, but not limited to, finasteride;

anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as, but not limited to, N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as, but not limited to, lapatinib); inhibitors of the hepatocyte growth factor family; inhibitors of the insulin growth factor family; inhibitors of the platelet-derived growth factor family such as, but not limited to, imatinib and/or nilotinib (AMN107); inhibitors of serine/threonine kinases (for example Ras/Raf signalling inhibitors such as, but not limited to, farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as, but not limited to, CDK2 and/or CDK4 inhibitors;

antiangiogenic agents such as, but not limited to, those which inhibit the effects of vascular endothelial growth factor, [for example the anti-vascular endothelial cell growth factor antibody bevacizumab (Avastin™) and for example, a VEGF receptor tyrosine kinase inhibitor such as, but not limited to, vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as, but not limited to, those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

vascular damaging agents such as, but not limited to, Combretastatin A4 and compounds disclosed in International Patent Applications WO 99/02166, WO 00/40529, WO 00/41669, WO 01/92224, WO 02/04434 and WO 02/08213;

an endothelin receptor antagonist, for example zibotentan (ZD4054) or atrasentan;

antisense therapies, for example those which are directed to the targets listed above, such as, but not limited to, ISIS 2503, an anti-ras antisense;

gene therapy approaches, including for example approaches to replace aberrant genes such as, but not limited to, aberrant p53 or aberrant BRCA1 or BRCA2, GDEPT (gene-directed enzyme pro-drug therapy) approaches such as, but not limited to, those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex-vivo and in-vivo approaches to increase the immunogenicity of patient tumour cells, such as, but not limited to, transfection with cytokines such as interleukin 2, interleukin 4 or granulocyte-macrophage colony stimulating factor, approaches to decrease T-cell anergy, approaches using transfected immune cells such as, but not limited to, cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

In a further embodiment, the antiproliferative treatment defined hereinbefore may involve, in addition to the compound of the invention, standard chemotherapy for the cancer concerned and/or therapy with a DNA damage repair inhibitors (e.g. PARP, ATM, ATR, WEE1, CHK1, USP1 and DNAPK inhibitors).

In a further embodiment, the antiproliferative treatment defined hereinbefore may involve, in addition to the compound of the invention, therapy with a PARP inhibitor.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as, but not limited to, cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination. In one embodiment, a combination refers to a combination product.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

Biological Activity

The biological assay described in the example section (Biological Assay 1) may be used to measure the pharmacological effects of the compounds of the present invention.

Although the pharmacological properties of the compounds of formula I vary with structural change, as expected, the compounds of the invention were found to be active in the assays described in Biological Assay 1. In general, the compounds of the invention demonstrate an $IC_{50}$ of 5000 nM or less in the assay described in Biological Assay 1, with preferred compounds of the invention demonstrating an $IC_{50}$ of 100 nM or less and the most preferred compounds of the invention demonstrating an $IC_{50}$ of 30 nM or less.

Additional Applications

The compounds of the present invention are also potentially useful agents for increasing the efficiency and robustness of CRISPR gene editing in vitro and in vivo.

In this regard, homologous recombination (HR) is primordial to ensure the correct modification of the DNA (insertion of DNA in the genome, base mutation, etc). Consistent with the hypothesis that TMEJ competes with HR for the access to resected DNA breaks (Mateos-Gomez P. A., et al., (2017), Nat. Struct. Mol. Biol. (2017) 24(12): 1116-1123), it has been shown that loss of Polθ leads to an increase of HR on CRISPR induced breaks and improves the fidelity and frequency of the genome modification (Mara K., et al., New Phyto. (2019); 222(3):1380-1391; Zelenski A. N., et al., Nat. Commun., (2017); 8(1):66). Therefore, a Polθ inhibitor can be used to increase efficiency and robustness of CRISPR genome editing in vitro, and potentially in vivo (Schimmel J. et al., Cell Rep. (2023) 42: 112019).

For this reason, a role for the loss of Polθ enhancing the efficacy of CRISPR mediated gene editing has been described in WO 2017/062754. Thus, the compounds of the invention are likely to be useful in enhancing the efficiency of CRISPR based editing methodologies and/or CRISPR based editing therapeutics. Furthermore, compound mediated Polθ inhibition is likely to reduce the frequency of random integration events and thus provide a route to ameliorate any safety concerns of CRISPR mediated technology. Thus, according to a further aspect of the invention, there is provided the use of a compound of formula (I) as defined herein in a CRISPR based editing methodology and/or CRISPR based editing therapeutics, such as the enhancement of efficiency of CRISPR based editing methodology and/or CRISPR based editing therapeutics.

For this reason, in a further aspect, the present invention provides the use of a compound of the invention (i.e. a compound of formula I or any sub-formulae thereof) or a salt, hydrate or solvate thereof, for CRISPR gene editing in vitro or in vivo.

In another aspect, the present invention provides the use of a compound of the invention (i.e. a compound of formula I or any sub-formulae thereof), or a salt, hydrate or solvate thereof, for increasing the efficiency of CRISPR gene editing in vitro or in vivo.

In another aspect, the present invention provides a compound of the invention (i.e. a compound of formula I or any sub-formulae thereof), or a salt, hydrate or solvate thereof, for use in CRISPR gene editing in vivo.

In another aspect, the present invention provides a compound of the invention (i.e. a compound of formula I or any sub-formulae thereof), or a salt, hydrate or solvate thereof, for use in increasing the efficiency of CRISPR gene editing in vivo.

EXAMPLES—PART A

The invention will now be illustrated, but not limited, by reference to the specific embodiments described in the following examples. Compounds are named using conventional IUPAC nomenclature, or as named by the chemical supplier.

The following synthetic procedures are provided for illustration of the methods used; for a given preparation or step the precursor used may not necessarily derive from the individual batch synthesized according to the step in the description given.

General

All solvents and chemical reagents were obtained from commercial sources and were used without further purification or drying. NMR spectra were recorded on either a Bruker Avance III HD 400 MHz, a Bruker NEO 400 MHz, a Bruker Avance III HD 500 MHz, a Bruker Avance NEO 500 MHz or a Bruker Avance III HD 600 MHz spectrometer. Chemical shifts are quoted in ppm using residual undeuterated solvent as the internal reference.

LCMS spectra were recorded on a Waters Aquity UPLC using:

Method A—Waters UPLC® BEH™ C18 2.1×50 mm 1.7 µm column at 40° C. eluting with 0.1% formic acid in acetonitrile and 0.1% formic acid in water using a gradient of 5-100% over 1.35 mins at a rate of 0.9 mL/min;

Method B—Phenomenex Kinetix-XB C18 2.1×100 mm, 1.7 µm column at 40° C. eluting with 0.1% formic acid in acetonitrile and 0.1% formic acid in water using a gradient of 5-100% over 5.8 mins at a rate of 0.6 mL/min;

Method C—Waters UPLC® BEH™ C18 2.1×50 mm 1.7 µm column at 55° C. eluting with 2 mM ammonium bicarbonate in water, buffered to pH 10 and acetonitrile using a gradient of 1-100% over 1.10 mins at a rate of 1 mL/min;

Method D—Waters UPLC® BEH™ C18 2.1×100 mm 1.7 µm column at 55° C. eluting with 2 mM ammonium bicarbonate in water, buffered to pH 10 and acetonitrile using a gradient of 5-100% over 5.30 mins at a rate of 0.6 mL/min;

Method E—Waters CSH C18 2.1×50 mm, 1.7 µm column at 55° C. eluting with 0.035% TFA in acetonitrile and 0.05% TFA in water using a gradient of 2% to 98% over 1.5 mins at a rate of 0.8 mL/min;

Method F—Waters CSH C18 2.1×50 mm, 1.7 µm column at 55° C. eluting with 0.035% TFA in acetonitrile and 0.05% TFA in water using a gradient of 2% to 98% over 2.4 mins at a rate of 0.8 mL/min;

Method G—Waters CSH C18 2.1×50 mm, 1.7 µm column at 55° C. eluting with 0.02% formic acid in acetonitrile and 0.02% formic acid in water using a gradient of 2% to 98% over 4.5 mins at a rate of 1 mL/min; or Method H; Waters CSH C18 2.1×50 mm, 1.7 µm column at 55° C. eluting with 0.02% formic acid in acetonitrile and 0.02% formic acid in water using a gradient of 2% to 98% over 2.4 mins at a rate of 0.8 mL/min.

Mass spectra were obtained using a Waters SQD, SQD2 or a QDA detector using electrospray ionisation in positive or negative mode. LCMS purity was assigned using AUC monitoring at 215, 254 or 280 nm.

Preparative HPLC was performed using either:

Method A—Waters Sunfire C18 30 mm×100 mm, 5 µm column at room temperature using 30% 0.1% formic acid in acetonitrile and 70% 0.1% formic acid in water for 1.9 mins then a gradient of 30-95% 0.1% formic acid in acetonitrile for 9.6 mins at a flow rate of 40 mL/min;

Method B—Waters XBridge C18 column 30 mm×100 mm, 5 µm at room temperature using 30% acetonitrile and 70% 0.2% ammonium hydroxide in water for 2 mins then a gradient of 30-95% acetonitrile for 9.5 mins at a flow rate of 40 mL/min; or Method C—Waters Sunfire™ C18 column (30 mm×100 mm, 5 µm; temperature: room temperature), with an injection volume of 1500 µL at a flow rate of 40 mL/min at 10% B for 1.90 min then a gradient of 10-95% B over 14.10 min and held for 2.0 min, where A=0.1% formic acid in water and B=0.1% formic acid in acetonitrile.
UV spectra were recorded at 215 nm using a Gilson detector.

List of Abbreviations

RT Room Temperature
DTBPF Ditertbutyl phosphino ferrocene
THF Tetrahydrofuran
TCFH Chloro-N,N,N',N'-tetramethylformamidinium hexafluorophosphate
DCM Dichloromethane
DIPEA N,N-diisopropylethylamine
DMF Dimethylformamide
DCE Dichloroethane
DPPF Diphenyl phosphino ferrocene
Sat. Saturated
Equiv. Equivalents
SPhos 2-Dicyclohexylphosphino-2',6'-dimethoxybiphenyl
$Pd_2(dba)_3$ Tris(dibenzylideneacetone)dipalladium(0)
Xantphos 4,5-Bis(diphenylphosphino)-9,9-dimethylxanthene
NMI N-methyl imidazole
NBS N-bromo succinimide
DPEPhos (Oxydi-2,1-phenylene)bis(diphenylphosphine)
THF tetrahydrofuran
DMAP N,N-dimethylaminopyridine
Rt Retention time General Scheme

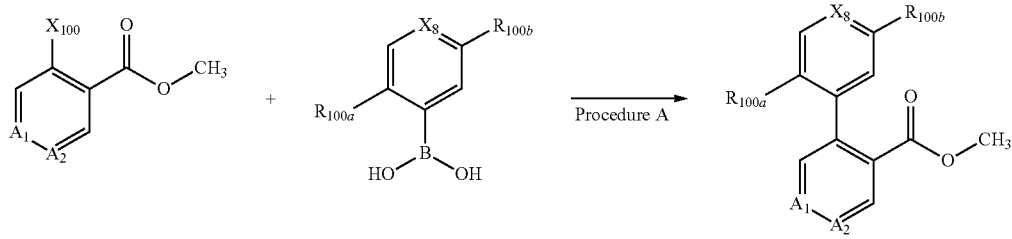

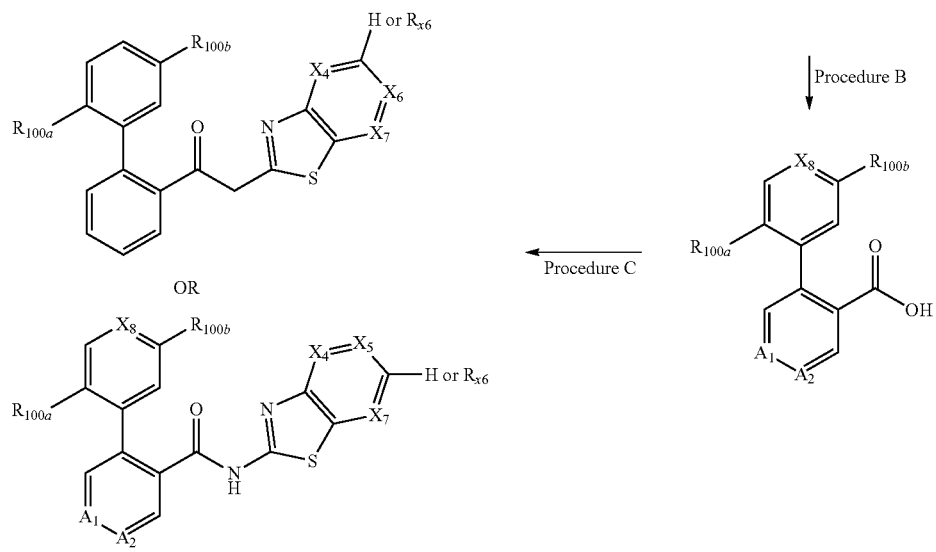

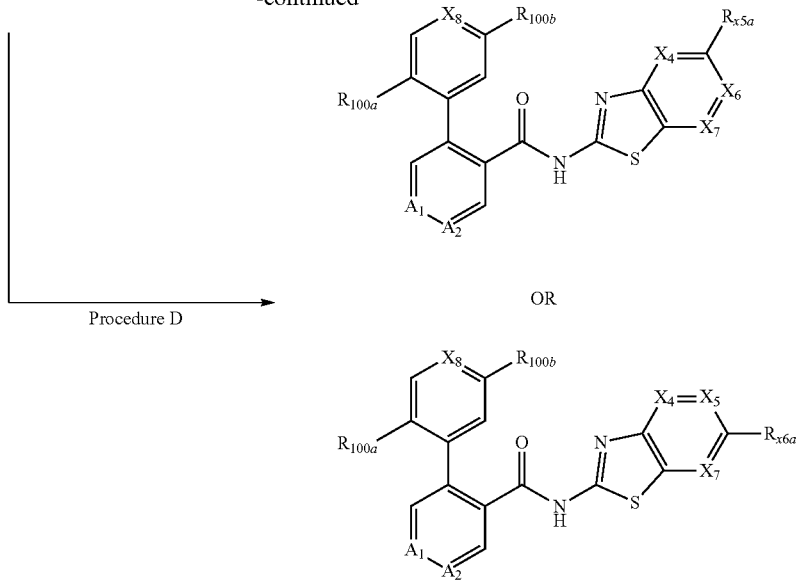

In the scheme above, $X_{100}$ is a halide; $A_1$ is N or C-Me; $A_2$ is N when $A_1$ is C-Me, or $A_2$ is C—H when A is N; the groups $R_{x5a}$ and $R_{x6a}$ are different groups $R_{x5}$ and $R_{x6}$ respectively formed by procedure D; the remaining groups are as defined hereinbefore.

General Procedure A for Suzuki Coupling

To a solution of the desired aryl halide (1 equiv) in 1,4-dioxane/water (3:1, 0.2 mmol/mL) in a round-bottom flask fitted with a magnetic stirrer bar were added the corresponding boronic acid (1.5 equiv), dipotassium carbonate (3.7 equiv) and palladium catalyst (10 mol %). The mixture was flushed with nitrogen, fitted with a condenser, and stirred at 90° C. for 18 h. The reaction was cooled to RT and the mixture was diluted with water and extracted with ethyl acetate. The organic extracts were combined, washed with brine, dried ($Na_2SO_4$) and concentrated under reduced pressure. The crude was purified by Biotage Isolera™ automated chromatography using a gradient of ethyl acetate in heptanes to give the desired biaryl products.

Intermediate 1 methyl 4-(2-chloro-5-methoxy-4-pyridyl-6-methyl-pyridine-3-carboxylate

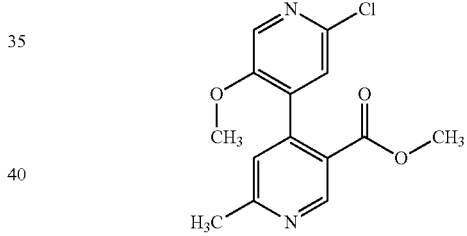

To a solution of methyl 4-chloro-6-methyl-pyridine-3-carboxylate (1.20 g, 6.47 mmol) in 1,4-dioxane (21 mL) and water (7 mL) in a 250 mL round-bottom flask fitted with a magnetic stirrer bar were added (2-chloro-5-methoxy-4-pyridyl)boronic acid (1.60 g, 8.54 mmol), dipotassium carbonate (3.30 g, 23.9 mmol) and palladium dichloride DTBPF (360 mg, 0.55 mmol). The mixture was flushed with nitrogen, fitted with a condenser, and stirred at 90° C. for 18 h. The reaction was cooled to RT and the mixture was diluted with water (50 mL) and extracted with ethyl acetate (3×50 mL). The organic extracts were combined, washed with brine, dried ($Na_2SO_4$) and the solvent was removed under reduced pressure. The crude was purified by Biotage Isolera™ automated chromatography (Sfar Duo, 100 g) using a gradient of 0-100% ethyl acetate in heptane. Fractions containing product were evaporated under reduced pressure to afford the title compound (5.03 g, 91% yield) as an off-white solid. $^1$H NMR (400 MHz, DMSO-$d_6$) δ 8.88 (s, 1H), 8.23 (s, 1H), 7.50 (s, 1H), 7.38 (s, 1H), 3.78 (s, 3H), 3.68 (s, 3H), 2.58 (s, 3H). LCMS (method B); RT 2.58 mins (100%), m/z 293.1/295.1 (M+H)$^+$.

The Intermediates 2 and 3 in Table 1 below were also synthesized using general procedure A detailed above.

TABLE 1

Intermediates 2 and 3 synthesized using general procedure A

| Intermediate | Yield | LCMS Purity (%) | LCMS RT (mins) | m/z | LCMS method | 1H NMR |
|---|---|---|---|---|---|---|
| Intermediate 2<br>methyl 3-(2-methoxyphenyl)pyridine-4-carboxylate | 65 | 90 | 0.76 | 244.2 | A | $^1$H NMR (500 MHZ, DMSO-$d_6$) δ 8.70 (d, J = 4.9 Hz, 1H), 8.59 (s, 1H), 7.64 (dd, J = 4.9, 0.8 Hz, 1H), 7.43-7.38 (m, 1H), 7.33 (dd, J = 7.4, 1.7 Hz, 1H), 7.09-7.04 (m, 2H), 3.66 (d, J = 2.7 Hz, 6H). |
| Intermediate 3<br>methyl 2'-chloro-5'-methoxy-6-methyl-[4,4'-bipyridine]-3-carboxylate | 91 | 100 | 2.58 | 293.1/295.1 | B | $^1$H NMR (400 MHZ, DMSO-d6) δ 8.88 (s, 1H), 8.23 (s, 1H), 7.50 (s, 1H), 7.38 (s, 1H), 3.78 (s, 3H), 3.68 (s, 3H), 2.58 (s, 3H) |

General Procedure B for Ester Hydrolysis

To a solution of methyl ester (1 equiv) in THF (0.2 mmol/mL) was added 1 M aqueous lithium hydroxide solution (2 equiv) and the mixture stirred for 18 h. The mixture was acidified to pH 3 using 1M aqueous HCl solution and extracted with ethyl acetate. The combined organic extracts were dried (Na$_2$SO$_4$) and solvent removed under reduced pressure. The resulting solid was dried in a vacuum oven at 40° C. overnight to give the desired carboxylic acid.

To a solution of methyl 4-(2-chloro-5-methoxy-4-pyridyl)-6-methyl-pyridine-3-carboxylate (5.03 g, 17.2 mmol) in THF (98 mL) was added 1 M aqueous lithium hydroxide (35 mL, 35.0 mmol) and the mixture stirred for 18 h. The mixture was acidified to pH 3 using 1M aqueous HCl solution and extracted with ethyl acetate (3×25 mL). The combined organic extracts were dried (Na$_2$SO$_4$) and concentrated under reduced pressure. The resulting solid was dried in a vacuum oven at 40° C. overnight to give the title compound (3.30 g, 69% yield) as a white solid. $^1$H NMR (400 MHz, DMSO-$d_6$) δ 13.06 (s, 1H), 8.89 (s, 1H), 8.21 (s, 1H), 7.44 (s, 1H), 7.30 (s, 1H), 3.79 (s, 3H), 2.56 (s, 3H). LCMS (method B); RT 1.63 mins (100%), m/z 279.1/281.1 (M+H)$^+$.

Intermediate 4

4-(2-chloro-5-methoxy-4-pyridyl)-6-methyl-pyridine-3-carboxylic Acid

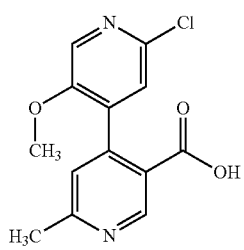 [SMILES: COc1cnc(Cl)cc1-c1cc(C)ncc1C(=O)O]

Intermediates 5 and 6 in Table 2 below were also synthesized using general procedure B detailed above.

TABLE 2

Intermediates 2 and 3 synthesized using general procedure A

| Intermediate | Yield | LCMS Purity (%) | LCMS RT (mins) | m/z | LCMS method | 1H NMR |
|---|---|---|---|---|---|---|
| Intermediate 5 3-(2-methoxyphenyl)pyridine-4-carboxylic acid | 70 | 95 | 0.4 | 230.2 | A | $^1$H NMR (400 MHZ, DMSO-d$_6$) δ 8.66 (d, J = 5.0 Hz, 1H), 8.53 (d, J = 0.7 Hz, 1H), 7.63 (dd, J = 5.0, 0.7 Hz, 1H), 7.40-7.36 (m, 1H), 7.28 (dd, J = 7.7, 1.7 Hz, 1H), 7.07-7.03 (m, 2H), 3.67 (s, 3H). |
| Intermediate 6 2'-chloro-5'-methoxy-6-methyl-[4,4'-bipyridine]-3-carboxylic acid | 69 | 100 | 1.63 | 279.1/281.1 | B | $^1$H NMR (400 MHZ, DMSO-d$_6$) δ 13.06 (s, 1H), 8.89 (s, 1H), 8.21 (s, 1H), 7.44 (s, 1H), 7.30 (s, 1H), 3.79 (s, 3H), 2.56 (s, 3H) |

General Procedure C for Amide Coupling

To a solution of carboxylic acid (1.1 equiv), amine (1 equiv) and 1-methylimidazole (5.1 equiv) in acetonitrile was added a solution of TCFH (1.1 equiv) in acetonitrile. The mixture was stirred for 18 h at RT.

Where the product precipitated from solution, it was filtered, washed with diethyl ether and dried in a vacuum oven at 40° C. to give the desired amide. Where the product did not precipitate the solution was diluted with ethyl acetate and washed with sat. NaHCO$_3$ aqueous solution. Organic extracts were combined, dried (Na$_2$SO$_4$) and concentrated under reduced pressure. The crude was purified by Biotage Isolera™ automated chromatography using a gradient of methanol in ethyl acetate or prep HPLC method A to give the desired amide.

Example 1—N-(6-chloro-1,3-benzothiazol-2-yl)-4-(2-chloro-5-methoxy-4-pyridyl)-6-methyl-pyridine-3-carboxamide To a solution of 4-(2-chloro-5-methoxy-4-pyridyl)-6-methyl-pyridine-3-carboxylic acid (50 mg, 0.18 mmol) in acetonitrile (1 mL) were added 6-chloro-1,3-benzothiazol-2-amine (36 mg, 0.20 mmol) and 1-methylimidazole (73 μL, 0.91 mmol) and flushed with nitrogen. To the above solution was added TCFH (53 mg, 0.20 mmol) in acetonitrile (1 mL) and the reaction mixture was stirred at room temperature for 18 h. The product precipitated from the reaction mixture and was filtered. The filter cake was washed sequentially with acetonitrile and diethyl ether then dried in a vacuum oven at 40° C. for 3 h to give the title compound (53 mg, 66% yield) as a colourless powder. $^1$H NMR (500 MHz, DMSO-d$_6$) δ 13.04 (s, 1H), 8.85 (s, 1H), 8.16 (s, 1H), 8.13 (d, J=2.2 Hz, 1H), 7.77 (d, J=8.6 Hz, 1H), 7.58 (s, 1H), 7.50-7.44 (m, 2H), 3.59 (s, 3H), 2.60 (s, 3H). LCMS (method B); RT 3.60 mins (99%), m/z 445.0/446.9 (M+H)$^+$

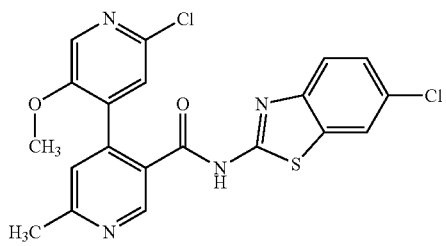 [SMILES: COc1cnc(Cl)cc1-c1cc(C)ncc1C(=O)Nc1nc2ccc(Cl)cc2s1]

Examples 2 to 18 in Table 3 below were also synthesized using general procedure C detailed above.

TABLE 3

Examples 2 to 18 synthesized using general procedure C

| Example | Yield | LCMS Purity (%) | LCMS RT (mins) | m/z | LCMS method | 1H NMR |
|---|---|---|---|---|---|---|
| Example 2<br>2'-chloro-N-(6-methanesulfonyl-1,3-benzothiazol-2-yl)-5'-methoxy-6-methyl-[4,4'-bipyridine]-3-carboxamide | 12 | 100 | 2.73 | 489.2/491.2 | B | $^1$H NMR (500 MHZ, DMSO-$d_6$) δ 13.26 (s, 1H), 8.87 (s, 1H), 8.65 (s, 1H), 8.16 (s, 1H), 7.99-7.95 (m, 2H), 7.60 (s, 1H), 7.48 (s, 1H), 3.58 (s, 3H), 3.25 (s, 3H), 2.61 (s, 3H). |
| Example 3<br>2'-chloro-N-(6-cyano-1,3-benzothiazol-2-yl)-5'-methoxy-6-methyl-[4,4'-bipyridine]-3-H3C | 15 | 100 | 3.1 | 436.2/438.2 | B | $^1$H NMR (500 MHZ, DMSO-$d_6$) δ 13.28 (s, 1H), 8.87 (s, 1H), 8.58 (s, 1H), 8.16 (s, 1H), 7.92 (d, J = 8.4 Hz, 1H), 7.86 (dd, J = 8.5, 1.8 Hz, 1H), 7.60 (s, 1H), 7.48 (s, 1H), 3.58 (s, 3H), 2.61 (s, 3H). |
| Example 4<br>2'-chloro-N-(6-iodo-1,3-benzothiazol-2-yl)-5'-methoxy-6-methyl-[4,4'-bipyridine]-3-carboxamide | 72 | 100 | 3.79 | 535.1/537.1 | B | $^1$H NMR (500 MHZ, DMSO-$d_6$) δ 13.02 (s, 1H), 8.85 (s, 1H), 8.39 (d, J = 1.8 Hz, 1H), 8.16 (s, 1H), 7.74 (dd, J = 8.4, 1.8 Hz, 1H), 7.59-7.55 (m, 2H), 7.46 (s, 1H), 3.59 (s, 3H), 2.60 (s, 3H). |
| Example 5<br>N-(6-bromo-1,3-benzothiazol-2-yl)-2'-chloro-5'-methoxy-6-methyl-[4,4'-bipyridine]-3-carboxamide | 65 | 98 | 3.73 | 489.1/491.1 | B | $^1$H NMR (400 MHZ, CDCl$_3$) δ 11.63 (s, 1H), 8.77 (s, 1H), 8.04 (s, 1H), 7.94 (d, J = 2.0 Hz, 1H), 7.29 (dd, J = 8.6, 2.0 Hz, 1H), 7.13 (s, 1H), 7.05 (s, 1H), 6.80 (d, J = 8.7 Hz, 1H), 3.70 (s, 3H), 2.64 (s, 3H) |

TABLE 3-continued

Examples 2 to 18 synthesized using general procedure C

| Example | Yield | LCMS Purity (%) | LCMS RT (mins) | m/z | LCMS method | 1H NMR |
|---|---|---|---|---|---|---|
| Example 6<br>2'-chloro-N-{5-chloro-[1,3]thiazolo[5,4-d]pyrimidin-2-yl}-5'-methoxy-6-methyl-[4,4'-bipyridine]-3-carboxamide | 22 | 95 | 3.08 | 447.0/449.0 | B | $^1$H NMR (400 MHZ, DMSO-d$_6$) δ 13.50 (s, 1H), 9.12 (s, 1H), 8.88 (s, 1H), 8.17 (s, 1H), 7.59 (s, 1H), 7.47 (s, 1H), 3.61 (s, 3H), 2.61 (s, 3H). |
| Example 7<br>2'-chloro-N-{5-chloro-[1,3]thiazolo[5,4-b]pyridin-2-yl}-5'-methoxy-6-methyl-[4,4'-bipyridine]-3-carboxamide | 4 | 85 | 3.29 | 446.0/448.0 | B | $^1$H NMR (400 MHZ, DMSO-d$_6$) δ 13.21 (s, 1H), 8.87 (s, 1H), 8.20-8.15 (m, 2H), 7.60-7.55 (m, 2H), 7.46 (s, 1H), 3.61 (s, 3H), 2.60 (s, 3H). |
| Example 8<br>3-(2-methoxyphenyl)-N-{[1,3]thiazolo[5,4-d]pyrimidin-2-yl}pyridine-4-carboxamide | 11 | 100 | 2.41 | 364 | B | $^1$H NMR (400 MHZ, DMSO-d$_6$) δ 13.33 (s, 1H), 9.20 (s, 1H), 9.03 (s, 1H), 8.76 (d, J = 4.9 Hz, 1H), 8.66 (s, 1H), 7.72 (d, J = 5.0 Hz, 1H), 7.44-7.36 (m, 2H), 7.09 (t, J = 6.9 Hz, 1H), 6.99 (d, J = 8.3 Hz, 1H), 3.51 (s, 3H). |
| Example 9<br>N-(6-bromo-1,3-benzothiazol-2-yl)-3-(2-methoxyphenyl)pyridine-4-carboxamide | 16 | 100 | 3.7 | 440.0/442.1 | B | $^1$H NMR (400 MHZ, DMSO-d$_6$) δ 8.72 (s, 1H), 8.62 (s, 1H), 8.23 (s, 1H), 7.68 (d, J = 5.1 Hz, 2H), 7.57 (s, 1H), 7.38 (s, 2H), 7.10-7.05 (m, 1H), 6.98 (d, J = 8.3 Hz, 1H), 3.49 (s, 3H). |

TABLE 3-continued

Examples 2 to 18 synthesized using general procedure C

| Example | Yield | LCMS Purity (%) | LCMS RT (mins) | m/z | LCMS method | 1H NMR |
|---|---|---|---|---|---|---|
| Example 10<br>3-(2-methoxyphenyl)-N-{[1,3]thiazolo[4,5-c]pyridin-2-yl}pyridine-4-carboxamide | 6 | 99 | 1.73 | 363.1 | B | ¹H NMR (400 MHZ, DMSO-$d_6$) δ 9.00 (s, 1H), 8.76-8.70 (m, 1H), 8.62 (s, 1H), 8.41-8.35 (m, 1H), 8.02 (s, 1H), 7.72-7.67 (m, 1H), 7.42-7.33 (m, 2H), 7.10-7.03 (m, 1H), 6.99-6.94 (m, 1H), 3.48 (s, 3H). |
| Example 11<br>3-(2-methoxyphenyl)-N-{[1,3]thiazolo[4,5-b]pyridin-2-yl}pyridine-4-carboxamide | 25 | 98 | 2.49 | 363.1 | B | ¹H NMR (400 MHZ, DMSO-$d_6$) δ 13.14 (s, 1H), 8.78-8.72 (m, 1H), 8.65 (s, 1H), 8.60-8.54 (m, 1H), 8.46-8.41 (m, 1H), 7.70 (d, J = 4.9Hz, 1H), 7.45-7.35 (m, 2H), 7.36-7.29 (m, 1H), 7.09 (t, J = 7.6 Hz, 1H), 6.98 (d, J = 8.3 Hz, 1H), 3.50 (s, 3H). |
| Example 12<br>3-(2-methoxyphenyl)-N-[5-(trifluoromethyl)-1,3-benzothiazol-2-yl]pyridine-4-carboxamide | 17 | 100 | 3.72 | 430.2 | B | ¹H NMR (500 MHZ, DMSO-$d_6$) δ 13.12 (s, 1H), 8.75 (d, J = 5.0 Hz, 1H), 8.65 (s, 1H), 8.24 (d, J = 8.2 Hz, 1H), 8.09 (s, 1H), 7.70 (d, J = 4.9 Hz, 1H), 7.65 (d, J = 10.4 Hz, 1H), 7.43-7.35 (m, 2H), 7.08 (t, J = 6.9 Hz, 1H), 6.97 (d, J = 8.4 Hz, 1H), 3.48 (s, 3H). |
| Example 13<br>N-(5-chloro-1,3-benzothiazol-2-yl)-3-(2-methoxyphenyl)pyridine-4-carboxamide | 18 | 100 | 3.58 | 396.0/397.9 | B | ¹H NMR (400 MHZ, DMSO-$d_6$) δ 13.00 (s, 1H), 8.74 (d, J = 4.9 Hz, 1H), 8.64 (s, 1H), 8.01 (d, J = 8.5 Hz, 1H), 7.84 (d, J = 2.0 Hz, 1H), 7.68 (d, J = 5.0 Hz, 1H), 7.43-7.34 (m, 3H), 7.08 (t, J = 6.9 Hz, 1H), 6.97 (d, J = 8.3 Hz, 1H), 3.48 (s, 3H). |
| Example 14<br>3-(2-methoxyphenyl)-N-{[1,3]thiazolo[5,4-b]pyridin-2-yl}pyridine-4-carboxamide | 10 | 100 | 2.57 | 363.1 | B | ¹H NMR (500 MHZ, DMSO-$d_6$) δ 13.00 (s, 1H), 8.75 (d, J = 5.0 Hz, 1H), 8.65 (s, 1H), 8.49 (dd, J = 4.7, 1.5 Hz, 1H), 8.16-8.12 (m, 1H), 7.69 (d, J = 5.0 Hz, 1H), 7.51 (dd, J = 8.2, 4.7 Hz, 1H), 7.43-7.35 (m, 2H), 7.11-7.07 (m, 1H), 6.98 (dd, J = 8.4, 1.0 Hz, 1H), 3.51 (s, 3H). |

TABLE 3-continued

Examples 2 to 18 synthesized using general procedure C

| Example | Yield | LCMS Purity (%) | LCMS RT (mins) | m/z | LCMS method | 1H NMR |
|---|---|---|---|---|---|---|
| Example 15<br>N-(1,3-benzothiazol-2-yl)-3-(2-methoxyphenyl)pyridine-4-carboxamide | 30 | 100 | 3.2 | 360.2 | B | $^1$H NMR (500 MHZ, DMSO-$d_6$) δ 8.75-8.66 (m, 1H), 8.65-8.56 (m, 1H), 7.98-7.88 (m, 1H), 7.77-7.70 (m, 1H), 7.68 (d, J = 4.9 Hz, 1H), 7.45-7.32 (m, 3H), 7.32-7.24 (m, 1H), 7.09-7.03 (m, 1H), 6.98 (d, J = 8.1 Hz, 1H), 3.51 (s, 3H). |
| Example 16<br>N-(5-cyano-1,3-benzothiazol-2-yl)-3-(2-methoxyphenyl)pyridine-4-carboxamide | 53 | 100 | 3.16 | 387.1 | B | $^1$H NMR (500 MHZ, DMSO-$d_6$) δ 13.13 (s, 1H), 8.75 (d, J = 4.9 Hz, 1H), 8.65 (s, 1H), 8.29 (d, J = 1.5 Hz, 1H), 8.22 (d, J = 8.2 Hz, 1H), 7.71 (dd, J = 8.2, 1.5 Hz, 1H), 7.69 (d, J = 5.0 Hz, 1H), 7.41 (dd, J = 7.5, 1.7 Hz, 1H), 7.40-7.36 (m, 1H), 7.08 (td, J = 7.5, 1.0 Hz, 1H), 6.97 (d, J = 7.9 Hz, 1H), 3.48 (s, 3H). |
| Example 17<br>2'-chloro-5'-methoxy-6-methyl-N-[6-(morpholin-4-yl)-1,3-benzothiazol-2-yl]-[4,4'-bipyridine]-3-carboxamide | 56 | 100 | 2.88 | 496.1/498.1 | B | $^1$H H NMR (500 MHz, DMSO-$d_6$) δ 8.83 (s, 1H), 8.16 (s, 1H), 7.61 (d, J = 8.9 Hz, 1H), 7.56 (s, 1H), 7.46 (d, J = 2.5 Hz, 1H), 7.44 (s, 1H), 7.15 (dd, J = 8.9, 2.5 Hz, 1H), 3.78-3.73 (m, 4H), 3.60 (s, 3H), 3.16-3.10 (m, 4H), 2.59 (s, 3H) |
| Example 18<br>2'-chloro-5'-methoxy-6-methyl-N-(6-nitro-1,3-benzothiazol-2-yl)-[4,4'-bipyridine]-3-carboxamide | 56 | 38 | 0.91 | 456.1/458.0 | A | $^1$H NMR (400 MHZ, DMSO-$d_6$) δ 13.38 (s, 1H), 9.06 (s, 1H), 8.88 (s, 1H), 8.32-8.29 (m, 1H), 8.17 (s, 1H), 7.93 (d, J = 8.9 Hz, 1H), 7.60 (s, 1H), 7.48 (s, 1H), 3.59 (s, 3H), 2.61 (s, 3H). |

General Procedure D for SNAr Reaction

To a solution of the required chloro-thiazolopyrimidine (1 equiv, made using general procedure C) in either DMF, ethanol, ethanol/DCE (1:1) or n-butanol was added the desired amine (5 equiv). The reaction was heated at either 80 or 100° C. and monitored by LCMS until complete. If required, additional amine (5 equiv) was added. When complete the reaction was concentrated under reduced pressure and the crude purified by preparative HPLC using either method A or method B.

Example 19—4-(2-chloro-5-methoxy-4-pyridyl)-N-[5-[(3R)-3-hydroxypyrrolidin-1-yl]thiazolo[5,4-d]pyrimidin-2-yl]-6-methyl-pyridine-3-carboxamide

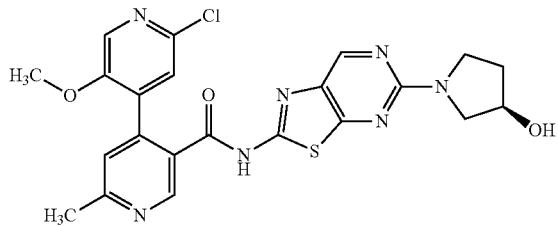

To a solution of 4-(2-chloro-5-methoxy-4-pyridyl)-N-(5-chlorothiazolo[5,4-d]pyrimidin-2-yl)-6-methyl-pyridine-3-carboxamide (30.0 mg, 0.07 mmol) in a mixture of ethanol (0.5 mL) and DCE (0.5 mL) was added (3R)-pyrrolidin-3-ol (30 mg, 0.34 mmol) and the reaction was stirred at 80° C. for 24 h. Another 5 equiv of (3R)-pyrrolidin-3-ol was added and heating continued for 8 h. Another 5 equiv of (3R)-pyrrolidin-3-ol was added and heating continued for 18 h. The reaction mixture was concentrated under reduced pressure and the residue dissolved in acetonitrile/water (1:1, 1 mL) and purified by prep HPLC method A. Product containing fractions were concentrated and freeze dried to give the title compound (7.0 mg, 21% yield) as a yellow powder. $^1$H NMR (500 MHz, DMSO-$d_6$) δ 8.84 (s, 1H), 8.71 (s, 1H), 8.16 (s, 1H), 7.54 (s, 1H), 7.42 (s, 1H), 4.96 (d, J=3.5 Hz, 1H), 4.41-4.36 (m, 1H), 3.63-3.54 (m, 6H), 3.49-3.46 (m, 1H), 2.59 (s, 3H), 2.05-1.98 (m, 1H), 1.92-1.86 (m, 1H). LCMS (method B); RT 2.41 mins (100%), m/z 498.1/500.1 (M+H)$^+$ Examples 20 to 35 in Table 4 below were all synthesised using general procedure D detailed above.

TABLE 4

| Examples 20 to 35 synthesized using general procedure D | | | | | | |
|---|---|---|---|---|---|---|
| Example | Yield | LCMS Purity (%) | LCMS RT (mins) | m/z | LCMS method | 1H NMR |
| Example 20[1]<br>2'-chloro-5'-methoxy-6-methyl-N-[5-(piperidin-1-yl)-[1,3]thiazolo[5,4-d]pyrimidin-2-yl]-[4,4'-bipyridine]-3-carboxamide | 9 | 100 | 3.86 | 496.5/<br>498.5 | B | $^1$H NMR (400 MHz, DMSO-$d_6$) δ 12.86 (s, 1H), 8.83 (s, 1H), 8.72 (s, 1H), 8.17 (s, 1H), 7.56 (s, 1H), 7.44 (s, 1H), 3.82-3.72 (m, 4H), 3.62 (s, 3H), 2.59 (s, 3H), 1.68-1.58 (m, 2H), 1.58-1.48 (m, 4H). |
| Example 21[2]<br>2'-chloro-N-[5-(4,4-difluoropiperidin-1-yl)-[1,3]thiazolo[5,4-d]pyrimidin-2-yl]-5'-methoxy-6-methyl-[4,4'-bipyridine]-3-carboxamide | 35 | 100 | 3.7 | 532.1/<br>534.1 | B | $^1$H NMR (500 MHz, DMSO-$d_6$) δ 12.93 (s, 1H), 8.84 (s, 1H), 8.79 (s, 1H), 8.17 (s, 1H), 7.56 (s, 1H), 7.45 (s, 1H), 3.99-3.87 (m, 4H), 3.63 (s, 3H), 2.60 (s, 3H), 2.07-1.97 (m, 4H). |
| Example 22[3]<br>2'-chloro-5'-methoxy-6-methyl-N-[5-(morpholin-4-yl)-[1,3]thiazolo[5,4-d]pyrimidin-2-yl]-[4,4'-bipyridine]-3-carboxamide | 28 | 97 | 3.03 | 498.1/<br>500.1 | B | $^1$H NMR (500 MHz, DMSO-$d_6$) δ 12.93 (s, 1H), 8.83 (s, 1H), 8.79 (s, 1H), 8.17 (s, 1H), 7.57 (s, 1H), 7.45 (s, 1H), 3.74-3.66 (m, 8H), 3.62 (s, 3H), 2.60 (s, 3H). |

TABLE 4-continued

Examples 20 to 35 synthesized using general procedure D

| Example | Yield | LCMS Purity (%) | LCMS RT (mins) | m/z | LCMS method | 1H NMR |
|---|---|---|---|---|---|---|
| Example 23[4]<br>2'-chloro-N-{5-[(3S)-3-hydroxypyrrolidin-1-yl]-[1,3]thiazolo[5,4-d]pyrimidin-2-yl}-5'-methoxy-6-methyl-[4,4'-bipyridine]-3-carboxamide | 22 | 90 | 2.4 | 498.1/<br>500.1 | B | $^1$H NMR (500 MHz, DMSO-$d_6$) δ 8.83 (s, 1H), 8.72 (s, 1H), 8.16 (s, 1H), 7.55 (s, 1H), 7.43 (s, 1H), 4.96 (d, J = 3.5 Hz, 1H), 4.41-4.36 (m, 1H), 3.65-3.53 (m, 6H), 3.50-3.45 (m, 1H), 2.59 (s, 3H), 2.05-1.98 (m, 1H), 1.93-1.87 (m, 1H). |
| Example 24[5]<br>2'-chloro-5'-methoxy-6-methyl-N-[5-(pyrrolidin-1-yl)-[1,3]thiazolo[5,4-d]pyrimidin-2-yl]-[4,4'-bipyridine]-3-carboxamide | 31 | 100 | 3.21 | 482.2/<br>484.2 | B | $^1$H NMR (500 MHz, DMSO-$d_6$) δ 12.84 (s, 1H), 8.82 (s, 1H), 8.75 (s, 1H), 8.17 (s, 1H), 7.57 (s, 1H), 7.46 (s, 1H), 3.63 (s, 3H), 3.55-3.49 (m, 4H), 2.60 (s, 3H), 1.98-1.91 (m, 4H). |
| Example 25[6]<br>2'-chloro-N-[5-(3,3-difluoropyrrolidin-1-yl)-[1,3]thiazolo[5,4-d]pyrimidin-2-yl]-5'-methoxy-6-methyl-[4,4'-bipyridine]-3-carboxamide | 42 | 98 | 3.33 | 518.2/<br>520.2 | B | $^1$H NMR (400 MHz, DMSO-$d_6$) δ 12.93 (s, 1H), 8.83 (m, 2H), 8.17 (s, 1H), 7.57 (s, 1H), 7.46 (s, 1H), 3.95 (t, J = 13.1 Hz, 2H), 3.77 (t, J = 7.4 Hz, 2H), 3.62 (s, 3H), 2.60 (m, 5H). |
| Example 26[7]<br>2'-chloro-N-{5-[(3R)-3-hydroxypyrrolidin-1-yl]-[1,3]thiazolo[5,4-d]pyrimidin-2-yl}-5'-methoxy-6-methyl-[4,4'-bipyridine]-3-carboxamide | 21 | 100 | 2.41 | 498.1/<br>500.1 | B | $^1$H NMR (500 MHz, DMSO-$d_6$) δ 8.84 (s, 1H), 8.71 (s, 1H), 8.16 (s, 1H), 7.54 (s, 1H), 7.42 (s, 1H), 4.96 (d, J = 3.5 Hz, 1H), 4.41-4.36 (m, 1H), 3.63-3.54 (m, 6H), 3.49-3.46 (m, 1H), 2.59 (s, 3H), 2.05-1.98 (m, 1H), 1.92-1.86 (m, 1H). |

TABLE 4-continued

Examples 20 to 35 synthesized using general procedure D

| Example | Yield | LCMS Purity (%) | LCMS RT (mins) | m/z | LCMS method | 1H NMR |
|---|---|---|---|---|---|---|
| Example 27[8] 2'-chloro-N-[5-(1,1-dioxo-1$\lambda^6$-thiomorpholin-4-yl)-[1,3]thiazolo[5,4-d]pyrimidin-2-yl]-5'-methoxy-6-methyl-[4,4'-bipyridine]-3-carboxamide 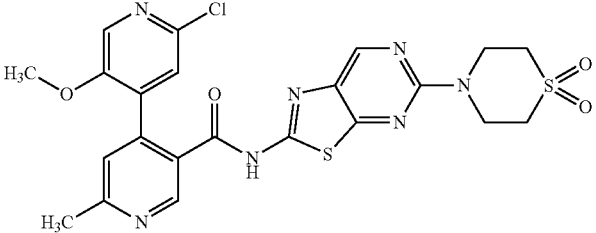 [SMILES: COc1cnc(Cl)cc1-c1cc(C)ncc1C(=O)Nc1nc2cnc(N3CCS(=O)(=O)CC3)nc2s1] | 9 | 100 | 2.78 | 546.1/ 548.0 | B | 1H NMR (400 MHz, DMSO-d$_6$) δ 12.98 (s, 1H), 8.87 (s, 1H), 8.16 (s, 1H), 7.56-7.37 (m, 3H), 4.23 (s, 4H), 3.61 (s, 3H), 3.17 (s, 4H), 2.59 (s, 3H). |
| Example 28[9] 2'-chloro-5'-methoxy-6-methyl-N-[5-(4-methylpiperazin-1-yl)-[1,3]thiazolo[5,4-d]pyrimidin-2-yl]-[4,4'-bipyridine]-3-carboxamide 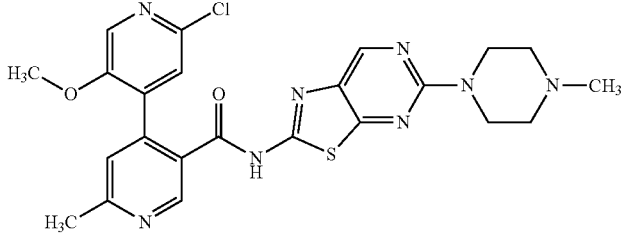 | 42 | 100 | 1.76 | 511/ 513.1 | B | 1H NMR (500 MHz, DMSO-d$_6$) δ 8.84 (s, 1H), 8.76 (s, 1H), 8.17 (s, 1H), 7.57 (s, 1H), 7.45 (s, 1H), 3.79-3.73 (m, 4H), 3.63 (s, 3H), 2.60 (s, 3H), 2.44-2.39 (m, 4H), 2.24 (s, 3H). |
| Example 29[10] 2'-chloro-5'-methoxy-6-methyl-N-(5-{2-oxa-6-azaspiro[3.3]heptan-6-yl}-[1,3]thiazolo[5,4-d]pyrimidin-2-yl)-[4,4'-bipyridine]-3-carboxamide 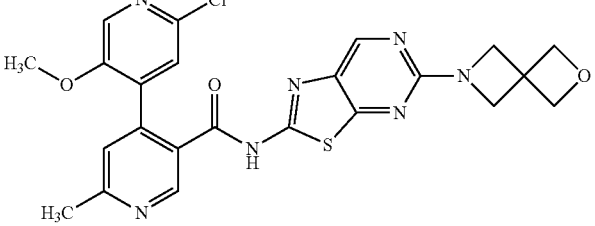 | 21 | 100 | 2.55 | 510.1/ 512.1 | B | 1H NMR (500 MHz, DMSO-d$_6$) δ 12.92 (s, 1H), 8.83 (s, 1H), 8.75 (s, 1H), 8.16 (s, 1H), 7.56 (s, 1H), 7.44 (s, 1H), 4.73 (s, 4H), 4.24 (s, 4H), 3.61 (s, 3H), 2.59 (s, 3H). |
| Example 30[11] 2'-chloro-5'-methoxy-N-{5-[(2-methoxyethyl)amino]-[1,3]thiazolo[5,4-d]pyrimidin-2-yl}-6-methyl-[4,4'-bipyridine]-3-carboxamide 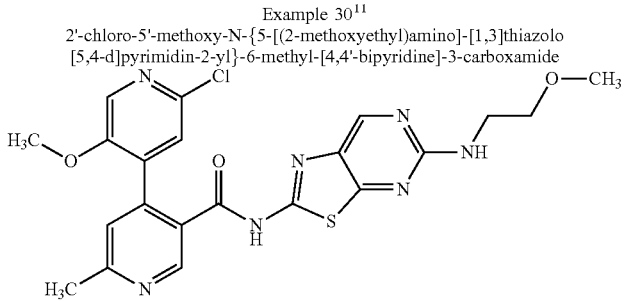 | 38 | 100 | 2.69 | 486.0/ 488.1 | B | 1H NMR (400 MHz, DMSO-d$_6$) δ 12.86 (s, 1H), 8.85 (s, 1H), 8.66 (s, 1H), 8.17 (s, 1H), 7.55 (s, 1H), 7.43 (s, 1H), 7.28 (s, 1H), 3.63 (s, 3H), 3.50-3.45 (m, 4H), 3.27 (s, 3H), 2.60 (s, 3H). |

TABLE 4-continued

Examples 20 to 35 synthesized using general procedure D

| Example | Yield | LCMS Purity (%) | LCMS RT (mins) | m/z | LCMS method | 1H NMR |
|---|---|---|---|---|---|---|
| Example 31[12] 2'-chloro-N-[5-(3-hydroxyazetidin-1-yl)-[1,3]thiazolo [5,4-d]pyrimidin-2-yl]-5'-methoxy-6-methyl-[4,'-bipyridine]-3-carboxamide | 7 | 100 | 2.27 | 484.1/ 486.0 | B | $^1$H NMR (500 MHz, DMSO-d$_6$) δ 12.87 (s, 1H), 8.88 (s, 1H), 8.64 (s, 1H), 8.15 (s, 1H), 7.50 (s, 1H), 7.37 (s, 1H), 5.67 (d, J = 6.7 Hz, 1H), 4.59-4.52 (m, 1H), 4.28-4.21 (m, 2H), 3.82-3.76 (m, 2H), 3.62 (s, 3H), 2.58 (s, 3H). |
| Example 32[13] 2'-chloro-5'-methoxy-N-[5-(3-methoxypyrrolidin-1-yl)-[1,3]thiazolo [5,4-d]pyrimidin-2-yl]-6-methyl-[4,4'-bipyridine]-3-carboxamide | 32 | 99 | 2.93 | 512.1/ 514.1 | B | $^1$H NMR (500 MHz, DMSO-d$_6$) δ 12.87 (s, 1H), 8.83 (s, 1H), 8.76 (s, 1H), 8.18 (s, 1H), 7.57 (s, 1H), 7.46 (s, 1H), 4.08 (s, 1H), 3.69-3.57 (m, 6H), 3.49 (q, J = 8.7 Hz, 1H), 3.27 (s, 3H), 2.60 (s, 3H), 2.10-2.04 (m, 2H) |
| Example 33[14] 2'-chloro-N-[5-(4-hydroxypiperidin-1-yl)-[1,3]thiazolo[5,4-d]pyrimidin-2-yl]-5'-methoxy-6-methyl-[4,4'-bipyridine]-3-carboxamide | 28 | 100 | 2.66 | 512.1/ 514.1 | B | $^1$H NMR (400 MHz, DMSO-d$_6$) δ 12.87 (s, 1H), 8.83 (s, 1H), 8.72 (s, 1H), 8.16 (s, 1H), 7.55 (s, 1H), 7.44 (s, 1H), 4.73 (d, J = 4.3 Hz, 1H), 4.33-4.22 (m, 2H), 3.74 (dq, J = 8.5, 4.1 Hz, 1H), 3.62 (s, 3H), 2.59 (s, 3H), 1.83-1.74 (m, 2H), 1.40-1.29 (m, 2H). |
| Example 34[15] 2'-chloro-5'-methoxy-6-methyl-N-{5-[(1S,4S)-2-oxa-5-azabicyclo[2.2.1]heptan-5-yl]-[1,3]thiazolo[5,4-d]pyrimidin-2-yl}-[4,4'-bipyridine]-3-carboxamide | 24 | 100 | 2.74 | 510.1/ 512.1 | B | $^1$H NMR (400 MHz, DMSO-d$_6$) δ 12.88 (s, 1H), 8.84 (s, 1H), 8.74 (s, 1H), 8.17 (s, 1H), 7.55 (s, 1H), 7.44 (s, 1H), 4.96 (s, 1H), 4.67 (s, 1H), 3.81 (d, J = 5.8 Hz, 1H), 3.68 (d, J = 7.3 Hz, 1H), 3.62 (s, 3H), 3.52 (d, J = 9.3 Hz, 1H), 3.42 (d, J = 11.4 Hz, 1H), 2.59 (s, 3H), 1.94 (d, J = 7.3 Hz, 1H), 1.87 (d, J = 9.5 Hz, 1H) |

TABLE 4-continued

Examples 20 to 35 synthesized using general procedure D

| Example | Yield | LCMS Purity (%) | LCMS RT (mins) | m/z | LCMS method | 1H NMR |
|---|---|---|---|---|---|---|
| Example 35[16]<br>2'-chloro-N-[5-(3-cyanopiperidin-1-yl)-[1,3]thiazolo[5,4-d]pyrimidin-2-yl]-5'-methoxy-6-methyl-[4,4'-bipyridine]-3-carboxamide | 18 | 100 | 3.27 | 521.1/ 523.1 | B | 1H NMR (400 MHz, DMSO-d6) δ 12.93 (s, 1H), 8.84 (s, 1H), 8.78 (s, 1H), 8.16 (s, 1H), 7.56 (s, 1H), 7.45 (s, 1H), 4.24-4.17 (m, 1H), 4.02-3.94 (m, 1H), 3.90-3.84 (m, 1H), 3.68-3.63 (m, 1H), 3.62 (s, 3H), 3.14-3.08 (m, 1H), 2.59 (s, 3H), 1.99-1.88 (m, 2H), 1.72-1.55 (m, 2H). |

TABLE 5

Reaction solvent and temperature used in the preparation of the Examples in Table 4 above

| Footnote in Table 4 above | Reaction Solvent | Reaction Temp (° C.) |
|---|---|---|
| 1 | DMF | 80 |
| 2 | Ethanol/DCE | 80 |
| 3 | Ethanol/DCE | 80 |
| 4 | Ethanol/DCE | 80 |
| 5 | Ethanol/DCE | 80 |
| 6 | Ethanol/DCE | 80 |
| 7 | Ethanol/DCE | 80 |
| 8 | Ethanol/DCE | 80 |
| 9 | Ethanol/DCE | 80 |
| 10 | Ethanol/DCE | 80 |
| 11 | n-Butanol | 100 |
| 12 | Ethanol | 80 |
| 13 | Ethanol | 80 |
| 14 | DMF | 80 |
| 15 | Ethanol | 80 |
| 16 | Ethanol/DCE | 80 |

Examples 36A and 36B—Synthesis of 2'-chloro-5'-methoxy-6-methyl-N-[6-(2-oxopiperidin-1-yl)-1,3-benzothiazol-2-yl]-[4,4'-bipyridine]-3-carboxamide

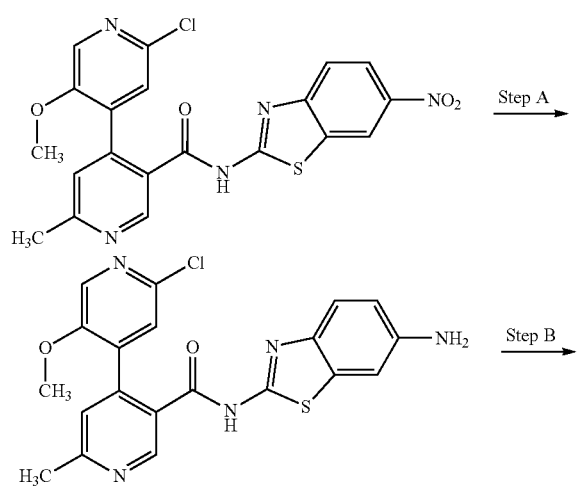

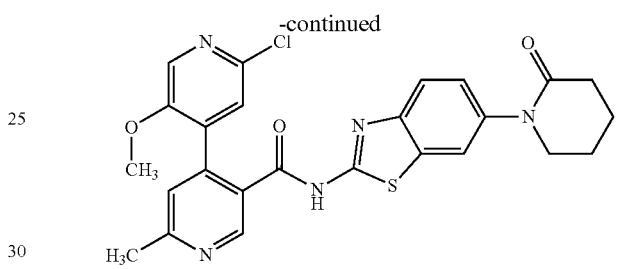

Step A—N-(6-amino-1,3-benzothiazol-2-yl)-4-(2-chloro-5-methoxy-4-pyridyl)-6-methyl-pyridine-3-carboxamide (Example 36A)

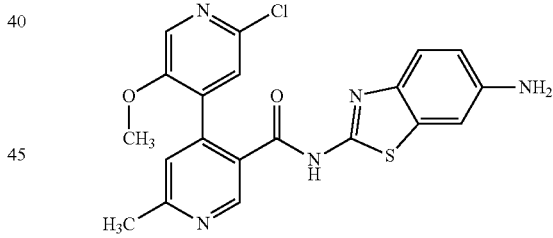

A stirred solution of 4-(2-chloro-5-methoxy-4-pyridyl)-6-methyl-N-(6-nitro-1,3-benzothiazol-2-yl)pyridine-3-carboxamide (1.1 g, 2.41 mmol, prepared using general procedure C) in ethanol (11 mL) and water (4.4 mL) was flushed with nitrogen for 5 minutes then iron powder (0.9 g, 16.1 mmol) and solid ammonium chloride (1.2 g, 22.4 mmol) were added. The reaction mixture was stirred at 60° C. for 30 min then filtered through a pad of celite, washing with ethyl acetate (20 mL), and the resultant filtrate was washed with water (15 mL). The organic layer was separated, dried (Na2SO4) and concentrated under reduced pressure. The residue was purified by Biotage Isolera™ automated chromatography (Sfar Duo 10 g) using a gradient of 0-10% methanol in DCM to give the title compound (454 mg, 44% yield) as a yellow-brown solid. 1H NMR (400 MHz, DMSO-d6) δ 12.59 (s, 1H), 8.82 (s, 1H), 8.17 (s, 1H), 7.55 (s, 1H), 7.46-7.41 (m, 2H), 7.00 (d, J=2.2 Hz, 1H), 6.73 (dd, J=8.6, 2.3 Hz, 1H), 5.17 (s, 2H), 3.62 (s, 3H), 2.60 (s, 3H). LCMS (method B); RT 1.93 mins (99%), m/z 424.5/426.5 (M+H)+

Step B 2'-chloro-5'-methoxy-6-methyl-N-[6-(2-oxopiperidin-1-yl)-1,3-benzothiazol-2-yl]-[4,4'-bipyridine]-3-carboxamide (Example 36B)

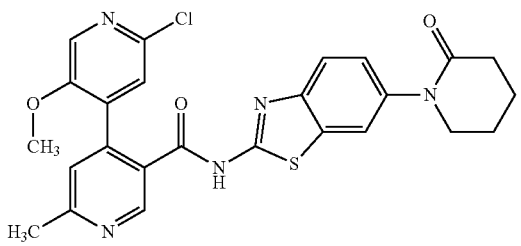 [SMILES: COc1cnc(Cl)cc1-c1cc(C)ncc1C(=O)Nc1nc2ccc(N3CCCCC3=O)cc2s1]

To an ice-cooled stirred solution of N-(6-amino-1,3-benzothiazol-2-yl)-4-(2-chloro-5-methoxy-4-pyridyl)-6-methyl-pyridine-3-carboxamide (30.0 mg, 0.07 mmol) and DIPEA (12 μL, 0.07 mmol) in THF (0.6 mL) was added a solution of 5-bromopentanoyl chloride (11 μL, 0.08 mmol) in THF (0.6 mL) dropwise and the reaction mixture was stirred for 15 min. It was then treated portion-wise with potassium tert-butoxide (30.0 mg, 0.27 mmol). Stirring was continued for 30 min. The mixture was treated with water (5 mL) and brine (5 mL) and the mixture was extracted with ethyl acetate (2×15 mL). The combined organic extracts were dried (MgSO4), filtered and evaporated under reduced pressure. The crude product was purified by prep HPLC method A. Product containing fractions were evaporated under reduced pressure and freeze-dried to give the title compound (6.8 mg, 19% yield) as a white powder. $^1$H NMR (500 MHz, DMSO-$d_6$) δ 12.97 (s, 1H), 8.87 (s, 1H), 8.16 (s, 1H), 7.87 (s, 1H), 7.75 (d, J=8.6 Hz, 1H), 7.58 (s, 1H), 7.46 (s, 1H), 7.34 (dd, J=8.5, 2.1 Hz, 1H), 3.64 (t, J=5.7 Hz, 2H), 3.60 (s, 3H), 2.61 (s, 3H), 2.41 (t, J=6.3 Hz, 2H), 1.92-1.83 (m, 4H). LCMS (method B); RT 2.79 mins (100%), m/z 508.2/510.1 (M+H)+.

Example 37—Synthesis of 2'-chloro-N-[5-(5,6-dihydro-2H-pyran-3-yl)-[1,3]thiazolo[5,4-b]pyridin-2-yl]-5'-methoxy-6-methyl-[4,4'-bipyridine]-3-carboxamide

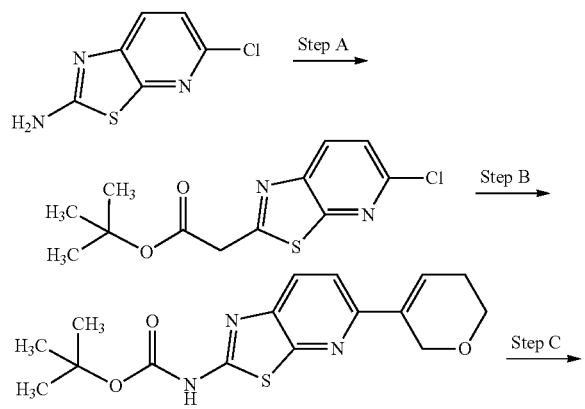

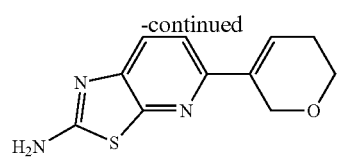

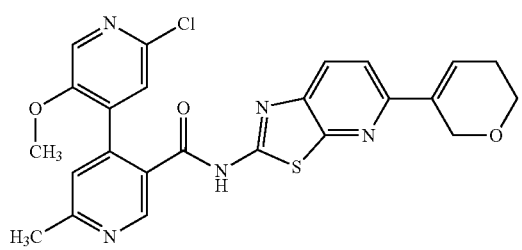 [SMILES: COc1cnc(Cl)cc1-c1cc(C)ncc1C(=O)Nc1nc2ccc(C3=CCCOC3)nc2s1]

Step A tert-butyl N-(5-chlorothiazolo[5,4-b]pyridin-2-yl)carbamate

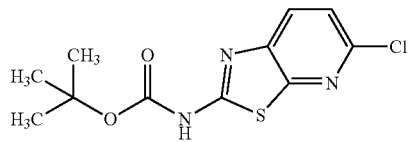 [SMILES: CC(C)(C)OC(=O)Nc1nc2ccc(Br)cc2s1]

To a solution of 5-chlorothiazolo[5,4-b]pyridin-2-amine (100 mg, 0.54 mmol) in DCE (2.5 mL), DIPEA (0.20 mL, 1.15 mmol) and N,N-dimethylpyridin-4-amine (6.17 mg, 0.05 mmol) was added at room temperature. To the prior solution, di-tert-butyl dicarbonate (124 mg, 0.57 mmol) was added and the resulting mixture was stirred at room temperature for 4 h. Another 0.5 equiv of N,N-dimethylpyridin-4-amine and di-tert-butyl dicarbonate were added and stirring continued for 18 h. The mixture was diluted with DCM and washed with water and brine solution (10 mL). Combined organic extracts were dried (Na2SO4) and concentrated under reduced pressure. The crude product was purified by Biotage Isolera™ automated chromatography (10 g, Sfar Duo) eluting with 0-50% ethyl acetate in heptanes to give the title compound (137 mg, 89% yield) as a colourless powder. $^1$H NMR (500 MHz, DMSO-$d_6$) δ 12.09 (s, 1H), 8.08 (d, J=8.5 Hz, 1H), 7.52 (d, J=8.4 Hz, 1H), 1.52 (s, 9H). LCMS (method A); 0.97 mins (100%), m/z 230.0/232.0 (M-$^t$Bu+H)+.

Step B tert-butyl N-[5-(3,6-dihydro-2H-pyran-5-yl)thiazolo[5,4-b]pyridin-2-yl]carbamate

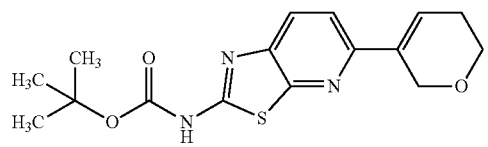

To a solution of tert-butyl N-(5-chlorothiazolo[5,4-b]pyridin-2-yl)carbamate (130 mg, 0.46 mmol) in 1,4-dioxane (1.8 mL) and water (0.45 mL) in a pressure vial were added 2-(3,6-dihydro-2H-pyran-5-yl)-4,4,5,5-tetramethyl-1,3,2-dioxaborolane (115 mg, 0.55 mmol) and dipotassium carbonate (157 mg, 1.14 mmol). The mixture was degassed under nitrogen before palladium dichloride DTBPF (30 mg, 0.05 mmol) was added, and the mixture was stirred at 90° C. for 3 h. The reaction mixture was cooled to RT and diluted with ethyl acetate (20 mL). The solution was washed with water and brine solution (10 mL) then dried (Na$_2$SO$_4$) and concentrated under reduced pressure. The crude product was purified by Biotage Isolera™ automated chromatography (25 g, Sfar Duo) eluting with 0-50% ethyl acetate in heptanes to give the title compound (92 mg, 58% yield) as a colourless powder. $^1$H NMR (500 MHz, DMSO-d$_6$) δ 11.91 (s, 1H), 7.97 (d, J=8.6 Hz, 1H), 7.64 (d, J=8.6 Hz, 1H), 6.82-6.78 (m, 1H), 4.58-4.54 (m, 2H), 3.75 (t, J=5.5 Hz, 2H), 2.33-2.29 (m, 2H), 1.52 (s, 9H). LCMS (method A); RT 0.96 mins (96%), m/z 334.1 (M+H)$^+$.

Step C (3,6-dihydro-2H-pyran-5-yl)thiazolo[5,4-b]pyridin-2-amine

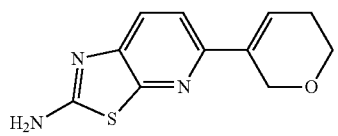

To a solution of tert-butyl N-[5-(3,6-dihydro-2H-pyran-5-yl)thiazolo[5,4-b]pyridin-2-yl]carbamate (20.0 mg, 0.06 mmol) in acetonitrile (0.25 mL) was added 4 M hydrogen chloride in 1,4-dioxane (0.22 mL, 0.86 mmol) and the mixture stirred at RT for 18 h.

The reaction mixture was concentrated under reduced pressure and the residue dissolved in 1:1 DCM/methanol (0.5 mL). 4 M hydrogen chloride in 1,4-dioxane (0.22 mL, 0.86 mmol) was added.

The mixture was left to stir at RT for 72 h. The reaction mixture was concentrated under reduced pressure and the resulting solid dissolved in methanol and loaded onto a 1 g SCX ion exchange cartridge. The cartridge was flushed with methanol (5 mL) and then 2M ammonia in methanol (5 mL). The ammonia filtrate was concentrated under reduced pressure to give (12 mg, 80% yield) as a colourless powder, which was used immediately without further purification. LCMS (method A) RT 0.60 mins (87%), m/z 234.5 (M+H)$^+$.

Step D 4-(2-chloro-5-methoxy-4-pyridyl)-N-[5-(3,6-dihydro-2H-pyran-5-yl)thiazolo[5,4-b]pyridin-2-yl]-6-methyl-pyridine-3-carboxamide

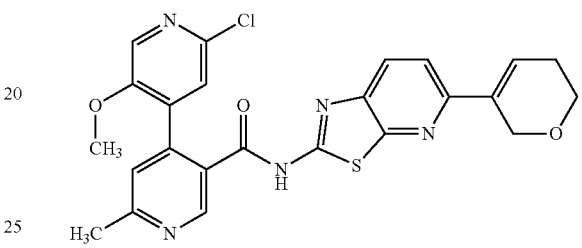

Prepared using general procedure C detailed above to give the title compound (3.5 mg, 15% yield) as a colourless powder. $^1$H NMR (500 MHz, DMSO-d$_6$) δ 13.05 (s, 1H), 8.85 (s, 1H), 8.16 (s, 1H), 8.08 (d, J=8.5 Hz, 1H), 7.72 (d, J=8.6 Hz, 1H), 7.58 (s, 1H), 7.47 (s, 1H), 6.87-6.80 (m, 1H), 4.58 (d, J=2.3 Hz, 2H), 3.75 (t, J=5.5 Hz, 2H), 3.61 (s, 3H), 2.60 (s, 3H), 2.34-2.31 (m, 2H). LCMS (method B) RT 3.22 mins (100%) m/z 494.1/496.1 (M+H)$^+$.

Example 38—Synthesis of 2'-chloro-N-[6-(5-chloropyridin-2-yl)-1,3-benzothiazol-2-yl]-5'-methoxy-6-methyl-[4,4'-bipyridine]-3-carboxamide

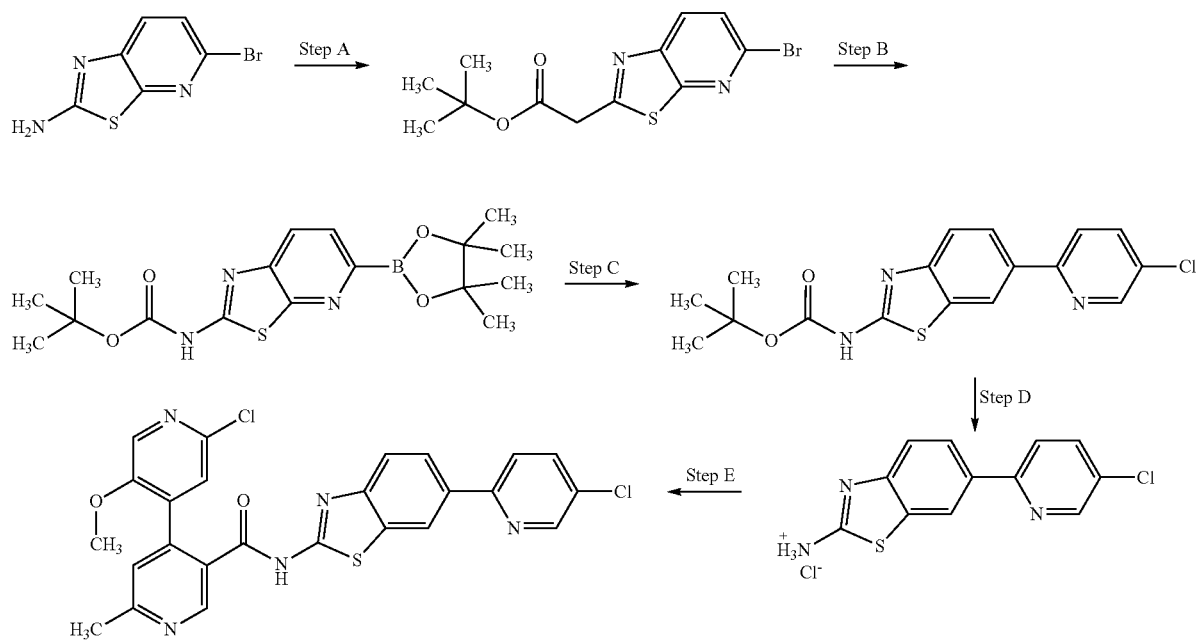

Step A tert-butyl N-(6-bromo-1,3-benzothiazol-2-yl)carbamate

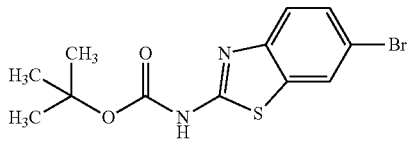

Prepared in an analogous manner to N-(5-chlorothiazolo[5,4-b]pyridin-2-yl)carbamate detailed above to give the title compound (665 mg, 58% yield) as a light orange solid. $^1$H NMR (400 MHz, DMSO-$d_6$) δ 8.18 (d, J=2.0 Hz, 1H), 7.60 (d, J=8.5 Hz, 1H), 7.52 (dd, J=8.5, 2.0 Hz, 1H), 1.51 (s, 9H). LCMS (method B) RT 4.09 mins (74%), m/z 329.0/331.0 (M+H)$^+$.

Step B tert-butyl N-[6-(4,4,5,5-tetramethyl-1,3,2-dioxaborolan-2-yl)-1,3-benzothiazol-2-yl]carbamate)

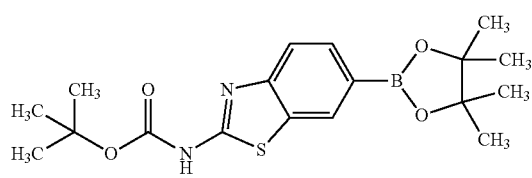 [SMILES: CC(C)(C)OC(=O)Nc1nc2ccc(B3OC(C)(C)C(C)(C)O3)cc2s1]

To a solution of tert-butyl N-(6-bromo-1,3-benzothiazol-2-yl)carbamate (150 mg, 0.46 mmol) in 1,4-dioxane (2.5 mL) in a pressure vial were added 4,4,4',4',5,5,5',5'-octamethyl-2,2'-bi-1,3,2-dioxaborolane (231 mg, 0.91 mmol) and potassium acetate (223 mg, 2.28 mmol). The mixture was degassed under nitrogen before palladium dichloride DPPF (33 mg, 0.05 mmol) was added. The mixture was stirred at 90° C. for 3 h. The reaction mixture was cooled to RT and filtered through celite. The celite pad was washed with ethyl acetate and the filtrate purified by Biotage Isolera™ automated chromatography (25 g, Sfar duo) eluting with 0-50% ethyl acetate in heptanes to give the title compound (210 mg, 86% yield) as a pale yellow glass that began to crystallise on standing at RT. $^1$H NMR (400 MHz, DMSO-$d_6$) δ 11.85 (br s, 1H), 8.22 (s, 1H), 7.68-7.63 (m, 2H), 1.51 (s, 9H), 1.31 (s, 12H). LCMS (method A); RT 1.16 mins (100%), m/z 377.2 (M+H)$^+$.

Step C tert-butyl N-[6-(5-chloro-2-pyridyl)-1,3-benzothiazol-2-yl]carbamate

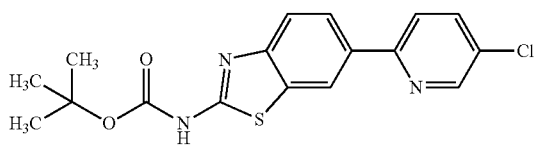 [SMILES: CC(C)(C)OC(=O)Nc1nc2ccc(-c3ccc(Cl)cn3)cc2s1]

To a solution of tert-butyl N-[6-(4,4,5,5-tetramethyl-1,3,2-dioxaborolan-2-yl)-1,3-benzothiazol-2-yl]carbamate (210 mg, 0.39 mmol) in 1,4-dioxane (1.6 mL) and water (0.4 mL) in a pressure vial were added 2-bromo-5-chloropyridine (98 mg, 0.51 mmol) and dipotassium carbonate (135 mg, 0.98 mmol). The mixture was degassed under nitrogen before palladium dichloride DTBPF (26 mg, 0.04 mmol) was added. The mixture was stirred at 90° C. for 3 h. The reaction was cooled to RT and diluted with ethyl acetate (20 mL) and washed with water and brine (10 mL). After the organic layer was separated a precipitate began to form. The solution was cooled in an ice bath for 30 mins then the precipitate filtered. The filter cake was washed with ether and dried under a flow of nitrogen. LCMS showed the solid to be pure product (45 mg). The filtrate was concentrated under reduced pressure and purified by Biotage Isolera™ automated chromatography (25 g, Sfar Duo) eluting with 0-100% ethyl acetate in heptanes to give a second crop of product. Both crops were combined to give the title compound (109 mg, 77% yield) as a beige powder. $^1$H NMR (500 MHz, DMSO-$d_6$) δ 11.88 (br s, 1H), 8.70 (d, J=2.5 Hz, 1H), 8.67 (d, J=1.9 Hz, 1H), 8.13 (dd, J=8.5, 1.9 Hz, 1H), 8.07 (d, J=8.7 Hz, 1H), 8.01 (dd, J=8.6, 2.5 Hz, 1H), 7.75 (d, J=8.5 Hz, 1H), 1.52 (s, 9H). LCMS (method A); RT 1.15 mins, m/z 362.364.0 (M+H)$^+$.

Step D 6-(5-chloro-2-pyridyl)-1,3-benzothiazol-2-amine; Dihydrochloride

To a suspension of tert-butyl N-[6-(5-chloro-2-pyridyl)-1,3-benzothiazol-2-yl]carbamate (109 mg, 0.3 mmol) in 1,4-dioxane (0.5 mL) at 0° C. was added 4 M hydrogen chloride in 1,4-dioxane (1.1 mL, 4.52 mmol) dropwise. Once addition was complete the mixture was warmed to RT and stirred for 18 h. The starting material had precipitated from solution. 1 mL of acetonitrile was added to aid solubility and stirring continued for 24 h. The mixture was concentrated under reduced pressure and the residue azeotropically dried with diethyl ether to give the title compound (109 mg, quantitative yield) as a colourless powder, which was used immediately without further purification. LCMS (method A); RT 0.75 mins (100%) m/z 262.1/264.1 (M+H)$^+$.

Step E 4-(2-chloro-5-methoxy-4-pyridyl)-N-[6-(5-chloro-2-pyridyl)-1,3-benzothiazol-2-yl]-6-methyl-pyridine-3-carboxamide

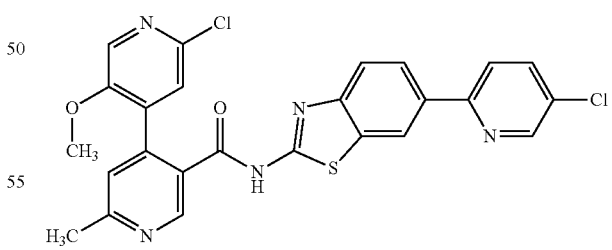

Prepared using general procedure C detailed above to give the title compound (83 mg, 54% yield) as a colourless powder. $^1$H NMR (500 MHz, DMSO-$d_6$) δ 13.08 (s, 1H), 8.87 (s, 1H), 8.73-8.70 (m, 2H), 8.20 (dd, J=8.5, 1.9 Hz, 1H), 8.17 (s, 1H), 8.09 (d, J=8.6 Hz, 1H), 8.03 (dd, J=8.6, 2.5 Hz, 1H), 7.86 (d, J=8.5 Hz, 1H), 7.59 (s, 1H), 7.47 (s, 1H), 3.61 (s, 3H), 2.61 (s, 3H). LCMS (method B); RT 3.92 mins (100%) m/z 522/524 (M+H)$^+$.

Example 39—Synthesis of N-[6-(5-chloropyridin-2-yl)-1,3-benzothiazol-2-yl]-3-(2-methoxyphenyl)pyridine-4-carboxamide

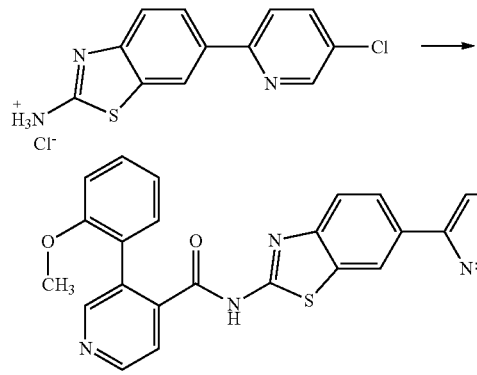

Synthesised using general procedure C from 6-(5-chloropyridin-2-yl)-1,3-benzothiazol-2-amine hydrochloride, prepared in an analogous manner to that shown above, to give the title compound (40 mg, 19% yield) as a colourless powder. $^1$H NMR (500 MHz, DMSO-$d_6$) δ 12.96 (br s, 1H), 8.5-8.9 (m, 4H), 8.19 (dd, 1H, J=1.8, 8.6 Hz), 8.0-8.1 (m, 1H), 8.02 (dd, 1H, J=2.6, 8.6 Hz), 7.85 (d, 1H, J=8.5 Hz), 7.69 (d, 1H, J=4.8 Hz), 7.3-7.4 (m, 2H), 7.0-7.1 (m, 1H), 6.9-7.0 (m, 1H), 3.4-3.6 (m, 3H). LCMS (method B) RT 2.72 mins (87%), m/z 473.1/475.1 (M+H)$^+$.

Example 40—Synthesis of 2'-chloro-N-[6-(3-hydroxyoxolan-3-yl)-1,3-benzothiazol-2-yl]-5'-methoxy-6-methyl-[4,4'-bipyridine]-3-carboxamide

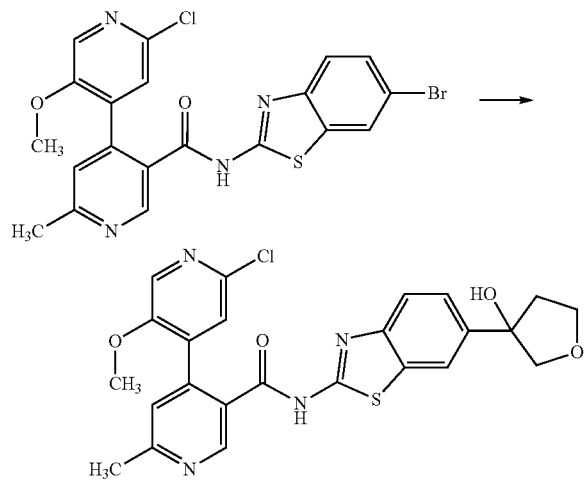

1.6 M butyllithium in hexane (50 μL, 0.08 mmol) was added dropwise to a solution of N-(6-bromo-1,3-benzothiazol-2-yl)-4-(2-chloro-5-methoxy-4-pyridyl)-6-methyl-pyridine-3-carboxamide (16 mg, 0.03 mmol, prepared using general procedure C detailed above) in THF (0.5 mL) at −78° C. The reaction mixture was stirred at −78° C. for a further 15 min. Then dihydrofuran-3(2H)-one (4.0 mg, 0.05 mmol) was added dropwise as a solution in THF (0.2 mL) to the reaction mixture and stirred for 2 h at −78° C. Sat. aqueous ammonium chloride solution was added (10 mL) and the mixture extracted with diethyl ether (2×10 mL) and ethyl acetate (1×10 mL) due to poor solubility of product. Organic extracts were combined, dried (Na$_2$SO$_4$), filtered and evaporated under reduced pressure. The crude product was purified by Biotage Isolera™ automated chromatography (Sfar Duo, 10 g) eluting with a gradient of 0-100% ethyl acetate in heptanes increasing to 10% methanol in ethyl acetate. Product containing fractions were concentrated under reduced pressure and the product purified further by prep HPLC method A to give the title compound (1.6 mg, 8% yield) as a white powder. $^1$H NMR (400 MHz, CDCl$_3$) δ 8.89 (s, 1H), 8.05 (s, 1H), 7.85-7.81 (m, 1H), 7.46-7.39 (m, 1H), 7.36-7.32 (m, 2H), 7.21 (d, J=3.0 Hz, 2H), 4.08-3.91 (m, 2H), 3.76-3.72 (m, 4H), 3.66 (d, J=9.2 Hz, 1H), 2.06-1.98 (m, 2H). LCMS (method B); RT 2.91 mins (86%), m/z 497.2/499.2 (M+H)$^+$.

Example 41—Synthesis of 2'-chloro-N-(6-methanesulfonamido-1,3-benzothiazol-2-yl)-5'-methoxy-6-methyl-[4,4'-bipyridine]-3-carboxamide

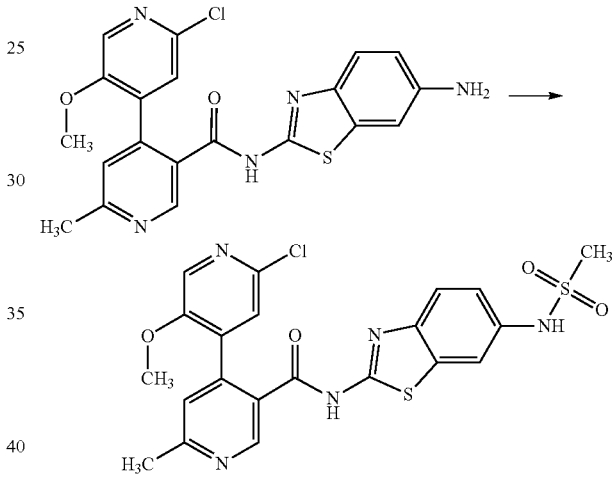

To a solution of N-(6-amino-1,3-benzothiazol-2-yl)-4-(2-chloro-5-methoxy-4-pyridyl)-6-methyl-pyridine-3-carboxamide (30.0 mg, 0.07 mmol), prepared in an analogous manner to that shown above, and DIPEA (15 μL, 0.08 mmol) in DCM (0.5 mL) was added methane sulfonyl chloride (6 μL, 0.08 mmol) at 0° C. Once addition was complete the reaction mixture was warmed to RT and stirred for 4 h. Another 1.2 equiv of DIPEA and methane sulfonyl chloride were added and the reaction continued at RT for 2 h. The mixture was diluted with DCM and washed with sat. aqueous NaHCO$_3$ solution. Organic extracts were dried (Na$_2$SO$_4$) and concentrated to give the crude product as a yellow glass. The crude was purified by prep HPLC method A to give the title compound (10 mg, 28% yield) as a colourless powder. $^1$H NMR (500 MHz, DMSO-$d_6$) δ 12.90 (s, 1H), 9.77 (s, 1H), 8.84 (s, 1H), 8.15 (s, 1H), 7.78 (s, 1H), 7.72 (d, J=8.8 Hz, 1H), 7.57 (s, 1H), 7.45 (s, 1H), 7.30 (d, J=8.8 Hz, 1H), 3.60 (s, 3H), 2.99 (s, 3H), 2.60 (s, 3H). LCMS (method B); RT 2.63 mins (100%) m/z 504.0/506.0 (M+H)$^+$.

Examples 42 to 44

Examples 42 to 4 listed in table 6 below were synthesised using general procedure C previously described.

TABLE 6

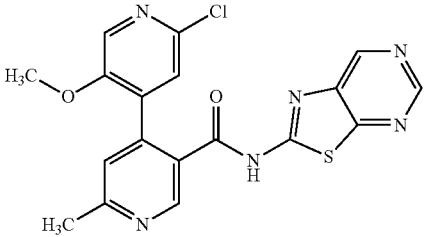 [SMILES: COc1cnc(Cl)cc1-c1cc(C)ncc1C(=O)Nc1nc2cncnc2s1]

| Example | Yield | LCMS Purity (%) | LCMS RT (mins) | m/z | LCMS method | 1H NMR |
|---|---|---|---|---|---|---|
| Example 42 2'-chloro-5'-methoxy-6-methyl-N-{[1,3]thiazolo[5,4-d]pyrimidin-2-yl}-[4,4'-bipyridine]-3-carboxamide | 6 | 100 | 2.46 | 413.0/ 415.0 | B | $^1$H NMR (500 MHz, DMSO-d$_6$) δ 13.38 (s, 1H), 9.15-8.89 (m, 3H), 8.15 (s, 1H), 7.53 (s, 1H), 7.40 (s, 1H), 3.61 (s, 3H), 2.59 (s, 3H). |
| Example 43 2'-chloro-5'-methoxy-6-methyl-N-[6-(methylsulfanyl)-1,3-benzothiazol-2-yl]-[4,4'-bipyridine]-3-carboxamide | 14 | 100 | 3.47 | 457.0/ 459.0 | B | $^1$H NMR (400 MHz, DMSO-d$_6$) δ 12.93 (s, 1H), 8.84 (s, 1H), 8.16 (s, 1H), 7.91 (d, J = 2.0 Hz, 1H), 7.69 (d, J = 8.5 Hz, 1H), 7.57 (s, 1H), 7.46 (s, 1H), 7.36 (dd, J = 8.6, 1.9 Hz, 1H), 3.59 (s, 3H), 2.60 (s, 3H), 2.53 (s, 3H). |
| Example 44 2'-chloro-5'-methoxy-6-methyl-N-{[1,3]thiazolo[5,4-c]pyridin-2-yl}-[4,4'-bipyridine]-3-carboxamide | 24 | 100 | 1.11 | 412.0/ 414.0 | D | $^1$H NMR (500 MHz, DMSO-d$_6$) δ 13.09 (s, 1H), 8.87 (s, 1H), 8.49 (dd, J = 4.7, 1.5 Hz, 1H), 8.17 (s, 1H), 8.14 (d, J = 8.2 Hz, 1H), 7.59 (s, 1H), 7.51 (dd, J = 8.2, 4.7 Hz, 1H), 7.47 (s, 1H), 3.62 (s, 3H), 2.61 (s, 3H). |

Examples 45 to 53

Examples 45 to 53 and intermediates 7 and 8 in table 7 below were synthesised using general procedure D previously described, using conditions described in the footnote table 8.

TABLE 7

| Example | Yield | LCMS Purity (%) | LCMS RT (mins) | m/z | LCMS method | 1H NMR |
|---|---|---|---|---|---|---|
| Example 45[3]<br>N-[5-(4-acetylpiperazin-1-yl)-[1,3]thiazolo[5,4-d]pyrimidin-2-yl]-2'-chloro-5'-methoxy-6-methyl-[4,4'-bipyridine]-3-carboxamide | 35 | 100 | 2.66 | 539.1/ 541.1 | B | ¹H NMR (400 MHz, DMSO-d₆) δ 12.82 (s, 1H), 8.83 (s, 1H), 8.79 (s, 1H), 8.17 (s, 1H), 7.57 (s, 1H), 7.45 (s, 1H), 3.85-3.77 (m, 2H), 3.77-3.71 (m, 2H), 3.62 (s, 3H), 3.57-3.50 (m, 4H), 2.60 (s, 3H), 2.05 (s, 3H). |
| Example 46[2]<br>2'-chloro-N-{5-[(2-hydroxyethyl)amino]-[1,3]thiazolo[5,4-d]pyrimidin-2-yl}-5'-methoxy-6-methyl-[4,4'-bipyridine]-3-carboxamide | 6 | 97 | 2.24 | 472.1/ 474.1 | B | ¹H NMR (400 MHz, DMSO-d₆) δ 8.87 (s, 1H), 8.58 (s, 1H), 8.15 (s, 1H), 7.50 (s, 1H), 7.37 (s, 1H), 7.11-7.03 (m, 1H), 4.67 (s, 1H), 3.63 (s, 3H), 3.52 (t, J = 6.3 Hz, 2H), 2.58 (s, 3H), one methylene obscured by water peak and one exchangeable proton not observed. |
| Example 47[4]<br>2'-chloro-5'-methoxy-N-[5-(3-methoxyazetidin-1-yl)-[1,3]thiazolo[5,4-d]pyrimidin-2-yl]-6-methyl-[4,4'-bipyridine]-3-carboxamide | 46 | 99 | 2.74 | 498.1/ 500.1 | B | ¹H NMR (400 MHz, DMSO-d₆) δ 12.92 (s, 1H), 8.86 (s, 1H), 8.72 (s, 1H), 8.17 (s, 1H), 7.54 (s, 1H), 7.42 (s, 1H), 4.35-4.29 (m, 1H), 4.26 (dd, J = 8.6, 6.5 Hz, 2H), 3.89 (dd, J = 10.1, 3.7 Hz, 2H), 3.63 (s, 3H), 3.26 (s, 3H), 2.59 (s, 3H). |
| Example 48[2]<br>2'-chloro-N-{5-[(4-hydroxycyclohexyl)amino]-[1,3]thiazolo[5,4-d]pyrimidin-2-yl}-5'-methoxy-6-methyl-[4,4'-bipyridine]-3-carboxamide | 13 | 100 | 2.42 | 526.1/ 528.1 | B | ¹H NMR (500 MHz, DMSO-d₆) δ 12.80 (s, 1H), 8.84 (s, 1H), 8.60 (s, 1H), 8.21-8.06 (m, 1H), 7.51 (s, 1H), 7.39 (s, 1H), 7.22-6.96 (m, 1H), 4.52 (d, J = 4.4 Hz, 1H), 3.72-3.38 (m, 5H), 2.57 (s, 3H), 1.95-1.76 (m, 4H), 1.32-1.16 (m, 4H). |

TABLE 7-continued

| Example | Yield | LCMS Purity (%) | LCMS RT (mins) | m/z | LCMS method | 1H NMR |
|---|---|---|---|---|---|---|
| Example 49[2] rac-2'-chloro-N-(5-{[(1R,3S)-3-hydroxycyclopentyl]amino}-[1,3]thiazolo[5,4-d]pyrimidin-2-yl)-5'-methoxy-6-methyl-[4,4'-bipyridine]-3-carboxamide | 18 | 100 | 2.50 | 512.1/ 514.1 | B | 1H NMR (500 MHz, DMSO-$d_6$) δ 12.83 (s, 1H), 8.84 (s, 1H), 8.65 (s, 1H), 8.29-8.05 (m, 1H), 7.55 (s, 1H), 7.43 (s, 1H), 7.22 (s, 1H), 4.64 (d, J = 4.1 Hz, 1H), 4.22-4.14 (m, 1H), 4.14-4.08 (m, 1H), 3.63 (s, 3H), 2.59 (s, 3H), 2.25-2.11 (m, 1H), 1.98-1.84 (m, 1H), 1.80-1.71 (m, 1H), 1.68-1.53 (m, 2H), 1.50-1.40 (m, 1H). |
| Example 50[5] 2'-chloro-5'-methoxy-6-methyl-N-{5-[(3R)-3-methylmorpholin-4-yl]-[1,3]thiazolo[5,4-d]pyrimidin-2-yl}-[4,4'-bipyridine]-3-carboxamide | 12 | 95 | 3.18 | 512.1/ 514.1 | B | 1H NMR (500 MHz, DMSO-$d_6$) δ 12.90 (s, 1H), 8.83 (s, 1H), 8.78 (s, 1H), 8.16 (s, 1H), 7.56 (s, 1H), 7.45 (s, 1H), 4.66-4.60 (m, 1H), 4.24 (d, J = 11.9 Hz, 1H), 3.95-3.90 (m, 1H), 3.72 (d, J = 11.4 Hz, 1H), 3.62 (s, 3H), 3.61-3.57 (m, 1H), 3.47-3.40 (m, 1H), 3.20 (dd, J = 13.2, 3.3 Hz, 1H), 2.59 (s, 3H), 1.19 (d, J = 6.9 Hz, 3H). |
| Example 51[5] 2'-chloro-5'-methoxy-6-methyl-N-{5-[(3S)-3-methylmorpholin-4-yl]-[1,3]thiazolo[5,4-d]pyrimidin-2-yl}-[4,4'-bipyridine]-3-carboxamide | 14 | 96 | 3.18 | 512.1/ 514.1 | B | 1H NMR (500 MHz, DMSO-$d_6$) δ 12.91 (s, 1H), 8.82 (s, 1H), 8.80 (s, 1H), 8.17 (s, 1H), 7.57 (s, 1H), 7.46 (s, 1H), 4.63 (dd, J = 6.9, 2.9 Hz, 1H), 4.24 (dd, J = 13.6, 2.9 Hz, 1H), 3.93 (dd, J = 11.1, 3.7 Hz, 1H), 3.72 (d, J = 11.4 Hz, 1H), 3.62 (s, 3H), 3.61-3.57 (m, 1H), 3.44 (td, J = 11.4, 3.1 Hz, 1H), 3.23-3.16 (m, 1H), 2.60 (s, 3H), 1.20 (d, J = 6.7 Hz, 3H). |

TABLE 7-continued

| Example | Yield | LCMS Purity (%) | LCMS RT (mins) | m/z | LCMS method | 1H NMR |
|---|---|---|---|---|---|---|
| Example 52[5]<br>2'-chloro-5'-methoxy-6-methyl-N-{5-[(propan-2-yl)amino]-[1,3]thiazolo[5,4-d]pyrimidin-2-yl}-[4,4'-bipyridine]-3-carboxamide | 3 | 97 | 2.07 | 470.3/ 472.3 | B | 1H NMR (500 MHz, DMSO-d6) δ 12.83 (s, 1H), 8.84 (s, 1H), 8.65 (s, 1H), 8.16 (s, 1H), 7.53 (s, 1H), 7.42 (s, 1H), 7.20 (s, 1H), 4.09-4.01 (m, 1H), 3.63 (s, 3H), 2.59 (s, 3H), 1.16 (d, J = 6.6 Hz, 6H). |
| Example 53[1]<br>2'-chloro-5'-methoxy-6-methyl-N-(5-{2-oxa-7-azaspiro[3.5]nonan-7-yl}-[1,3]thiazolo[5,4-d]pyrimidin-2-yl)-[4,4'-bipyridine]-3-carboxamide | 10 | 96 | 3.12 | 538.1/ 540.1 | B | 1H NMR (500 MHz, DMSO-d6) 12.86 (s, 1H), 8.86 (s, 1H), 8.67 (s, 1H), 8.15 (s, 1H), 7.52 (s, 1H), 7.39 (s, 1H), 4.35 (s, 4H), 3.74-3.67 (m, 4H), 3.62 (s, 3H), 2.58 (s, 3H), 1.85-1.76 (m, 4H) |
| Intermediate 7[2]<br>tert-butyl 3-(2-{2'-chloro-5'-methoxy-6-methyl-[4,4'-bipyridine]-3-amido}-[1,3]thiazolo[5,4-d]pyrimidin-5-yl)-3,8-diazabicyclo[3.2.1]octane-8-carboxylate | 96 | 88 | 1.08 | 623.3/ 625.3 | A | |
| Intermediate 8[2]<br>tert-butyl 4-(2-{2'-chloro-5'-methoxy-6-methyl-[4,4'-bipyridine]-3-amido}-[1,3]thiazolo[5,4-d]pyrimidin-5-yl)piperazine-1-carboxylate | 88 | 100 | 1.03 | 597.2/ 599.2 | A | |

TABLE 8

Reaction solvent and temperature used in the preparation of the Examples in the table 7 above

| Footnote in Table x above | Reaction Solvent | Reaction Temp (° C.) |
|---|---|---|
| 1 | Ethanol | 80 |
| 2 | n-Butanol | 100 |
| 3 | Ethanol/DCE | 80 |
| 4 | n-Butanol | 80 |
| 5 | n-Butanol | 110 |

General Procedure E for Boc Deprotection 4M hydrogen chloride solution in 1,4-dioxane (10 equiv) was added to the required Boc protected amine pre-cursor (derived using general method D, 1 equiv) at RT. The mixture was stirred at RT and monitored via LCMS until the reaction was complete. The mixture was concentrated under reduced pressure and the residue purified by preparative HPLC method B to give the desired products.

Example 54 Synthesis of 2'-chloro-N-(5-{3,8-diazabicyclo[3.2.1]octan-3-yl}-[1,3]thiazolo[5,4-d]pyrimidin-2-yl)-5'-methoxy-6-methyl-[4,4'-bipyridine]-3-carboxamide

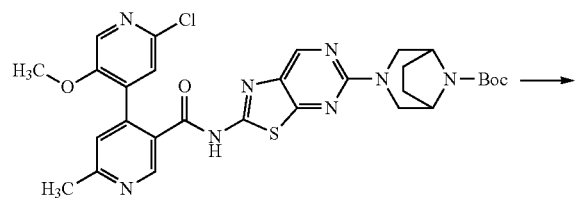

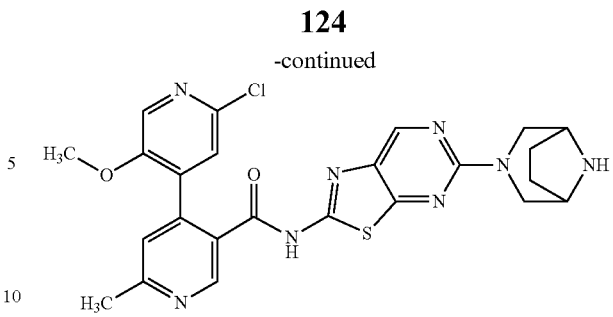

4M hydrogen chloride in 1,4-dioxane (250 µL, 1 mmol) was added to tert-butyl 3-(2-{2'-chloro-5'-methoxy-6-methyl-[4,4'-bipyridine]-3-amido}-[1,3]thiazolo[5,4-d]pyrimidin-5-yl)-3,8-diazabicyclo[3.2.1]octane-8-carboxylate (200 mg, 0.1 mmol, intermediate 7 prepared using general procedure D) and the mixture stirred at RT for 1 h. The reaction mixture was concentrated and the residue purified by preparative HPLC method B to give the title compound (15 mg, 30% yield) as a yellow powder. $^1$H NMR (400 MHz, DMSO-$d_6$) δ 8.93 (s, 1H), 8.56 (s, 1H), 8.13 (s, 1H), 7.44 (s, 1H), 7.29 (s, 1H), 4.26 (dd, J=13.1, 2.4 Hz, 2H), 3.81-3.75 (m, 2H), 3.62 (s, 3H), 3.08 (dd, J=13.0, 2.1 Hz, 2H), 2.56 (s, 3H), 1.83-1.61 (m, 4H), two exchangeable protons not observed. LCMS (method D); RT 1.83 mins (99%), m/z 523.4/525.3 (M+H)$^+$ Example 55 in table 9 below was prepared using general procedure E described above.

TABLE 9

| Example | Yield | LCMS Purity (%) | LCMS RT (mins) | m/z | LCMS method | 1H NMR |
|---|---|---|---|---|---|---|
| Example 55 2'-chloro-5'-methoxy-6-methyl-N-[5-(piperazin-1-yl)-[1,3]thiazolo[5,4-d]pyrimidin-2-yl]-[4,4'-bipyridine]-3-carboxamide | 23 | 100 | 1.64 | 497.2/ 499.2 | B | $^1$H NMR (400 MHz, DMSO-$d_6$) δ 8.93 (s, 1H), 8.57 (s, 1H), 8.14 (s, 1H), 7.44 (s, 1H), 7.29 (s, 1H), 3.74 (t, J = 5.0 Hz, 4H), 3.62 (s, 3H), 2.90 (t, J = 5.1 Hz, 4H), 2.56 (s, 3H), two exchangeable protons not observed. |

Examples 56 and 57

Examples 56 and 57 in table 10 below were prepared in the same manner as example 36B above.

TABLE 10

| Example | Yield | LCMS Purity (%) | LCMS RT (mins) | m/z | LCMS method | 1H NMR |
|---|---|---|---|---|---|---|
| 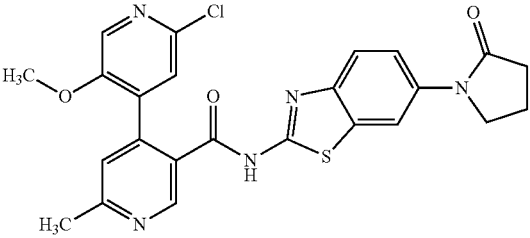 [SMILES: COc1cnc(Cl)cc1-c1cc(C)ncc1C(=O)Nc1nc2ccc(N3CCCC3=O)cc2s1]<br>Example 56<br>2'-chloro-5'-methoxy-6-methyl-N-[6-(2-oxopyrrolidin-1-yl)-1,3-benzothiazol-2-yl]-[4,4'-bipyridine]-3-carboxamide | 14 | 90 | 2.77 | 494.1/ 496.1 | B | $^1$H NMR (500 MHz, DMSO-$d_6$) δ 8.88 (s, 1H), 8.17-8.04 (m, 2H), 7.78-7.63 (m, 2H), 7.50 (s, 1H), 7.37 (s, 1H), 3.88 (t, J = 7.0 Hz, 2H), 3.59 (s, 3H), 2.58 (s, 3H), 2.08 (p, J = 7.6 Hz, 2H), one methylene signal obscured by solvent peak and one exchangeable proton not observed. |
| 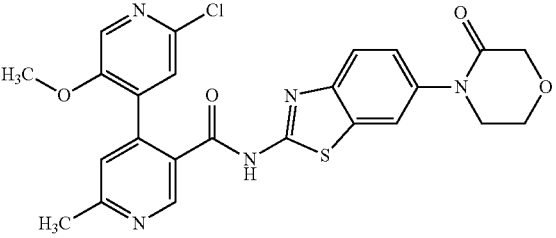 [SMILES: COc1cnc(Cl)cc1-c1cc(C)ncc1C(=O)Nc1nc2ccc(N3CCOCC3=O)cc2s1]<br>Example 57<br>2'-chloro-5'-methoxy-6-methyl-N-[6-(3-oxomorpholin-4-yl)-1,3-benzothiazol-2-yl]-[4,4'-bipyridine]-3-carboxamide | 25 | 99 | 2.50 | 510.1/ 512.1 | B | $^1$H NMR (400 MHz, DMSO-$d_6$) δ 13.00 (s, 1H), 8.86 (s, 1H), 8.16 (s, 1H), 8.01 (d, J = 2.0 Hz, 1H), 7.80 (d, J = 8.6 Hz, 1H), 7.59 (s, 1H), 7.51-7.42 (m, 2H), 4.23 (s, 2H), 4.04-3.96 (m, 2H), 3.81-3.74 (m, 2H), 3.60 (s, 3H), 2.61 (s, 3H). |

General Procedure F for Ullman Coupling

To a solution of the desired iodobenzothiazole (1 equiv) in DMSO was added the required amide (2 equiv), caesium carbonate (3 equiv) and copper(I) iodide (3 equiv). The mixture was degassed under nitrogen and then 1,2-dimethylethylenediamine (3 equiv) added. The mixture was stirred at 100° C. and monitored via LCMS until complete. The mixture was cooled to RT, diluted with DCM and washed with saturated ammonium chloride solution then water. The organic phase was treated with SMOPEX™ scavenger resin. The resin was filtered and the filtrate concentrated under reduced pressure. The residue was purified by Biotage Isolera™ automated chromatography to give the desired products.

Example 58 Synthesis of 2'-chloro-5'-methoxy-6-methyl-N-[6-(3-methyl-2-oxoimidazolidin-1-yl)-1,3-benzothiazol-2-yl]-[4,4'-bipyridine]-3-carboxamide

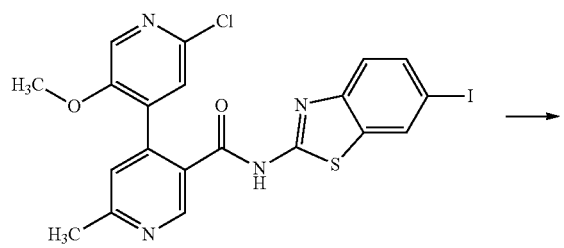

-continued

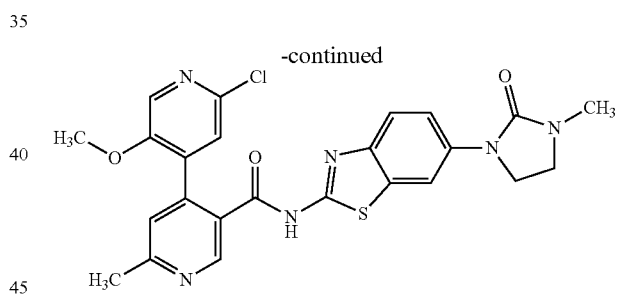

To a solution of 2'-chloro-N-(6-iodo-1,3-benzothiazol-2-yl)-5'-methoxy-6-methyl-[4,4'-bipyridine]-3-carboxamide (Example 4, 100 mg, 0.17 mmol) in DMSO (2 mL) was added 1-methylimidazolidin-2-one (35 mg, 0.35 mmol), caesium carbonate (169 mg, 0.52 mmol) and copper(I) iodide (99 mg, 0.52 mmol). The mixture was degassed under a flow of nitrogen then 1,2-dimethylethylenediamine (56 μL, 0.52 mmol) was added and the mixture heated at 100° C. for 2 h. The reaction mixture was cooled to RT, diluted with DCM (25 mL) and washed sequentially with sat. ammonium chloride solution (20 mL then 2×10 mL), water (10 mL) and brine (10 mL). The organic phase was passed through a Telos™ phase separator, treated with SMOPEX™ metal scavenger resin and stirred overnight. The solution was filtered and concentrated under reduced pressure. The crude residue was purified by Biotage Isolera™ automated chromatography (C18 Duo, 12 g) using a gradient of 0-100% acetonitrile in water (0.1% formic acid). Product containing fractions were combined and purified further by Biotage Isolera™ automated chromatography (Sfar Duo 10 g) using a gradient of 0-10% methanol in DCM to give the title compound (8.7 mg, 10% yield) as a colourless powder. ¹H NMR (500 MHz, DMSO-d₆) δ 12.83 (s, 1H), 8.84 (s, 1H), 8.15 (s, 1H), 8.01 (s, 1H), 7.84-7.76 (m, 1H), 7.76-7.65 (m, 1H), 7.56 (s, 1H), 7.44 (s, 1H) 3.92-3.79 (m, 2H), 3.60 (s, 3H), 3.51-3.41 (m, 2H), 2.78 (s, 3H), 2.59 (s, 3H). LCMS (method D); RT 1.57 mins (99%), m/z 509.3/511.2 (M+H)⁺.

Examples 59 and 60 in table 11 below were prepared using general procedure F described above.

TABLE 11

| Example | Yield | LCMS Purity (%) | LCMS RT (mins) | m/z | LCMS method | 1H NMR |
|---|---|---|---|---|---|---|
| Example 59<br>2'-chloro-5'-methoxy-6-methyl-N-[6-(2-oxo-1,3-oxazolidin-3-yl)-1,3-benzothiazol-2-yl]-[4,4'-bipyridine]-3-carboxamide | 18 | 100 | 1.39 | 496.2/498.2 | D | ¹H NMR (500 MHz DMSO-d₆) δ 12.92 (s, 1H), 8.85 (s, 1H), 8.15 (s, 1H), 8.08 (s, 1H), 7.84-7.68 (m, 2H), 7.57 (s, 1H), 7.45 (s, 1H), 4.53-4.39 (m, 2H), 4.22-4.06 (m, 2H), 3.60 (s, 3H), 2.60 (s, 3H). |
| Example 60<br>2'-chloro-5'-methoxy-6-methyl-N-[6-(2-oxoimidazolidin-1-yl)-1,3-benzothiazol-2-yl]-[4,4'-bipyridine]-3-carboxamide | 12 | 100 | 2.39 | 495.1/497.0 | B | ¹H NMR (400 MHz, DMSO) d 12.84 (s, 1H), 8.84 (s, 1H), 8.16 (s, 1H), 8.01 (s, 1H), 7.83-7.73 (m, 1H), 7.73-7.63 (m, 1H), 7.56 (s, 1H), 7.44 (s, 1H), 6.98 (s, 1H), 3.95-3.85 (m, 2H), 3.60 (s, 3H), 3.46-3.39 (m, 2H), 2.60 (s, 3H). |

Examples 61 to 75

Examples 61 to 75 listed in table 12 below were prepared in a manner analogous to general procedure C previously described. In parenthesis, (1) indicates the reaction was carried out at RT, (2) at 80° C., (3) at 90° C. and (4) at 50° C. Where the reactions were heated, components were first mixed at RT.

TABLE 12

| Example | Yield | LCMS Purity (%) | LCMS Rt (mins) | m/z | LCMS method | 1H NMR |
|---|---|---|---|---|---|---|
| 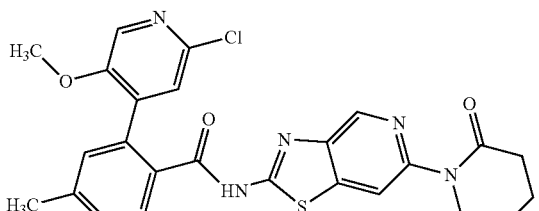<br>Example 61 (2)<br>2'-chloro-5'-methoxy-6-methyl-N-[6-(2-oxopiperidin-1-yl)-[1,3]thiazolo[4,5-c]pyridin-2-yl]-[4,4'-bipyridine]-3-carboxamide | 15 | 100 | 2.64 | 509.4/ 507.4 | B | $^1$H NMR (400 MHz, DMSO-$d_6$) δ 13.16 (s, 1H), 8.89 (s, 2H), 8.16 (s, 2H), 7.58 (s, 1H), 7.46 (s, 1H), 3.88-3.81 (m, 2H), 3.61 (s, 3H), 2.61 (s, 3H), 2.46-2.43 (m, 2H), 1.92-1.83 (m, 4H). |
| 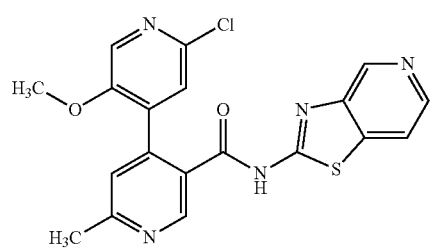<br>Example 62 (2)<br>2'-chloro-5'-methoxy-6-methyl-N-{[1,3]thiazolo[4,5-c]pyridin-2-yl}-[4,4'-bipyridine]-3-carboxamide | 20 | 99 | 1.17 | 412.2/ 414.1 | D | $^1$H NMR (500 MHz, DMSO-$d_6$) δ 13.54 (s, 1H), 9.36 (s, 1H), 8.90 (s, 1H), 8.60 (d, J = 6.0 Hz, 1H), 8.50 (d, J = 5.9 Hz, 1H), 8.17 (s, 1H), 7.61 (s, 1H), 7.51 (s, 1H), 3.59 (s, 3H), 2.62 (s, 3H). |
| 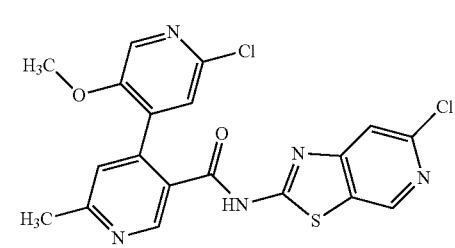 [SMILES: COc1cnc(Cl)cc1-c1cc(C)ncc1C(=O)Nc1nc2cc(Cl)ncc2s1]<br>Example 63 (1)<br>2'-chloro-N-{6-chloro-[1,3]thiazolo[5,4-c]pyridin-2-yl}-5'-methoxy-6-methyl-[4,4'-bipyridine]-3-carboxamide | 5 | 100 | 3.01 | 446.0/ 448.0 | D | $^1$H NMR (500 MHz, CDCl$_3$) δ 8.83 (s, 1H), 8.79 (s, 1H), 8.07 (s, 1H), 7.24 (s, 1H), 7.09 (s, 1H), 6.57 (s, 1H), 3.70 (s, 3H), 2.69 (s, 3H). |
| 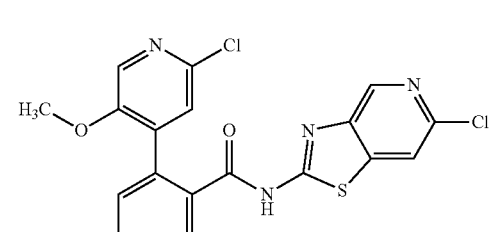<br>Example 64 (2)<br>2'-chloro-N-{6-chloro-[1,3]thiazolo[4,5-c]pyridin-2-yl}-5'-methoxy-6-methyl-[4,4'-bipyridine]-3-carboxamide | 83 | 100 | 3.12 | 446.0/ 448.0 | B | $^1$H NMR (500 MHz, DMSO-$d_6$) δ 13.29 (s, 1H), 8.88 (s, 1H), 8.83 (s, 1H), 8.19 (s, 1H), 8.16 (s, 1H), 7.58 (s, 1H), 7.46 (s, 1H), 3.59 (s, 3H), 2.60 (s, 3H). |

TABLE 12-continued

| Example | Yield | LCMS Purity (%) | LCMS Rt (mins) | m/z | LCMS method | 1H NMR |
|---|---|---|---|---|---|---|
| Example 65 (2)<br>2'-chloro-5'-methoxy-6-methyl-N-[6-(morpholin-4-yl)-[1,3]thiazolo[4,5-c]pyridin-2-yl]-[4,4'-bipyridine]-3-carboxamide | 56 | 100 | 2.57 | 497.1/ 499.1 | B | $^1$H NMR (500 MHz, DMSO-$d_6$) δ 12.88 (s, 1H), 8.83 (s, 1H), 8.63 (s, 1H), 8.16 (s, 1H), 7.57 (s, 1H), 7.45 (s, 1H), 7.45 (s, 1H), 7.40 (s, 1H), 3.80-3.69 (m, 4H), 3.61 (s, 3H), 3.46-3.43 (m, 4H), 2.60 (s, 3H). |
| Example 66 (1)<br>2'-chloro-N-[6-(dimethylsulfamoyl)-1,3-benzothiazol-2-yl]-5'-methoxy-6-methyl-[4,4'-bipyridine]-3-carboxamide | 26 | 99 | 3.07 | 518.1/ 520.1 | B | $^1$H NMR (400 MHz, DMSO-$d_6$) δ 13.25 (s, 1H), 8.87 (s, 1H), 8.51 (d, J = 2.0 Hz, 1H), 8.17 (s, 1H), 7.96 (d, J = 8.6 Hz, 1H), 7.79 (d, J = 8.5 Hz, 1H), 7.60 (s, 1H), 7.48 (s, 1H), 3.60 (s, 3H), 2.63 (s, 6H), 2.61 (s, 3H). |
| Example 67 (2)<br>2'-chloro-5'-methoxy-6-methyl-N-[6-(morpholin-4-yl)-[1,3]thiazolo[4,5-b]pyridin-2-yl]-[4,4'-bipyridine]-3-carboxamide | 73 | 98 | 2.65 | 497.1/ 499.1 | B | $^1$H NMR (500 MHz, DMSO-$d_6$) δ 13.00 (s, 1H), 8.85 (s, 1H), 8.38 (d, J = 2.8 Hz, 1H), 8.16 (s, 1H), 7.97 (d, J = 2.8 Hz, 1H), 7.58 (s, 1H), 7.46 (s, 1H), 3.81-3.75 (m, 4H), 3.60 (s, 3H), 3.20-3.16 (m, 4H), 2.60 (s, 3H). |
| Example 68 (2)<br>2'-chloro-N-[6-(4-hydroxypiperidin-1-yl)-[1,3]thiazolo[4,5-c]pyridin-2-yl]-5'-methoxy-6-methyl-[4,4'-bipyridine]-3-carboxamide | 11 | 100 | 2.05 | 511.2/ 513.2 | B | $^1$H NMR (500 MHz, DMSO-$d_6$) δ 12.82 (s, 1H), 8.83 (s, 1H), 8.58 (s, 1H), 8.16 (s, 1H), 7.56 (s, 1H), 7.45 (s, 1H), 7.38 (s, 1H), 4.48 (d, J = 4.3 Hz, 1H), 4.05-3.95 (m, 2H), 3.75-3.64 (m, 1H), 3.61 (s, 3H), 3.16-3.00 (m, 2H), 2.60 (s, 3H), 1.85-1.73 (m, 2H), 1.47-1.30 (m, 2H). |
| Example 69 (1)<br>N-(1,3-benzothiazol-2-yl)-2'-chloro-5'-methoxy-6-methyl-[4,4'-bipyridine]-3-carboxamide | 17 | 100 | 2.22 | 411.1/ 413.1 | F | $^1$H NMR (600 MHz, DMSO-$d_6$) δ 12.92 (s, 1H), 8.85 (s, 1H), 8.15 (s, 1H), 7.97 (d, J = 7.9 Hz, 1H), 7.77 (d, J = 8.1Hz, 1H), 7.57 (s, 1H), 7.50-7.39 (m, 2H), 7.39-7.19 (m, 1H), 3.59 (s, 3H), 2.60 (s, 3H). |

TABLE 12-continued

| Example | Yield | LCMS Purity (%) | LCMS Rt (mins) | m/z | LCMS method | 1H NMR |
|---|---|---|---|---|---|---|
| 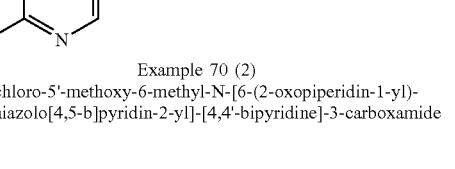<br>Example 70 (2)<br>2'-chloro-5'-methoxy-6-methyl-N-[6-(2-oxopiperidin-1-yl)-<br>[1,3]thiazolo[4,5-b]pyridin-2-yl]-[4,4'-bipyridine]-3-carboxamide | 72 | 98 | 2.57 | 509.1/ 511.1 | B | $^1$H NMR (500 MHz, DMSO-$d_6$) δ 13.25 (s, 1H), 8.88 (s, 1H), 8.48 (d, J = 2.5 Hz, 1H), 8.38 (d, J = 2.5 Hz, 1H), 8.16 (s, 1H), 7.60 (s, 1H), 7.47 (s, 1H), 3.68 (t, J = 5.7 Hz, 2H), 3.60 (s, 3H), 2.61 (s, 3H), 2.44 (t, J = 6.3 Hz, 2H), 1.93-1.85 (m, 4H). |
| 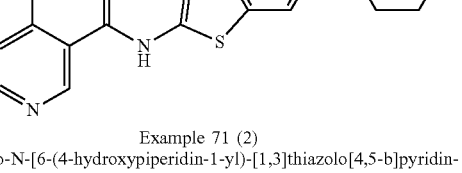<br>Example 71 (2)<br>2'-chloro-N-[6-(4-hydroxypiperidin-1-yl)-[1,3]thiazolo[4,5-b]pyridin-<br>2-yl]-5'-methoxy-6-methyl-[4,4'-bipyridine]-3-carboxamide | 26 | 98 | 2.32 | 511.1/ 513.1 | B | $^1$H NMR (500 MHz, DMSO-$d_6$) δ 12.97 (s, 1H), 8.85 (s, 1H), 8.36 (d, J = 2.8 Hz, 1H), 8.17 (s, 1H), 7.95 (d, J = 2.8 Hz, 1H), 7.58 (s, 1H), 7.46 (s, 1H), 4.71 (d, J = 4.1 Hz, 1H), 3.69-3.63 (m, 1H), 3.61 (s, 3H), 3.59-3.52 (m, 2H), 2.93-2.90 (m, 2H), 2.61 (s, 3H), 1.88-1.82 (m, 2H), 1.56-1.49 (m, 2H). |
| 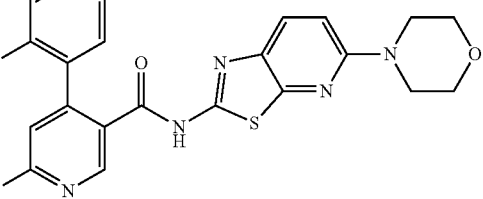<br>Example 72 (2)<br>2'-chloro-5'-methoxy-6-methyl-N-[5-(morpholin-4-yl)-<br>[1,3]thiazolo[5,4-b]pyridin-2-yl]-[4,4'-bipyridine]-3-carboxamide | 25 | 100 | 2.82 | 497.1/ 499.1 | B | $^1$H NMR (500 MHz, DMSO-$d_6$) δ 8.84 (s, 1H), 8.15 (s, 1H), 7.87 (d, J = 9.0 Hz, 1H), 7.53 (s, 1H), 7.41 (s, 1H), 6.97 (d, J = 9.0 Hz, 1H), 3.74-3.69 (m, 4H), 3.61 (s, 3H), 3.49-3.44 (m, 4H), 2.59 (s, 3H). |
| 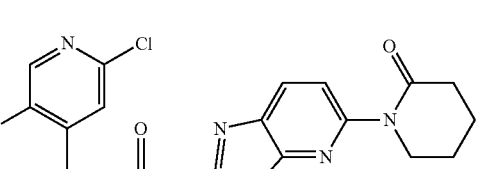<br>Example 73 (4)<br>2'-chloro-5'-methoxy-6-methyl-N-[5-(2-oxopiperidin-1-yl)-<br>[1,3]thiazolo[5,4-b]pyridin-2-yl]-[4,4'-bipyridine]-3-carboxamide | 84 | 100 | 2.69 | 509.3/ 511.3 | B | $^1$H NMR (500 MHz, DMSO-$d_6$) δ 13.06 (s, 1H), 8.87 (s, 1H), 8.16 (s, 1H), 8.09 (d, J = 8.5 Hz, 1H), 7.70 (d, J = 8.8 Hz, 1H), 7.57 (s, 1H), 7.45 (s, 1H), 3.85 (t, J = 5.9 Hz, 2H), 3.61 (s, 3H), 2.60 (s, 3H), 2.48-2.45 (m, 2H), 1.93-1.78 (m, 4H). |

TABLE 12-continued

| Example | Yield | LCMS Purity (%) | LCMS Rt (mins) | m/z | LCMS method | 1H NMR |
|---|---|---|---|---|---|---|
| Example 74 (4)<br>2'-chloro-N-[5-(4-hydroxypiperidin-1-yl)-[1,3]thiazolo[5,4-b]pyridin-2-yl]-5'-methoxy-6-methyl-[4,4'-bipyridine]-3-carboxamide | 20 | 99 | 2.46 | 511.1/ 513.1 | B | $^1$H NMR (500 MHz, DMSO-d$_6$) δ 12.67 (s, 1H), 8.82 (s, 1H), 8.16 (s, 1H), 7.83 (d, J = 9.0 Hz, 1H), 7.55 (s, 1H), 7.43 (s, 1H), 6.98 (d, J = 9.1 Hz, 1H), 4.70 (d, J = 4.3 Hz, 1H), 4.07-3.96 (m, 2H), 3.75-3.65 (m, 1H), 3.62 (s, 3H), 3.19-3.05 (m, 2H), 2.59 (s, 3H), 1.86-1.74 (m, 2H), 1.44-1.30 (m, 2H). |
| Example 75 (3)<br>2'-chloro-5'-methoxy-N-{5-methoxy-[1,3]thiazolo[5,4-d]pyrimidin-2-yl}-6-methyl-[4,4'-bipyridine]-3-carboxamide | 59 | 99 | 1.77 | 443.2/ 445.2 | G | $^1$H NMR (600 MHz, DMSO-d$_6$) δ 13.15 (s, 1H), 8.99 (s, 1H), 8.85 (s, 1H), 8.17 (s, 1H), 7.58 (s, 1H), 7.47 (s, 1H), 3.97 (s, 3H), 3.61 (s, 3H), 2.60 (s, 3H). |

Examples 76 to 82

Examples 76 to 82 in table 13 below were prepared in a manner analogous to general procedure D previously described. In parenthesis (1) indicates the use of nBuOH at 100° C. and (2) the use of EtOH at 80° C.

TABLE 13

| Example | Yield | LCMS Purity (%) | LCMS Rt (mins) | m/z | LCMS method | $^1$H NMR |
|---|---|---|---|---|---|---|
| Example 76 (2)<br>2'-chloro-5'-methoxy-6-methyl-N-(5-{2-oxa-6-azaspiro[3.4]octan-6-yl}-[1,3]thiazolo[5,4-d]pyrimidin-2-yl)-[4,4'-bipyridine]-3-carboxamide | 43 | 100 | 2.72 | 524.1/526.1 | B | $^1$H NMR (400 MHz, DMSO-d$_6$) δ 12.87 (s, 1H), 8.83 (s, 1H), 8.74 (s, 1H), 8.17 (s, 1H), 7.55 (s, 1H), 7.44 (s, 1H), 4.61 (d, J = 6.0 Hz, 2H), 4.51 (d, J = 6.0 Hz, 2H), 3.77 (s, 2H), 3.62 (s, 3H), 3.55 (d, J = 6.9 Hz, 2H), 2.59 (s, 3H), 2.25 (t, J = 7.0 Hz, 2H). |

TABLE 13-continued

| Example | Yield | LCMS Purity (%) | LCMS Rt (mins) | m/z | LCMS method | ¹H NMR |
|---|---|---|---|---|---|---|
| Example 77 (1) 2'-chloro-N-{5-[(2-hydroxy-2-methylpropyl)amino]-[1,3]thiazolo[5,4-d]pyrimidin-2-yl}-5'-methoxy-6-methyl-[4,4'-bipyridine]-3-carboxamide | 31 | 100 | 2.54 | 500.1/502.1 | B | ¹H NMR (400 MHz, DMSO-$d_6$) δ 12.85 (s, 1H), 8.82 (s, 1H), 8.67 (s, 1H), 8.17 (s, 1H), 7.56 (s, 1H), 7.44 (s, 1H), 6.97 (s, 1H), 4.52 (s, 1H), 3.63 (s, 3H), 2.59 (s, 3H), 1.12 (s, 6H). |
| Example 78 (1) 2'-chloro-5'-methoxy-6-methyl-N-{5-[(2-methylpropyl)amino]-[1,3]thiazolo[5,4-d]pyrimidin-2-yl}-[4,4'-bipyridine]-3-carboxamide | 29 | 98 | 3.33 | 484.1/486.1 | B | ¹H NMR (400 MHz, DMSO-$d_6$) δ 12.84 (s, 1H), 8.83 (s, 1H), 8.67 (s, 1H), 8.17 (s, 1H), 7.57 (s, 1H), 7.45 (s, 2H), 3.63 (s, 3H), 3.19-3.07 (m, 2H), 2.60 (s, 3H), 1.88 (hept, J = 6.6 Hz, 1H), 0.92-0.88 (m, 6H). |
| Example 79 (1) 2'-chloro-N-[5-(cyclobutylamino)-[1,3]thiazolo[5,4-d]pyrimidin-2-yl]-5'-methoxy-6-methyl-[4,4'-bipyridine]-3-carboxamide | 27 | 91 | 3.20 | 482.1/484.1 | B | ¹H NMR (400 MHz, DMSO-$d_6$) δ 8.85 (s, 1H), 8.61 (s, 1H), 8.15 (s, 1H), 7.45 (s, 1H), 7.37 (s, 1H), 7.28 (br s, 1H), 4.42-4.36 (m, 1H), 3.67 (s, 3H), 2.60 (s, 3H), 2.31-2.24 (m, 2H), 2.04-1.96 (m, 2H), 1.72-1.64 (m, 2H). |
| Example 80 (2) 2'-chloro-5'-methoxy-N-[5-(4-methoxypiperidin-1-yl)-[1,3]thiazolo[5,4-d]pyrimidin-2-yl]-6-methyl-[4,4'-bipyridine]-3-carboxamide | 17 | 100 | 3.34 | 526.2/528.2 | B | ¹H NMR (400 MHz, CDCl$_3$) δ 10.47 (s, 1H), 8.81 (s, 1H), 8.10-7.95 (m, 2H), 7.20-7.13 (m, 2H), 4.36-4.24 (m, 2H), 3.74 (s, 3H), 3.52-3.41 (m, 3H), 3.40 (s, 3H), 2.67 (s, 3H), 2.00-1.90 (m, 2H), 1.65-1.58 (m, 2H). |

TABLE 13-continued

| Example | Yield | LCMS Purity (%) | LCMS Rt (mins) | m/z | LCMS method | $^1$H NMR |
|---|---|---|---|---|---|---|
| 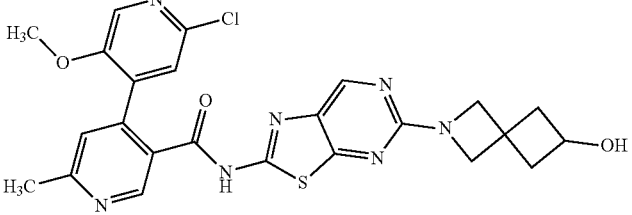<br>Example 81 (2)<br>2'-chloro-N-(5-{6-hydroxy-2-azaspiro[3.3]heptan-2-yl}-[1,3]thiazolo[5,4-d]pyrimidin-2-yl)-5'-methoxy-6-methyl-[4,4'-bipyridine]-3-carboxamide | 38 | 100 | 1.22 | 524.3/526.3 | B | $^1$H NMR (500 MHz, DMSO-d$_6$) δ 12.90 (s, 1H), 8.84 (s, 1H), 8.71 (s, 1H), 8.17 (s, 1H), 7.55 (s, 1H), 7.44 (s, 1H), 5.06 (d, J = 6.2 Hz, 1H), 4.08-3.98 (m, 5H), 3.62 (s, 3H), 2.60 (s, 3H), 2.05-1.99 (m, 2H). |
| 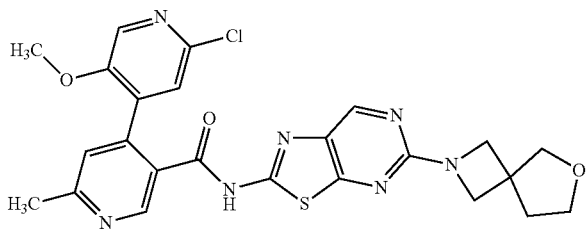 [SMILES: COc1cnc(Cl)cc1-c1cc(C)ncc1C(=O)Nc1nc2cnc(N3CC4(CCOC4)C3)nc2s1]<br>Example 82 (2)<br>2'-chloro-5'-methoxy-6-methyl-N-(5-{6-oxa-2-azaspiro[3.4]octan-2-yl}-[1,3]thiazolo[5,4-d]pyrimidin-2-yl)-[4,4'-bipyridine]-3-carboxamide | 8 | 100 | 2.77 | 524.1/526.1 | B | 1H NMR (400 MHz, CDCl3) δ 8.84 (s, 1H), 8.04 (s, 1H), 7.19 (s, 1H), 7.16 (s, 1H), 4.17 (s, 4H), 3.94 (s, 2H), 3.90 (t, J = 7.0 Hz, 3H), 3.74 (s, 3H), 2.69 (s, 3H), 2.23 (t, J = 7.0 Hz, 2H). |

Example 83

Example 83—2'-chloro-N-{6-[imino(methyl)oxo-λ$^6$-sulfanyl]-1,3-benzothiazol-2-yl}-5'-methoxy-6-methyl-[4,4'-bipyridine]-3-carboxamide Scheme 1 Synthesis of Example 83

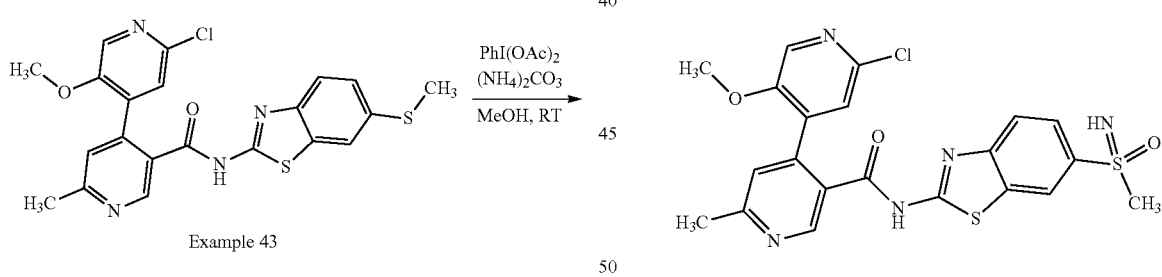

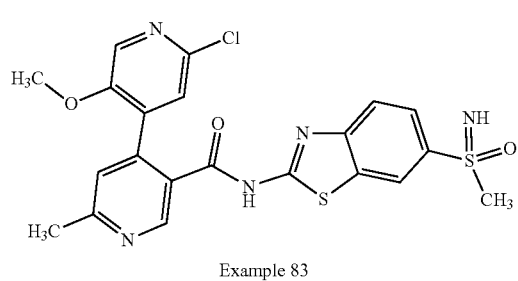

Example 83

2'-chloro-5'-methoxy-6-methyl-N-[6-(methylsulfanyl)-1,3-benzothiazol-2-yl]-[4,4'-bipyridine]-3-carboxamide (Example 43, 170 mg, 0.37 mmol) was dissolved in methanol (5.7 mL) and the mixture purged with N$_{2(g)}$. To the stirred mixture was added ammonium carbonate (54 mg, 0.56 mmol) in methanol (2.8 mL) followed by diacetoxyiodo benzene (275 mg, 0.85 mmol) in methanol (2.8 mL). The mixture was stirred at RT under N$_{2(g)}$ for 18 h. The mixture was filtered and the filtrate concentrated under reduced pressure. The residue was purified by Biotage Isolera™ automated chromatography (Sfar Duo 10 g) using a gradient of 0-10% methanol in DCM. The partially purified product was further purified using Biotage Isolera™ automated chromatography (C18 Duo, 12 g) using a gradient of 0-100% acetonitrile in water (0.1% formic acid) to give the title compound (16 mg, 9%) as a colourless powder. $^1$H NMR (500 MHz, DMSO-d$_6$) δ 13.19 (s, 1H), 8.89 (s, 1H), 8.58 (s, 1H), 8.16 (s, 1H), 7.96 (d, J=7.9 Hz, 1H), 7.90 (d, J=8.2 Hz, 1H), 7.58 (s, 1H), 7.46 (s, 1H), 4.22 (s, 1H), 3.59 (s, 3H), 3.10 (s, 3H), 2.60 (s, 3H). LCMS (method B); Rt 2.24 mins (100%), m/z 488.1/490.0 (M+H)$^+$ General Procedure G for Ullman Coupling
(Described Previously)

To a solution of the desired iodobenzothiazole (1 equiv) in DMSO was added the required amide (2 equiv), caesium carbonate (3 equiv) and copper (1) iodide (3 equiv). The mixture was degassed under N$_{2(g)}$ and then 1,2-dimethylethylenediamine (3 equiv) added. The mixture was heated at 100° C. and monitored by LCMS until complete. The mixture was cooled to RT, diluted with DCM and washed with saturated ammonium chloride solution and water. Organic extracts were combined and treated with SMOPEX™ scavenger resin. The resin was filtered and the filtrate concentrated under reduced pressure. The residue was purified by Biotage Isolera™ automated chromatography to give the desired coupling products.

The following examples were prepared in analogous fashion:

| Example | Yield | LCMS Purity (%) | LCMS Rt (mins) | m/z | LCMS method | 1H NMR |
|---|---|---|---|---|---|---|
| 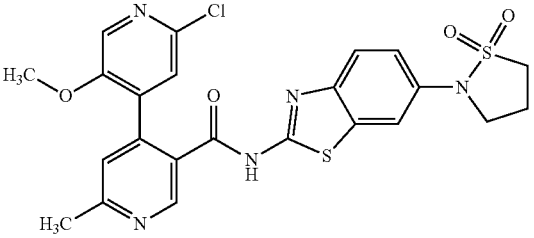 [SMILES: COc1cnc(Cl)cc1-c1cc(C)ncc1C(=O)Nc1nc2ccc(N3CCCS3(=O)=O)cc2s1] Example 84 2'-chloro-N-[6-(1,1-dioxo-1λ$^6$, 2-thiazolidin-2-yl)-1,3-benzothiazol-2-yl]-5'-methoxy-6-methyl-[4,4'-bipyridine]-3-carboxamide | 9 | 99 | 2.84 | 530.1/ 532.1 | B | $^1$H NMR (500 MHz, DMSO-d$_6$) δ 12.93 (s, 1H), 8.88 (s, 1H), 8.14 (s, 1H), 7.76 (s, 1H), 7.74-7.68 (m, 1H), 7.53 (s, 1H), 7.41 (s, 1H), 7.38-7.33 (m, 1H), 3.78 (t, J = 6.5 Hz, 2H), 3.60 (s, 3H), 3.51 (t, J = 7.5 Hz, 2H), 2.59 (s, 3H), 2.46-2.39 (m, 2H). |
| 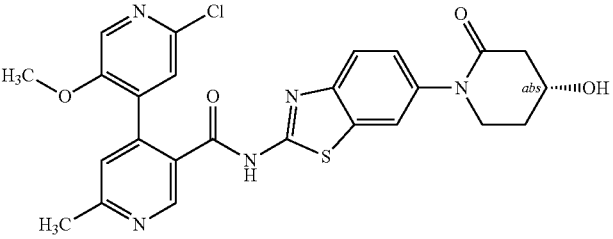 [SMILES: COc1cnc(Cl)cc1-c1cc(C)ncc1C(=O)Nc1nc2ccc(N3CC[C@@H](O)CC3=O)cc2s1] Example 85 2'-chloro-N-{6-[(4R)-4-hydroxy-2-oxopiperidin-1-yl]-1,3-benzothiazol-2-yl}-5'-methoxy-6-methyl-[4,4'-bipyridine]-3-carboxamide | 3 | 97 | 2.29 | 524.1/ 526.1 | B | $^1$H NMR (400 MHz, CDCl$_3$) δ 12.15 (s, 1H), 8.75 (s, 1H), 8.01 (s, 1H), 7.67 (d, J = 2.0 Hz, 1H), 7.13 (s, 1H), 7.09-7.01 (m, 2H), 6.91-6.80 (m, 1H), 4.43-4.34 (m, 1H), 3.98-3.87 (m, 1H), 3.65 (s, 3H), 3.62-3.52 (m, 1H), 2.82 (dd, J = 17.6, 4.5 Hz, 1H), 2.64-2.56 (m, 4H), 2.21-2.01 (m, 2H). |
| 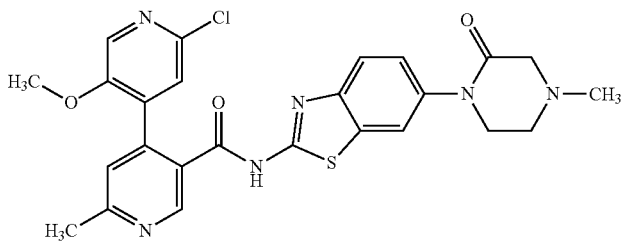 Example 86 2'-chloro-5'-methoxy-6-methyl-N-[6-(4-methyl-2-oxopiperazin-1-yl)-1,3-benzothiazol-2-yl]-[4,4'-bipyridine]-3-carboxamide | 6 | 100 | 1.31 | 523.3/ 525.3 | D | $^1$H NMR (500 MHz, DMSO-d$_6$) δ 12.96 (s, 1H), 8.86 (s, 1H), 8.16 (s, 1H), 7.95 (d, J = 2.2 Hz, 1H), 7.77 (d, J = 8.6 Hz, 1H), 7.59 (s, 1H), 7.47 (s, 1H), 7.39 (dd, J = 8.6, 2.2 Hz, 1H), 3.72-3.67 (m, 2H), 3.60 (s, 3H), 3.14 (s, 2H), 2.79-2.72 (m, 2H), 2.61 (s, 3H), 2.31 (s, 3H). |

Example 87

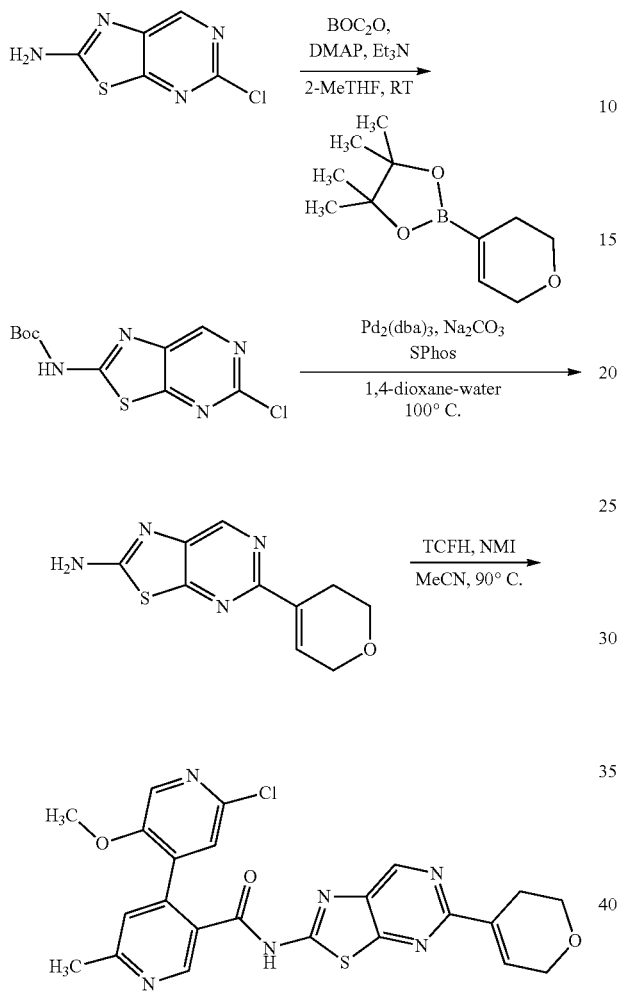

Intermediate I1—tert-butyl N-{5-chloro-[1,3]thiazolo[5,4-d]pyrimidin-2-yl}carbamate

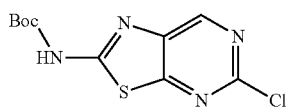 [SMILES: CC(C)(C)OC(=O)Nc1nc2cnc(Cl)nc2s1]

5-chloro-[1,3]thiazolo[5,4-d]pyrimidin-2-amine (1.53 g, 8.2 mmol), DMAP (200 mg, 1.64 mmol) and Et$_3$N (1.14 mL, 8.2 mmol) in 2-Methyl THF (120 mL) was treated portion wise with tert-butoxycarbonyl tert-butyl carbonate (3.65 g, 16.4 mmol). The reaction was stirred at RT for 3 days then concentrated under reduced pressure. The resulting solid was triturated with n-heptane (30 mL) and the resulting solid filtered and dried in vacuo to give the title compound (2.42 g, 93%) as a white powder. LCMS (method H); Rt 1.68 mins (90%), m/z 231.1 (M-t-bu)$^+$ Intermediate I2—5-(3,6-dihydro-2H-pyran-4-yl)-[1,3]thiazolo[5,4-d]pyrimidin-2-amine

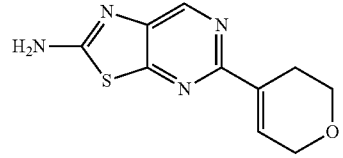 [SMILES: Nc1nc2cnc(C3=CCOCC3)nc2s1]

A stirred suspension of tert-butyl N-(5-chlorothiazolo[5,4-d]pyrimidin-2-yl)carbamate (intermediate I1, 200 mg, 0.670 mmol), 2-(3,6-dihydro-2H-pyran-4-yl)-4,4,5,5-tetramethyl-1,3,2-dioxaborolane (296 mg, 1.34 mmol) and 2 M K$_2$CO$_{3(aq)}$ (1.0 mL, 2.01 mmol) in 1,4-Dioxane (8 mL) and Water (1.5 mL) was degassed under N$_{2(g)}$ for 5 min. SPhos (56 mg, 0.134 mmol) and Pd$_2$(dba)$_3$ (65 mg, 0.067 mmol) were added and the mixture stirred at 100° C. overnight in a sealed pressure vessel. The mixture was cooled to RT and partitioned between water and EtOAc. The layers were separated, and the aqueous layer further extracted with EtOAc (×2). Combined organics were dried over hydrophobic filter paper and concentrated under reduced pressure. Reverse phase column chromatography (30 g, Redisep gold C18 aq, 0-100% acetonitrile in water, neutral) afforded the title compound (64 mg, 41%) as an off-white solid. $^1$H NMR (500 MHz, DMSO-d$_6$) δ 8.59 (s, 1H), 8.10 (s, 2H), 7.06-7.05 (m, 1H), 4.30-4.28 (m, 2H), 3.81 (t, J=5.5 Hz, 2H), 2.59-2.56 (m, 2H). LCMS (method E); Rt 0.54 mins (100%), m/z 235.2 (M+H)$^+$ Example 87—2'-chloro-N-[5-(3,6-dihydro-2H-pyran-4-yl)-[1,3]thiazolo[5,4-d]pyrimidin-2-yl]-5'-methoxy-6-methyl-[4,4'-bipyridine]-3-carboxamide

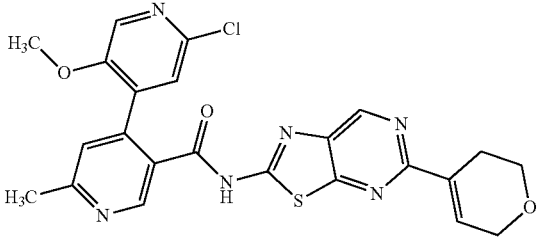 [SMILES: COc1cnc(Cl)cc1-c1cc(C)ncc1C(=O)Nc1nc2cnc(C3=CCOCC3)nc2s1]

Prepared in a manner analogous to general procedure C at 90° C., followed by reverse phase column chromatography (30 g, Redisep Aq18, 0-100% acetonitrile in water, neutral) then trituration with methanol to give the title compound (70 mg, 47%) as a white powder. $^1$H NMR (600 MHz, DMSO-d$_6$) δ 13.30 (s, 1H), 9.16 (s, 1H), 8.86 (s, 1H), 8.17 (s, 1H), 7.59 (s, 1H), 7.48 (s, 1H), 7.25-7.24 (m, 1H), 4.32 (br d, 2H, J=2.8 Hz), 3.83 (s, 2H), 3.61 (s, 3H), 2.61 (s, 5H). LCMS (method G); Rt 2.19 mins (97%), m/z 495.1/497.1 (M+H)$^+$

Example 88

Scheme 3 Synthesis of Example 88

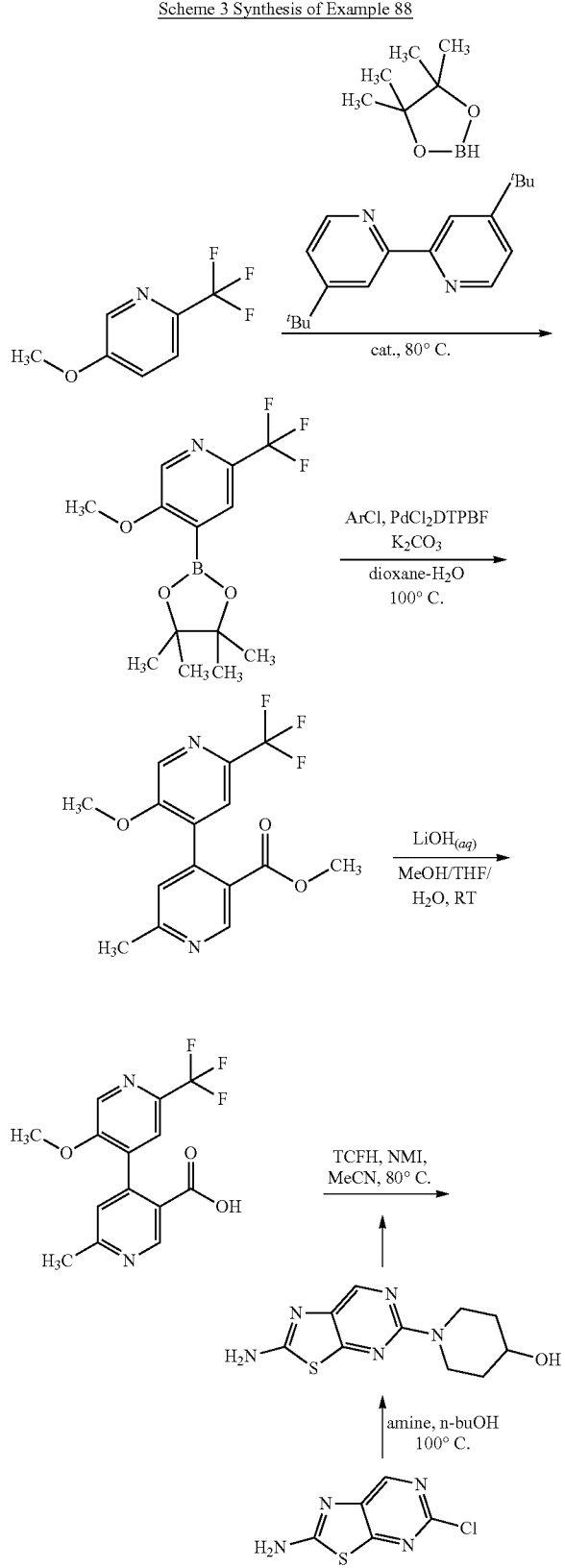

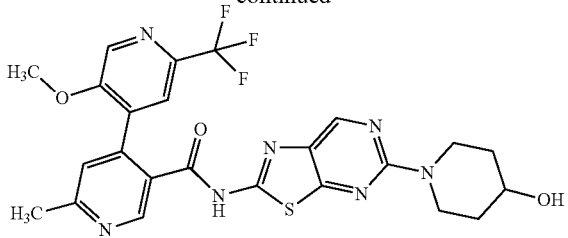

Intermediate I3—5-methoxy-4-(4,4,5,5-tetramethyl-1,3,2-dioxaborolan-2-yl)-2-(trifluoromethyl)pyridine

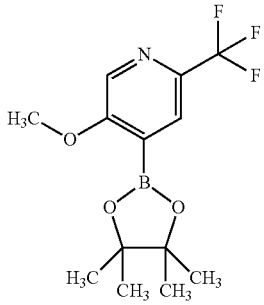

Di-Mµ-methanolatodiiridium(Ir—Ir)-cycloocta-1,5-diene (1:2) (37 mg, 0.057 mmol) and 4-tert-butyl-2-(4-tert-butyl-2-pyridyl)pyridine (30 mg, 0.113 mmol) were added to a Schlenk flask which had been evacuated and filled with $N_{2(g)}$ three times. 4,4,5,5-tetramethyl-1,3,2-dioxaborolane (1.23 mL, 8.47 mmol) and 5-methoxy-2-(trifluoromethyl)pyridine (0.79 mL, 5.65 mmol) were added via syringe. The flask was closed, and the mixture was heated at 80° C. for 2 h. The mixture was cooled to RT and diluted with EtOAc. The resulting mixture was concentrated under reduced pressure. The crude product thus obtained was purified by column chromatography (SiO$_2$, 40 g Redisep gold, 0-100% of EtOAc-EtOH (3:1) in heptane) to afford the title compound (1.66 g, 81%) as a beige solid. $^1$H NMR (400 MHz, DMSO-d$_6$) δ 8.56 (s, 1H), 7.80 (d, J=0.6 Hz, 1H), 3.98 (s, 3H), 1.31 (s, 12H). LCMS (method F); Rt 0.93 mins (94%), m/z 222.2.

Intermediate I4—methyl 5'-methoxy-6-methyl-2'-(trifluoromethyl)-[4,4'-bipyridine]-3-carboxylate

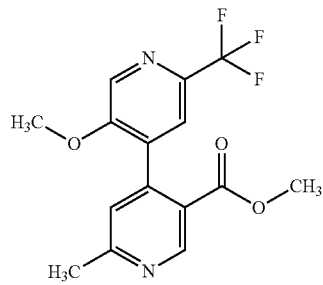

In a sealed vial, a stirred suspension of 5-methoxy-4-(4,4,5,5-tetramethyl-1,3,2-dioxaborolan-2-yl)-2-(trifluoromethyl)pyridine (intermediate I3, 640 mg, 1.82 mmol), methyl 4-bromo-6-methylpyridine-3-carboxylate (220 mg, 0.956 mmol) and K₂CO₃ (396 mg, 2.87 mmol) in 1,4-Dioxane (17.2 mL) and Water (5.0 mL) was degassed under N$_{2(g)}$ for 5 min. Palladium dichloride DTBPF (125 mg, 0.191 mmol) was added, and the mixture stirred at 100° C. for 3 h. The mixture was cooled to RT and diluted with water and EtOAc. The organic layer was washed with brine, dried over hydrophobic filter paper then concentrated under reduced pressure. Reverse phase column chromatography (0-100% ACN in water, redisep C18 aq 50 g) afforded the title compound (316 mg, 96%) as a brown gum. LCMS (method F); Rt 1.23 mins (94%), m/z 327.3 (M+H)⁺.

Intermediate I5—5'-methoxy-6-methyl-2'-(trifluoromethyl)-[4,4'-bipyridine]-3-carboxylic Acid

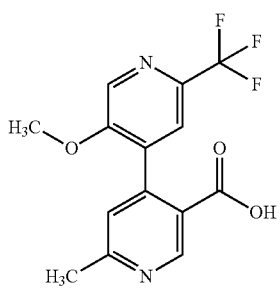 [SMILES: COc1cnc(C(F)(F)F)cc1-c1cc(C)ncc1C(=O)O]

Prepared in a fashion analogous to general procedure B with intermediate I4 giving the title compound (300 mg, quantitative) as a brown foam. ¹H NMR (500 MHz, DMSO-d₆) δ 12.3-13.5 (m, 1H), 8.92 (s, 1H), 8.59 (s, 1H), 7.81 (s, 1H), 7.34 (s, 1H), 3.90 (s, 3H), 2.57 (s, 3H). LCMS (method F); Rt 0.91 mins (96%), m/z 313.2 (M+H)⁺.

Intermediate I6—1-{2-amino-[1,3]thiazolo[5,4-d]pyrimidin-5-yl}piperidin-4-ol

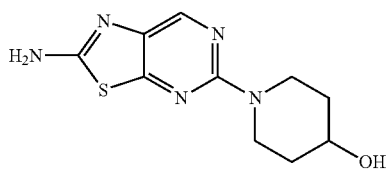 [SMILES: Nc1nc2cnc(N3CCC(O)CC3)nc2s1]

Piperidin-4-ol (130 mg, 1.29 mmol) was added to a suspension of 5-chlorothiazolo[5,4-d]pyrimidin-2-amine (50 mg, 0.26 mmol) in n-butanol (1.3 mL). The reaction was stirred at 100° C. overnight. Upon cooling to RT, the mixture was diluted with EtOAc and washed with water then brine. The organic phase was dried (Na₂SO₄) and concentrated under reduced pressure to give an orange solid. The solid was co-evaporated with diethylether to remove residual n-butanol and the resulting solid triturated with diethylether and filtered under vacuum. The filter cake was dried under a flow of N$_{2(g)}$ to give the title compound (56 mg, 82%) as an orange powder. ¹H NMR (500 MHz, DMSO-d₆) δ 8.25 (s, 1H), 7.48 (s, 2H), 4.68 (d, J=4.3 Hz, 1H), 4.19 (dt, J=12.7, 4.4 Hz, 2H), 3.73-3.66 (m, 1H), 3.21-3.15 (m, 2H), 1.78-1.72 (m, 2H), 1.35-1.27 (m, 2H). LCMS (Method A); Rt 0.43 mins (100%), m/z 252.1 (M+H)⁺

Example 88—N-[5-(4-hydroxypiperidin-1-yl)-[1,3]thiazolo[5,4-d]pyrimidin-2-yl]-5'-methoxy-6-methyl-2'-(trifluoromethyl)-[4,4'-bipyridine]-3-carboxamide

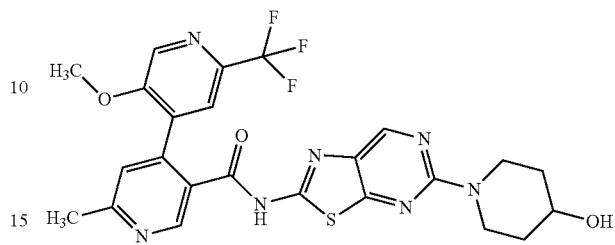

Prepared in a manner analogous to general procedure C with intermediates I5 and I6 at 80° C. Purified by reverse-phase chromatography (30 g Redisep Aq18) using a gradient of acetonitrile in water from 0% to 100% (neutral). To afford the title compound (23 mg, 28%) as a brown powder. ¹H NMR (600 MHz, DMSO-d₆) δ 12.89 (s, 1H), 8.84 (s, 1H), 8.74 (s, 1H), 8.54 (s, 1H), 7.94 (s, 1H), 7.51 (s, 1H), 4.72 (d, J=4.25 Hz, 1H), 4.27 (dt, J=13.3, 4.6 Hz, 2H), 3.71-3.76 (m, 4H), 3.29-3.30 (m, 2H), 2.61 (s, 3H), 1.75-1.82 (m, 2H), 1.31-1.38 (m, 2H). LCMS (method G); Rt 1.9 mins (99%), m/z 546.3 (M+H)⁺

Example 89

Scheme 4 Synthesis of Example 89

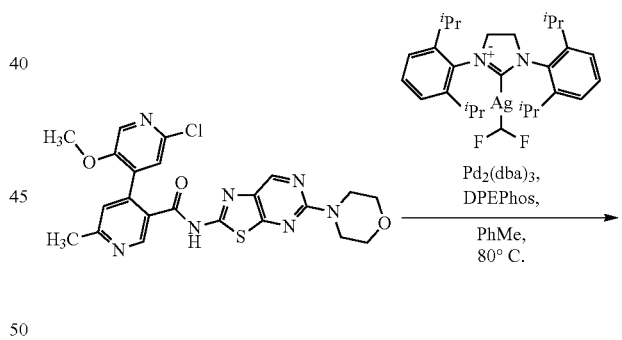

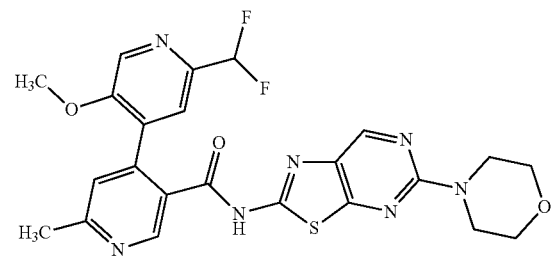

149

Example 89—N-[5-(4-hydroxypiperidin-1-yl)-[1,3]thiazolo[5,4-d]pyrimidin-2-yl]-5'-methoxy-6-methyl-2'-(trifluoromethyl)-[4,4'-bipyridine]-3-carboxamide

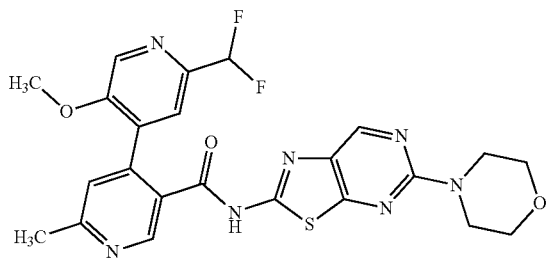 [SMILES: COc1cnc(C(F)F)cc1-c1cc(C)ncc1C(=O)Nc1nc2cnc(N3CCOCC3)nc2s1]

To a stirred solution 4-(2-chloro-5-methoxy-4-pyridyl)-6-methyl-N-(5-morpholinothiazolo[5,4-d]pyrimidin-2-yl)pyridine-3-carboxamide (Example 22, 70 mg, 0.141 mmol) in anhydrous toluene (1.8 mL, degassed for 10 min under $N_{2(g)}$ sparge prior to use) under $N_{2(g)}$ was added $Pd_2(dba)_3$ (13 mg, 0.01 mmol) and DPEPhos (15 mg, 0.028 mmol) followed by [1,3-bis(2,6-diisopropylphenyl)-4,5-dihydroimidazol-1-ium-2-yl]-(difluoromethyl)silver (100 mg, 0.183 mmol). The mixture was stirred at 80° C. for 18 h. Upon cooling to RT, the mixture was concentrated under reduced pressure and the gum was then purified by normal phase column chromatography (10 g sfar, 0-100% EtOAc in heptane then 0-20% methanol in EtOAc). The partially purified product was further purified via preparative HPLC (method C) then further purified via preparative HPLC under the following conditions: Column; Sunfire C18, 150× 19 mm, 5 μm. Flow rate; 20 mL/min, 5-95% 0.1% formic acid in acetonitrile-0.1% formic acid in water over 18 min. This afforded the title compound (4 mg, 6%) following lyophilisation from 1:1 acetonitrile-water as an off-white solid. $^1$H NMR (500 MHz, DMSO-$d_6$) δ 8.99 (s, 1H), 8.47 (s, 1H), 8.41 (s, 1H), 8.29 (s, 1H), 7.55 (s, 1H), 7.21 (s, 1H), 6.95 (t, J=55.2 Hz, 1H), 3.70 (s, 3H), 3.68-3.61 (m, 8H), 2.54 (s, 3H). LCMS (Method B); Rt 2.79 mins (94%), m/z 514.1 (M+H)$^+$ Example 90

Scheme 5 Synthesis of Example 90

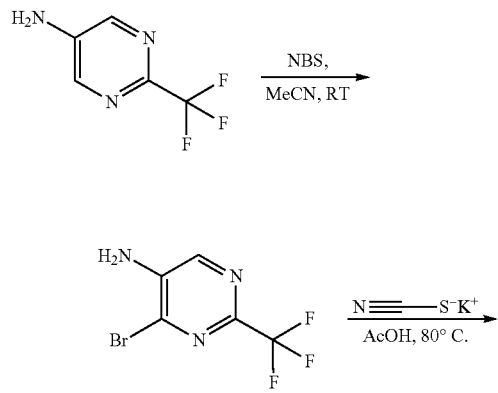

150

-continued

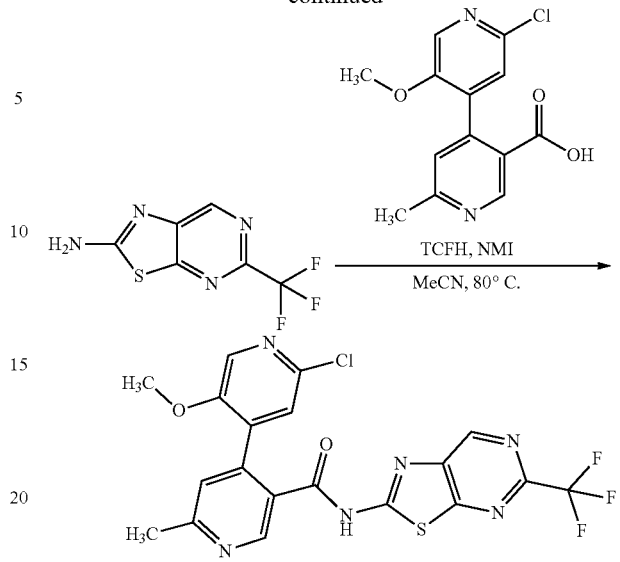

Intermediate I11—4-bromo-2-(trifluoromethyl)pyrimidin-5-amine

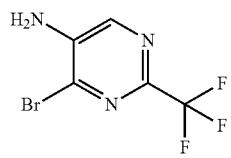

To a stirred solution of 2-(trifluoromethyl)pyrimidin-5-amine (500 mg, 2.91 mmol) in anhydrous acetonitrile (5 mL) was added 1-bromopyrrolidine-2,5-dione (628 mg, 3.49 mmol) in portions. The mixture was stirred at RT for 17 h. Under stirring, the mixture was poured into a solution of 1 N $Na_2S_2O_{3(aq)}$ and EtOAc. The organic layer was dried over $Na_2SO_4$ anhydrous, filtered and concentrated under reduced pressure. The residue was purified via normal phase chromatography ($SiO_2$, Biotage, Redisep 24 g) using a gradient of 70-100% DCM in heptane to give the title compound (266 mg, 38%) as an orange powder. $^1$H NMR (600 MHz, DMSO-$d_6$) δ 8.22 (s, 1H), 6.63 (s, 2H).

Intermediate I12—5-(trifluoromethyl)-[1,3]thiazolo[5,4-d]pyrimidin-2-amine

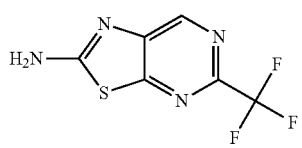 [SMILES: Nc1nc2cnc(C(F)(F)F)nc2s1]

To a stirred suspension of thiocyanatopotassium (120 mg, 1.17 mmol) in acetic acid (1.5 mL) was added 4-bromo-2-(trifluoromethyl)pyrimidin-5-amine (intermediate I11, 257 mg, 1.06 mmol). The mixture was stirred at 80° C. overnight. The mixture was poured into diethylether, the resulting solid was filtered, and the filtrate treated with water and 17 ml 2 M NaOH$_{(aq)}$ were added. The organic layer was dried over Na$_2$SO$_4$ then concentrated to dryness. The residue was triturated with DCM, filtered, rinsed several times with n-pentane and dried in vacuo at 50° C. overnight to give the title compound (146 mg, 62%) as a beige powder. $^1$H NMR (600 MHz, DMSO-d$_6$) δ 8.76 (s, 1H), 8.56 (s, 2H). LCMS (method E); Rt 0.64 mins (99%), m/z 221.1 (M+H)$^+$ Example 90—2'-chloro-5'-methoxy-6-methyl-[5-(trifluoromethyl)-[1,3]thiazolo[5,4-d]pyrimidin-2-yl]-[4,4'-bipyridine]-3-carboxamide

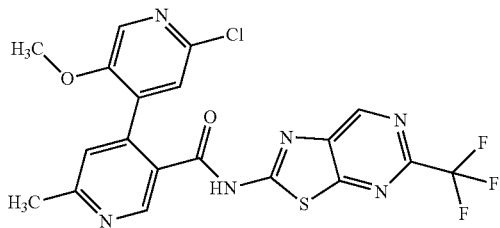 [SMILES: COc1cnc(Cl)cc1-c1cc(C)ncc1C(=O)Nc1nc2cnc(C(F)(F)F)nc2s1]

Prepared in a manner analogous to general procedure C at 80° C. giving the title compound (33 mg, 16%) as a white powder. $^1$H NMR (600 MHz, DMSO-d$_6$) δ 13.65 (br s, 1H), 9.39 (s, 1H), 8.89 (s, 1H), 8.17 (s, 1H), 7.61 (s, 1H), 7.50 (s, 1H), 3.60 (s, 3H), 2.61 (s, 3H). LCMS (method F); Rt 1.51 mins (100%), m/z 481.1/482.9 (M+H)$^+$ Example 91

Scheme 6 Synthesis of Example 91

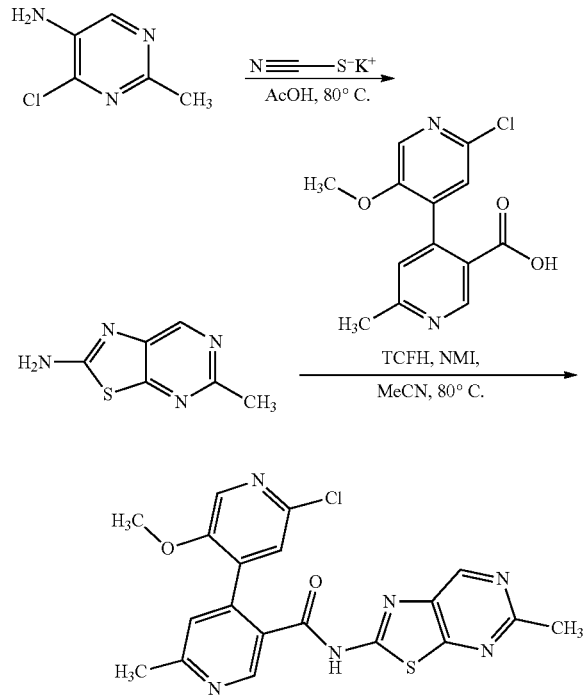

Intermediate I7—5-methyl-[1,3]thiazolo[5,4-d]pyrimidin-2-amine

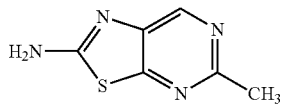

Prepared in a fashion analogous to intermediate I12 employing the corresponding commercial aryl chloride as a starting material. $^1$H NMR (500 MHz, DMSO-d$_6$) δ 8.51 (s, 1H), 8.00 (s, 2H), 2.58 (s, 3H).

Example 91—2'-chloro-5'-methoxy-6-methyl-N-{5-methyl-[1,3]thiazolo[5,4-d]pyrimidin-2-yl}-[4,4'-bipyridine]-3-carboxamide

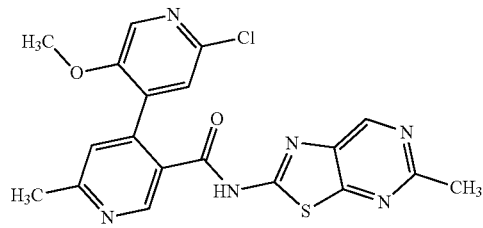

Prepared in a manner analogous to general procedure C at 80° C. The mixture contained a precipitate which was filtered and sequentially washed with water and acetonitrile to give a white solid. Purification via reverse phase column chromatography (10-100 acetonitrile in water, 0.1% AcOH) to give the title compound (100 mg, 39%) as a white solid. $^1$H NMR (400 MHz, DMSO-d$_6$) δ 13.26 (s, 1H), 9.08 (s, 1H), 8.86 (s, 1H), 8.17 (s, 1H), 7.59 (s, 1H), 7.48 (s, 1H), 3.61 (s, 3H), 2.72 (s, 3H), 2.61 (s, 3H). LCMS (method G); Rt 1.86 mins (100%), m/z 427.1/429.1 (M+H)$^+$ Example 92

Scheme 7 Synthesis of Example 92

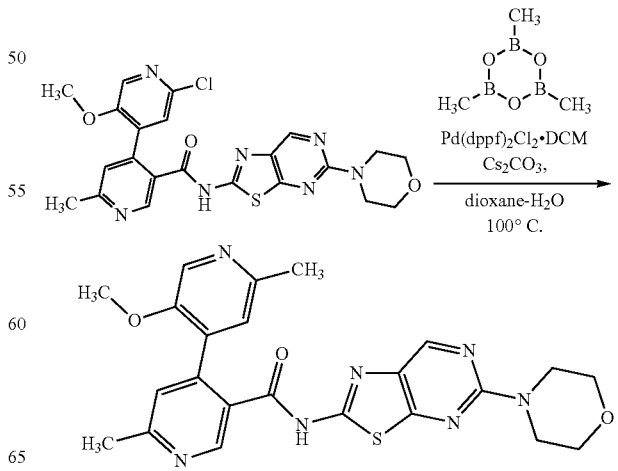

Example 92—5'-methoxy-2',6-dimethyl-N-[5-(morpholin-4-yl)-[1,3]thiazolo[5,4-d]pyrimidin-2-yl]-[4,4'-bipyridine]-3-carboxamide

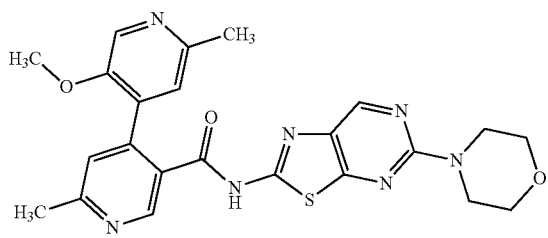 [SMILES: COc1cnc(C)cc1-c1cc(C)ncc1C(=O)Nc1nc2cnc(N3CCOCC3)nc2s1]

4-(2-chloro-5-methoxy-4-pyridyl)-6-methyl-N-(5-morpholinothiazolo[5,4-d]pyrimidin-2-yl)pyridine-3-carboxamide (Example 22, 120 mg, 0.241 mmol), trimethylboroxin (121 mg, 0.964 mmol) and Cs$_2$CO$_2$ (236 mg, 0.723 mmol) were stirred in 1,4-dioxane (0.66 mL) and water (0.28 mL) and the mixture degassed under N$_{2(g)}$ sparge for 5 min. Pd(dppf)Cl$_2$·DCM (20 mg, 0.0241 mmol) was added and the mixture further degassed under N$_{2(g)}$ for 5 min. The mixture was stirred at 100° C. (in pressure vial) for 18 h. Upon cooling to RT, the mixture was further treated with trimethylboroxin (121 mg, 0.964 mmol), Cs$_2$CO$_2$ (236 mg, 0.723 mmol) and Pd(dppf)Cl$_2$·DCM (20 mg, 0.0241 mmol). The mixture was degassed for 5 min under N$_{2(g)}$ sparge then stirred at 100° C. for 6 h. Upon cooling to RT, the mixture was diluted with DCM (6 mL), upon which a precipitate formed. The mixture was filtered and the filter cake washed with DCM. The filtrate was treated as follows; The organic phase was separated and concentrated under reduced pressure. The residue was dissolved in DMSO (2.5 mL with 1 drop of water). Preparative HPLC (method A) followed by lyophilisation from acetonitrile/water afforded the partially purified product. Normal phase column chromatography (0-10% MeOH in DCM) followed by lyophilisation from acetonitrile/water afforded the title compound (24 mg, 20%) as an off-white powder. $^1$H NMR (400 MHz, CDCl$_3$) 10.18-9.99 (m, 1H), 8.75 (s, 1H), 8.17-8.08 (m, 2H), 7.09 (s, 1H), 6.94 (s, 1H), 3.79-3.70 (m, 8H), 3.69 (s, 3H), 2.60 (s, 3H), 2.48 (s, 3H). LCMS (method B); Rt 1.89 mins (100%), m/z 478.1 (M+H)$^+$ Example 93

Scheme 8 Synthesis of Example 93

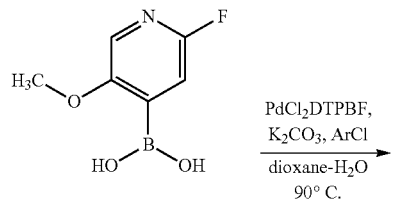

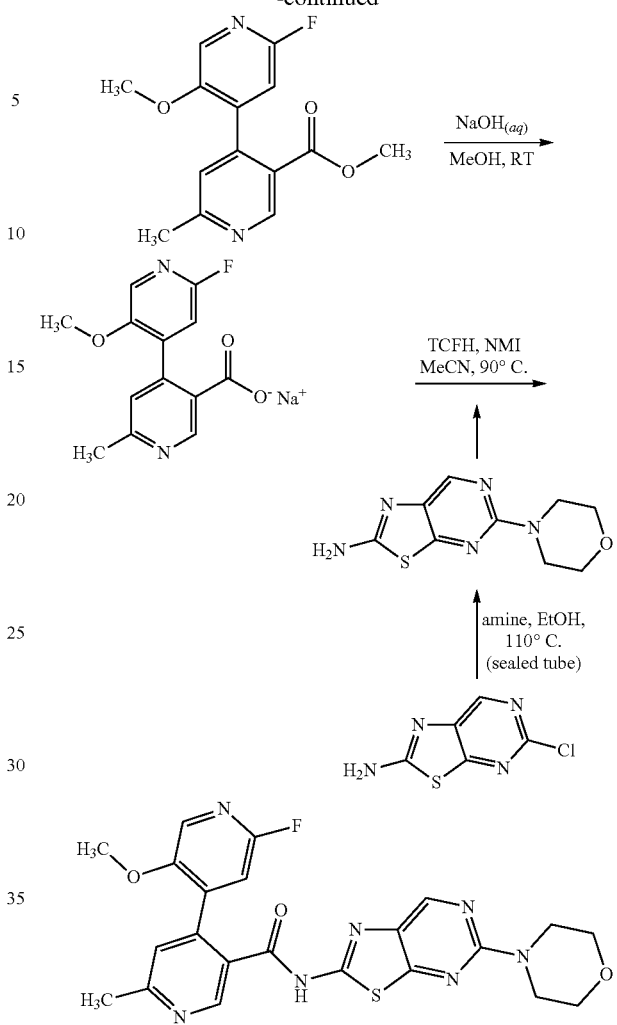

Intermediate I8—methyl 2'-fluoro-5'-methoxy-6-methyl-[4,4'-bipyridine]-3-carboxylate

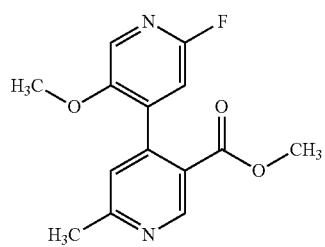

Prepared in a fashion analogous to general procedure A giving the title compound (296 mg, 65%) as a light yellow oil. $^1$H NMR (400 MHz, DMSO-d$_6$) δ 8.88 (s, 1H), 7.97 (d, J=1.9 Hz, 1H), 7.37 (s, 1H), 7.22 (d, J=2.9 Hz, 1H), 3.75 (s, 3H), 3.67 (s, 3H), 2.58 (s, 3H). LCMS (method F); Rt 0.96 mins (98%), m/z 277.2 (M+H)$^+$ Intermediate I9—sodium 2'-fluoro-5'-methoxy-6-methyl-[4,4'-bipyridine]-3-carboxylate

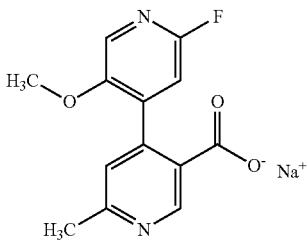 [SMILES: COc1cnc(F)cc1-c1cc(C)ncc1C(=O)[O-] ; [Na+]]

To a stirred solution of methyl 4-(2-fluoro-5-methoxy-4-pyridyl)-6-methyl-pyridine-3-carboxylate (intermediate I8, 296 mg, 1.05 mmol) in methanol (3 mL) was added at 1 M NaOH$_{(aq)}$ (3.0 mL, 3.0 mmol) at RT. The mixture was stirred 2 h at RT and concentrated under reduced pressure to afford the title compound (406 mg, 95%) as a yellow solid. $^1$H NMR (400 MHz, DMSO-d$_6$) δ 8.73 (s, 1H), 7.83 (d, J=1.8 Hz, 1H), 6.94 (s, 1H), 6.87 (d, J=2.8 Hz, 1H), 3.72 (s, 3H), 2.44 (s, 3H). LCMS (method F); Rt 0.72 mins (97%), m/z (free acid) 263.3 (M+H)$^+$ Intermediate I10—5-(morpholin-4-yl)-[1,3]thiazolo[5,4-d]pyrimidin-2-amine

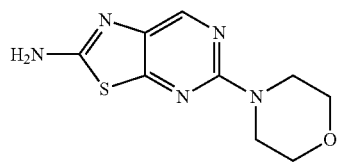 [SMILES: Nc1nc2cnc(N3CCOCC3)nc2s1]

To a suspension of 5-chloro-[1,3]thiazolo[5,4-d]pyrimidin-2-amine (2.25 g, 11.5 mmol) in ethanol (43 mL) at RT was added morpholine (9.88 mL, 115 mmol). The vial was sealed, and the mixture was stirred at 110° C. for 6 h. The mixture was allowed to cool to RT and stirred at RT overnight. The precipitate was filtered, washed with Ethanol (×2), diethylether (×3) and dried in vacuo overnight, to give a pink powder. This was triturated with water (×3), filtered and dried in vacuo at 45° C. to give the title compound (1.27 g, 47%) as a pink powder. $^1$H NMR (400 MHz, DMSO-d$_6$) δ 8.29 (s, 1H), 7.54 (s, 2H), 3.75-3.51 (m, 8H). LCMS (method E); Rt 0.55 mins (95%), m/z 238.2 (M+H)$^+$ Example 93—2'-fluoro-5'-methoxy-6-methyl-N-[5-(morpholin-4-yl)-[1,3]thiazolo[5,4-d]pyrimidin-2-yl]-[4,4'-bipyridine]-3-carboxamide

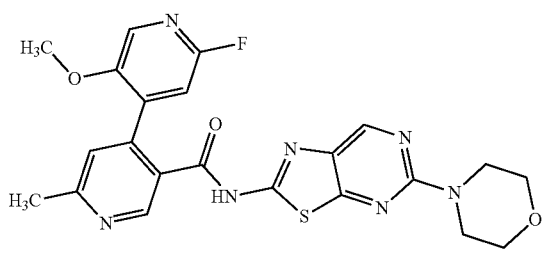 [SMILES: COc1cnc(F)cc1-c1cc(C)ncc1C(=O)Nc1nc2cnc(N3CCOCC3)nc2s1]

Prepared in a manner analogous to general procedure C at 90° C. followed by column chromatography (SiO$_2$, 0-100% of EtOAc/EtOH (3/1) in heptane) to give the title compound (94 mg, 47%) as a white solid. $^1$H NMR (400 MHz, DMSO-d$_6$) δ 12.93 (s, 1H), 8.84 (s, 1H), 8.80 (s, 1H), 7.92 (d, J=1.6 Hz, 1H), 7.45 (s, 1H), 7.30 (d, J=2.7 Hz, 1H), 3.77-3.64 (m, 8H), 3.60 (s, 3H), 2.61 (s, 3H). LCMS (method F); Rt 1.23 mins (100%), m/z 482.3 (M+H)$^+$ Example 94

Scheme 9 Synthesis of Example 94

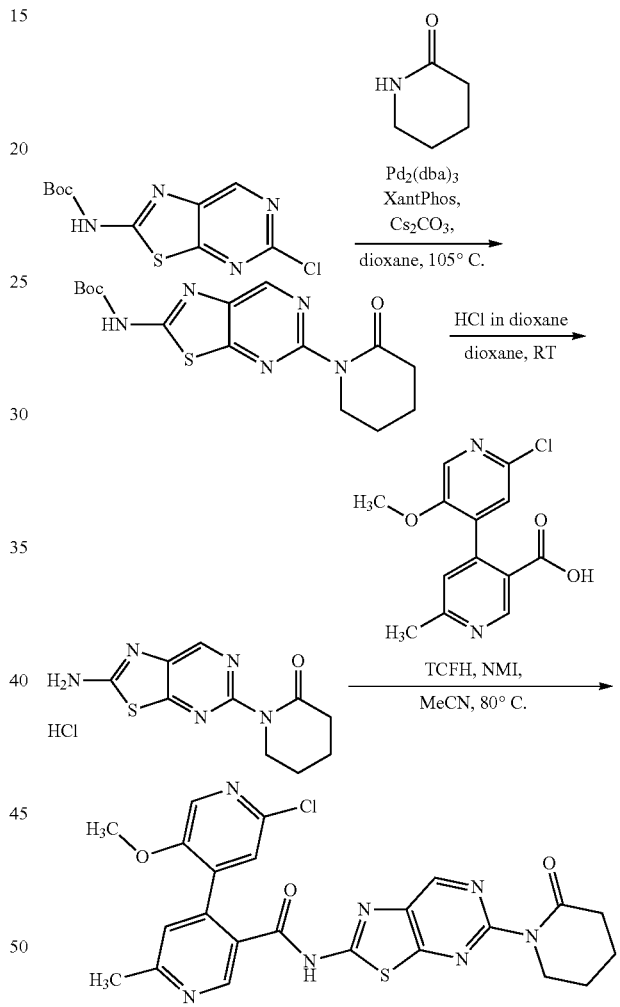

Intermediate I13—tert-butyl N-[5-(2-oxopiperidin-1-yl)-[1,3]thiazolo[5,4-d]pyrimidin-2-yl]carbamate

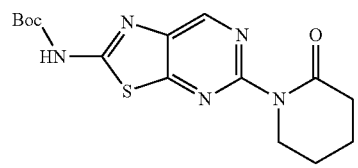 [SMILES: CC(C)(C)OC(=O)Nc1nc2cnc(N3CCCCC3=O)nc2s1]

tert-butyl N-(5-chlorothiazolo[5,4-d]pyrimidin-2-yl)carbamate (intermediate I1, 750 mg, 2.48 mmol), piperidin-2-one (493 mg, 4.97 mmol) and Cs$_2$CO$_3$ (2.89 g, 8.70 mmol) were stirred in anhydrous 1,4-dioxane (28 mL) and degassed under N$_{2(g)}$ sparge for 10 mins. Pd$_2$(dba)$_3$ (228 mg, 0.248 mmol) and Xantphos (288 mg, 0.497 mmol) were added and the mixture further degassed under N$_{2(g)}$ sparge for 5 mins. The mixture was stirred at 105° C. under N$_{2(g)}$ for 18 h. Upon cooling to RT, the mixture was diluted with water (6 mL) and EtOAc (20 mL). The organic phase was separated and the aqueous phase further extracted with EtOAc (2×20 mL). The combined organics were washed with brine (20 mL). The aqueous phase was extracted with EtOAc (2×20 mL) and the combined organics dried (MgSO$_4$) then concentrated under reduced pressure. Column chromatography (0-10% methanol in DCM) afforded the title compound (812 mg, 61%). $^1$H NMR (400 MHz, DMSO-d$_6$) δ 12.27 (s, 1H), 9.05 (s, 1H), 3.77 (t, J=5.6 Hz, 2H), 2.44 (t, J=6.2 Hz, 2H), 1.95-1.80 (m, 4H), 1.53 (s, 9H). LCMS (method A); Rt 0.76 mins (96%), m/z 350.1 (M+H)$^+$ Intermediate I14—1-{2-amino-[1,3]thiazolo[5,4-d]pyrimidin-5-yl}piperidin-2-one Hydrochloride

tert-butyl N-[5-(2-oxo-1-piperidyl)thiazolo[5,4-d]pyrimidin-2-yl]carbamate (intermediate I13 390 mg, 0.726 mmol) was stirred in 4 M HCl in 1,4-dioxane (5.0 mL, 20.0 mmol) for 1 h at RT. The mixture was diluted with anhydrous 1,4-dioxane (5 mL) and stirred for 24 h. The reaction was concentrated under reduced pressure and co-evaporated sequentially with acetonitrile (10 mL) and heptane (10 mL) to give the title compound (406 mg, 92%). $^1$H NMR (400 MHz, DMSO-d$_6$) δ 8.58 (s, 1H), 7.62-7.24 (m, 3H), 3.69 (t, J=5.6 Hz, 2H), 2.40 (t, J=6.3 Hz, 2H), 1.91-1.78 (m, 4H). LCMS (method A); Rt 0.43 mins (86%), m/z 250.0 (M+H)$^+$ Example 94—2'-chloro-5'-methoxy-6-methyl-N-[5-(2-oxopiperidin-1-yl)-[1,3]thiazolo[5,4-d]pyrimidin-2-yl]-[4,4'-bipyridine]-3-carboxamide

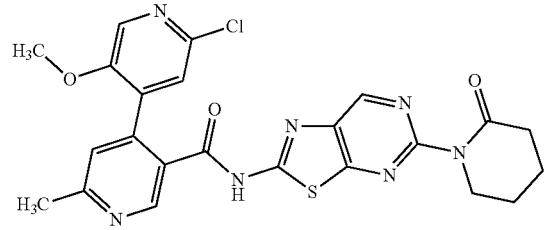 [SMILES: COc1cnc(Cl)cc1-c1cc(C)ncc1C(=O)Nc1nc2cnc(N3CCCCC3=O)nc2s1]

Prepared in a manner analogous to general procedure C at 80° C. to give the title compound (23 mg, 13%) as an off-white solid. $^1$H NMR (400 MHz, CDCl$_3$) δ 10.34 (s, 1H), 8.94 (s, 1H), 8.74 (s, 1H), 8.05 (s, 1H), 7.29 (s, 1H), 7.20 (s, 1H), 3.92 (t, J=5.6 Hz, 2H), 3.75 (s, 3H), 2.71 (s, 3H), 2.60 (t, J=6.4 Hz, 2H), 2.06-1.92 (m, 4H). LCMS (method B); Rt 2.58 mins (99%), m/z 510.2/512.1 (M+H)$^+$.

Biological Assay 1

The Polθ ATPase assay was used to evaluate inhibitors of Polθ ATPase activity, in vitro. Experiments were performed using a truncated Polθ protein (Polθ-Hel containing the helicase domain (67-894), ATP and a DNA single strand Oligo (5'-CTGTCCTGCATGATG-3') in the Polθ assay buffer (20 mM Tris-HCl (pH 8.8), MgCl2 5 mM, tween20 0.01%, NP40 0.01%, BSA 0.01%, DTT 1 mM). 2 μL of assay buffer containing Polθ-Hel protein (0.5 nM) and DNA substrate (500 nM) was transferred into assay ready plates, containing 0.04 μL of compounds diluted in DMSO. After a 30 minutes incubation at 23° C. in the dark, the reaction was triggered by adding 2 μL of ATP (60 μM), in assay buffer. After 60 minutes at 23° C., 4 μl of ADP-Glo™ Reagent (Glo 1) was added followed by 40 minutes of incubation, then 8 μl of ADP-Glo™ kinase Detection Reagent (Glo 2) followed by 60 minutes of incubation at 23° C. Luminescence was then measured using Tecan F200 infinite plate reader. Raw data were analysed using GeneData to generate IC50 values.

The results are shown in Table A below.

TABLE A

| | Polθ ATPase assay IC50 results | |
|---|---|---|
| Example No. | Compound | Polθ ATPase assay IC50 |
| 1 | N-(6-chloro-1,3-benzothiazol-2-yl)-4-(2-chloro-5-methoxy-4-pyridyl)-6-methyl-pyridine-3-carboxamide | *** |

TABLE A-continued

Polθ ATPase assay IC50 results

| Example No. | Compound | Polθ ATPase assay IC50 |
|---|---|---|
| 2 | 2'-chloro-N-(6-methanesulfonyl-1,3-benzothiazol-2-yl)-5'-methoxy-6-methyl-[4,4'-bipyridine]-3-carboxamide | *** |
| 3 | 2'-chloro-N-(6-cyano-1,3-benzothiazol-2-yl)-5'-methoxy-6-methyl-[4,4'-bipyridine]-3-carboxamide | *** |
| 4 | 2'-chloro-N-(6-iodo-1,3-benzothiazol-2-yl)-5'-methoxy-6-methyl-[4,4'-bipyridine]-3-carboxamide | *** |
| 5 | N-(6-bromo-1,3-benzothiazol-2-yl)-2'-chloro-5'-methoxy-6-methyl-[4,4'-bipyridine]-3-carboxamide | *** |
| 6 | 2'-chloro-N-{5-chloro-[1,3]thiazolo[5,4-d]pyrimidin-2-yl}-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 7 | 2'-chloro-N-{5-chloro-[1,3]thiazolo[5,4-b]pyridin-2-yl}-5'-methoxy-6-methyl-[4,4'-bipyridine]-3-carboxamide | *** |
| 8 | 3-(2-methoxyphenyl)-N-{[1,3]thiazolo[5,4-d]pyrimidin-2-yl}pyridine-4-carboxamide | ** |
| 9 | N-(6-bromo-1,3-benzothiazol-2-yl)-3-(2-methoxyphenyl)pyridine-4-carboxamide | ** |
| 10 | 3-(2-methoxyphenyl)-N-{[1,3]thiazolo[4,5-c]pyridin-2-yl}pyridine-4-carboxamide | * |
| 11 | 3-(2-methoxyphenyl)-N-{[1,3]thiazolo[4,5-b]pyridin-2-yl}pyridine-4-carboxamide | * |

TABLE A-continued

Polθ ATPase assay IC50 results

| Example No. | Compound | Polθ ATPase assay IC50 |
|---|---|---|
| 12 | 3-(2-methoxyphenyl)-N-[5-(trifluoromethyl)-1,3-benzothiazol-2-yl]pyridine-4-carboxamide | * |
| 13 | N-(5-chloro-1,3-benzothiazol-2-yl)-3-(2-methoxyphenyl)pyridine-4-carboxamide | * |
| 14 | 3-(2-methoxyphenyl)-N-{[1,3]thiazolo[5,4-b]pyridin-2-yl}pyridine-4-carboxamide | * |
| 15 | N-(1,3-benzothiazol-2-yl)-3-(2-methoxyphenyl)pyridine-4-carboxamide | * |
| 16 | N-(5-cyano-1,3-benzothiazol-2-yl)-3-(2-methoxyphenyl)pyridine-4-carboxamide | ND |

TABLE A-continued

Polθ ATPase assay IC50 results

| Example No. | Compound | Polθ ATPase assay IC50 |
|---|---|---|
| 17 | 2'-chloro-5'-methoxy-6-methyl-N-[6-(morpholin-4-yl)-1,3-benzothiazol-2-yl]-[4,4'-bipyridine]-3-carboxamide | *** |
| 18 | 2'-chloro-5'-methoxy-6-methyl-N-(6-nitro-1,3-benzothiazol-2-yl)-[4,4'-bipyridine]-3-carboxamide | ND |
| 19 | 4-(2-chloro-5-methoxy-4-pyridyl)-N-[5-[(3R)-3-hydroxypyrrolidin-1-yl]thiazolo[5,4-d]pyrimidin-2-yl]-6-methyl-pyridine-3-carboxamide | *** |
| 20 | 2'-chloro-5'-methoxy-6-methyl-N-[5-(piperidin-1-yl)-[1,3]thiazolo[5,4-d]pyrimidin-2-yl]-[4,4'-bipyridine]-3-carboxamide | *** |
| 21 | 2'-chloro-N-[5-(4,4-difluoropiperidin-1-yl)-[1,3]thiazolo[5,4-d]pyrimidin-2-yl]-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 22 | 2'-chloro-5'-methoxy-6-methyl-N-[5-(morpholin-4-yl)-[1,3]thiazolo[5,4-d]pyrimidin-2-yl]-[4,4'-bipyridine]-3-carboxamide | *** |
| 23 | 2'-chloro-N-{5-[(3S)-3-hydroxypyrrolidin-1-yl]-[1,3]thiazolo[5,4-d]pyrimidin-2-yl}-5'-methoxy-6-methyl-[4,4'-bipyridine]-3-carboxamide | *** |
| 24 | 2'-chloro-5'-methoxy-6-methyl-N-[5-(pyrrolidin-1-yl)-[1,3]thiazolo[5,4-d]pyrimidin-2-yl]-[4,4'-bipyridine]-3-carboxamide | *** |
| 25 | 2'-chloro-N-[5-(3,3-difluoropyrrolidin-1-yl)-[1,3]thiazolo[5,4-d]pyrimidin-2-yl]-5'-methoxy-6-methyl-[4,4'-bipyridine]-3-carboxamide | *** |
| 26 | 2'-chloro-N-{5-[(3R)-3-hydroxypyrrolidin-1-yl]-[1,3]thiazolo[5,4-d]pyrimidin-2-yl}-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 27 | 2'-chloro-N-[5-(1,1-dioxo-1$\lambda^6$-thiomorpholin-4-yl)-[1,3]thiazolo[5,4-d]pyrimidin-2-yl]-5'-methoxy-6-methyl-[4,4'-bipyridine]-3-carboxamide | *** |
| 28 | 2'-chloro-5'-methoxy-6-methyl-N-[5-(4-methylpiperazin-1-yl)-[1,3]thiazolo[5,4-d]pyrimidin-2-yl]-[4,4'-bipyridine]-3-carboxamide | *** |
| 29 | 2'-chloro-5'-methoxy-6-methyl-N-(5-{2-oxa-6-azaspiro[3.3]heptan-6-yl}-[1,3]thiazolo[5,4-d]pyrimidin-2-yl)-[4,4'-bipyridine]-3-carboxamide | *** |
| 30 | 2'-chloro-5'-methoxy-N-{5-[(2-methoxyethyl)amino]-[1,3]thiazolo[5,4-d]pyrimidin-2-yl}-6-methyl-[4,4'-bipyridine]-3-carboxamide | *** |
| 31 | 2'-chloro-N-[5-(3-hydroxyazetidin-1-yl)-[1,3]thiazolo[5,4-d]pyrimidin-2-yl]-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 32 | 2'-chloro-5'-methoxy-N-[5-(3-methoxypyrrolidin-1-yl)-[1,3]thiazolo[5,4-d]pyrimidin-2-yl]-6-methyl-[4,4'-bipyridine]-3-carboxamide | *** |
| 33 | 2'-chloro-N-[5-(4-hydroxypiperidin-1-yl)-[1,3]thiazolo[5,4-d]pyrimidin-2-yl]-5'-methoxy-6-methyl-[4,4'-bipyridine]-3-carboxamide | *** |
| 34 | 2'-chloro-5'-methoxy-6-methyl-N-{5-[(1S,4S)-2-oxa-5-azabicyclo[2.2.1]heptan-5-yl]-[1,3]thiazolo[5,4-d]pyrimidin-2-yl}-[4,4'-bipyridine]-3-carboxamide | *** |
| 35 | 2'-chloro-N-[5-(3-cyanopiperidin-1-yl)-[1,3]thiazolo[5,4-d]pyrimidin-2-yl]-5'-methoxy-6-methyl-[4,4'-bipyridine]-3-carboxamide | *** |
| 36A | N-(6-amino-1,3-benzothiazol-2-yl)-4-(2-chloro-5-methoxy-4-pyridyl)-6-methyl-pyridine-3-carboxamide | ** |

TABLE A-continued

Polθ ATPase assay IC50 results

| Example No. | Compound | Polθ ATPase assay IC50 |
|---|---|---|
| 36B | 2'-chloro-5'-methoxy-6-methyl-N-[6-(2-oxopiperidin-1-yl)-1,3-benzothiazol-2-yl]-[4,4'-bipyridine]-3-carboxamide | *** |
| 37 | 4-(2-chloro-5-methoxy-4-pyridyl)-N-[5-(3,6-dihydro-2H-pyran-5-yl)thiazolo[5,4-b]pyridin-2-yl]-6-methyl-pyridine-3-carboxamide | *** |
| 38 | 4-(2-chloro-5-methoxy-4-pyridyl)-N-[6-(5-chloro-2-pyridyl)-1,3-benzothiazol-2-yl]-6-methyl-pyridine-3-carboxamide | *** |
| 39 | N-[6-(5-chloropyridin-2-yl)-1,3-benzothiazol-2-yl]-3-(2-methoxyphenyl)pyridine-4-carboxamide | ** |
| 40 | 2'-chloro-N-[6-(3-hydroxyoxolan-3-yl)-1,3-benzothiazol-2-yl]-5'-methoxy-6-methyl-[4,4'-bipyridine]-3-carboxamide | ** |

TABLE A-continued

Polθ ATPase assay IC50 results

| Example No. | Compound | Polθ ATPase assay IC50 |
|---|---|---|
| 41 | 2'-chloro-N-(6-methanesulfonamido-1,3-benzothiazol-2-yl)-5'-methoxy-6-methyl-[4,4'-bipyridine]-3-carboxamide 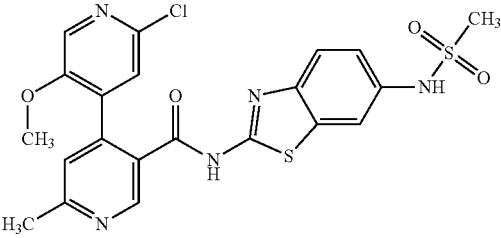 [SMILES: COc1cnc(Cl)cc1-c1cc(C)ncc1C(=O)Nc1nc2ccc(NS(C)(=O)=O)cc2s1] | *** |
| 42 | 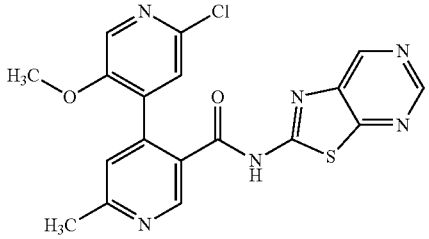 2'-chloro-5'-methoxy-6-methyl-N-{[1,3]thiazolo[5,4-d]pyrimidin-2-yl}-[4,4'-bipyridine]-3-carboxamide | *** |
| 43 | 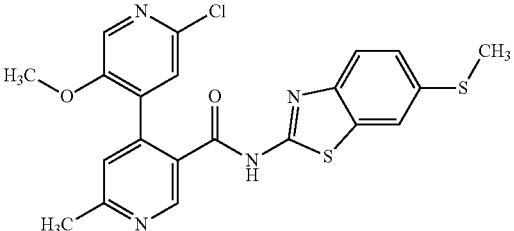 2'-chloro-5'-methoxy-6-methyl-N-[6-(methylsulfanyl)-1,3-benzothiazol-2-yl]-[4,4'-bipyridine]-3-carboxamide | *** |
| 44 | 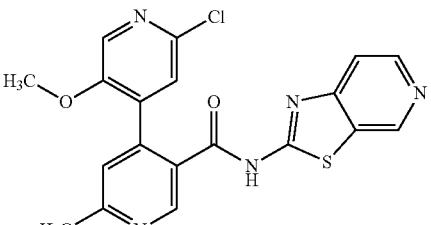 2'-chloro-5'-methoxy-6-methyl-N-{[1,3]thiazolo[5,4-c]pyridin-2-yl}-[4,4'-bipyridine]-3-carboxamide | *** |
| 45 | 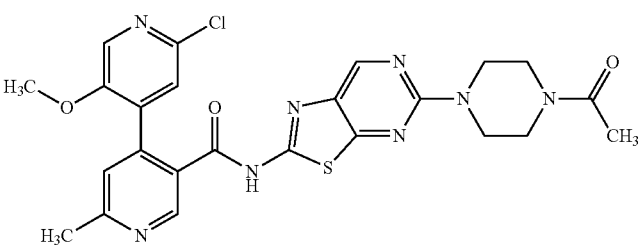 [SMILES: COc1cnc(Cl)cc1-c1cc(C)ncc1C(=O)Nc1nc2cnc(N3CCN(C(C)=O)CC3)nc2s1] N-[5-(4-acetylpiperazin-1-yl)-[1,3]thiazolo[5,4-d]pyrimidin-2-yl]-2'-chloro-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 46 | 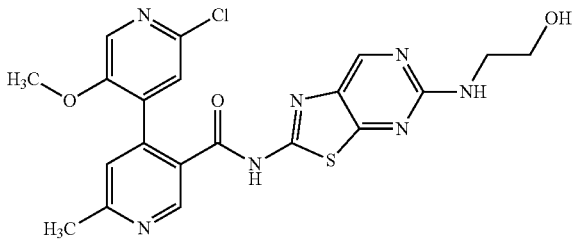 [SMILES: COc1cnc(Cl)cc1-c1cc(C)ncc1C(=O)Nc1nc2cnc(NCCO)nc2s1]<br>2'-chloro-N-{5-[(2-hydroxyethyl)amino]-[1,3]thiazolo[5,4-d]pyrimidin-2-yl}-5'-methoxy-6-methyl-[4,4'-bipyridine]-3-carboxamide | *** |
| 47 | 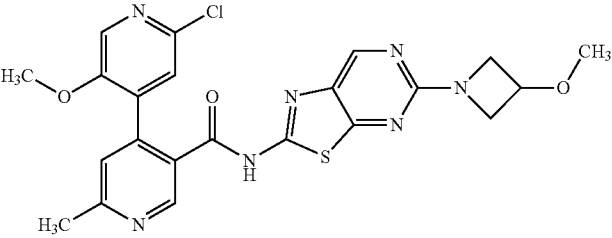<br>2'-chloro-5'-methoxy-N-[5-(3-methoxyazetidin-1-yl)-[1,3]thiazolo[5,4-d]pyrimidin-2-yl]-6-methyl-[4,4'-bipyridine]-3-carboxamide | *** |
| 48 | 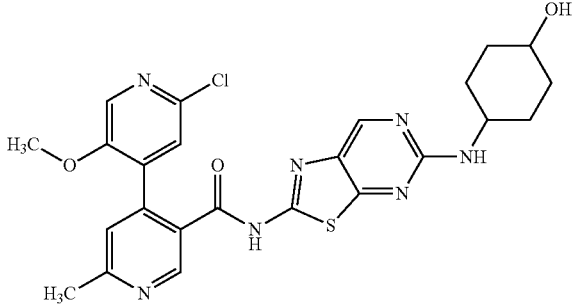 [SMILES: COc1cnc(Cl)cc1-c1cc(C)ncc1C(=O)Nc1nc2cnc(NC3CCC(O)CC3)nc2s1]<br>2'-chloro-N-{5-[(4-hydroxycyclohexyl)amino]-[1,3]thiazolo[5,4-d]pyrimidin-2-yl}-5'-methoxy-6-methyl-[4,4'-bipyridine]-3-carboxamide | *** |
| 49 | 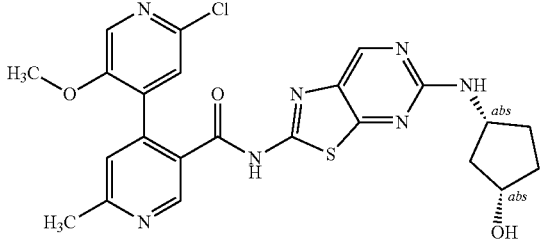 [SMILES: COc1cnc(Cl)cc1-c1cc(C)ncc1C(=O)Nc1nc2cnc(N[C@@H]3CC[C@H](O)C3)nc2s1]<br>rac-2'-chloro-N-(5-{[(1R,3S)-3-hydroxycyclopentyl]amino}-[1,3]thiazolo[5,4-d]pyrimidin-2-yl)-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 50 | 2'-chloro-5'-methoxy-6-methyl-N-{5-[(3R)-3-methylmorpholin-4-yl]-[1,3]thiazolo[5,4-d]pyrimidin-2-yl}-[4,4'-bipyridine]-3-carboxamide | *** |
| 51 | 2'-chloro-5'-methoxy-6-methyl-N-{5-[(3S)-3-methylmorpholin-4-yl]-[1,3]thiazolo[5,4-d]pyrimidin-2-yl}-[4,4'-bipyridine]-3-carboxamide | *** |
| 52 | 2'-chloro-5'-methoxy-6-methyl-N-{5-[(propan-2-yl)amino]-[1,3]thiazolo[5,4-d]pyrimidin-2-yl}-[4,4'-bipyridine]-3-carboxamide | *** |
| 53 | 2'-chloro-5'-methoxy-6-methyl-N-(5-{2-oxa-7-azaspiro[3.5]nonan-7-yl}-[1,3]thiazolo[5,4-d]pyrimidin-2-yl)-[4,4'-bipyridine]-3-carboxamide | *** |
| 54 | 2'-chloro-N-(5-{3,8-diazabicyclo[3.2.1]octan-3-yl}-[1,3]thiazolo[5,4-d]pyrimidin-2-yl)-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 55 | 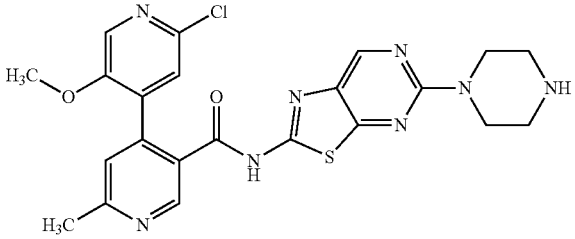 [SMILES: COc1cnc(Cl)cc1-c1cc(C)ncc1C(=O)Nc1nc2cnc(N3CCNCC3)nc2s1]<br>2'-chloro-5'-methoxy-6-methyl-N-[5-(piperazin-1-yl)-[1,3]thiazolo[5,4-d]pyrimidin-2-yl]-[4,4'-bipyridine]-3-carboxamide | *** |
| 56 | 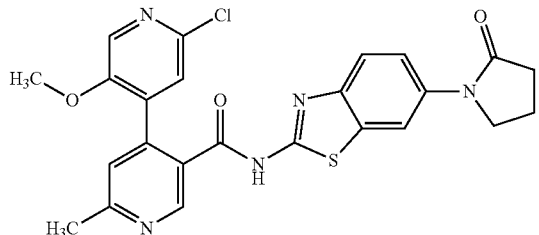<br>2'-chloro-5'-methoxy-6-methyl-N-[6-(2-oxopyrrolidin-1-yl)-1,3-benzothiazol-2-yl]-[4,4'-bipyridine]-3-carboxamide | *** |
| 57 | 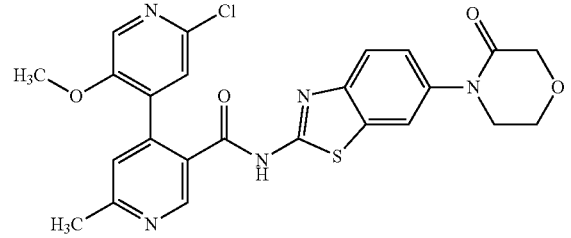 [SMILES: COc1cnc(Cl)cc1-c1cc(C)ncc1C(=O)Nc1nc2ccc(N3CCOCC3=O)cc2s1]<br>2'-chloro-5'-methoxy-6-methyl-N-[6-(3-oxomorpholin-4-yl)-1,3-benzothiazol-2-yl]-[4,4'-bipyridine]-3-carboxamide | *** |
| 58 | 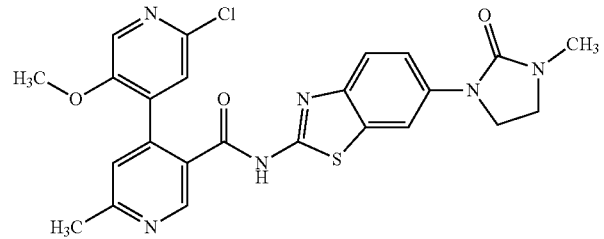<br>2'-chloro-5'-methoxy-6-methyl-N-[6-(3-methyl-2-oxoimidazolidin-1-yl)-1,3-benzothiazol-2-yl]-[4,4'-bipyridine]-3-carboxamide | *** |
| 59 | 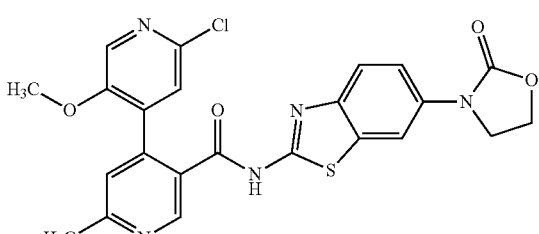<br>2'-chloro-5'-methoxy-6-methyl-N-[6-(2-oxo-1,3-oxazolidin-3-yl)-1,3-benzothiazol-2-yl]-[4,4'-bipyridine]-3-carboxamide | *** |

TABLE A-continued

Polθ ATPase assay IC50 results

| Example No. | Compound | Polθ ATPase assay IC50 |
|---|---|---|
| 60 | 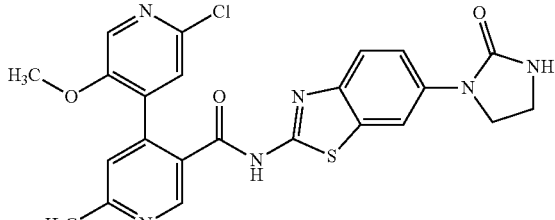2'-chloro-5'-methoxy-6-methyl-N-[6-(2-oxoimidazolidin-1-yl)-1,3-benzothiazol-2-yl]-[4,4'-bipyridine]-3-carboxamide | *** |
| 61 | 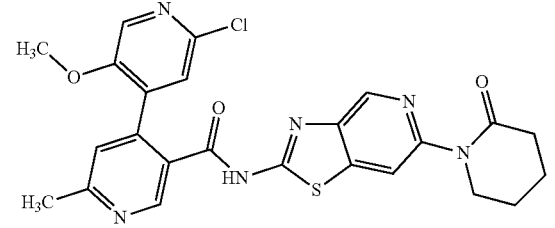 [SMILES: COc1cnc(Cl)cc1-c1cc(C)ncc1C(=O)Nc1nc2cnc(N3CCCCC3=O)cc2s1]2'-chloro-5'-methoxy-6-methyl-N-[6-(2-oxopiperidin-1-yl)-[1,3]thiazolo[4,5-c]pyridin-2-yl]-[4,4'-bipyridine]-3-carboxamide | *** |
| 62 | 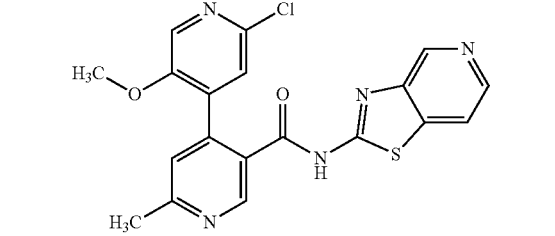2'-chloro-5'-methoxy-6-methyl-N-{[1,3]thiazolo[4,5-c]pyridin-2-yl}-[4,4'-bipyridine]-3-carboxamide | *** |
| 63 | 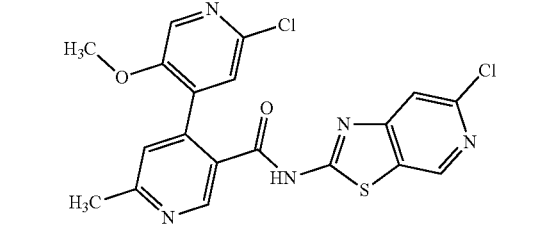 [SMILES: COc1cnc(Cl)cc1-c1cc(C)ncc1C(=O)Nc1nc2cc(Cl)ncc2s1]2'-chloro-N-{6-chloro-[1,3]thiazolo[5,4-c]pyridin-2-yl}-5'-methoxy-6-methyl-[4,4'-bipyridine]-3-carboxamide | *** |
| 64 | 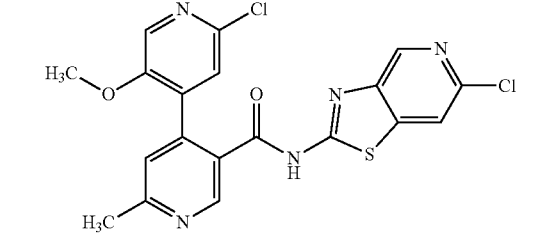 [SMILES: COc1cnc(Cl)cc1-c1cc(C)ncc1C(=O)Nc1nc2cnc(Cl)cc2s1]2'-chloro-N-{6-chloro-[1,3]thiazolo[4,5-c]pyridin-2-yl}-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 65 | 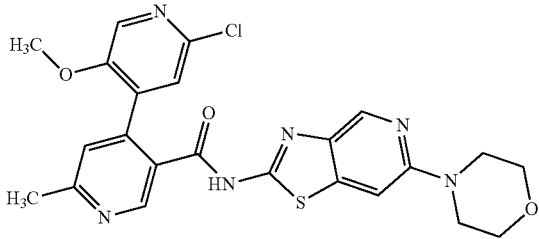 [SMILES: COc1cnc(Cl)cc1-c1cc(C)ncc1C(=O)Nc1nc2cnc(N3CCOCC3)cc2s1] 2'-chloro-5'-methoxy-6-methyl-N-[6-(morpholin-4-yl)-[1,3]thiazolo[4,5-c]pyridin-2-yl]-[4,4'-bipyridine]-3-carboxamide | *** |
| 66 | 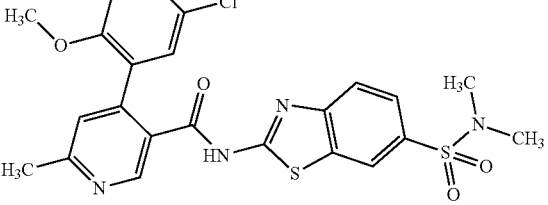 2'-chloro-N-[6-(dimethylsulfamoyl)-1,3-benzothiazol-2-yl]-5'-methoxy-6-methyl-[4,4'-bipyridine]-3-carboxamide | *** |
| 67 | 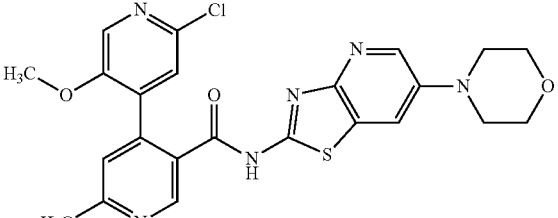 2'-chloro-5'-methoxy-6-methyl-N-[6-(morpholin-4-yl)-[1,3]thiazolo[4,5-b]pyridin-2-yl]-[4,4'-bipyridine]-3-carboxamide | *** |
| 68 | 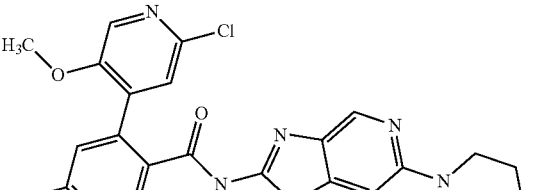 2'-chloro-N-[6-(4-hydroxypiperidin-1-yl)-[1,3]thiazolo[4,5-c]pyridin-2-yl]-5'-methoxy-6-methyl-[4,4'-bipyridine]-3-carboxamide | *** |
| 69 | 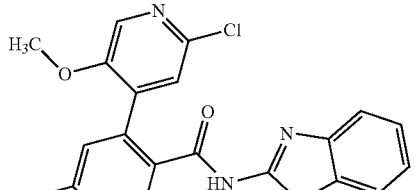 N-(1,3-benzothiazol-2-yl)-2'-chloro-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 70 | 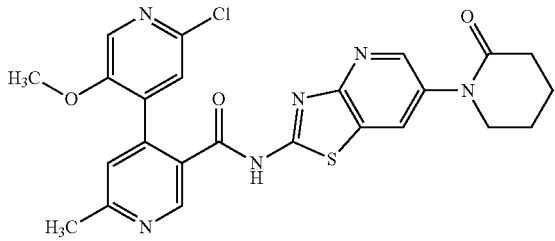 [SMILES: COc1cnc(Cl)cc1-c1cc(C)ncc1C(=O)Nc1nc2ncc(N3CCCCC3=O)cc2s1]<br>2'-chloro-5'-methoxy-6-methyl-N-[6-(2-oxopiperidin-1-yl)-[1,3]thiazolo[4,5-b]pyridin-2-yl]-[4,4'-bipyridine]-3-carboxamide | *** |
| 71 | 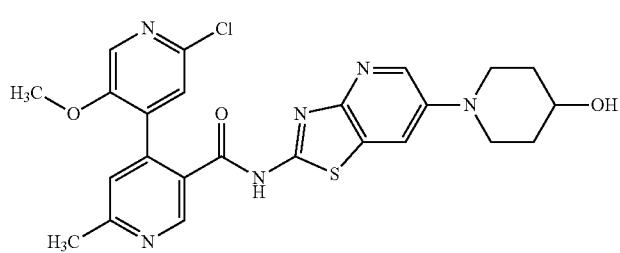 [SMILES: COc1cnc(Cl)cc1-c1cc(C)ncc1C(=O)Nc1nc2ncc(N3CCC(O)CC3)cc2s1]<br>2'-chloro-N-[6-(4-hydroxypiperidin-1-yl)-[1,3]thiazolo[4,5-b]pyridin-2-yl]-5'-methoxy-6-methyl-[4,4'-bipyridine]-3-carboxamide | *** |
| 72 | 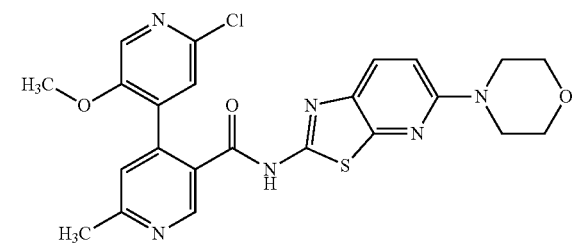 [SMILES: COc1cnc(Cl)cc1-c1cc(C)ncc1C(=O)Nc1nc2ccc(N3CCOCC3)nc2s1]<br>2'-chloro-5'-methoxy-6-methyl-N-[5-(morpholin-4-yl)-[1,3]thiazolo[5,4-b]pyridin-2-yl]-[4,4'-bipyridine]-3-carboxamide | *** |
| 73 | 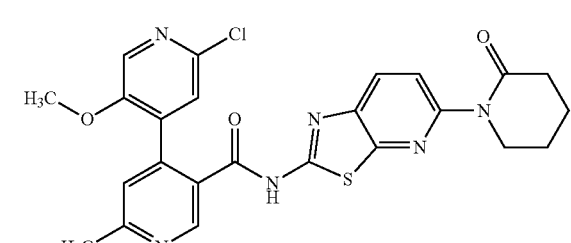<br>2'-chloro-5'-methoxy-6-methyl-N-[5-(2-oxopiperidin-1-yl)-[1,3]thiazolo[5,4-b]pyridin-2-yl]-[4,4'-bipyridine]-3-carboxamide | *** |
| 74 | 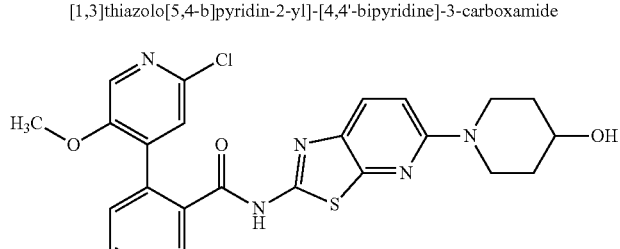<br>2'-chloro-N-[5-(4-hydroxypiperidin-1-yl)-[1,3]thiazolo[5,4-b]pyridin-2-yl]-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 75 | 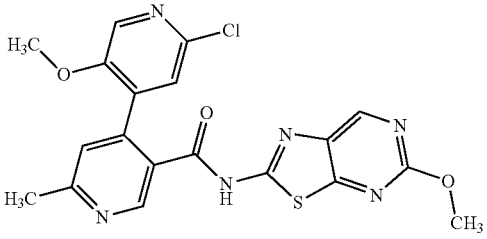<br>2'-chloro-5'-methoxy-N-{5-methoxy-[1,3]thiazolo[5,4-d]pyrimidin-2-yl}-6-methyl-[4,4'-bipyridine]-3-carboxamide | *** |
| 76 | 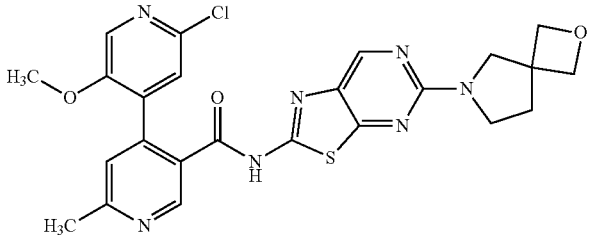 [SMILES: COc1cnc(Cl)cc1-c1cc(C)ncc1C(=O)Nc1nc2cnc(N3CCC4(COC4)C3)nc2s1]<br>2'-chloro-5'-methoxy-6-methyl-N-(5-{2-oxa-6-azaspiro[3.4]octan-6-yl}-[1,3]thiazolo[5,4-d]pyrimidin-2-yl)-[4,4'-bipyridine]-3-carboxamide | *** |
| 77 | 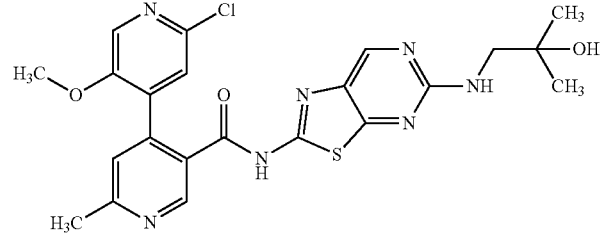 [SMILES: COc1cnc(Cl)cc1-c1cc(C)ncc1C(=O)Nc1nc2cnc(NCC(C)(C)O)nc2s1]<br>2'-chloro-N-{5-[(2-hydroxy-2-methylpropyl)amino]-[1,3]thiazolo[5,4-d]pyrimidin-2-yl}-5'-methoxy-6-methyl-[4,4'-bipyridine]-3-carboxamide | *** |
| 78 | 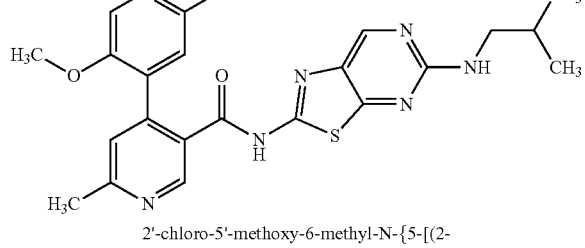<br>2'-chloro-5'-methoxy-6-methyl-N-{5-[(2-methylpropyl)amino]-[1,3]thiazolo[5,4-d]pyrimidin-2-yl}-[4,4'-bipyridine]-3-carboxamide | *** |
| 79 | 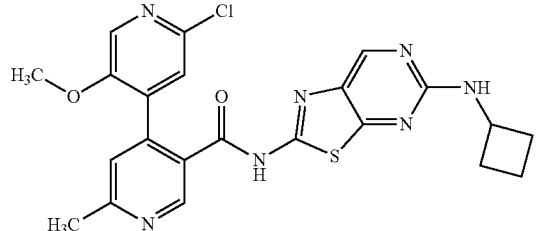<br>2'-chloro-N-[5-(cyclobutylamino)-[1,3]thiazolo[5,4-d]pyrimidin-2-yl]-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 80 | 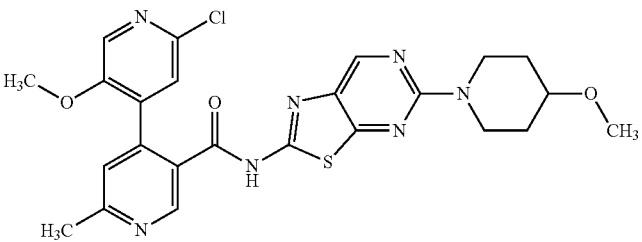<br>2'-chloro-5'-methoxy-N-[5-(4-methoxypiperidin-1-yl)-[1,3]thiazolo[5,4-d]pyrimidin-2-yl]-6-methyl-[4,4'-bipyridine]-3-carboxamide | *** |
| 81 | 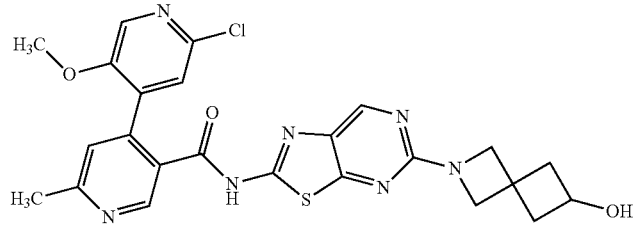 [SMILES: COc1cnc(Cl)cc1-c1cc(C)ncc1C(=O)Nc1nc2cnc(N3CC4(CC(O)C4)C3)nc2s1]<br>2'-chloro-N-(5-{6-hydroxy-2-azaspiro[3.3]heptan-2-yl}-[1,3]thiazolo[5,4-d]pyrimidin-2-yl)-5'-methoxy-6-methyl-[4,4'-bipyridine]-3-carboxamide | *** |
| 82 | 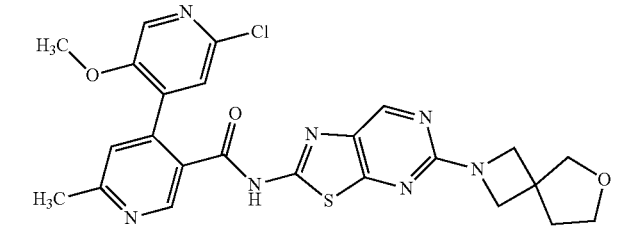 [SMILES: COc1cnc(Cl)cc1-c1cc(C)ncc1C(=O)Nc1nc2cnc(N3CC4(CCOC4)C3)nc2s1]<br>2'-chloro-5'-methoxy-6-methyl-N-(5-{6-oxa-2-azaspiro[3.4]octan-2-yl}-[1,3]thiazolo[5,4-d]pyrimidin-2-yl)-[4,4'-bipyridine]-3-carboxamide | *** |
| 83 | 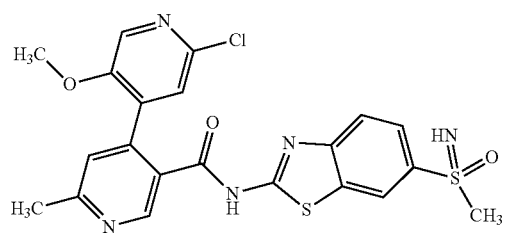 [SMILES: COc1cnc(Cl)cc1-c1cc(C)ncc1C(=O)Nc1nc2ccc(S(C)(=N)=O)cc2s1]<br>2'-chloro-N-{6-[imino(methyl)oxo-λ⁶-sulfanyl]-1,3-benzothiazol-2-yl}-5'-methoxy-6-methyl-[4,4'-bipyridine]-3-carboxamide | *** |
| 84 | 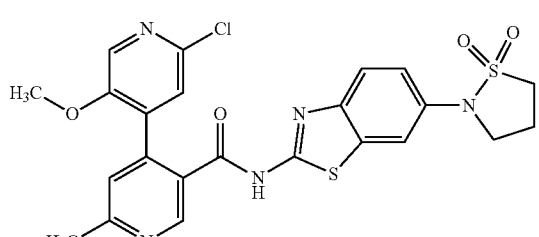<br>2'-chloro-N-[6-(1,1-dioxo-1λ⁶,2-thiazolidin-2-yl)-1,3-benzothiazol-2-yl]-5'-methoxy-6-methyl-[4,4'-bipyridine]-3-carboxamide | *** |

TABLE A-continued

Polθ ATPase assay IC50 results

| Example No. | Compound | Polθ ATPase assay IC50 |
|---|---|---|
| 85 | 2'-chloro-N-{6-[(4R)-4-hydroxy-2-oxopiperidin-1-yl]-1,3-benzothiazol-2-yl}-5'-methoxy-6-methyl-[4,4'-bipyridine]-3-carboxamide | *** |
| 86 | 2'-chloro-5'-methoxy-6-methyl-N-[6-(4-methyl-2-oxopiperazin-1-yl)-1,3-benzothiazol-2-yl]-[4,4'-bipyridine]-3-carboxamide | *** |
| 87 | 2'-chloro-N-[5-(3,6-dihydro-2H-pyran-4-yl)-[1,3]thiazolo[5,4-d]pyrimidin-2-yl]-5'-methoxy-6-methyl-[4,4'-bipyridine]-3-carboxamide | *** |
| 88 | N-[5-(4-hydroxypiperidin-1-yl)-[1,3]thiazolo[5,4-d]pyrimidin-2-yl]-5'-methoxy-6-methyl-2'-(trifluoromethyl)-[4,4'-bipyridine]-3-carboxamide | *** |
| 89 | N-[5-(4-hydroxypiperidin-1-yl)-[1,3]thiazolo[5,4-d]pyrimidin-2-yl]-5'-methoxy-6-methyl-2'-(trifluoromethyl)-[4,4'-bipyridine]-3-carboxamide | *** |

TABLE A-continued

Polθ ATPase assay IC50 results

| Example No. | Compound | Polθ ATPase assay IC50 |
|---|---|---|
| 90 | 2'-chloro-5'-methoxy-6-methyl-N-[5-(trifluoromethyl)-[1,3]thiazolo[5,4-d]pyrimidin-2-yl]-[4,4'-bipyridine]-3-carboxamide | *** |
| 91 | 2'-chloro-5'-methoxy-6-methyl-N-{5-methyl-[1,3]thiazolo[5,4-d]pyrimidin-2-yl}-[4,4'-bipyridine]-3-carboxamide | *** |
| 92 | 5'-methoxy-2',6-dimethyl-N-[5-(morpholin-4-yl)-[1,3]thiazolo[5,4-d]pyrimidin-2-yl]-[4,4'-bipyridine]-3-carboxamide | *** |
| 93 | 2'-fluoro-5'-methoxy-6-methyl-N-[5-(morpholin-4-yl)-[1,3]thiazolo[5,4-d]pyrimidin-2-yl]-[4,4'-bipyridine]-3-carboxamide | *** |
| 94 | 2'-chloro-5'-methoxy-6-methyl-N-[5-(2-oxopiperidin-1-yl)-[1,3]thiazolo[5,4-d]pyrimidin-2-yl]-[4,4'-bipyridine]-3-carboxamide | *** |

\*\*\* denotes an IC50 of less than 100 nM
\*\* denotes an IC50 of 100 nM to 1000 nM
\* denotes an IC50 of greater than 1000 nM

EXAMPLES—PART B

Analytical

All solvents and chemical reagents were obtained from commercial sources and were used without further purification or drying. NMR spectra were recorded on either a Bruker Avance III HD 400 MHz, a Bruker NEO 400 MHz, a Bruker Avance III HD 500 MHz, a Bruker Avance NEO 500 MHz or a Bruker Avance III HD 600 MHz spectrometer. Chemical shifts are quoted in ppm using residual undeuterated solvent as the internal reference.

LCMS spectra were recorded on a Waters Aquity UPLC using method A; Waters UPLC® BEH™ C18 2.1×50 mm 1.7 μm column at 40° C. eluting with 0.1% formic acid in acetonitrile and 0.1% formic acid in water using a gradient of 5-100% over 1.35 mins at a rate of 0.9 mL/min, method B; Phenomenex Kinetix-XB C18 2.1×100 mm, 1.7 μm column at 40° C. eluting with 0.1% formic acid in acetonitrile and 0.1% formic acid in water using a gradient of 5-100% over 5.8 mins at a rate of 0.6 mL/min, method C; Waters UPLC® BEH™ C18 2.1×50 mm 1.7 μm column at 55° C. eluting with 2 mM ammonium bicarbonate in water, buffered to pH 10 and acetonitrile using a gradient of 1-100% over 1.10 mins at a rate of 1 mL/min, method D; Waters UPLC® BEH™ C18 2.1×100 mm 1.7 μm column at 55° C. eluting with 2 mM ammonium bicarbonate in water, buffered to pH 10 and acetonitrile using a gradient of 5-100% over 5.30 mins at a rate of 0.6 mL/min, method E; Waters CSH C18 2.1×50 mm, 1.7 μm column at 55° C. eluting with 0.035% TFA in acetonitrile and 0.05% TFA in water using a gradient of 2% to 98% over 1.5 mins at a rate of 0.8 mL/min, method F; Waters CSH C18 2.1×50 mm, 1.7 μm column at 55° C. eluting with 0.035% TFA in acetonitrile and 0.05% TFA in water using a gradient of 2% to 98% over 2.4 mins at a rate of 0.8 mL/min, method G; Waters CSH C18 2.1×50 mm, 1.7 μm column at 55° C. eluting with 0.02% formic acid in acetonitrile and 0.02% formic acid in water using a gradient of 2% to 98% over 4.5 mins at a rate of 1 mL/min, or method H; Waters CSH C18 2.1×50 mm, 1.7 μm column at 55° C. eluting with 0.02% formic acid in acetonitrile and 0.02% formic acid in water using a gradient of 2% to 98% over 2.4 mins at a rate of 0.8 mL/min. Mass spectra were obtained using a Waters SQD, SQD2 or a QDA detector using electrospray ionisation in positive or negative mode. LCMS purity was assigned using AUC monitoring at 215, 220, 254 or 280 nm.

Preparative HPLC was performed using either method A: Waters Sunfire C18 30 mm×100 mm, 5 μm column at room temperature using 30% 0.1% formic acid in acetonitrile and 70% 0.1% formic acid in water for 1.9 mins then a gradient of 30-95% 0.1% formic acid in acetonitrile for 9.6 mins at a flow rate of 40 mL/min, method B; Waters XBridge C18 column 30 mm×100 mm, 5 μm at room temperature using 30% acetonitrile and 70% 0.2% ammonium hydroxide in water for 2 mins then a gradient of 30-95% acetonitrile for 9.5 mins at a flow rate of 40 mL/min, or method C; Waters Sunfire™ C18 column (30 mm×100 mm, 5 μm; temperature: room temperature), with an injection volume of 1500 μL at a flow rate of 40 mL/min at 10% B for 1.90 min then a gradient of 10-95% B over 14.10 min and held for 2.0 min, where A=0.1% formic acid in water and B=0.1% formic acid in acetonitrile. UV spectra were recorded at 215 nm using a Gilson detector.

Experimental

Examples listed in the table below were prepared in a manner analogous to general procedure D previously described.

| Example | Yield | LCMS Purity (%) | LCMS Rt (mins) | m/z | LCMS method | $^1$H NMR |
|---|---|---|---|---|---|---|
| 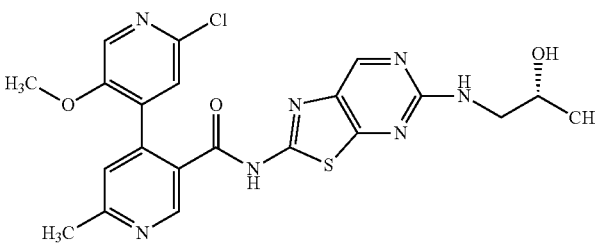<br>Example 95<br>2'-chloro-N-(5-{[(2R)-2-hydroxypropyl]amino}-[1,3]thiazolo[5,4-d]pyrimidin-2-yl)-5'-methoxy-6-methyl-[4,4'-bipyridine]-3-carboxamide | 6.5 | 95 | 2.41 | 486.3/488.3 | B | $^1$H NMR (400 MHz, DMSO-d$_6$) δ 12.85 (s, 1H), 8.85 (s, 1H), 8.66 (s, 1H), 8.17 (s, 1H), 7.55 (s, 1H), 7.43 (s, 1H), 7.20 (s, 1H), 4.70 (d, J = 4.8 Hz, 1H), 3.86-3.75 (m, 1H), 3.63 (s, 3H), 3.28-3.22 (m, 2H), 2.60 (s, 3H), 1.08 (d, J = 6.2 Hz, 3H). |

| Example | Yield | LCMS Purity (%) | LCMS Rt (mins) | m/z | LCMS method | 1H NMR |
|---|---|---|---|---|---|---|
| 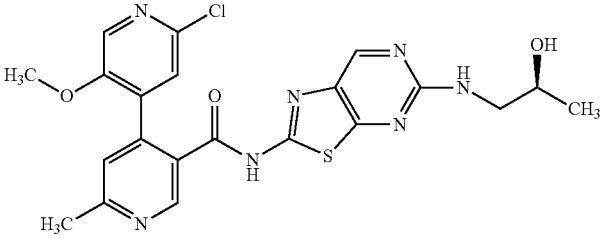 [SMILES: COc1cnc(Cl)cc1-c1cc(C)ncc1C(=O)Nc1nc2cnc(NC[C@H](C)O)nc2s1] Example 96 2'-chloro-N-(5-{[(2S)-2-hydroxypropyl]amino}-[1,3]thiazolo[5,4-d]pyrimidin-2-yl)-5'-methoxy-6-methyl-[4,4'-bipyridine]-3-carboxamide | 8.8 | 95 | 2.43 | 486.3/488.3 | B | 1H NMR (400 MHz, DMSO-$d_6$) δ 8.84 (s, 1H), 8.62 (s, 1H), 8.15 (s, 1H), 7.56-7.36 (m, 2H), 4.68 (d, J = 4.8 Hz, 1H), 3.86-3.72 (m, 1H), 3.62 (s, 3H), 3.28-3.18 (m, 3H), 2.58 (s, 3H), 2.06-1.94 (m, 1H), 1.06 (d, J = 6.2 Hz, 3H). |
| 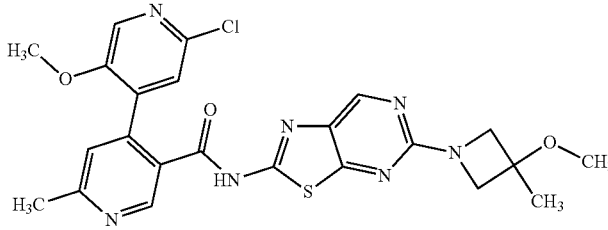 Example 97 2'-chloro-5'-methoxy-N-[5-(3-methoxy-3-methylazetidin-1-yl)-[1,3]thiazolo[5,4-d]pyrimidin-2-yl]-6-methyl-[4,4'-bipyridine]-3-carboxamide | 41 | 100 | 2.92 | 512.3/514.3 | B | 1H NMR (400 MHz, DMSO-$d_6$) δ 12.93 (s, 1H), 8.82 (s, 1H), 8.77 (s, 1H), 8.17 (s, 1H), 7.57 (s, 1H), 7.46 (s, 1H), 4.06-3.97 (m, 2H), 3.94-3.86 (m, 2H), 3.62 (s, 3H), 3.21 (s, 3H), 2.60 (s, 3H), 1.47 (s, 3H). |

General Procedure H for the Preparation of 5-alkoxy-1,3-benzothiazole-2-amines

To a solution of 2-amino-1,3-benzothiazole-5-ol (1 equiv) and either potassium carbonate or caesium carbonate (2 equiv) in acetone, DMF or acetonitrile (0.2 mmol/mL) was added the required alkyl halide (1.2 equiv) and the reaction stirred at 50° C. until the reaction was deemed complete by LCMS. The reaction mixture was diluted with water, if the product precipitated it was filtered and dried in a vacuum oven. If the product did not precipitate the aqueous mix was extracted with ethyl acetate. The organic extracts were washed with brine solution, dried, and concentrated under reduced pressure. The residue was either used crude in the next stage or purified by Biotage Isolera™ automated chromatography to give the desired alkylated products.

Intermediate I15 2-[(2-amino-1,3-benzothiazol-5-yl)oxy]acetonitrile

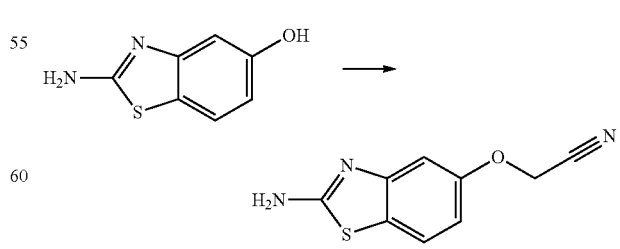

To a stirred suspension of 2-amino-1,3-benzothiazol-5-ol (202 mg, 1.2 mmol) and potassium carbonate (330 mg, 2.4 mmol) in acetone (6.0 mL) was added bromoacetonitrile (100 uL, 1.39 mmol). The mixture was stirred at 50° C. for 16 h. The reaction mixture was diluted with water (10 mL) and extracted with ethyl acetate (2×10 mL). Organic extracts were washed with brine and dried by filtration through a hydrophobic filter paper. The crude residue was purified by Biotage Isolera™ automated chromatography (25 g, Sfar Duo) eluting with a solvent gradient of 0-10% methanol in DCM to give the title compound (45 mg, 19%) as beige powder. $^1$H NMR (400 MHz, DMSO-$d_6$) δ 7.58 (d, J=8.6 Hz, 1H), 7.53 (s, 2H), 7.06 (d, J=2.6 Hz, 1H), 6.74 (dd, J=8.6, 2.6 Hz, 1H), 5.16 (s, 2H). LCMS (method F) Rt 0.57 mins (100%), m/z 206.2 (M+H)$^+$.

Intermediates in the table below were prepared in an analogous manner to general procedure H described above.

| Intermediate | Yield | LCMS Purity (%) | LCMS Rt (mins) | m/z | LCMS method | $^1$H NMR |
|---|---|---|---|---|---|---|
| 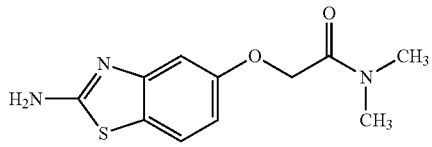 [SMILES: CN(C)C(=O)COc1ccc2sc(N)nc2c1]<br>Intermediate 116<br>2-[(2-amino-1,3-benzothiazol-5-yl)oxy]-N,N-dimethylacetamide | 93 | 61 | 0.53 | 252.2 | F | Not recorded |
| 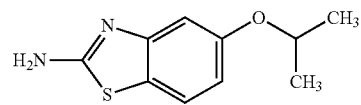<br>Intermediate 117<br>5-(propan-2-yloxy)-1,3-benzothiazol-2-amine | 73 | 75 | 0.80 | 209.0 | F | Not recorded |
| 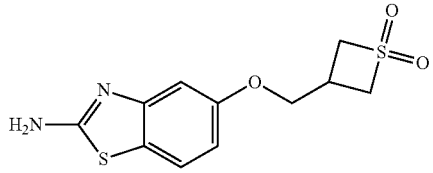 [SMILES: Nc1nc2cc(OCC3CS(=O)(=O)C3)ccc2s1]<br>Intermediate 118<br>3-{[(2-amino-1,3-benzothiazol-5-yl)oxy]methyl}-1-λ-6-thietane-1,1-dione | 2.6 | 70 | 0.58 | 285.2 | F | Not recorded |
| 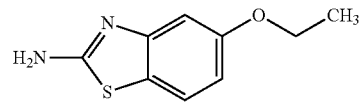<br>Intermediate 119<br>5-ethoxy-1,3-benzothiazol-2-amine | quant | unknown | 0.50 | 195.2 | E | Not recorded |
| 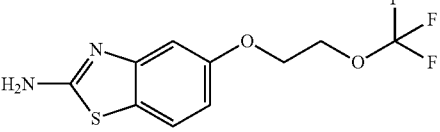<br>Intermediate 120<br>5-[2-(trifluoromethoxy)ethoxy]-1,3-benzothiazol-2-amine | 19 | 95 | 0.93 | 279.2 | F | $^1$H NMR (400 MHz, DMSO-$d_6$) δ 7.51 (d, J = 8.6 Hz, 1H), 7.46 (s, 2H), 6.94 (d, J = 2.5 Hz, 1H), 6.66 (dd, J = 8.5, 2.5 Hz, 1H), 4.43-4.36 (m, 2H), 4.27-4.20 (m, 2H). |

Intermediate I21 1-(4-{[(2-amino-1,3-benzothiazol-5-yl)oxy]methyl}piperidin-1-yl)ethan-1-one

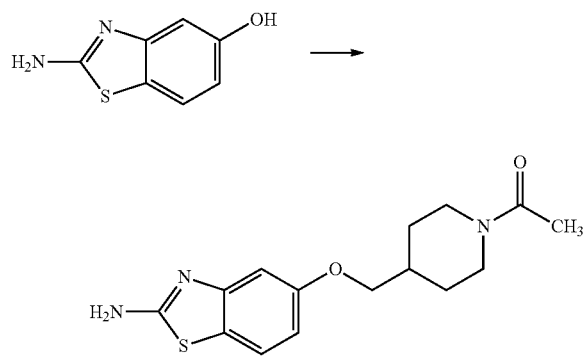

To a stirred solution of N,N-isopropoxycarbonyliminocarbamate (338 uL, 1.71 mmol) in THF (9 mL) was added triphenylphosphine (1.07 g, 1.71 mmol). The reaction mixture was cooled to 0° C. then 2-amino-1,3-benzothiazol-5-ol (250 mg, 1.43 mmol) and 1-[4-(hydroxymethyl)piperidin-1-yl]ethanone (260 mg, 1.57 mmol) were added. The reaction mixture was allowed to warm to RT and stirred overnight. The reaction mixture was heated to reflux for 4 h then allowed to cool to RT overnight. The reaction mixture was filtered, and the filtrate was concentrated under reduced pressure. The crude residue was purified by reverse phase Biotage Isolera™ automated chromatography (15 g, C18) using a solvent gradient of 0-100% acetonitrile in water with 0.1% acetic acid additive to give the title compound (335 mg, 65%) as a brown semi-solid. LCMS (method F) Rt 0.78 mins (85%), m/z 306.3 (M+H)$^+$.

Intermediate I22 2-[(2-amino-1,3-benzothiazol-5-yl)oxy]-2,2-difluoro-N-methylacetamide

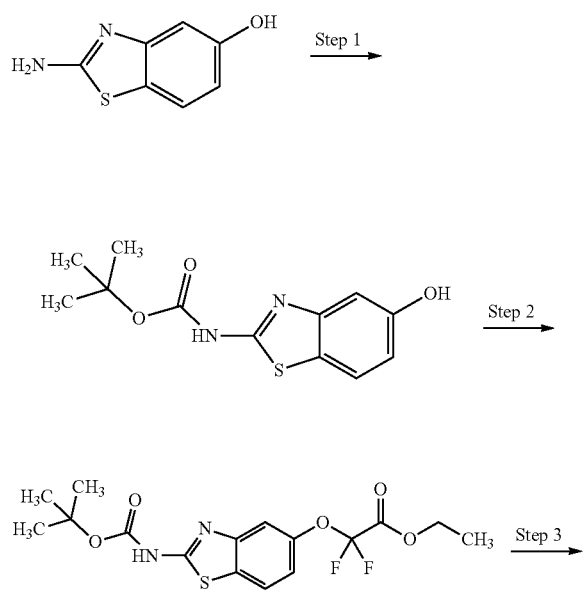

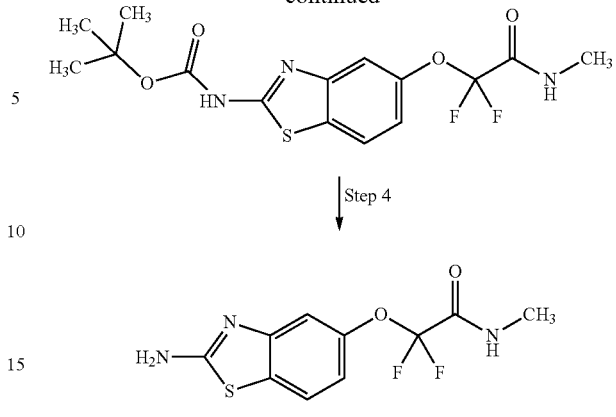

Step 1—Tert-butyl N-(5-hydroxy-1,3-benzothiazol-2-yl)carbamate

To a solution of 2-amino-1,3-benzothiazol-5-ol (1.00 g, 5.7 mmol) in cyclopentyl methyl ether (80 mL) was Boc anhydride (2.50 g, 11.4 mmol), triethylamine (1.59 mL, 11.4 mmol) and N,N-dimethylpyridin-4-amine (35 mg, 0.29 mmol) and the mixture was stirred for 16 hours at RT. The reaction mixture was then concentrated in vacuo and ethyl acetate was added. The solution was washed with water and the organic layer separated, then filtered over hydrophobic filter paper. The filtrate was concentrated in vacuo to give a white solid. The solid was dissolved in methanol (80 mL) and potassium carbonate (1.96 g, 14.2 mmol) was added. The mixture was stirred at RT for 16 h. 1M aqueous hydrogen chloride (14.3 mL, 14.3 mmol) was then added and the mixture was concentrated in vacuo. The crude product was partitioned between ethyl acetate and water. Organics were separated and filtered over hydrophobic filter paper. The filtrate was concentrated in vacuo to give the title compound (1.28 g, 67%) as an off-white solid. $^1$H NMR (400 MHz, DMSO-d$_6$) δ: 11.59 (s, 1H), 9.44 (s, 1H), 7.64 (d, J=8.5 Hz, 1H), 7.02 (d, J=2.3 Hz, 1H), 6.77-6.70 (m, 1H), 1.50 (s, 9H). LCMS (method F) Rt 1.30 mins (80%) m/z 267.0 (M+H)$^+$.

Step 2—ethyl 2-[(2-{[(tert-butoxy)carbonyl]amino}-1,3-benzothiazol-5-yl)oxy]-2,2-difluoroacetate To a solution of tert-butyl N-(5-hydroxy-1,3-benzothiazol-2-yl)carbamate (200 mg, 0.75 mmol) in acetone (5.0 mL) was added ethyl 2-bromo-2,2-difluoro-acetate (295 μL, 2.25 mmol) followed by DBU (347 μL, 2.25 mmol) and the mixture stirred at RT for 16 h. The reaction mixture was concentrated in vacuo and purified directly by Biotage Isolera™ automated chromatography (25 g. Sfar Duo) eluting with a solvent gradient of 0-50% ethyl acetate in heptanes to give the title compound (44 mg, 14%) as a colourless solid. LCMS (method F) Rt 1.73 mins (70%), m/z 375.0 (M+H)$^+$ (methyl ester), Rt 1.82 mins (21%), m/z 389.0 (M+H)$^+$ (ethyl ester). N.B Partial transesterification occurred during concentration from methanol.

Step 3—tert-butyl N-{5-[difluoro(methylcarbamoyl)methoxy]-1,3-benzothiazol-2-yl}carbamate To a solution of ethyl 2-[(2-{[(tert-butoxy)carbonyl]amino}-1,3-benzothiazol-5-yl)oxy]-2,2-difluoroacetate (44 mg, 0.11 mmol) in cyclopentyl methyl ether (2.0 mL) was added 2M methylamine in THF (2.0 mL, 4.0 mmol) and the mixture was stirred at 50° C. for 5 h, then at RT for 72 hours. The reaction mixture was then concentrated in vacuo and purified directly by Biotage Isolera™ automated chromatography (10 g, Sfar Duo) eluting with a solvent gradient of 0-80% ethyl acetate/ethanol (3:1) in heptanes to give the title compound (40 mg, 91%) as a colourless solid. LCMS (method F) Rt 1.47 mins (91%), m/z 374.0 (M+H)⁺.

Step 4—2-[(2-amino-1,3-benzothiazol-5-yl)oxy]-2,2-difluoro-N-methylacetamide

To a stirred suspension of tert-butyl N-{5-[difluoro(methylcarbamoyl)methoxy]-1,3-benzothiazol-2-yl}carbamate (40 mg, 0.1 mmol) in DCM (3.0 mL) at RT was added trifluoroacetic acid (75 uL, 1.0 mmol) and the reaction mixture was stirred at RT for 5 h. Additional trifluoroacetic acid (0.2 mL, 2.6 mmol) was added and the reaction mixture was stirred for 16 h at RT. The volatiles were removed under reduced pressure to afford the title compound (31 mg, 97%) as a light brown solid. LCMS (method F) Rt 0.64 mins (83%), m/z 274.1 (M+H)⁺.

Intermediate I23 2-[(2-amino-1,3-benzothiazol-5-yl)oxy]-2,2-difluoro-N,N-dimethylacetamide

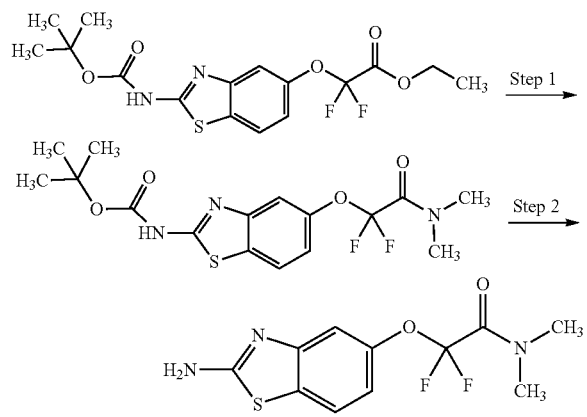

Step 1—tert-butyl N-{5-[(dimethylcarbamoyl)difluoromethoxy]-1,3-benzothiazol-2-yl}carbamate The title compound was prepared in an analogous manner to that described for step 3 intermediate I22, starting from ethyl 2-[(2-{[(tert-butoxy)carbonyl]amino}-1,3-benzothiazol-5-yl)oxy]-2,2-difluoroacetate (46 mg, 0.1 mmol) and 2M dimethylamine in THF (1 mL, 2 mmol) to give 40 mg, 93% as a colourless solid. LCMS (method F) Rt 1.6 mins (91%), m/z 388.0 (M+H)⁺.

Step 2—2-[(2-amino-1,3-benzothiazol-5-yl)oxy]-2,2-difluoro-N,N-dimethylacetamide The title compound was prepared in a manner analogous to that described for step 4 intermediate I22, starting from tert-butyl N-{5-[(dimethylcarbamoyl)difluoromethoxy]-1,3-benzothiazol-2-yl}carbamate (40 mg, 0.1 mmol) and tri-fluoroacetic acid (38 equiv) to give 25 mg, 61% as a colourless oil. LCMS (method F) Rt 0.79 mins (66%), m/z 288.1 (M+H)⁺.

Intermediate I24 2-amino-N-methyl-1,3-benzothiazole-5-carboxamide

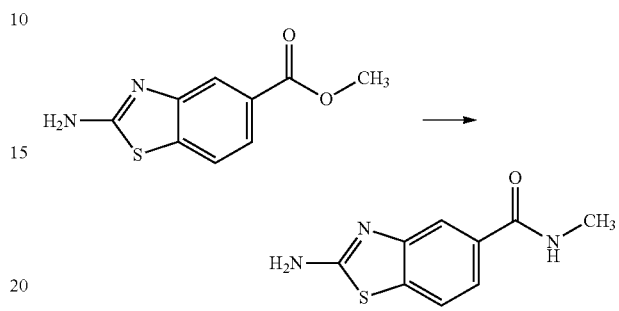

Methyl 2-amino-1,3-benzothiazole-5-carboxylate (150 mg, 0.7 mmol) was suspended in Ethanol (3.0 mL) and an aqueous solution of 1M lithium hydroxide (1.40 mL, 1.40 mmol) was added. The mixture was stirred at 50° C. for 3 h. 1M aqueous hydrogen chloride (1.4 mL) was then added and the resulting mixture was concentrated in vacuo, to give a white solid. HATU (298 mg, 0.77 mmol) was added and the resulting mixture suspended in Dimethyl carbonate (5.0 mL). DIPEA (0.24 mL, 1.40 mmol) was added and the mixture was stirred for 10 mins before 2M methylamine in THF (1.05 mL, 2.10 mmol) was added. The reaction was stirred at RT for 3 h. Additional HATU (271 mg, 0.7 mmol), DIPEA (0.24 mL, 1.40 mmol) and 2M methylamine in THF (3.49 mL, 6.99 mmol) was added to the mixture and the reaction was stirred at RT for 16 h. The reaction mixture was concentrated in vacuo and the residue was partitioned between THF and a sat. NaHCO₃ solution. Phases were separated, and the organic layer was filtered over hydrophobic filter paper. The filtrate was concentrated in vacuo to give the title compound (190 mg, quant.) as a colourless oil. LCMS (method F) Rt 0.45 mins (80%), m/z 208.0 (M+H)⁺.

Intermediate I25 2-amino-N-(2-methoxyethyl)-1,3-benzothiazole-5-carboxamide

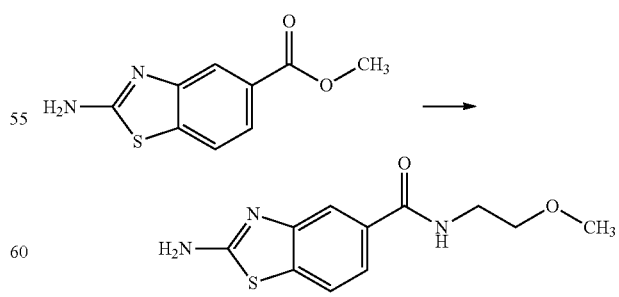

The title compound was prepared in an analogous manner to intermediate I24 described above to give 141 mg, 55% as a colourless oil. LCMS (method F) Rt 0.41 mins (68%) m/z 252.0 (M+H)⁺.

Intermediate I26 2-({2-amino-[1,3]thiazolo[5,4-d]pyrimidin-7-yl}oxy)-N,N dimethylacetamide

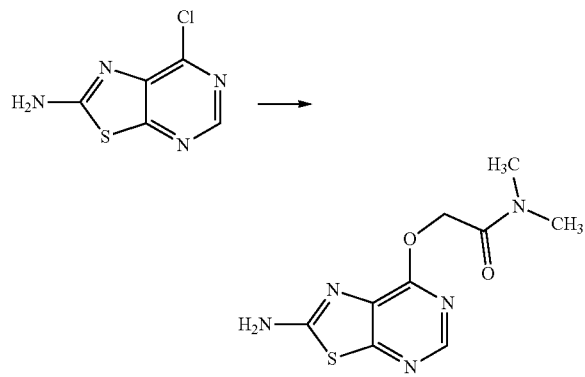

Sodium hydride (17 mg, 0.43 mmol, 60% in mineral oil) was added in one portion to 2-hydroxy-N,N-dimethylacetamide (30 mg, 0.29 mmol) in anhydrous THF (3.1 mL) at 0° C. The resulting suspension was stirred at 0° C. for 10 mins and then 7-chloro-[1,3]thiazolo[5,4-d]pyrimidin-2-amine (56 mg, 0.29 mmol) was added as a suspension in dry THF (1.0 mL), dropwise over 1 minute. The mixture was stirred at 0° C. for 15 mins, then allowed to warm to RT and stirred overnight. The mixture was then heated at 65° C. for 48 h. Additional 2-hydroxy-N,N-dimethylacetamide (15.0 mg, 0.14 mmol) and sodium hydride (11 mg, 0.29 mmol, 60% in mineral oil) were premixed together in dry THF (1.0 mL) at 0° C. for 5 mins then added to the reaction mixture at RT. The reaction was stirred at 60° C. for a further 24 h. The reaction was quenched by addition of aqueous 1M Citric acid solution (5 mL) and the mixture extracted with ethyl acetate (2×20 mL). The product remained in the aqueous phase, so the aqueous phase was further extracted with 2-methyl THF (2×30 mL) and IPA/chloroform (1:3, 2×30 mL). Organic extracts were combined and concentrated in vacuo. The crude residue was purified by Biotage Isolera™ automated chromatography (12 g, Sfar Duo) eluting with a solvent gradient of 30-100% ethyl acetate/ethanol (3:1) in heptanes to give the title compound (30 mg, 41%) as a yellow solid. $^1$H NMR (400 MHz, DMSO-$d_6$) δ: 8.27 (s, 1H), 7.90 (s, 2H), 5.19 (s, 2H), 3.00 (s, 3H), 2.82 (s, 3H). LCMS (method F) Rt 0.63 mins (98%), m/z 254.3 (M+H)$^+$.

Intermediate I27 3-(2-amino-1,3-benzothiazol-4-yl)-N,N-dimethylpropanamide

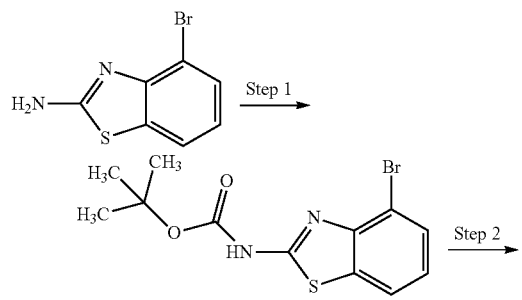

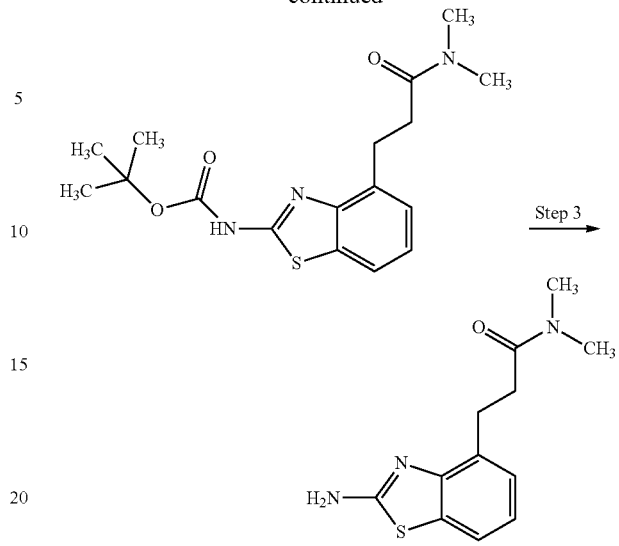

Step 1—tert-butyl N-(4-bromo-1,3-benzothiazol-2-yl)carbamate

To a solution of 2-amino-1,3-benzothiazol-5-ol (1.00 g, 5.72 mmol) in cyclopentyl methyl ether (80 mL) was added Boc anhydride (2.50 g, 11.4 mmol), triethylamine (1.59 mL, 11.4 mmol), and N,N-dimethylpyridin-4-amine (34.9 mg, 0.29 mmol) and the mixture was stirred at RT overnight. The solvent was then removed under reduced pressure and replaced with 2-methyl THF. The 2-methyl THF solution was washed with water and brine solution. The organic layer was filtered over hydrophobic filter paper and concentrated in vacuo to give the title compound (759 mg, 94%) as a yellow solid. $^1$H NMR (400 MHz, DMSO-$d_6$) δ: 12.12 (s, 1H), 7.94 (dd, J=7.8, 1.2 Hz, 1H), 7.62 (dd, J=7.8, 1.1 Hz, 1H), 7.17 (td, J=7.9, 1.7 Hz, 1H), 1.58-1.47 (m, 9H). LCMS (method F) Rt 1.8 mins (88%), m/z 329.1/331.3 (M+H)$^+$, 273.0/275.0 (M-$^t$Bu+H)$^+$.

Step 2—tert-butyl N-{4-[2-(dimethylcarbamoyl)ethyl]-1,3-benzothiazol-2-yl}carbamate To a 5 mL vial was added the photocatalyst ditert-butyl-tetrafluoro-bis(trifluoromethyl)spiro[BLAH] hexafluorophosphate (8.6 mg, 7.6 μmol), tert-butyl N-(4-bromo-1,3-benzothiazol-2-yl)carbamate (250 mg, 0.76 mmol), 3-bromo-N,N-dimethyl-propanamide (205 mg, 1.14 mmol), tris(trimethylsilyl)silane (351 μL, 1.14 mmol), 4,4'-di-tert-butyl-2,2'-bipyridyl nickel dichloride (16 mg, 38 μmol) and anhydrous sodium carbonate (169 mg, 1.52 mmol). The vial was sealed and placed under nitrogen before DME (4 mL) was added. The solution was degassed by sparging with nitrogen with stirring for 10 mins. The reaction was then stirred and irradiated with a 34 W blue LED lamp (6 cm away, with cooling fan to keep the reaction temperature at 25° C.) for 20 hours. The reaction was quenched by exposure to air and concentration in vacuo. The crude material was purified by Biotage Isolera™ automated chromatography (24 g, Sfar Duo) using a solvent gradient of 0-100% ethyl acetate in heptanes to give the title compound (53 mg, 20%) as a yellow solid. LCMS (method F) Rt 1.55 mins (100%) m/z 350.3 (M+H)$^+$.

Step 3—3-(2-amino-1,3-benzothiazol-4-yl)-N,N-dimethylpropanamide

To a solution of tert-butyl N-{4-[2-(dimethylcarbamoyl)ethyl]-1,3-benzothiazol-2-yl}carbamate (53 mg, 0.15 mmol) in DCM (1.5 mL) was added trifluoroacetic acid (232 uL, 3.0 mmol) and the mixture stirred at RT for 7 h. The mixture was concentrated under reduce pressure and the residue dissolved in 2-methyl THF. The 2-methyl THF solution was washed with sat. NaHCO$_3$ solution, the organic phase was separated and filtered through hydrophobic filter paper before being concentrated under reduce pressure to give the title compound (28 mg, 72%) as a yellow-beige solid. $^1$H NMR (400 MHz, DMSO-d$_6$) δ 7.49 (t, 2H), 7.47 (d, 1H), 7.06 (dd, 1H), 6.92 (t, 1H), 3.04-2.95 (m, 2H), 2.92 (s, 3H), 2.81 (s, 3H), 2.66-2.57 (m, 2H). LCMS (method F) Rt 0.66 mins (99%), m/z 250.2 (M+H)$^+$.

Intermediate I28 5-[2-(morpholin-4-yl)ethoxy]-1,3-benzothiazol-2-amine

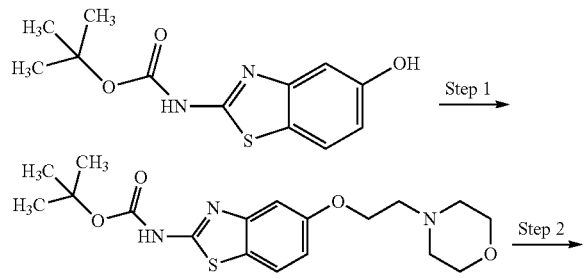

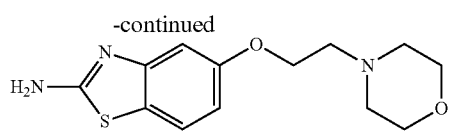

Step 1—tert-butyl N-{5-[3-(morpholin-4-yl)propoxy]-1,3-benzothiazol-2-yl}carbamate The title compound was prepared in an analogous manner to general procedure H starting from tert-butyl N-(5-hydroxy-1,3-benzothiazol-2-yl)carbamate (198 mg, 0.6 mmol, prepared as in step 1 intermediate I22) to give 325 mg, 53% as a yellow oil. LCMS (method E) Rt 0.59 mins (37%), m/z 380.3 (M+H)$^+$.

Step 2—5-[3-(morpholin-4-yl)propoxy]-1,3-benzothiazol-2-amine

The title compound was prepared in a manner analogous to step 3 intermediate I27 to give 247 mg, 44% as a yellow oil. LCMS (method E) Rt 0.45 mins (40%), m/z 280.2 (M+H)$^+$.

All examples in the table below we prepared using general procedure C previously described, starting from either commercially available 2-amino benzothiazoles or the intermediates described above. Reactions were heated to 60° C. if no reaction occurred at RT.

| Example | Yield | LCMS Purity (%) | LCMS Rt (mins) | m/z | LCMS method | $^1$H NMR |
|---|---|---|---|---|---|---|
| Example 99<br>N-(4-bromo-1,3-benzothiazol-2-yl)-2'-chloro-5'-methoxy-6-methyl-[4,4'-bipyridine]-3-carboxamide | 86 | 98 | 1.53 | 489.0/491.1 | F | $^1$H NMR (400 MHz, DMSO-d6) δ: 13.32 (s, 1H), 8.88 (s, 1H), 8.15 (s, 1H), 7.99 (s, 1H), 7.69 (d, J = 8.0 Hz, 1H), 7.56 (s, 1H), 7.44 (s, 1H), 7.24 (s, 1H), 3.60 (s, 3H), 2.60 (s, 3H) |

| Example | Yield | LCMS Purity (%) | LCMS Rt (mins) | m/z | LCMS method | ¹H NMR |
|---|---|---|---|---|---|---|
| Example 100<br>2'-chloro-N-{4-[2-(dimethylcarbamoyl)ethyl]-1,3-benzothiazol-2-yl}-5'-methoxy-6-methyl-[4,4'-bipyridine]-3-carboxamide | Quant. | 99 | 1.36 | 510.2/512.2 | F | ¹H NMR (600 MHz DMSO-$d_6$) δ 12.96 (s, 1H), 8.85 (s, 1H), 8.15 (s, 1H), 7.80 (br d,) J = 7.7 Hz, 1H), 7.56 (s, 1H), 7.44 (s, 1H), 7.31 (br d,) J = 7.1 Hz, 1H) 7.10-7.30 (m, 1H), 3.59 (s, 3H), 3.1-3.2 (m, 2H), 2.93 (s, 3H), 2.83 (s, 3H), 2.70-2.80 (m, 2H), 2.59 (s, 3H) |
| Example 101<br>2'-chloro-N-[5-(cyanomethoxy)-1,3-benzothiazol-2-yl]-5'-methoxy-6-methyl-[4,4'-bipyridine]-3-carboxamide | 63 | 100 | 1.33 | 466.1/468.1 | F | ¹H NMR (600 MHz, DMSO-d6,) δ 12.94 (br s, 1H), 8.84 (s, 1H), 8.15 (s, 1H), 7.92 (d, J = 8.7 Hz 1H,), 7.57 (s, 1H), 7.3-7.5 (m, 2H), 7.07 (dd, J = 2.5, 8.7 Hz, 1H,), 5.26 (s, 2H), 3.59 (s, 3H), 2.60 (s, 3H) |

| Example | Yield | LCMS Purity (%) | LCMS Rt (mins) | m/z | LCMS method | ¹H NMR |
|---|---|---|---|---|---|---|
| Example 102<br>2'-chloro-N-{5-[difluoro(methylcarbamoyl)methoxy]-1,3-benzothiazol-2-yl}-5'-methoxy-6-methyl-[4,4'-bipyridine]-3-carboxamide | 13 | 99 | 1.30 | 534.2/536.2 | F | ¹H NMR (600 MHz, DMSO-$d_6$,) δ 13.06 (br s, 1H), 9.08 (br d, J = 4.5 Hz 1H,), 8.85 (s, 1H), 8.15 (s, 1H), 8.03 (br d, J = 8.3 Hz), 1H, 7.5-7.7 (m, 2H), 7.45 (s, 1H), 7.23 (br d, J = 8.3 Hz 1H,), 3.60 (s, 3H), 2.72 (d, J = 4.6 Hz 3H,), 2.60 (s, 3H) |
| Example 103<br>N-(5-bromo-1,3-benzothiazol-2-yl)-2'-chloro-5'-methoxy-6-methyl-[4,4'-bipyridine]-3-carboxamide | 84 | 100 | 1.54 | 489.0/491.1 | F | ¹H NMR (400 MHz, DMSO-$d_6$) δ 13.08 (s, 1H), 8.87 (s, 1H), 8.15 (s, 1H), 7.93 (d, J = 9.7 Hz, 2H), 7.56 (s, 1H), 7.45 (d, J = 15.9 Hz, 2H), 3.59 (s, 3H), 2.60 (s, 3H) |
| Example 104<br>2'-chloro-N-{5-[(dimethylcarbamoyl)difluoromethoxy]-1,3-benzothiazol-2-yl}-5'-methoxy-6-methyl-[4,4'-bipyridine]-3-carboxamide | 19 | 98 | 1.41 | 548.3/550.3 | F | ¹H NMR (600 MHz, DMSO-$d_6$,) δ 13.05 (br s, 1H), 8.87 (br s, 1H), 8.15 (s, 1H), 7.86-8.10 (m, 1H), 7.56 (br s, 2H), 7.44 (br s, 1H), 7.16-7.32 (m, 1H), 3.59 (s, 3H), 3.26 (s, 3H), 2.97 (s, 3H), 2.59 (s, 3H) |

| Example | Yield | LCMS Purity (%) | LCMS Rt (mins) | m/z | LCMS method | ¹H NMR |
|---|---|---|---|---|---|---|
| 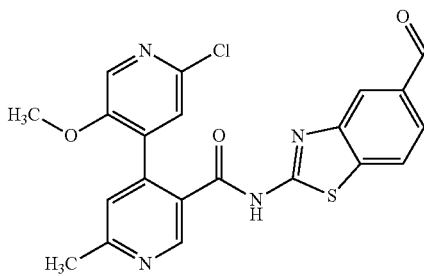<br>Example 105<br>2'-chloro-5'-methoxy-6-methyl-N-[5-(methylcarbamoyl)-1,3-benzothiazol-2-yl]-[4,4'-bipyridine]-3-carboxamide | 10 | 98 | 1.12 | 468.0/470.0 | F | ¹H NMR (600 MHz, DMSO-d6,): δ (ppm) 12.83-13.30 (m, 1H), 8.87 (s, 1H), 8.53 (br d, J = 4.4 Hz, 1H), 8.20 (br s, 1H), 8.15 (s, 1H), 8.03 (br d, J = 7.9 Hz, 1H), 7.77 (br d, J = 7.8 Hz, 1H), 7.56 (s, 1H), 7.44 (br s, 1H), 3.58-3.61 (m, 3H), 2.82 (d, J = 4.5 Hz, 3H), 2.60 (s, 3H |
| 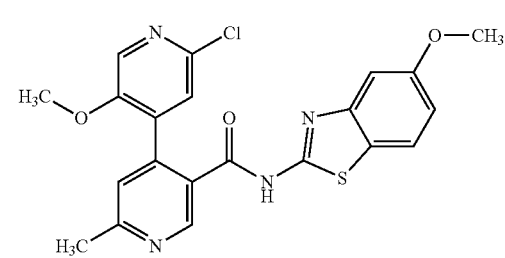<br>Example 106<br>2'-chloro-5'-methoxy-N-(5-methoxy-1,3-benzothiazol-2-yl)-6-methyl-[4,4'-bipyridine]-3-carboxamide | 70 | 100 | 1.35 | 441.2/444.2 | F | ¹H NMR (600 MHz, DMSO-d6) δ ppm 12.44-13.02 (m, 1 H) 8.85 (s, 1 H) 8.15 (s, 1 H) 7.80 (br d, J = 8.60 Hz, 1 H) 7.55 (s, 1 H) 7.43 (s, 1 H) 7.27 (br s, 1 H) 6.94 (br d, J = 7.35 Hz, 1 H) 3.82 (s, 3 H) 3.59 (s, 3 H) 2.59 (s, 3 H) |

| Example | Yield | LCMS Purity (%) | LCMS Rt (mins) | m/z | LCMS method | 1H NMR |
|---|---|---|---|---|---|---|
| Example 107<br>2'-chloro-5'-methoxy-N-{5-[(2-methoxyethyl)carbamoyl]-1,3-benzothiazol-2-yl}-6-methyl-[4,4'-bipyridine]-3-carboxamide | 10 | 98 | 1.30 | 512.0/514.0 | F | 1H NMR (600 MHz, DMSO-d6) δ 13.04 (br s, 1H), 8.90 (br s, 1H), 8.61 (br s, 1H), 8.21 (br s, 1H), 8.15 (s, 1H), 8.00 (br s, 1H), 7.78 (br s, 1H), 7.54 (br s, 1H), 7.42 (br s, 1H), 3.60 (s, 3H), 3.51-3.44 (m, 4H), 3.29-3.27 (m, 3H), 2.60 (s, 3H) |
| Example 108<br>2'-chloro-N-{7-[(dimethylcarbamoyl)methoxy]-[1,3]thiazolo[5,4-d]pyrimidin-2-yl}-5'-methoxy-6-methyl-[4,4'-bipyridine]-3-carboxamide | 45 | 99 | 1.13 | 514.4/516.4 | F | 1H NMR (600 MHz, DMSO-d6,) δ 13.1-13.6 (m, 1H), 8.88 (br s, 1H), 8.57 (br s, 1H), 8.16 (s, 1H), 7.20-7.70 (m, 2H), 5.30 (s, 2H), 3.62 (s, 3H), 3.02 (s, 3H), 2.84 (s, 3H), 2.60 (s, 3H) |

-continued

| Example | | Yield | LCMS Purity (%) | LCMS Rt (mins) | m/z | LCMS method | ¹H NMR |
|---|---|---|---|---|---|---|---|
| 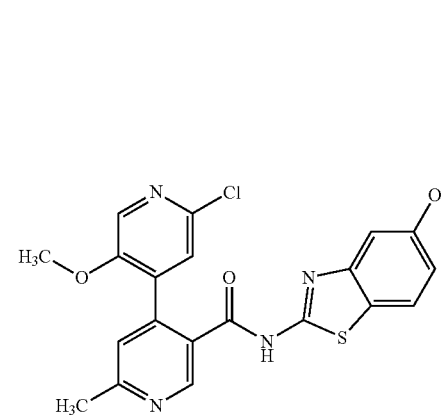 [SMILES: COc1cnc(Cl)cc1-c1cc(C)ncc1C(=O)Nc1nc2cc(Br)ccc2s1]<br>Example 109<br>N-{5-[(1-acetylpiperidin-4-yl)methoxy]-1,3-benzothiazol-2-yl}-2'-chloro-5'-methoxy-6-methyl-[4,4'-bipyridine]-3-carboxamide | | 9 | 90 | 1.37 | 566.4/568.4 | F | ¹H NMR (600 MHz, DMSO-d₆) δ ppm 12.43-13.43 (m, 1 H) 8.86 (s, 1 H) 8.15 (s, 1 H) 7.78 (br d, J = 7.4 Hz, 1 H) 7.53 (s, 1 H) 7.41 (br s, 1 H) 7.12-7.31 (m, 1 H) 6.93 (br d, J = 7.91 Hz, 1 H) 4.41 (br d, J = 12.97 Hz, 1 H) 3.91 (d, J = 6.31 Hz, 2 H) 3.84 (br d, J = 12.48 Hz, 1 H) 3.59 (s, 3 H) 2.98-3.13 (m, 1 H) 2.59 (s, 4 H) 2.00 (s, 4 H) 1.74-1.87 (m, 2 H) 1.23 (br s, 2 H) |
| 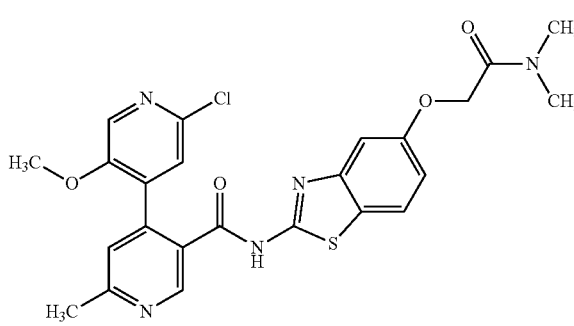<br>Example 110<br>2'-chloro-N-{5-[(dimethylcarbamoyl)methoxy]-1,3-benzothiazol-2-yl}-5'-methoxy-6-methyl-[4,4'-bipyridine]-3-carboxamide | | 42 | 100 | 1.18 | 512.2/514.2 | F | ¹H NMR (600 MHz, DMSO-d₆) δ 12.82 (br s, 1H), 8.85 (s, 1H), 8.14 (s, 1H), 7.79 (br d, J = 8.3 Hz, 1H), 7.55 (s, 1H), 7.43 (br s, 1H), 7.25 (br s, 1H), 6.94 (br d, J = 8.3 Hz, 1H), 4.86 (s, 2H), 3.59 (s, 3H), 3.05-2.78 (m, 6H), 2.59 (s, 3H) |

| Example | Yield | LCMS Purity (%) | LCMS Rt (mins) | m/z | LCMS method | ¹H NMR |
|---|---|---|---|---|---|---|
| 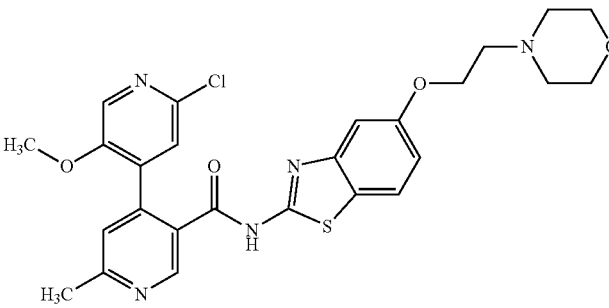 Example 111 2'-chloro-5'-methoxy-6-methyl-N-{5-[2-(morpholin-4-yl)ethoxy]-1,3-benzothiazol-2-yl}-[4,4'-bipyridine]-3-carboxamide | 3 | 100 | 0.91 | 541.1/543.1 | F | ¹H NMR (600 MHz, DMSO-$d_6$) δ ppm 12.88 (br s, 1 H) 8.79-8.93 (m, 1 H) 8.15 (s, 1 H) 7.80 (br d, 1 H) 7.55 (s, 1 H) 7.44 (br s, 1 H) 7.20-7.36 (m, 1 H) 6.95 (br d, 1 H) 4.16 (t, 2 H) 3.52-3.67 (m, 7 H) 2.72 (t, 2 H) 2.60 (s, 3 H) 2.44-2.49 (m, 4 H) |
| 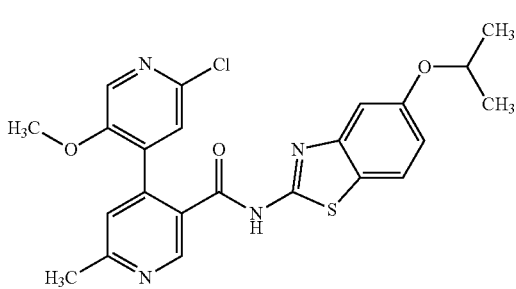 [SMILES: COc1cnc(Cl)cc1-c1cc(C)ncc1C(=O)Nc1nc2cc(OC(C)C)ccc2s1] Example 112 2'-chloro-5'-methoxy-6-methyl-N-[5-(propan-2-yloxy)-1,3-benzothiazol-2-yl]-[4,4'-bipyridine]-3-carboxamide | 36 | 99 | 1.52 | 469.0/471.0 | F | ¹H NMR (500 MHz, DMSO-$d_6$,) δ 12.86 (br s, 1H), 8.84 (br s, 1H), 8.16 (d, J = 2.1 Hz, 1H), 7.81 (br d, J = 8.8 Hz, 1H), 7.57 (s, 1H), 7.45 (br s, 1H), 7.28 (br s, 1H), 6.87-7.03 (m, 1H), 4.55-4.83 (m, 1H), 3.60 (d, J = 2.1 Hz, 3H), 2.60 (d, J = 1.9 Hz, 3H), 1.23-1.37 (m, 6H) |

| Example | Yield | LCMS Purity (%) | LCMS Rt (mins) | m/z | LCMS method | ¹H NMR |
|---|---|---|---|---|---|---|
| Example 113<br>2'-chloro-N-{5-[(1,1-dioxo-1-A6-thietan-3-yl)methoxy]-1,3-benzothiazol-2-yl}-5'-methoxy-6-methyl-[4,4'-bipyridine]-3-carboxamide | 66 | 97 | 1.37 | 545.4/547.4 | F | ¹H NMR (600 MHz, DMSO-d₆) δ 12.90 (br s, 1H), 8.86 (br s, 1H), 8.14 (s, 1H), 7.82 (br d, J = 7.3 Hz, 1H), 7.54 (s, 1H), 7.42 (br s, 1H), 7.30 (br s, 1H), 6.95 (br d, J = 8.0 Hz, 1H), 4.28-4.40 (m, 2H), 4.22 (d, J = 7.0 Hz, 2H), 3.98-4.12 (m, 2H), 3.59 (s, 3H), 2.99 (tt, J = 9.6, 6.4 Hz, 1H), 2.59 (s, 3H) |
| Example 114<br>2'-chloro-N-(5-ethoxy-1,3-benzothiazol-2-yl)-5'-methoxy-6-methyl-[4,4'-bipyridine]-3-carboxamide | 14 | 95 | 1.44 | 455.2/457.2 | F | ¹H NMR (600 MHz, DMSO-d₆) δ 12.86 (br s, 1H), 8.84 (br s, 1H), 8.15 (s, 1H), 7.81 (d, J = 8.6 Hz, 1H), 7.56 (s, 1H), 7.44 (s, 1H), 7.27 (br s, 1H), 6.94 (dd, J = 8.7, 2.4 Hz, 1H), 4.09 (q, J = 6.9 Hz, 2H), 3.59 (s, 3H), 2.60 (s, 3H), 1.36 (t, J = 7.0 Hz, 3H) |

| Example | Yield | LCMS Purity (%) | LCMS Rt (mins) | m/z | LCMS method | ¹H NMR |
|---|---|---|---|---|---|---|
| 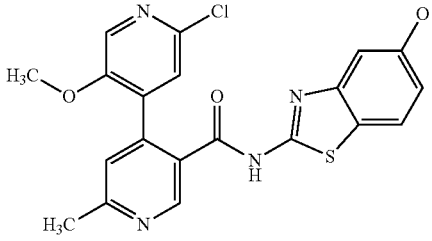 Example 115 2'-chloro-5'-methoxy-6-methyl-N-{5-[2-(trifluoromethoxy)ethoxy]-1,3-benzothiazol-2-yl}-[4,4'-bipyridine]-3-carboxamide | 23 | 98 | 1.58 | 539.2/541.2 | F | ¹H NMR (500 MHz, DMSO-d$_6$,) δ 12.91 (s, 1H), 8.85 (s, 1H), 8.16 (s, 1H), 7.86 (d, J = 8.8 Hz, 1H), 7.57 (s, 1H), 7.46 (s, 1H), 7.35 (d, J = 1.9 Hz, 1H), 7.00 (dd, J = 8.7, 2.4 Hz, 1H), 4.40-4.49 (m, 2H), 4.28-4.38 (m, 2H), 3.60 (s, 3H), 2.61 (s, 3H) |
| 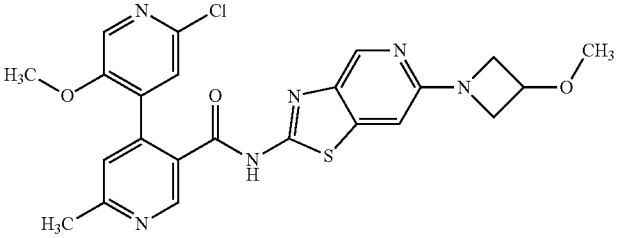 Example 129 2'-chloro-5'-methoxy-N-[6-(3-methoxyazetidin-1-yl)-[1,3]thiazolo[4,5-c]pyridin-2-yl]-6-methyl-[4,4'-bipyridine]-3-carboxamide | 28 | 100 | 2.26 | 497.2/499.2 | B | ¹H NMR (400 MHz, DMSO-d$_6$) δ 12.96 (s, 1H), 8.83 (s, 1H), 8.59 (s, 1H), 8.17 (s, 1H), 7.57 (s, 1H), 7.47 (s, 1H), 7.11 (s, 1H), 4.39-4.32 (m, 1H), 4.26-4.18 (m, 2H), 3.86-3.80 (m, 2H), 3.61 (s, 3H), 3.26 (s, 3H), 2.60 (s, 3H) |

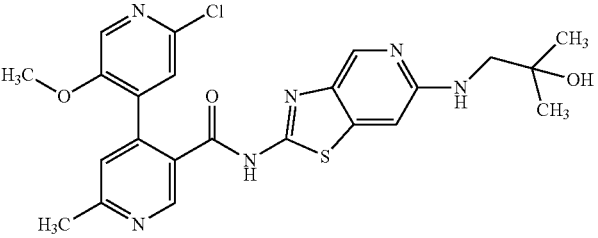 [SMILES: COc1cnc(Cl)cc1-c1cc(C)ncc1C(=O)Nc1nc2cnc(NCC(C)(C)O)cc2s1]

| Example | Yield | LCMS Purity (%) | LCMS Rt (mins) | m/z | LCMS method | ¹H NMR |
|---|---|---|---|---|---|---|
| Example 130 2'-chloro-N-{6-[(2-hydroxy-2-methylpropyl)amino]-[1,3]thiazolo[4,5-c]pyridin-2-yl}-5'-methoxy-6-methyl-[4,4'-bipyridine]-3 carboxamide | 20 | 99 | 1.96 | 499.2/501.2 | B | ¹H NMR (400 MHz, DMSO-d₆) δ 12.76 (br s, 1H), 8.83 (s, 1H), 8.44 (d, J = 0.9 Hz, 1H), 8.17 (s, 1H), 7.56 (s, 1H), 7.45 (s, 1H), 7.04 (s, 1H), 6.26 (t, J = 5.9 Hz, 1H), 3.63 (s, 3H), 3.25 (d, J = 5.9 Hz, 2H), 2.60 (s, 3H), 1.14 (s, 6H). |
| Example 131 2'-chloro-5'-methoxy-N-[6-(3-methoxy-3-methylazetidin-1-yl)-[1,3]thiazolo[4,5-c]pyridin-2-yl]-6-methyl-[4,4'-bipyridine]-3-carboxamide | 6 | 100 | 2.40 | 511.2/513.2 | B | ¹H NMR (400 MHz, DMSO-d₆) δ 12.85 (s, 1H), 8.82 (s, 1H), 8.57 (s, 1H), 8.17 (s, 1H), 7.57 (s, 1H), 7.46 (s, 1H), 6.98 (br s, 1H), 3.90-3.86 (m, 2H), 3.80-3.76 (m, 2H), 3.61 (s, 3H), 3.20 (s, 3H), 2.60 (s, 3H), 1.48 (s, 3H). |

Example 116—6-[(dimethylcarbamoyl)methyl]-5'-methoxy-N-{[1,3]thiazolo[5,4d]pyrimidin-2-yl}-2'-(trifluoromethyl)-[4,4'-bipyridine]-3-carboxamide

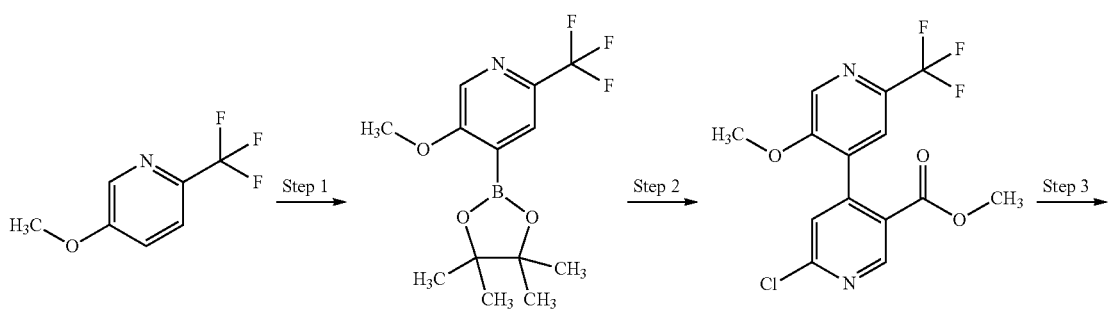

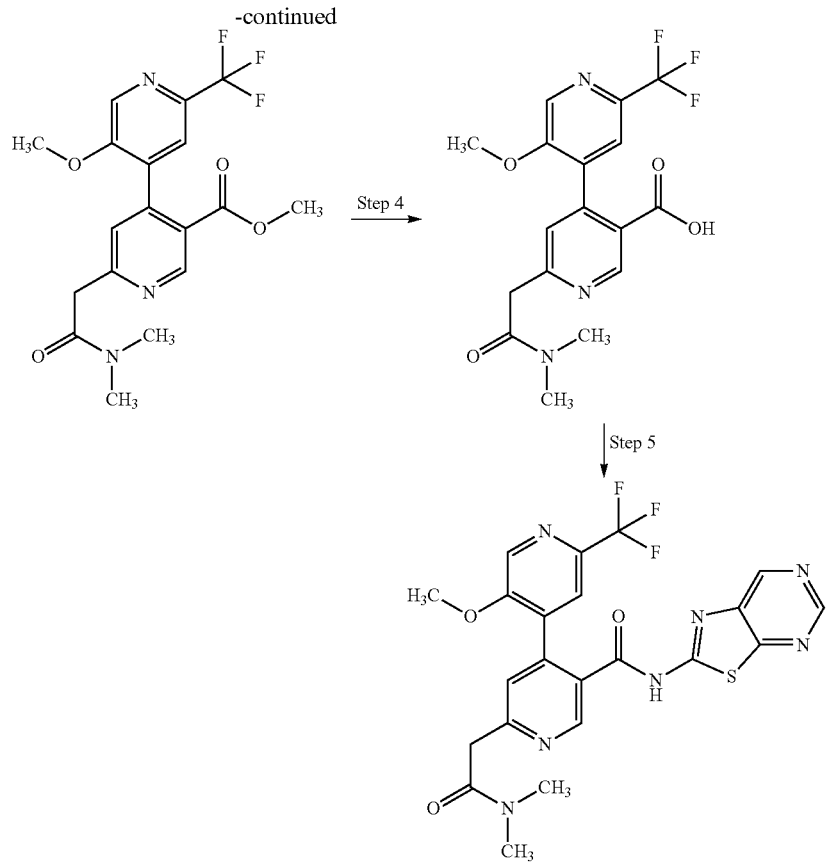

Step 1—5-methoxy-4-(4,4,5,5-tetramethyl-1,3,2-dioxaborolan-2-yl)-2-(trifluoromethyl)pyridine To a pressure vial was added dimethanolato-diiridium-cycloocta-1,5-diene (1:2) (38 mg, 0.06 mmol) and 4,4'-di-tert-butyl-2,2'-bipyridine (31 mg, 0.11 mmol) and the vial evacuated and filled with nitrogen. 5-Methoxy-2-(trifluoromethyl)pyridine (0.80 mL, 5.70 mmol) and 4,4,5,5-tetramethyl-1,3,2-dioxaborolane (1.3 mL, 8.61 mmol) were then added via syringe. The mixture was degassed with nitrogen for 5 mins then sealed and heated at 80° C. for 4.5 h. The reaction was retreated with dimethanolato-diiridium-cycloocta-1,5-diene (1:2) (38 mg, 0.06 mmol) and 4,4'-di-tert-butyl-2,2'-bipyridine (31 mg, 0.11 mmol), degassed with nitrogen for 5 mins and heating continued at 80° C. for 2 h. The reaction mixture was cooled to RT and transferred to a round bottom flask using a mixture of DCM and ethyl acetate and absorbed directly onto silica. The crude was purified by Biotage Isolera™ automated chromatography (Sfar Duo, 10 g) eluting with a solvent gradient of 0-50% TBME in heptanes to give the title compound (1.16 g, 55%) as a beige solid. $^1$H NMR (400 MHz, CDCl$_3$) δ 8.35 (s, 1H), 7.88 (s, 1H), 4.00 (s, 3H), 1.37 (s, 12H). LCMS (method A) Rt 0.63 mins (100%), m/z 222.2 (M-C$_6$H$_{10}$+H)$^+$.

Step 2—methyl 6-chloro-5'-methoxy-2'-(trifluoromethyl)-[4,4'-bipyridine]-3-carboxylate The title compound was prepared in a manner analogous to general procedure A, described previously, to give 420 mg, 30% as a colourless solid. $^1$H NMR (400 MHz, CDCl$_3$) δ 8.99-8.94 (m, 1H), 8.41 (s, 1H), 7.52 (s, 1H), 7.29-7.27 (m, 1H), 3.91 (s, 3H), 3.76 (s, 3H). LCMS (method A) Rt 0.98 mins (95%), m/z 347.2/349.2 (M+H)$^+$.

Step 3—methyl 6-[(dimethylcarbamoyl)methyl]-5'-methoxy-2'-(trifluoromethyl)-[4,4'-bipyridine]-3-carboxylate Methyl 6-chloro-4-[5-methoxy-2-(trifluoromethyl)-4-pyridyl]pyridine-3-carboxylate (307 mg, 0.886 mmol) and palladium tetrakistriphenylphosphine (210 mg, 0.182 mmol) were added to a 40 mL pressure release vial under nitrogen. 2-Methyl-THF (1 mL) was added and the mixture degassed under a flow of nitrogen for 2 mins. 0.46M chloro-[2-(dimethylamino)-2-oxo-ethyl]zinc$^1$ in THF (8.3 mL, 3.80 mmol) was added to the reaction vial. The reaction mixture was stirred at RT for further 10 mins before being heated at 90° C. for 2 h. The reaction was allowed to cool to RT and diluted with methanol (20 mL). The methanol solution was stirred for 30 mins and a yellow precipitate formed. The mixture was filtered under vacuum through celite, washing with methanol (30 mL). The filtrate was concentrated onto silica and purified by Biotage Isolera™ automated chromatography (Sfar Duo, 10 g) eluting with 0-10% methanol in DCM. Product containing fractions were combined and concentrated to give 600 mg of a green residue. This was dissolved in ethyl acetate (8 mL) and washed with water (3×5 mL), the organics were filtered through a hydrophobic frit and concentrated under reduced pressure to give the title compound (348 mg, 65%) as a green viscous oil. $^1$H NMR (400 MHz, CDCl$_3$) δ 9.14-9.05 (m, 1H), 8.37 (s, 1H), 7.55 (s, 1H), 7.32-7.28 (m, 1H), 4.03 (s, 2H), 3.88 (s, 3H), 3.74

(s, 3H), 3.16 (s, 3H), 2.99 (s, 3H). LCMS (method A) Rt 0.74 mins (66%), m/z 398.3 (M+H)+.

1) N-(5-substituted-[(1,3,4-thiadiazolyl) or (thiazolyl)])(substituted)carboxamide compounds and use thereof for inhibiting human polymerase theta, Liu, Bingcan et al, WO2023050007 A1 2023 Apr. 6

Step 4—6-[(dimethylcarbamoyl)methyl]-5'-methoxy-2'-(trifluoromethyl)-[4,4'-bipyridine]-3-carboxylic Acid The title compound was prepared using general procedure B previously described to give 300 mg, 98% as a green glass. $^1$H NMR (400 MHz, CDCl$_3$) δ 9.12 (s, 1H), 8.36 (s, 1H), 7.56 (s, 1H), 7.28 (s, 1H), 4.02 (s, 2H), 3.87 (s, 3H), 3.13 (s, 3H), 2.98 (s, 3H). CO$_2$H not observed. LCMS (method A) 0.62 mins (91%) m/z 384.3 (M+H)+.

Step 5—6-[(dimethylcarbamoyl)methyl]-5'-methoxy-N-{[1,3]thiazolo[5,4d]pyrimidin-2-yl}-2'-(trifluoromethyl)-[4,4'-bipyridine]-3-carboxamide The title compound was prepared using general procedure C previously described, with heating at 60° C. to give 43 mg, 25% as an off-white powder. $^1$H NMR (400 MHz, DMSO-d$_6$) δ 13.43 (s, 1H), 9.21 (s, 1H), 9.04 (s, 1H), 8.92 (s, 1H), 8.56 (s, 1H), 7.91 (s, 1H), 7.55 (s, 1H), 4.04 (s, 2H), 3.73 (s, 3H), 3.10 (s, 3H), 2.86 (s, 3H). LCMS (method B) Rt 2.53 mins (100%), m/z 518.4 (M+H)+.

Example 117—N-[5-(4-hydroxypiperidin-1-yl)-[1,3]thiazolo[5,4-d]pyrimidin-2-yl]-5'-methoxy-2',6-dimethyl-[4,4'-bipyridine]-3-carboxamide

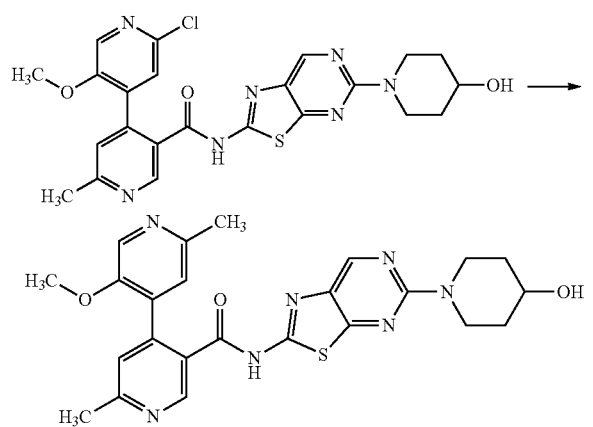

2'-Chloro-N-[5-(4-hydroxypiperidin-1-yl)-[1,3]thiazolo[5,4-d]pyrimidin-2-yl]-5'-methoxy-6-methyl-[4,4'-bipyridine]-3-carboxamide (150 mg, 0.29 mmol, example 95), trimethylboroxine (121 mg, 0.96 mmol) and caesium carbonate (236 mg, 0.72 mmol) were stirred in 1,4-Dioxane (2 mL) and Water (0.2 mL) and degassed with a stream of nitrogen for 5 mins. Bis(diphenylphosphino)ferrocene dichloropalladium(II) (20 mg, 0.024 mmol) was added and the mixture degassed for further 5 mins. The reaction was stirred at 80° C. for 18 hours. The reaction was cooled to RT and diluted with ethyl acetate. The mixture was washed with sat. NaHCO$_3$ solution and brine. Organics were separated, dried (Na$_2$SO$_4$) and concentrated. The crude residue was absorbed onto silica and purified by Biotage Isolera™ automated chromatography (25 g, Sfar Duo) eluting with 0-10% methanol in ethyl acetate. Product containing fractions were concentrated and the residue freeze dried from acetonitrile/water (1:1) to give the title compound (44 mg, 29%) as a pale yellow powder. $^1$H NMR (400 MHz, DMSO-d$_6$) δ 12.83 (s, 1H), 8.77 (s, 1H), 8.74 (s, 1H), 8.18 (s, 1H), 7.39 (s, 1H), 7.28 (s, 1H), 4.74 (d, J=4.2 Hz, 1H), 4.32-4.23 (m, 2H), 3.78-3.71 (m, 1H), 3.58 (s, 3H), 2.59 (s, 3H), 2.48 (s, 3H), 1.84-1.73 (m, 2H), 1.41-1.29 (m, 2H). CH$_2$ obscured by water peak. LCMS (method B) Rt 1.73 mins (95%), m/z 492.4 (M+H)+.

Example 118—2'-chloro-5'-methoxy-6-methyl-N-[5-(2-oxopiperidin-1-yl)-[1,3]thiazolo[5,4-b]pyridin-2-yl]-[4,4'-bipyridine]-3-carboxamide

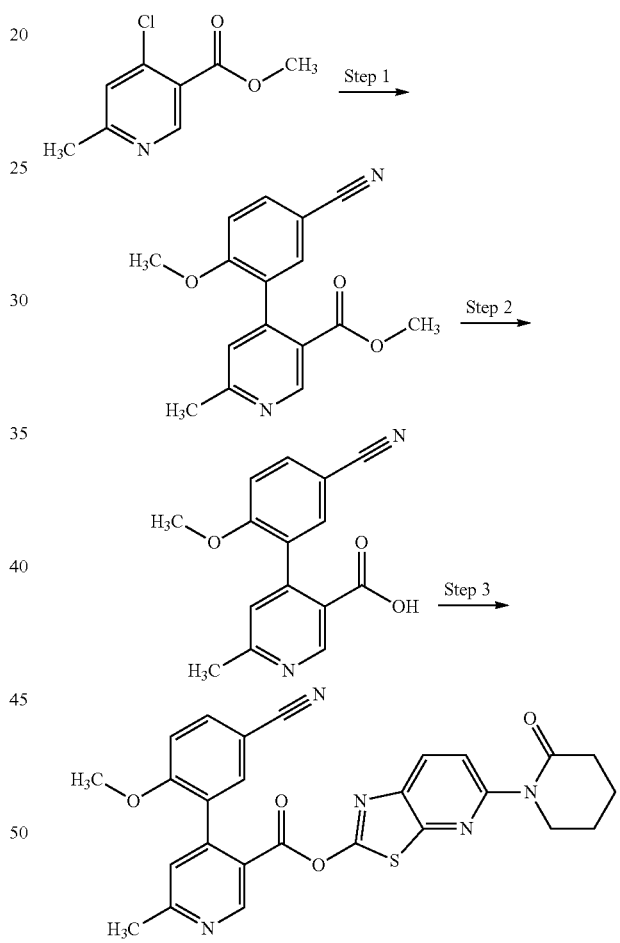

Step 1—4-(5-cyano-2-methoxyphenyl)-6-methylpyridine-3-carboxylate

The title compound was prepared using general procedure A, described previously to give 563 mg, 70% as a pale yellow powder. $^1$H NMR (500 MHz, DMSO-d$_6$) δ 8.82 (s, 1H), 7.92 (dd, J=8.7, 2.1 Hz, 1H), 7.79 (d, J=2.1 Hz, 1H), 7.34 (s, 1H), 7.24 (d, J=8.7 Hz, 1H), 3.75 (s, 3H), 3.64 (s, 3H), 2.56 (s, 3H). LCMS (method A) Rt 0.74 mins (95%), m/z 283.3 (M+H)+.

Step 2—4-(5-cyano-2-methoxyphenyl)-6-methylpyridine-3-carboxylic Acid

The title compound was prepared using general procedure B, described previously to give 427 mg, 81% as a colourless powder. LCMS (method A) Rt 0.5 mins (95%), m/z 269.3 (M+H)+.

Step 3—2'-chloro-5'-methoxy-6-methyl-N-[5-(2-oxopiperidin-1-yl)-[1,3]thiazolo[5,4-b]pyridin-2-yl]-[4,4'-bipyridine]-3-carboxamide The title compound was prepared using general procedure C, described previously with heating at 80° C. to give 20 mg, 20% as a pale yellow powder. $^1$H NMR (400 MHz, DMSO-d$_6$) δ 12.93 (s, 1H), 8.78 (s, 1H), 8.11 (d, J=8.8 Hz, 1H), 7.94-7.87 (m, 2H), 7.72 (d, J=8.7 Hz, 1H), 7.43 (s, 1H), 7.17 (d, J=9.3 Hz, 1H), 3.86 (t, J=5.7 Hz, 2H), 3.58 (s, 3H), 2.60 (s, 3H), 2.48-2.45 (m, 2H), 1.92-1.81 (m, 4H). LCMS (method B) Rt 2.80 mins (95%), m/z 499.4 (M+H)+.

Example 119—5-[(2-{2'-chloro-5'-methoxy-6-methyl-[4,4'-bipyridine]-3-amido}-[1,3]thiazolo[4,5-c]pyridin-6-yl)amino]pentanoic Acid

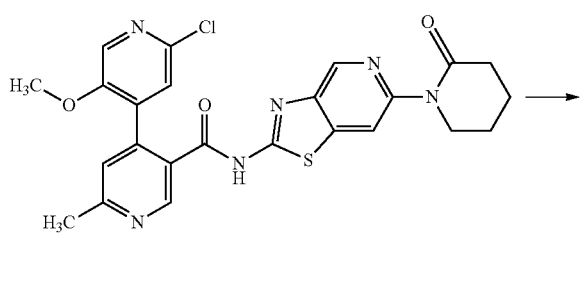

2'-Chloro-5'-methoxy-6-methyl-N-[6-(2-oxopiperidin-1-yl)-[1,3]thiazolo[4,5-c]pyridin-2-yl]-[4,4'-bipyridine]-3-carboxamide (50 mg, 0.01 mmol, example 95) was dissolved in 0.1M aqueous hydrogen chloride solution (99.5 mL, 9.95 mmol) and the mixture stirred at RT for 65 h. The mixture was then heated at 55° C. for a further 17 h. The reaction mixture was concentrated under reduced pressure and the residue purified by preparative HPLC method C to give the title compound (23 mg, 42%) as a yellow powder. $^1$H NMR (400 MHz, DMSO-d$_6$) δ 12.73 (br s, 1H), 11.99 (br s, 1H), 8.83 (s, 1H), 8.44 (s, 1H), 8.16 (s, 1H), 7.54 (s, 1H), 7.43 (s, 1H), 6.90 (s, 1H), 6.49-6.38 (m, 1H), 3.62 (s, 3H), 3.22 (m, 2H), 2.59 (s, 3H), 2.28-2.21 (m, 2H), 1.63-1.46 (m, 4H). LCMS (method B) Rt 1.93 mins (94%), m/z 527.3/529.3 (M+H)+.

Example 120—5-[(2-{2'-chloro-5'-methoxy-6-methyl-[4,4'-bipyridine]-3-amido}-[1,3]thiazolo[5,4-b]pyridin-5-yl)amino]pentanoic Acid

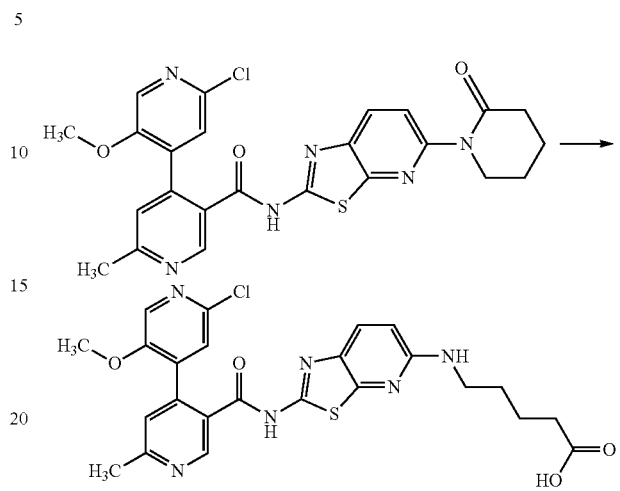

The title compound was prepared in manner analogous to example 119 above to give 22 mg, 42% as a yellow powder. $^1$H NMR (400 MHz, DMSO-d$_6$) δ 12.55 (br s, 1H), 12.02 (br s, 1H), 8.80 (s, 1H), 8.16 (s, 1H), 7.71 (d, J=8.8 Hz, 1H), 7.54 (s, 1H), 7.43 (s, 1H), 6.88-6.77 (m, 1H), 6.58 (d, J=8.9 Hz, 1H), 3.62 (s, 3H), 3.28-3.21 (m, 2H), 2.59 (s, 3H), 2.28-2.21 (m, 2H), 1.65-1.48 (m, 4H). LCMS (method B) Rt 2.54 mins (100%), m/z 527.3/529.3 (M+H)+.

Example 121—2'-chloro-5'-methoxy-6-methyl-N-{5-[(2H-1,2,3,4-tetrazol-5-yl)methoxy]-1,3-benzothiazol-2-yl}-[4,4'-bipyridine]-3-carboxamide

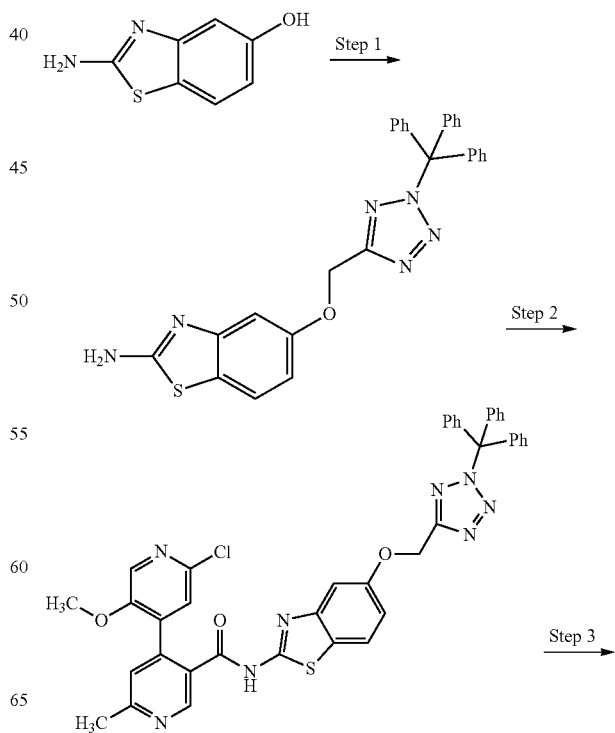

-continued

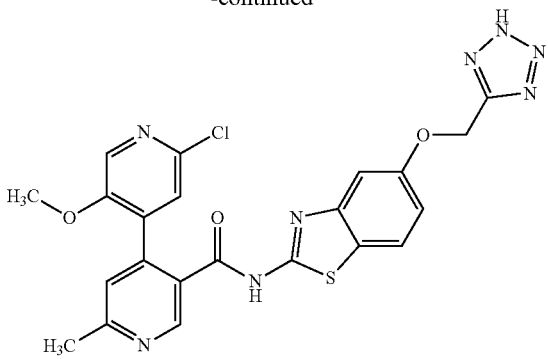

Step 1—5-{[2-(triphenylmethyl)-2H-1,2,3,4-tetrazol-5-yl]methoxyl}-1,3-benzothiazol-2-amine The title compound was prepared using general procedure H, described previously, to give 405 mg, 45% as an off white solid. LCMS (method F) Rt 1.46 mins (47%), m/z 513.1 (M+Na)⁺.

Step 2—2'-chloro-5'-methoxy-6-methyl-N-(5-{[2-(triphenylmethyl)-2H-1,2,3,4-tetrazol-5-yl]oxyl}-1,3-benzothiazol-2-yl)-[4,4'-bipyridine]-3-carboxamide The title compound was prepared using general procedure C, with heating at 80° C., to give 93 mg, 34% as a colourless oil. LCMS (method F) Rt 1.96 mins (97%), m/z 751.5/753.5 (M+H)⁺.

Step 3—2'-chloro-5'-methoxy-6-methyl-N-{5-[(2H-1,2,3,4-tetrazol-5-yl)methoxy]-1,3-benzothiazol-2-yl}-[4,4'-bipyridine]-3-carboxamide 2'-Chloro-5'-methoxy-6-methyl-N-(5-{[2-(triphenylmethyl)-2H-1,2,3,4-tetrazol-5-yl]oxyl}-1,3-benzothiazol-2-yl)-[4,4'-bipyridine]-3-carboxamide (94.0 mg, 0.12 mmol) was dissolved in a mixture of cyclopentyl methyl ether (3.0 mL) and Ethanol (1.0 mL). 3M hydrogen chloride in cyclopentyl methyl ether (0.20 mL, 0.61 mmol) was added and the mixture was stirred for 30 mins at RT. The reaction mixture was concentrated under reduced pressure and the crude residue purified by reverse phase Biotage Isolera™ automated chromatography (C18, 12 g) eluting with a solvent gradient of 20-100% acetonitrile in water to give the title compound (29 mg, 46%) as a colourless solid. ¹H NMR (DMSO-d₆, 500 MHz): δ 16.46-17.35 (m, 1H), 12.67-13.10 (m, 1H), 8.85 (s, 1H), 8.16 (s, 1H), 7.89 (d, J=8.7 Hz, 1H), 7.58 (s, 1H), 7.41-7.53 (m, 2H), 7.08 (br dd, J=8.4, 1.4 Hz, 1H), 5.57 (s, 2H), 3.60 (s, 3H), 2.61 (s, 3H). LCMS (method F) Rt 1.18 mins (100%), m/z 509.2/511.2 (M+H)⁺.

Example 122—2'-chloro-N-(5-hydroxy-1,3-benzothiazol-2-yl)-5'-methoxy-6-methyl-[4,4'-bipyridine]-3-carboxamide Example 123—2-[(2-{2'-chloro-5'-methoxy-6-methyl-[4,4'-bipyridine]-3-amido}-1,3-benzothiazol-5-yl)oxy]ethyl Acetate; and Example 124—2'-chloro-N-[5-(2-hydroxyethoxy)-1,3-benzothiazol-2-yl]-5'-methoxy-6-methyl-[4,4'-bipyridine]-3-carboxamide

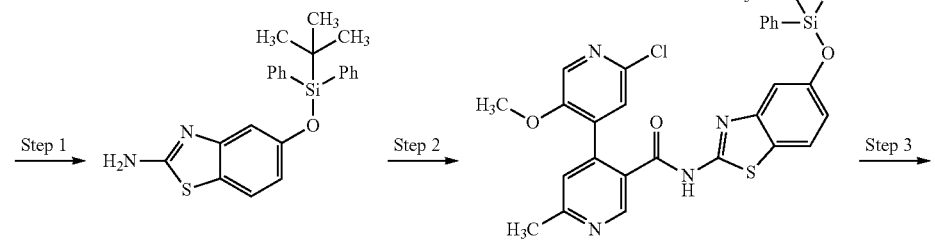

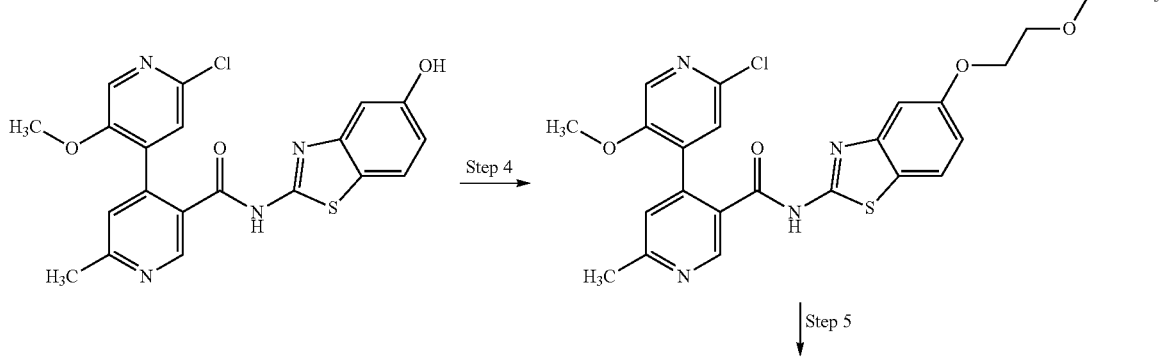

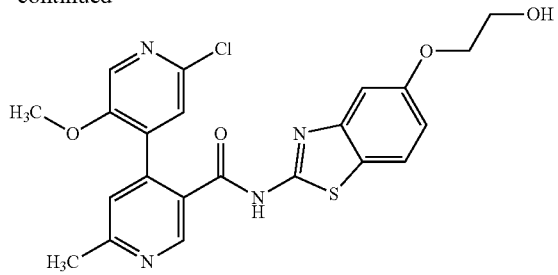

Step 1—5-[(tert-butyldiphenylsilyl)oxy]-1,3-benzothiazol-2-amine 2-amino-1,3-benzothiazol-5-ol (500 mg, 2.86 mmol), imidazole (253 mg, 3.72 mmol) and N,N-dimethylpyridin-4-amine (70 mg, 0.57 mmol) were dissolved in DMF (15.0 mL) at RT. tert-butyldiphenyl silyl chloride (907 uL, 3.43 mmol) was added and the reaction mixture was stirred at RT overnight. The reaction mixture was diluted with water (25 mL) and the suspension was extracted with ethyl acetate. Organic extracts were combined, washed with brine solution, dried ($Na_2SO_4$), filtered and concentrated. The crude residue was purified by Biotage Isolera™ automated chromatography (25 g, Sfar Duo) eluting with a solvent gradient of 0-50% ethyl acetate in heptanes to give the title compound (329 mg, 27%) as a colourless solid. $^1$H NMR (400 MHz, DMSO-$d_6$) δ: 7.70-7.66 (m, 4H), 7.50-7.41 (m, 6H), 7.39-7.33 (m, 3H), 6.63 (d, J=2.4 Hz, 1H), 6.48 (dd, J=8.5, 2.4 Hz, 1H), 1.04 (s, 9H). LCMS (method E) Rt 0.91 mins (95%), m/z 405.4 (M+H)$^+$.

Step 2—N-{5-[(tert-butyldiphenylsilyl)oxy]-1,3-benzothiazol-2-yl}-2'-chloro-5'-methoxy-6-methyl-[4,4'-bipyridine]-3-carboxamide The title compound was prepared according to general procedure C, with heating at 60° C. to give 526 mg, 99% as a colourless solid. $^1$H NMR (400 MHz, DMSO-$d_6$) δ: 12.80 (s, 1H), 8.79 (s, 1H), 8.14 (s, 1H), 7.75-7.67 (m, 5H), 7.54 (s, 1H), 7.53-7.40 (m, 7H), 6.96 (d, J=1.8 Hz, 1H), 6.84 (dd, J=8.6, 2.1 Hz, 1H), 3.57 (s, 3H), 2.58 (s, 3H), 1.07 (s, 9H). LCMS (method E) Rt 1.16 mins (97%), m/z 665.4/667.4 (M+H)$^+$.

Step 3—2'-chloro-N-(5-hydroxy-1,3-benzothiazol-2-yl)-5'-methoxy-6-methyl-[4,4'-bipyridine]-3-carboxamide N-{5-[(tert-butyldiphenylsilyl)oxy]-1,3-benzothiazol-2-yl}-2'-chloro-5'-methoxy-6-methyl-[4,4'-bipyridine]-3-carboxamide (506 mg, 0.74 mmol) was dissolved in THF (7.0 mL) at RT. Tetrabutylammonium fluoride (75% w/w in water) (540 uL, 1.48 mmol) was added and the reaction mixture was stirred at RT for 1 minute. The reaction mixture was partitioned between Ethyl acetate and a saturated ammonium chloride solution. Organic extracts were combined, washed with brine solution, dried ($Na_2SO_4$), filtered and concentrated. The crude residue was dissolved in DCM, which caused a white precipitate to form. The solid was collected by filtration, washed with DCM and dried under vacuum to give the title compound (319 mg, 99%) as a colourless solid. $^1$H NMR (DMSO-$d_6$) δ 12.81 (s, 1H), 9.53 (s, 1H), 8.83 (s, 1H), 8.16 (s, 1H), 7.70 (d, J=8.6 Hz, 1H), 7.56 (s, 1H), 7.45 (s, 1H), 7.11 (s, 1H), 6.81 (dd, J=8.4, 2.3 Hz, 1H), 3.60 (s, 3H), 2.60 (s, 3H). LCMS (method F) Rt 1.14 mins (98%), m/z 427.3/429.2 (M+H)$^+$.

Step 4—2-[(2-{2'-chloro-5'-methoxy-6-methyl-[4,4'-bipyridine]-3-amido}-1,3-benzothiazol-5-yl)oxy]ethyl Acetate The title compound was prepared using general procedure H, described previously to give 52 mg, 14% as a colourless solid. $^1$H NMR (DMSO-$d_6$) δ: 12.90 (s, 1H), 8.85 (s, 1H), 8.15 (s, 1H), 7.82 (d, J=8.7 Hz, 1H), 7.56 (s, 1H), 7.44 (s, 1H), 7.32 (s, 1H), 6.97 (dd, J=8.6, 2.4 Hz, 1H), 4.36 (dd, J=5.8, 3.2 Hz, 2H), 4.26 (dd, J=5.7, 3.3 Hz, 2H), 3.60 (s, 3H), 2.60 (s, 3H), 2.05 (s, 3H). LCMS (method F) Rt 1.35 mins (98%), m/z 513.2/515.2 (M+H)$^+$.

Step 5—2'-chloro-N-[5-(2-hydroxyethoxy)-1,3-benzothiazol-2-yl]-5'-methoxy-6-methyl-[4,4'-bipyridine]-3-carboxamide To 2-[(2-{2'-chloro-5'-methoxy-6-methyl-[4,4'-bipyridine]-3-amido}-1,3-benzothiazol-5-yl)oxy]ethyl acetate (42.0 mg, 0.08 mmol) was added a solution of 0.5M sodium methoxide in methanol (0.32 mL, 0.16 mmol) and the reaction stirred at RT for 1 h. The reaction mixture was quenched by addition of saturated ammonium chloride solution and extracted with ethyl acetate. Organic extracts were combined, washed with brine solution, dried ($Na_2SO_4$), filtered and concentrated. The residue was dissolved in acetonitrile/water (1:1) and lyophilised overnight to give the title compound (37 mg, 97%) as a colourless solid. $^1$H NMR (DMSO-$d_6$) δ 12.87 (s, 1H), 8.84 (s, 1H), 8.16 (s, 1H), 7.82 (d, J=8.7 Hz, 1H), 7.57 (s, 1H), 7.45 (s, 1H), 7.30 (s, 1H), 6.96 (dd, J=8.7, 2.4 Hz, 1H), 4.87 (t, J=5.5, 5.5 Hz, 1H), 4.06 (t, J=5.0, 5.0 Hz, 2H), 3.75 (q, J=5.2, 5.2, 5.2 Hz, 2H), 3.60 (s, 3H), 2.60 (s, 3H). LCMS (method F) Rt 1.16 mins (99%), m/z 471.2/473.2 (M+H)$^+$.

Example 125—5-(4-hydroxypiperidin-1-yl)-[1,3]thiazolo[5,4-d]pyrimidin-2-yl 2'-chloro-5'-methoxy-1-methyl-6-oxo-1,6-dihydro-[3,4'-bipyridine]-4-carboxylate

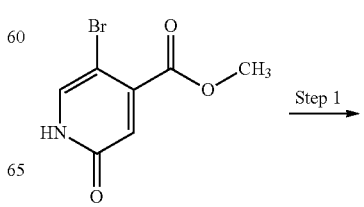

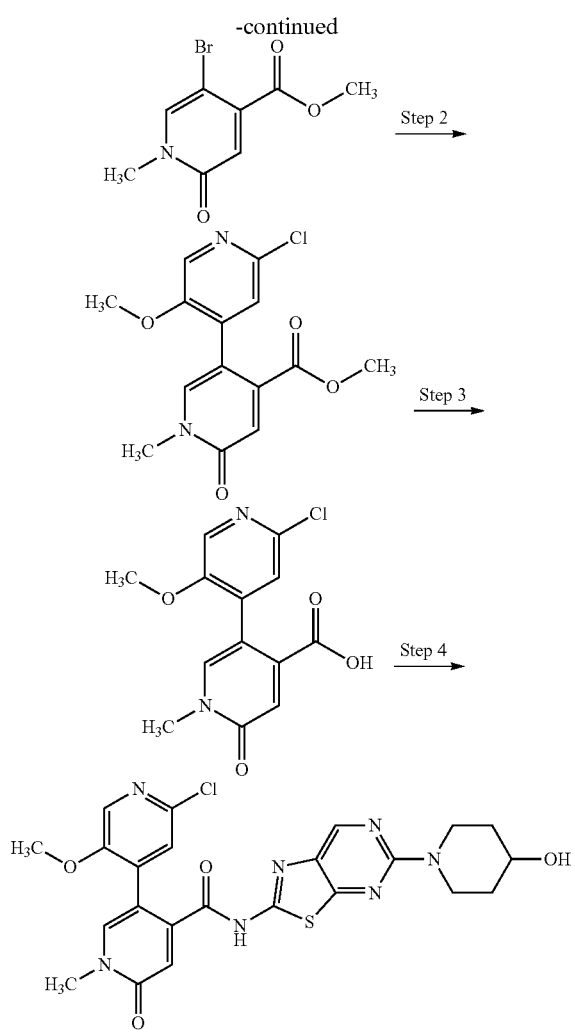

a yellow powder. ¹H NMR (400 MHz, DMSO-d₆) δ 13.34 (s, 1H), 8.12 (s, 1H), 7.94 (s, 1H), 7.43 (s, 1H), 6.70 (s, 1H), 3.77 (s, 3H), 3.49 (s, 3H). LCMS (method A) Rt 0.46 mins (100%), m/z 295.0/297.0 (M+H)⁺.

Step 4—5-(4-hydroxypiperidin-1-yl)-[1,3]thiazolo[5,4-d]pyrimidin-2-yl 2'-chloro-5'-methoxy-1-methyl-6-oxo-1,6-dihydro-[3,4'-bipyridine]-4-carboxylate The title compound was prepared according to general procedure C, described previously. Purification was performed using the following preparative HPLC method; Waters CSH 100×30 mm, 5 um column eluting with acetonitrile in water (0.1% formic acid additive) at RT with a gradient of; 5-30% over 2 mins, 30-32% over 8 mins, 32-95% over 2 mins at a flow rate of 40 mL/min. The title compound (24 mg, 13%) was isolated as a yellow powder. ¹H NMR (500 MHz, DMSO-d₆) δ 12.94 (s, 1H), 8.74 (s, 1H), 8.04 (s, 1H), 8.01 (s, 1H), 7.50 (s, 1H), 6.78 (s, 1H), 4.73 (d, J=4.2 Hz, 1H), 4.28 (dt, J=13.3, 4.6 Hz, 2H), 3.78-3.70 (m, 1H), 3.56 (s, 3H), 3.52 (s, 3H), 1.82-1.76 (m, 2H), 1.39-1.31 (m, 2H). 2H obscured by water peak. LCMS (method B) Rt 2.34 mins (100%), m/z 528.3/530.3 (M+H)⁺.

Example 126—2'-chloro-N-[7-(cyanomethoxy)-[1,3]thiazolo[5,4-d]pyrimidin-2-yl]-5'-methoxy-6-methyl-[4,4'-bipyridine]-3-carboxamide; and Example 127—N-[7-carbamoylmethoxy)-[1,3]thiazolo[5,4-d]pyrimidin-2-yl]-2'-chloro-5'-methoxy-6-methyl-[4,4'-bipyridine]-3-carboxamide

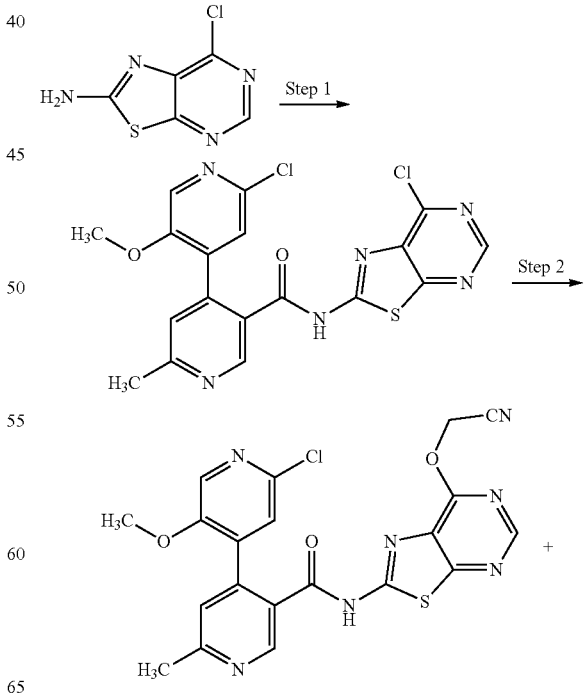

Step 1—methyl 5-bromo-1-methyl-2-oxo-1,2-dihydropyridine-4-carboxylate

To a stirred suspension of methyl 5-bromo-2-oxo-1,2-dihydropyridine-4-carboxylate (1.0 g, 4.31 mmol) in acetonitrile (20 mL) was added cesium carbonate (1.69 g, 5.17 mmol) followed by iodomethane (295 uL, 4.74 mmol). The reaction mixture was stirred at RT for 16 h. The reaction mixture was filtered and the solid was washed with MeCN (20 mL). The filtrates were combined and concentrated under reduced pressure to give the title compound (1.39 g, quant.) as a brown solid. ¹H NMR (400 MHz, DMSO-d₆) δ 8.21 (s, 1H), 6.72 (s, 1H), 3.85 (s, 3H), 3.44 (s, 3H). LCMS (method A) Rt 0.51 mins (98%), m/z 247.9 (M+H)⁺.

Step 2—methyl 2'-chloro-5'-methoxy-1-methyl-6-oxo-1,6-dihydro-[3,4'-bipyridine]-4-carboxylate The title compound was prepared according to general procedure A, described previously to give 507 mg, 29% as a yellow powder. LCMS (method A) Rt 0.58 mins (99%), m/z 309.0/311.0 (M+H)⁺.

Step 3—2'-chloro-5'-methoxy-1-methyl-6-oxo-1,6-dihydro-[3,4'-bipyridine]-4-carboxylic Acid The title compound was prepared according to general procedure B, described previously to give 380 mg, 90% as -continued

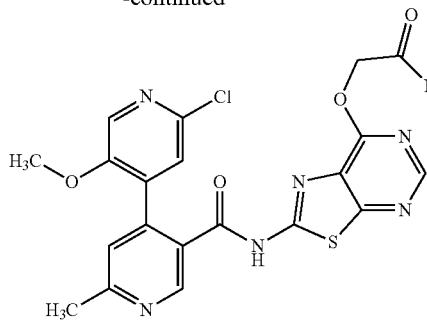

Step 1—2'-chloro-N-{7-chloro-[1,3]thiazolo[5,4-d]pyrimidin-2-yl}-5'-methoxy-6-methyl-[4,4'-bipyridine]-3-carboxamide The title compound was prepared according to general procedure C, with heating at 60° C. to give 293 mg, 38% as a purple powder. LCMS (method E) Rt 0.77 mins (88%), m/z 447.1/449.1 (M+H)⁺.

Step 2—2'-chloro-N-[7-(cyanomethoxy)-[1,3]thiazolo[5,4-d]pyrimidin-2-yl]-5'-methoxy-6-methyl-[4,4'-bipyridine]-3-carboxamide; and N-[7-(carbamoylmethoxy)-[1,3]thiazolo[5,4-d]pyrimidin-2-yl]-2'-chloro-5'-methoxy-6-methyl-[4,4'-bipyridine]-3-carboxamide 2'-chloro-N-{7-chloro-[1,3]thiazolo[5,4-d]pyrimidin-2-yl}-5'-methoxy-6-methyl-[4,4'-bipyridine]-3-carboxamide (150 mg, 0.34 mmol), potassium hydroxide (38 mg, 0.67 mmol) and hydroxyacetonitrile (150 uL, 1.98 mmol) were added to a solution of (hydroxypropyl)methyl cellulose (3.7 mg, 5.95 μmol) in water (3.8 mL). The resulting mixture was sonicated and then heated at 50° C. overnight. Additional hydroxyacetonitrile (150 uL, 1.98 mmol) and (hydroxypropyl)methyl cellulose (0.5 mg, 0.8 μM) were added and heating continued for a further 4 h. The mixture was cooled to RT and concentrated under reduced pressure. The residue was purified by reverse phase Biotage Isolera™ automated chromatography (C18, 30 g) eluting with a solvent gradient of 10-80% acetonitrile in water. Product containing fraction were combined and purified further by preparative HPLC using the following method; Waters CSH C18 30 mm×100 mm, 1.7 μm column at room temperature using 30% 0.1% formic acid in acetonitrile and 70% 0.1% formic acid in water for 1.9 mins then a gradient of 30-95% 0.1% formic acid in acetonitrile for 9.6 mins at a flow rate of 40 mL/min, to give 2'-chloro-N-[7-(cyanomethoxy)-[1,3]thiazolo[5,4-d]pyrimidin-2-yl]-5'-methoxy-6-methyl-[4,4'-bipyridine]-3-carboxamide (3.2 mg, 2%) as a colourless solid, ¹H NMR (600 MHz, DMSO-d₆) δ 13.41 (s, 1H) 8.87 (br s, 1H) 8.76 (br s, 1H) 8.16 (s, 1H) 7.60 (br s, 1H) 7.39-7.53 (m, 1H) 5.48 (s, 2H) 3.61 (s, 3H) 2.61 (s, 3H), LCMS (method F) Rt 1.23 mins (100%), m/z 468.2/470.1 (M+H)⁺, and N-[7-(carbamoylmethoxy)-[1,3]thiazolo[5,4-d]pyrimidin-2-yl]-2'-chloro-5'-methoxy-6-methyl-[4,4'-bipyridine]-3-carboxamide (2.3 mg, 1%) as a colourless solid, ¹H NMR (600 MHz, DMSO-d6) δ 13.33 (s, 1H), 8.86 (br s, 1H), 8.61 (br s, 1H), 8.17 (s, 1H), 7.59 (br s, 1H), 7.53 (br s, 1H), 7.48 (br s, 1H), 7.25 (br s, 1H), 4.94 (s, 2H), 3.62 (s, 3H), 2.61 (s, 3H), LCMS (method F) Rt 1.04 mins (98%), m/z 486.3/488.3 (M+H)⁺.

Example 128—2'-chloro-5'-methoxy-6-methyl-N-[6-(morpholin-3-yl)-1,3-benzothiazol-2-yl]-[4,4'-bipyridine]-3-carboxamide

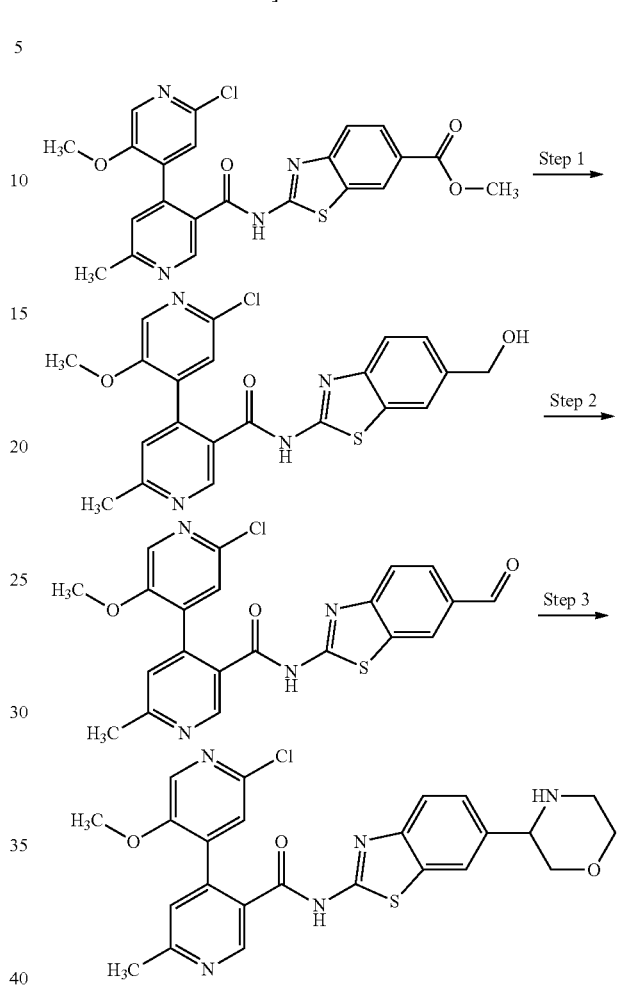

Step 1—2'-chloro-N-[6-(hydroxymethyl)-1,3-benzothiazol-2-yl]-5'-methoxy-6-methyl-[4,4'-bipyridine]-3-carboxamide To a stirred suspension of methyl 2-{2'-chloro-5'-methoxy-6-methyl-[4,4'-bipyridine]-3-amido}-1,3-benzothiazole-6-carboxylate (53 mg, 0.110 mmol) in THF (2 mL) at 0° C. was added 2M lithium aluminium hydride in THF (1.0 mL, 2.0 mmol). The reaction mixture was warmed to RT and stirred 2 h. The reaction was quenched by addition of water and the mixture was extracted twice with ethyl acetate. Combined organic layers were washed with saturated aqueous ammonium chloride solution, dried through a hydrophobic phase separator and concentrated under reduced pressure to afford the title compound (44 mg, 77%) as a yellow oil. ¹H NMR (400 MHz, DMSO-d₆) δ: 12.89 (s, 1H), 8.85 (s, 1H), 8.16 (s, 1H), 7.89 (s, 1H), 7.71 (d, J=8.3 Hz, 1H), 7.57 (s, 1H), 7.47-7.35 (m, 2H), 5.25 (t, J=5.7 Hz, 1H), 4.59 (d, J=5.7 Hz, 2H), 3.60 (s, 3H), 2.60 (s, 3H). LCMS (method F) Rt 1.07 mins (85%), m/z 441.2 (M+H)⁺.

Step 2—2'-chloro-N-(6-formyl-1,3-benzothiazol-2-yl)-5'-methoxy-6-methyl-[4,4'-bipyridine]-3-carboxamide To a stirred solution of 2'-chloro-N-[6-(hydroxymethyl)-1,3-benzothiazol-2-yl]-5'-methoxy-6-methyl-[4,4'-bipyridine]-3-carboxamide (44 mg, 0.08 mmol) in DCM (1 mL) and methanol (0.2 mL) was added manganese dioxide (58 mg, 0.67 mmol) and the mixture stirred at RT overnight. Additional manganese dioxide (58 mg, 0.67 mmol) was added and the mixture stirred for 3 h at RT, 3 h at 50° C. and finally 12 h at RT. The reaction mixture was filtered through a pad of celite. The filtrate was concentrated under reduced pressure to give the title compound (53 mg, 99%) as a yellow solid. LCMS (method F) Rt 1.27 mins (70%), m/z 439.2 (M+H)$^+$.

Step 3—2'-chloro-5'-methoxy-6-methyl-N-[6-(morpholin-3-yl)-1,3-benzothiazol-2-yl]-[4,4'-bipyridine]-3-carboxamide To a stirred suspension of 2'-chloro-N-(6-formyl-1,3-benzothiazol-2-yl)-5'-methoxy-6-methyl-[4,4'-bipyridine]-3-carboxamide (53 mg, 0.0845 mmol) in DCM (1 mL) was added (2-aminoethoxy)methyl tributylstannane (41 mg, 0.11 mmol) and 4 Å molecular sieves. The mixture was stirred at RT for 2 h. In a separate vessel, 2,6-dimethylpyridine (10 uL, 0.08 mmol) was added in one portion to a suspension of copper(II) triflate (33 mg, 0.09 mmol) in hexafluoro-isopropanol (1 mL) and stirred for 1 h at RT, during which time a homogeneous green suspension was formed. The mixture containing molecular sieves was filtered through a syringe filter and added to the hexafluoro-isopropanol solution. The resulting homogeneous green suspension was stirred at RT for 16 h. Additional (2-aminoethoxy)methyl tributylstannane (50 mg, 0.13 mmol) and molecular sieves were added to the reaction mixture and stirred at RT for 1 h before a solution of copper(II) triflate (33.0 mg, 0.09 mmol) and 2,6-dimethylpyridine (10 uL, 0.09 mmol) in hexafluoro-isopropanol (1 mL, prepared as previously described) was added and stirring continued at RT for 12 h. The reaction was quenched by addition of saturated aqueous ammonium chloride solution. Organics were separated and the aqueous was extracted twice with DCM. Combined organic extracts were washed with a saturated aqueous ammonium chloride solution, dried through a hydrophobic phase separator and concentrated under reduced pressure. The crude residue was successively purified by Biotage Isolera™ automated chromatography (C18, 12 g) using a solvent gradient of 0% to 100% acetonitrile in water (0.1% acetic acid additive) and preparative HPLC using the following method; Interchim C18 HQ column, 150×21.2 mm, 10 μm using a gradient of 5% to 50% acetonitrile in water (0.1% TFA additive) at a flow rate of 40 mL/min. Desired fractions were concentrated to dryness. The resulting residue was dissolved in DCM and washed with a saturated sodium bicarbonate solution. Organics were dried through a hydrophobic phase separator and concentrated under reduced pressure. The residue was freeze dried to give the title compound (3.3 mg, 8%) as a colourless solid. $^1$H NMR (400 MHz, DMSO-d$_6$) δ 8.86 (s, 1H), 8.15 (s, 1H), 7.98 (s, 1H), 7.68 (d, J=8.2 Hz, 1H), 7.56 (s, 1H), 7.50-7.41 (m, 2H), 3.89 (dd, J=10.1, 3.2 Hz, 1H), 3.79-3.68 (m, 2H), 3.59 (s, 3H), 3.53-3.42 (m, 1H), 3.30-3.15 (m, 1H), 2.97-2.84 (m, 2H), 2.60 (s, 3H). 2×NH not observed. LCMS (method F) Rt 0.83 mins (100%), m/z 496.3/498.3 (M+H)$^+$.

Example 132—2'-chloro-N-[5-(4-hydroxypiperidin-1-yl)-7-methyl-[1,3]thiazolo[5,4-d]pyrimidin-2-yl]-5'-methoxy-6-methyl-[4,4'-bipyridine]-3-carboxamide

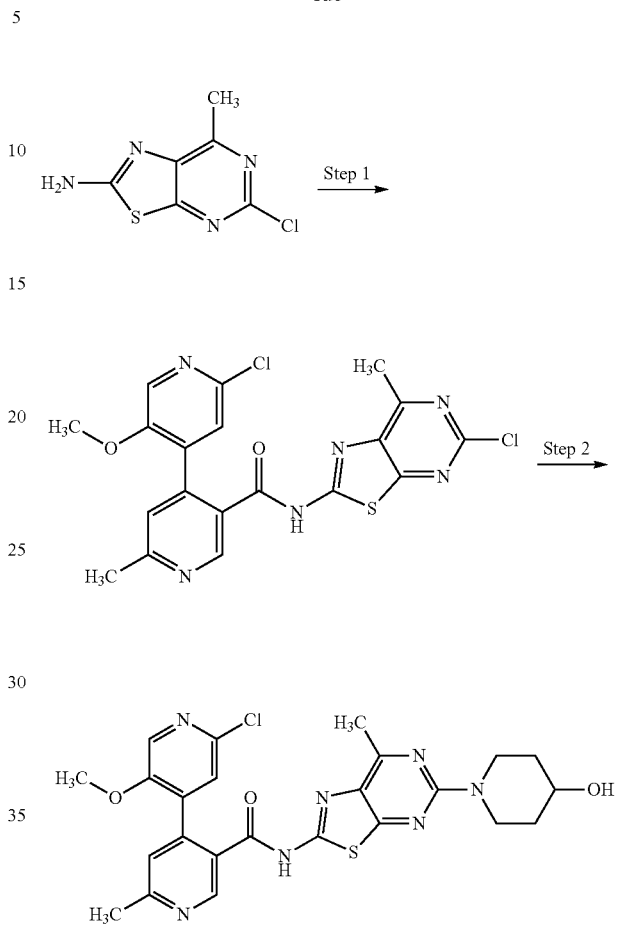

Step 1—2'-chloro-N-{5-chloro-7-methyl-[1,3]thiazolo[5,4-d]pyrimidin-2-yl}-5'-methoxy-6-methyl-[4,4'-bipyridine]-3-carboxamide The title compound was prepared according to general procedure C, with heating at 80° C. The product precipitated from solution, it was filtered and dried in a vacuum oven at 40° C. for 2 h to give 274 mg, 62% as a colourless powder. $^1$H NMR (400 MHz, DMSO-d$_6$) δ 13.53 (s, 1H), 8.88 (s, 1H), 8.18 (s, 1H), 7.59 (s, 1H), 7.47 (s, 1H), 3.62 (s, 3H), 2.77 (s, 3H), 2.61 (s, 3H). LCMS (method F) Rt 1.38 mins (99%), m/z 461.1/463.1 (M+H)$^+$.

Step 2—2'-chloro-N-[5-(4-hydroxypiperidin-1-yl)-7-methyl-[1,3]thiazolo[5,4-d]pyrimidin-2-yl]-5'-methoxy-6-methyl-[4,4'-bipyridine]-3-carboxamide The title compound was prepared according to general procedure D, previously described, to give 145 mg, 86% as a yellow powder. $^1$H NMR (600 MHz, DMSO-d$_6$) δ 12.92 (s, 1H), 8.82 (s, 1H), 8.16 (s, 1H), 7.55 (s, 1H), 7.43 (s, 1H), 4.70 (d, J=4.2 Hz, 1H), 4.28 (dt, J=13.2, 4.5 Hz, 2H), 3.72 (m, 1H), 3.62 (s, 3H), 3.25-3.30 (m, 2H), 2.58 (m, 6H), 1.74-1.82 (m, 2H), 1.37-1.34 (m, 2H). LCMS (method F) Rt 1.20 mins (98%), m/z 526.3/528.3 (M+H)$^+$.

Example 133—2'-chloro-N-[5-(2-hydroxy-2-methyl-propoxy)-[1,3]thiazolo[5,4-d]pyrimidin-2-yl]-5'-methoxy-6-methyl-[4,4'-bipyridine]-3-carboxamide

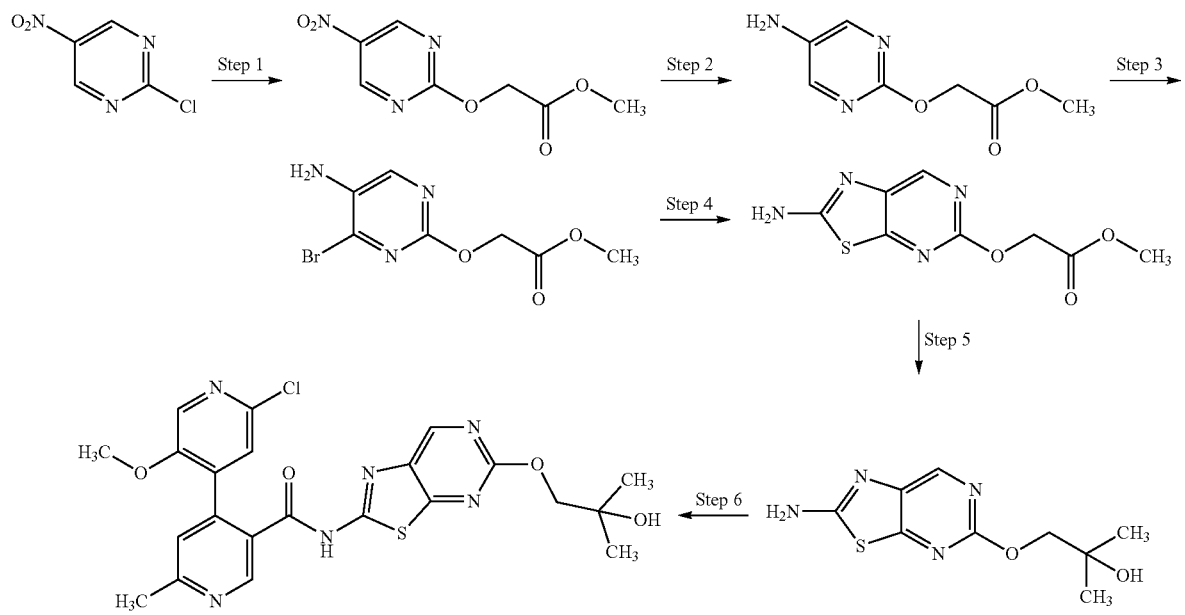

Step 1—methyl 2-[(5-nitropyrimidin-2-yl)oxy]acetate

Ethyl hydroxyacetate (16.5 mL, 0.21 mol) was added to 2-chloro-5-nitropyrimidine (4.00 g, 25.1 mmol) and stirred to give a yellow/orange suspension. DIPEA (13.1 mL, 75.2 mmol) was added and the reaction mixture heated at 80° C. for 25 mins. The reaction was cooled to RT and diluted with ethyl acetate (50 mL) and water (50 mL). The layers were separated and the aqueous extracted again with ethyl acetate (3×50 mL), the combined organics were washed with brine (25 mL), dried (MgSO$_4$), filtered and concentrated under a reduced pressure. The crude residue was purified by Biotage Isolera™ automated chromatography (Sfar Duo 50 g) eluting with 0-100% TBME in heptanes. Product containing fractions were combined and concentrated under reduced pressure to give the title compound (2.54 g, 45%) as a yellow oil that solidified on standing at RT. $^1$H NMR (500 MHz, DMSO-d$_6$) δ 9.41 (s, 2H), 5.15 (s, 2H), 3.69 (s, 3H). LCMS (method A) Rt 0.60 mins (94%), m/z 214.1 (M+H)$^+$.

Step 2—methyl 2-[(5-aminopyrimidin-2-yl)oxy]acetate

Iron powder (2.29 g, 40.9 mmol) was added to a stirred solution of methyl 2-(5-nitropyrimidin-2-yl)oxyacetate (3.27 g, 13.6 mmol) and ammonium chloride (730 mg, 13.6 mmol) in ethanol (40 mL) and water (10 mL) at 60° C., and the mixture stirred vigorously for 2.5 h. The mixture was cooled to RT and methanol (30 mL) added to the reaction mixture. Solids were filtered through celite, washing with hot methanol (2×30 mL). The filtrate was partially concentrated under reduced pressure, diluted with water (20 mL) and extracted with ethyl acetate (10 mL). The aqueous phase was basified with sat. aqueous NaHCO$_3$ solution (7 mL) and extracted again with ethyl acetate (3×40 mL). The combined organic extracts were washed with brine (30 mL), dried (MgSO$_4$) and concentrated under reduced pressure to give the title compound (2.13 g, 82%) as a yellow solid. $^1$H NMR (400 MHz, DMSO-d$_6$) δ 7.93 (s, 2H), 5.04 (s, 2H), 4.79 (s, 2H), 3.64 (s, 3H). LCMS (method A) Rt 0.35 mins (96%), m/z 184.1 (M+H)$^+$.

Step 3—methyl 2-[(5-amino-4-bromopyrimidin-2-yl)oxy]acetate

Benzyltrimethylazanium tribroman-2-ium (2.72 g, 6.97 mmol) was added in several portions over 30 mins to a stirred solution of methyl 2-(5-aminopyrimidin-2-yl)oxyacetate (1.33 g, 6.97 mmol) in anhydrous methanol (8 mL) and anhydrous DCM (32 mL) at −4° C. The resulting mixture was stirred at −4° C. for 45 mins. Further Benzyltrimethyl-azanium tribroman-2-ium (270 mg, 0.70 mmol) was added in 3 portions over 2 mins and the mixture was stirred at −4° C. for 30 mins. The reaction was quenched with solid NaHCO$_3$ (1 g) and stirred for 10 mins before sat. aqueous NaHCO$_3$ solution (20 mL) was added. The mixture was stirred vigorously for 10 mins then extracted with DCM (3×25 mL). The combined extracts were dried (Na$_2$SO$_4$), filtered and concentrated under reduced pressure. The crude residue was purified by Biotage Isolera™ automated chromatography (50 g, Sfar Duo) eluting with 0-100% TBME in heptanes, increasing to 0-30% methanol in TBME to give the title compound (220 mg, 11%) as a yellow solid. $^1$H NMR (400 MHz, DMSO-d$_6$) δ 8.02 (s, 1H), 5.28 (s, 2H), 4.84 (s, 2H), 3.67 (s, 3H). LCMS (method C) Rt 0.49 mins (94%), m/z 262.1/264.1 (M+H)$^+$.

Step 4—methyl 2-({2-amino-[1,3]thiazolo[5,4-d]pyrimidin-5-yl}oxy)acetate

A mixture of methyl 2-(5-amino-4-bromo-pyrimidin-2-yl)oxyacetate (254 mg, 0.90 mmol) and potassium thiocyanate (88 mg, 0.90 mmol) in acetic acid (920 μL) and 1,4-dioxane (5.5 mL) was stirred at 120° C. for 30 mins. The suspension was allowed to cool to RT and solution decanted off. The remaining solids were stirred in a mixture of ethyl acetate (5 mL) and water (0.25 mL) to form a solution. The layers were separated and aqueous phase extracted with ethyl acetate (2×2 mL). The combined organics were filtered through a hydrophobic frit and retained. The previously decanted solution was concentrated under reduced pressure and the residue stirred in ethyl acetate (20 mL) to give a brown suspension. 1M aqueous HCl solution (2 mL) added. The organics were separated and the aqueous phase extracted with ethyl acetate (2×10 mL). The combined extracts were washed with water (5 mL) and filtered through a hydrophobic frit. All organics were then combined and concentrated under reduced pressure to give the title compound (148 mg, 63%) as an orange solid. $^1$H NMR (400 MHz, DMSO-$d_6$) δ 8.41 (s, 1H), 7.89 (s, 2H), 4.94 (s, 2H), 3.68 (s, 3H). LCMS (method C) Rt 0.41 mins (92%), m/z 241.2 (M+H)$^+$.

Step 5—1-({2-amino-[1,3]thiazolo[5,4-d]pyrimidin-5-yl}oxy)-2-methylpropan-2-ol 3M methyl magnesium bromide in ether (1.50 mL, 4.50 mmol) was added dropwise to a stirred solution of methyl 2-(2-aminothiazolo[5,4-d]pyrimidin-5-yl)oxyacetate (193 mg, 0.75 mmol) in anhydrous 2-Methyl-THF (6 mL) at 0° C. The reaction was stirred for 30 mins at 0° C., then at room temperature overnight. The reaction mixture was diluted with sat. aqueous ammonium chloride (5 mL) and water (5 ml) then extracted into ethyl acetate (5×10 mL). The organic extract was washed with water (5 mL) and brine solution, then concentrated under reduced pressure to give the title compound (123 mg, 55%) as a tan gum, which was used without further purification. $^1$H NMR (400 MHz, DMSO-$d_6$) δ 8.40 (s, 1H), 7.81 (s, 2H), 4.03 (s, 2H), 1.19 (s, 6H). O$\overline{\text{H}}$ not observed. LCMS (method D) Rt 1.36 mins (70%), m/z 241.2 (M+H)$^+$.

Step 6—2'-chloro-N-[5-(2-hydroxy-2-methyl-propoxy)-[1,3]thiazolo[5,4-d]pyrimidin-2-yl]-5'-methoxy-6-methyl-[4,4'-bipyridine]-3-carboxamide The title compound was prepared using general procedure C, with heating at 60° C., to give 17 mg, 8% as a colourless powder. $^1$H NMR (400 MHz, DMSO-$d_6$) δ 13.17 (s, 1H), 8.98 (s, 1H), 8.86 (s, 1H), 8.18 (s, 1H), 7.59 (s, 1H), 7.47 (s, 1H), 4.70 (s, 1H), 4.14 (s, 2H), 3.63 (s, 3H), 2.61 (s, 3H), 1.22 (s, 6H). LCMS (method B) Rt 2.68 mins (99%), m/z 501.2/503.2 (M+H)$^+$.

Part B—Biological Assay 1

The Polθ ATPase assay described in Biological Assay 1 above was used to evaluate inhibitors of Polθ ATPase activity for the compounds described in the Experimental Part B above, in vitro.

The results are shown in Table B below.

TABLE B

Polθ ATPase assay IC50 results

| Example No. | Compound | Polθ ATPase assay IC50 |
|---|---|---|
| 95 | 2'-chloro-N-(5-{[(2R)-2-hydroxypropyl]amino}-[1,3]thiazolo[5,4-d]pyrimidin-2-yl)-5'-methoxy-6-methyl-[4,4'-bipyridine]-3-carboxamide | *** |
| 96 | 2'-chloro-N-(5-{[(2S)-2-hydroxypropyl]amino}-[1,3]thiazolo[5,4-d]pyrimidin-2-yl)-5'-methoxy-6-methyl-[4,4'-bipyridine]-3-carboxamide | *** |
| 97 | 2'-chloro-5'-methoxy-N-[5-(3-methoxy-3-methylazetidin-1-yl)-[1,3]thiazolo[5,4-d]pyrimidin-2-yl]-6-methyl-[4,4'-bipyridine]-3-carboxamide | *** |
| 99 | N-(4-bromo-1,3-benzothiazol-2-yl)-2'-chloro-5'-methoxy-6-methyl-[4,4'-bipyridine]-3-carboxamide | *** |
| 100 | 2'-chloro-N-{4-[2-(dimethylcarbamoyl)ethyl]-1,3-benzothiazol-2-yl}-5'-methoxy-6-methyl-[4,4'-bipyridine]-3-carboxamide | *** |
| 101 | 2'-chloro-N-[5-(cyanomethoxy)-1,3-benzothiazol-2-yl]-5'-methoxy-6-methyl-[4,4'-bipyridine]-3-carboxamide | *** |
| 102 | 2'-chloro-N-{5-[difluoro(methylcarbamoyl)Methoxy]-1,3-benzothiazol-2-yl}-5'-methoxy-6-methyl-[4,4'-bipyridine]-3-carboxamide | *** |
| 103 | N-(5-bromo-1,3-benzothiazol-2-yl)-2'-chloro-5'-methoxy-6-methyl-[4,4'-bipyridine]-3-carboxamide | *** |
| 104 | 2'-chloro-N-{5-[(dimethylcarbamoyl)difluoromethoxy]-1,3-benzothiazol-2-yl}-5'-methoxy-6-methyl-[4,4'-bipyridine]-3-carboxamide | *** |
| 105 | 2'-chloro-5'-methoxy-6-methyl-N-[5-(methylcarbamoyl)-1,3-benzothiazol-2-yl]-[4,4'-bipyridine]-3-carboxamide | *** |
| 106 | 2'-chloro-5'-methoxy-N-(5-methoxy-1,3-benzothiazol-2-yl)-6-methyl-[4,4'-bipyridine]-3-carboxamide | *** |
| 107 | 2'-chloro-5'-methoxy-N-{5-[(2-methoxyethyl)carbamoyl]-1,3-benzothiazol-2-yl}-6-methyl-[4,4'-bipyridine]-3-carboxamide | *** |
| 108 | 2'-chloro-N-{7-[(dimethylcarbamoyl)methoxy]-[1,3]thiazolo[5,4-d]pyrimidin-2-yl}-5'-methoxy-6-methyl-[4,4'-bipyridine]-3-carboxamide | *** |
| 109 | N-{5-[(1-acetylpiperidin-4-yl)methoxy]-1,3-benzothiazol-2-yl}-2'-chloro-5'-methoxy-6-methyl-[4,4'-bipyridine]-3-carboxamide | *** |
| 110 | 2'-chloro-N-{5-[(dimethylcarbamoyl)methoxy]-1,3-benzothiazol-2-yl}-5'-methoxy-6-methyl-[4,4'-bipyridine]-3-carboxamide | *** |
| 111 | 2'-chloro-5'-methoxy-6-methyl-N-{5-[2-(morpholin-4-yl)ethoxy]-1,3-benzothiazol-2-yl}-[4,4'-bipyridine]-3-carboxamide | *** |
| 112 | 2'-chloro-5'-methoxy-6-methyl-N-[5-(propan-2-yloxy)-1,3-benzothiazol-2-yl]-[4,4'-bipyridine]-3-carboxamide | *** |
| 113 | 2'-chloro-N-{5-[(1,1-dioxo-1-λ6-thietan-3-yl)methoxy]-1,3-benzothiazol-2-yl}-5'-methoxy-6-methyl-[4,4'-bipyridine]-3-carboxamide | ** |
| 114 | 2'-chloro-N-(5-ethoxy-1,3-benzothiazol-2-yl)-5'-methoxy-6-methyl-[4,4'-bipyridine]-3-carboxamide | ** |
| 115 | 2'-chloro-5'-methoxy-6-methyl-N-{5-[2-(trifluoromethoxy)ethoxy]-1,3-benzothiazol-2-yl}-[4,4'-bipyridine]-3-carboxamide | ** |

TABLE B-continued

Polθ ATPase assay IC50 results

| Example No. | Compound | Polθ ATPase assay IC50 |
|---|---|---|
| 116 | 6-[(dimethylcarbamoyl)methyl]-5'-methoxy-N-{[1,3]thiazolo[5,4d]pyrimidin-2-yl}-2'-(trifluoromethyl)-[4,4'-bipyridine]-3-carboxamide | *** |
| 117 | N-[5-(4-hydroxypiperidin-1-yl)-[1,3]thiazolo[5,4-d]pyrimidin-2-yl]-5'-methoxy-2',6-dimethyl-[4,4'-bipyridine]-3-carboxamide | *** |
| 118 | 2'-chloro-5'-methoxy-6-methyl-N-[5-(2-oxopiperidin-1-yl)-[1,3]thiazolo[5,4-b]pyridin-2-yl]-[4,4'-bipyridine]-3-carboxamide | *** |
| 119 | 5-[(2-{2'-chloro-5'-methoxy-6-methyl-[4,4'-bipyridine]-3-amido}-[1,3]thiazolo[4,5-c]pyridin-6-yl)amino]pentanoic acid | *** |
| 120 | 5-[(2-{2'-chloro-5'-methoxy-6-methyl-[4,4'-bipyridine]-3-amido}-[1,3]thiazolo[5,4-b]pyridin-5-yl)amino]pentanoic acid | *** |
| 121 | 2'-chloro-5'-methoxy-6-methyl-N-{5-[(2H-1,2,3,4-tetrazol-5-yl)methoxy]-1,3-benzothiazol-2-yl}-[4,4'-bipyridine]-3-carboxamide | *** |
| 122 | 2'-chloro-N-(5-hydroxy-1,3-benzothiazol-2-yl)-5'-methoxy-6-methyl-[4,4'-bipyridine]-3-carboxamide | *** |
| 123 | 2-[(2-{2'-chloro-5'-methoxy-6-methyl-[4,4'-bipyridine]-3-amido}-1,3-benzothiazol-5-yl)oxy]ethyl acetate | *** |
| 124 | 2'-chloro-N-[5-(2-hydroxyethoxy)-1,3-benzothiazol-2-yl]-5'-methoxy-6-methyl-[4,4'-bipyridine]-3-carboxamide | *** |
| 125 | 5-(4-hydroxypiperidin-1-yl)-[1,3]thiazolo[5,4-d]pyrimidin-2-yl 2'-chloro-5'-methoxy-1-methyl-6-oxo-1,6-dihydro-[3,4'-bipyridine]-4-carboxylate | *** |
| 126 | 2'-chloro-N-[7-(cyanomethoxy)-[1,3]thiazolo[5,4-d]pyrimidin-2-yl]-5'-methoxy-6-methyl-[4,4'-bipyridine]-3-carboxamide; | *** |
| 127 | N-[7-(carbamoylmethoxy)-[1,3]thiazolo[5,4-d]pyrimidin-2-yl]-2'-chloro-5'-methoxy-6-methyl-[4,4'-bipyridine]-3-carboxamide | *** |
| 128 | 2'-chloro-5'-methoxy-6-methyl-N-[6-(morpholin-3-yl)-1,3-benzothiazol-2-yl]-[4,4'-bipyridine]-3-carboxamide | *** |
| 129 | 2'-chloro-5'-methoxy-N-[6-(3-methoxyazetidin-1-yl)-[1,3]thiazolo[4,5-c]pyridin-2-yl]-6-methyl-[4,4'-bipyridine]-3-carboxamide | *** |
| 130 | 2'-chloro-N-{6-[(2-hydroxy-2-methylpropyl)amino]-[1,3]thiazolo[4,5-c]pyridin-2-yl}-5'-methoxy-6-methyl-[4,4'-bipyridine]-3 carboxamide | *** |
| 131 | 2'-chloro-5'-methoxy-N-[6-(3-methoxy-3-methylazetidin-1-yl)-[1,3]thiazolo[4,5-c]pyridin-2-yl]-6-methyl-[4,4'-bipyridine]-3-carboxamide | *** |
| 132 | 2'-chloro-N-[5-(4-hydroxypiperidin-1-yl)-7-methyl-[1,3]thiazolo[5,4-d]pyrimidin-2-yl]-5'-methoxy-6-methyl-[4,4'-bipyridine]-3-carboxamide | *** |
| 133 | 2'-chloro-N-[5-(2-hydroxy-2-methylpropoxy)-[1,3]thiazolo[5,4-d]pyrimidin-2-yl]-5'-methoxy-6-methyl-[4,4'-bipyridine]-3-carboxamide | *** |

\*\*\* denotes an IC50 of less than 100 nM
\*\* denotes an IC50 of 100 nM to 1000 nM
\* denotes an IC50 of greater than 1000 nM

The invention claimed is:

1. A compound having the structure shown below:

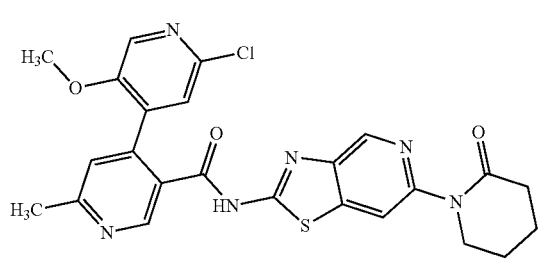

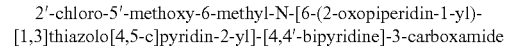

2'-chloro-5'-methoxy-6-methyl-N-[6-(2-oxopiperidin-1-yl)-[1,3]thiazolo[4,5-c]pyridin-2-yl]-[4,4'-bipyridine]-3-carboxamide or a pharmaceutically acceptable salt thereof.

2. A pharmaceutical composition comprising a compound according to claim 1, or a pharmaceutically acceptable salt thereof, and at least one pharmaceutically acceptable excipient.

3. A method of treating lymphoma, rhabdoid tumor, multiple myeloma, uterine cancer, gastric cancer, peripheral nervous system cancer, rhabdomyosarcoma, bone cancer, colorectal cancer, mesothelioma, breast cancer, ovarian cancer, lung cancer, fibroblast cancer, central nervous system cancer, urinary tract cancer, upper aerodigestive cancer, leukemia, kidney cancer, skin cancer, esophageal cancer, and pancreatic cancer; the method comprising administering to a patient in need of such treatment a therapeutically effective amount of a compound according to claim 1.

4. A method of treating lymphoma, rhabdoid tumor, multiple myeloma, uterine cancer, gastric cancer, peripheral nervous system cancer, rhabdomyosarcoma, bone cancer, colorectal cancer, mesothelioma, breast cancer, ovarian cancer, lung cancer, fibroblast cancer, central nervous system cancer, urinary tract cancer, upper aerodigestive cancer, leukemia, kidney cancer, skin cancer, esophageal cancer, and pancreatic cancer; the method comprising administering to a patient in need of such treatment a therapeutically effective amount of a pharmaceutical composition according to claim 2.

\* \* \* \* \*